United States Patent
Yasuda et al.

(10) Patent No.: US 6,806,230 B1
(45) Date of Patent: Oct. 19, 2004

(54) PYRIMIDINE DERIVATIVES AND HERBICIDES CONTAINING THEM

(75) Inventors: Atsushi Yasuda, Chiba (JP); Fumiaki Takabe, Shizuoka (JP); Ikumi Urushibata, Chiba (JP); Mikio Yamaguchi, Shizuoka (JP); Yoshihiro Yamaji, Shizuoka (JP); Makoto Fujinami, Shizuoka (JP); Takeshige Miyazawa, Shizuoka (JP)

(73) Assignees: Kumiai Chemical Industry Co., Ltd., Tokyo (JP); Ihara Chemical Industry Co., Ltd., Tokyo (JP)

( * ) Notice: Subject to any disclaimer, the term of this patent is extended or adjusted under 35 U.S.C. 154(b) by 156 days.

(21) Appl. No.: 10/070,804

(22) PCT Filed: Sep. 8, 2000

(86) PCT No.: PCT/JP00/06165

§ 371 (c)(1),
(2), (4) Date: Mar. 11, 2002

(87) PCT Pub. No.: WO01/17975

PCT Pub. Date: Mar. 15, 2001

(30) Foreign Application Priority Data

Sep. 9, 1999 (JP) .............................. 11-255029

(51) Int. Cl.$^7$ .................. A01N 43/54; A01N 43/84; A61K 31/505; C07D 239/02
(52) U.S. Cl. .............. 504/239; 504/225; 544/297; 544/298; 544/315; 514/256; 514/269; 514/274
(58) Field of Search .................. 514/269, 274, 514/256; 544/297, 298, 315; 504/239, 225

(56) References Cited

FOREIGN PATENT DOCUMENTS

| EP | 764641 | 3/1997 |
| WO | 96/22980 | 8/1996 |

OTHER PUBLICATIONS

Bargar, T. M. et. al., Pesticide Sciences, 1999, vol. 55, No. 11, pp. 1059–1069.*
T. M. Bargar, et al., Pesticide Science, vol. 55, pp. 1059–1069, XP–002154128, "A Comparative Molecular Field Analysis Study of Obtusifoliol 14α–Methyl Demethylase Inhibitos", 1999.

Patent Abstracts of Japan, JP 42–012906, Jul. 24, 1967.
A. G. Beaman, et al., Database CA 'Online! Chemical Abstracts Service, AN 1969:422065, XP–002208032, "Studies in the Nitroimidazole Series. III. 2–Nitroimidazole Derivatives Substituted in the 1–Position", 1968.
P. R. Bovy, et al., Database CA 'Online! Chemical Abstracts Service, AN 1994–299228, XP–002208033, "Synthesis of Heterocyclic.Beta.Amino Acids. A Convenient Preparation of Beta.–Amino–5–Pyrimidinepropanoic Acid and Derivatives", 1993.
A. Takamizawa et al.: "Studies on pyrimidine derivaties and rerated compounds LXXVII" Chemical & Pharmaceutical Bulletin, vol. 21, No. 4, pp. 770–784 1983.

* cited by examiner

Primary Examiner—Richard L. Raymond
Assistant Examiner—Tamthom N. Truong
(74) Attorney, Agent, or Firm—Oblon, Spivak, McClelland, Maier & Neustadt, P.C.

(57) ABSTRACT

Pyrimidine derivatives having excellent herbicidal activities for crop plants and selectivity between crop plants and weeds, are presented. Pyrimidine derivatives represented by the following formula (I):

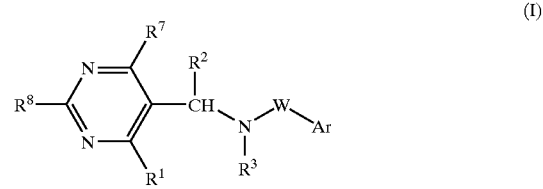

(I)

wherein $R^1$ is a hydrogen atom, an alkyl group, a haloalkyl group or the like; $R^2$ is an alkyl group, a phenyl group which may be substituted, or the like; $R^3$ is a hydrogen atom, an alkyl group, an alkynyl group or the like; $R^7$ is a hydrogen atom, a halogen atom, an alkyl group or the like; $R^8$ is a hydrogen atom, an alkyl group or the like, W is a —C(=Q)Z— group or a —SO$_2$— group; Q is O or S; Z is O, S, a —C(R$^4$)R$^5$—, a —NR$^6$ group or the like; each of $R^4$ and $R^5$ is a hydrogen atom, an alkyl group, an alkoxy group or the like; $R^6$ is a hydrogen atom or an alkyl group; and Ar is a phenyl group which may be substituted, a pyridyl group which may be substituted, or the like, and herbicides containing such pyrimidine derivatives as active ingredients.

10 Claims, No Drawings

PYRIMIDINE DERIVATIVES AND HERBICIDES CONTAINING THEM

TECHNICAL FIELD

The present invention relates to novel pyrimidine derivatives and herbicides containing them as active ingredients.

BACKGROUND ART

Pyrimidine derivatives are known, for example, by the specification of international application WO95/12582, the specification of international application WO96/22980 and the specification of international application WO97/12877. However, the pyrimidine derivatives of the present invention have not been known.

A herbicide to be used for crop plants is desired to be a chemical which exhibits a sufficient herbicidal effect at a low dose and yet provides selectivity between crop plants and weeds, when applied to an upland field or to a paddy field. Accordingly, it is an object of the present invention to provide a compound which has an excellent herbicidal activity and selectivity between crop plants and weeds.

DISCLOSURE OF THE INVENTION

Under these circumstances, the present inventors have synthesized various substituted pyrimidine derivatives and have studied their physiological activities. As a result, it has been found that novel substituted pyrimidine derivatives as the compounds of the present invention have excellent herbicidal activities and selectivity between crop plants and weeds, and the present invention has been accomplished. Namely, the present invention provides a pyrimidine derivative represented by the formula (I)

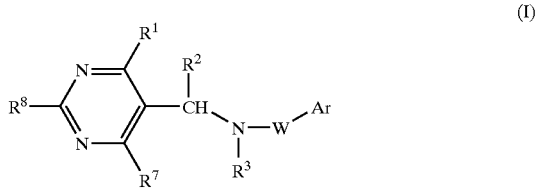

(I)

wherein $R^1$ is a hydrogen atom (except for a case where $R^2$=hydrogen atom, and W=SO$_2$), a halogen atom, a $C_1$–$C_6$ alkyl group, a $C_1$–$C_6$ alkylcarbonyl $C_1$–$C_6$ alkyl group, a hydroxyl group, a $C_2$–$C_6$ alkenyl group, a $C_2$–$C_6$ alkynyl group, a $C_3$–$C_6$ cycloalkyl group (this group may be substituted by a halogen atom, a $C_1$–$C_6$ alkyl group, a $C_1$–$C_6$ alkoxy group or a $C_1$–$C_4$ haloalkyl group), a $C_1$–$C_4$ haloalkyl group, a $C_1$–$C_6$ alkoxy group, a $C_1$–$C_4$ haloalkoxy group, a $C_2$–$C_6$ alkenyloxy group, a $C_2$–$C_6$ alkynyloxy group, a $C_3$–$C_6$ cycloalkyloxy group, a phenyl group (this group may be substituted by a halogen atom, a $C_1$–$C_6$ alkyl group, a $C_1$–$C_6$ alkoxy group, a $C_1$–$C_4$ haloalkyl group, a $C_1$–$C_4$ haloalkoxy group, a cyano group, a cyano $C_1$–$C_6$ alkyl group, a nitro group, a $C_1$–$C_6$ alkylthio group, a $C_1$–$C_6$ alkylsulfinyl group or a $C_1$–$C_6$ alkylsulfonyl group), a $C_1$–$C_6$ alkylthio group (except for a case where $R^2$=phenyl group, and W=SO$_2$), a $C_2$–$C_6$ alkenylthio group, a $C_2$–$C_6$ alkynylthio group, a $C_3$–$C_6$ cycloalkylthio group, a $C_1$–$C_6$ alkylsulfinyl group, a $C_2$–$C_6$ alkenylsulfinyl group, a $C_2$–$C_6$ alkynylsulfinyl group, a $C_3$–$C_6$ cycloalkylsulfinyl group, a $C_1$–$C_6$ alkylsulfonyl group, a $C_2$–$C_6$ alkenylsulfonyl group, a $C_2$–$C_6$ alkynylsulfonyl group, a $C_3$–$C_6$ cycloalkylsulfonyl group, a $C_1$–$C_6$ hydroxyalkyl group, a $C_2$–$C_7$ acyl group, a $C_1$–$C_6$ alkoxy $C_1$–$C_6$ alkyl group, a cyano group, a $C_1$–$C_6$ alkoxycarbonyl group, a $C_1$–$C_6$ alkoxycarbonyl $C_1$–$C_6$ alkyl group, a $C_1$–$C_6$ alkoxycarbonyl $C_2$–$C_6$ alkenyl group, a carboxyl group, a carboxyl $C_1$–$C_6$ alkyl group, a di $C_1$–$C_6$ alkoxy $C_1$–$C_6$ alkyl group, a $C_1$–$C_6$ alkoxyimino $C_1$–$C_6$ alkyl group, a hydroxyimino $C_1$–$C_6$ alkyl group, a dioxolanyl group (this group may be substituted by a $C_1$–$C_6$ alkyl group), an aldehyde group, an oxiranyl group, a NR$^9$R$^{10}$ group or a CONR$^9$R$^{10}$ group, R$^9$ is a hydrogen atom, a $C_1$–$C_6$ alkyl group, a $C_2$–$C_6$ alkenyl group, a $C_2$–$C_6$ alkynyl group, a $C_1$–$C_4$ haloalkyl group, a $C_1$–$C_6$ alkoxy $C_1$–$C_6$ alkyl group, a $C_1$–$C_6$ alkylthio $C_1$–$C_6$ alkyl group, a $C_3$–$C_6$ cycloalkyl group, a $C_2$–$C_7$ acyl group or a $C_1$–$C_6$ alkylsulfonyl group, R$^{10}$ is a $C_1$–$C_6$ alkyl group, a $C_2$–$C_6$ alkenyl group, a $C_2$–$C_6$ alkynyl group, a $C_1$–$C_4$ haloalkyl group, a $C_1$–$C_6$ alkoxy $C_1$–$C_6$ alkyl group, a $C_1$–$C_6$ alkylthio $C_1$–$C_6$ alkyl group, a $C_3$–$C_6$ cycloalkyl group, a $C_2$–$C_7$ acyl group, a $C_1$–$C_6$ alkylsulfonyl group, a $C_1$–$C_6$ alkoxycarbonyl group or a benzyloxycarbonyl group, here R$^9$ and R$^{10}$ may, together with the carbon atom to which they are bonded, form a 5- to 7-membered saturated ring, $R^2$ is a hydrogen atom, a $C_1$–$C_6$ alkyl group, a $C_2$–$C_6$ alkenyl group, a $C_2$–$C_6$ alkynyl group, a $C_1$–$C_6$ alkylthio group, a $C_1$–$C_4$ haloalkyl group, a $C_1$–$C_6$ alkoxy group, a $C_1$–$C_6$ alkoxy $C_1$–$C_6$ alkyl group, a $C_1$–$C_6$ alkylthio $C_1$–$C_6$ alkyl group, a $C_3$–$C_6$ cycloalkyl group (this group may be substituted by a halogen atom, a $C_1$–$C_6$ alkyl group, a $C_1$–$C_6$ alkoxy group or a $C_1$–$C_4$ haloalkyl group), a $C_2$–$C_7$ acyl group, a cyano group, a di $C_1$–$C_6$ alkoxy $C_1$–$C_6$ alkyl group, a $C_1$–$C_6$ alkoxyimino $C_1$–$C_6$ alkyl group, a hydroxyimino $C_1$–$C_6$ alkyl group, a dioxolanyl group (this group may be substituted by a $C_1$–$C_6$ alkyl group), a cyano $C_1$–$C_6$ alkyl group, a $C_1$–$C_6$ hydroxyalkyl group, a $C_1$–$C_6$ alkoxycarbonyl group, a $C_1$–$C_6$ alkoxycarbonyl $C_1$–$C_6$ alkyl group, a CR$^{11}$R$^{12}$NR$^9$R$^{10}$ group, a CONR$^9$R$^{10}$ group, a CR$^{11}$R$^{12}$CONR$^9$R$^{10}$ group or a group represented by any one of the formulae R$^2$-1 to R$^2$-13:

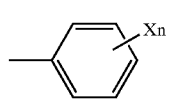

R$^2$-1

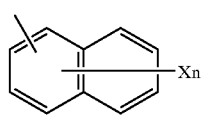

R$^2$-2

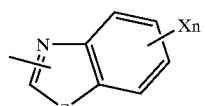

R$^2$-3

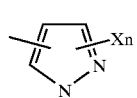

R$^2$-4

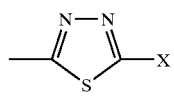

R$^2$-5

-continued

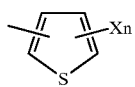 R²-6

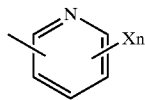 R²-7

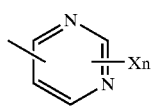 R²-8

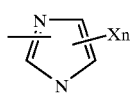 R²-9

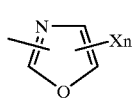 R²-10

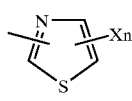 R²-11

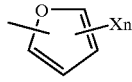 R²-12

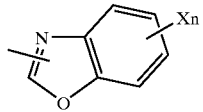 R²-13

(wherein X is a hydrogen atom, a halogen atom, a $C_1$–$C_6$ alkyl group, a $C_2$–$C_6$ alkenyl group, a $C_2$–$C_6$ alkynyl group, a $C_1$–$C_6$ alkoxy group, a $C_1$–$C_6$ alkoxy $C_1$–$C_6$ alkyl group, a $NR^9R^{10}$ group, a $CONR^9R^{10}$ group, a $C_1$–$C_4$ haloalkoxy group, a $C_2$–$C_6$ alkenyloxy group, a $C_3$–$C_6$ cycloalkyloxy group, a s $C_2$–$C_7$ acyl group, a $C_1$–$C_6$ alkoxycarbonyl group, a $C_1$–$C_6$ alkylthio group, a $C_1$–$C_6$ alkylsulfinyl group, a $C_1$–$C_6$ alkylsufonyl group, a cyano group, a nitro group or a $C_1$–$C_4$ haloalkyl group, n is an integer of from 1 to 3, when n is an integer of 2 or 3, the plurality of X may be the same or different, and two adjacent lower alkoxy groups may be bonded to each other to form a $C_1$–$C_3$ alkylenedioxy group), each of $R^{11}$ and $R^{12}$ is a hydrogen atom, a $C_1$–$C_6$ alkyl group, a $C_2$–$C_6$ alkenyl group, a $C_2$–$C_6$ alkynyl group or a $C_1$–$C_6$ alkoxy group, $R^3$ is a hydrogen atom, a $C_1$–$C_6$ alkyl group, a $C_2$–$C_6$ alkenyl group, a $C_2$–$C_6$ alkynyl group, a $C_1$–$C_6$ alkoxy group, a di $C_1$–$C_6$ alkylamino group, a $C_3$–$C_6$ cycloalkyl group, a $C_1$–$C_6$ alkoxy $C_1$–$C_6$ alkyl group, a cyano $C_1$–$C_6$ alkyl group, a $C_3$–$C_6$ cycloalkyl $C_1$–$C_6$ alkyl group, an oxiranyl $C_1$–$C_6$ alkyl group or a $C_1$–$C_6$ alkoxycarbonyl $C_1$–$C_6$ alkyl group, W is a —C(=Q)Z— group or a —SO$_2$— group, Q is an oxygen atom or a sulfur atom, Z is an oxygen atom, a sulfur atom, a —NR$^6$— group, a —CH$_2$CH$_2$— group, a —CH=CH— group, a —C(R$^4$)R$^5$— group, a —C(R$^4$)R$^5$—Q— group, a —Q—C(R$^4$)R$^5$— group, a —C(=Q)— group, a —NR$^6$NR$^{6a}$— group or a —NR$^6$C(R$^4$)R$^5$— group, each of $R^4$ and $R^5$ is a hydrogen atom, a $C_1$–$C_6$ alkyl group, a halogen atom, a $C_1$–$C_6$ alkoxy group or a $C_1$–$C_6$ alkylthio group, each of $R^6$ and $R^{6a}$ is a hydrogen atom, a $C_1$–$C_6$ alkyl group, a $C_2$–$C_6$ alkenyl group or a $C_2$–$C_6$ alkynyl group, here $R^3$ and $R^6$ may, together with the carbon atom to which they are bonded, form a 5- to 7-membered cyclic urea, Ar is a group represented by any one of the formulae Ar-1 to Ar-17:

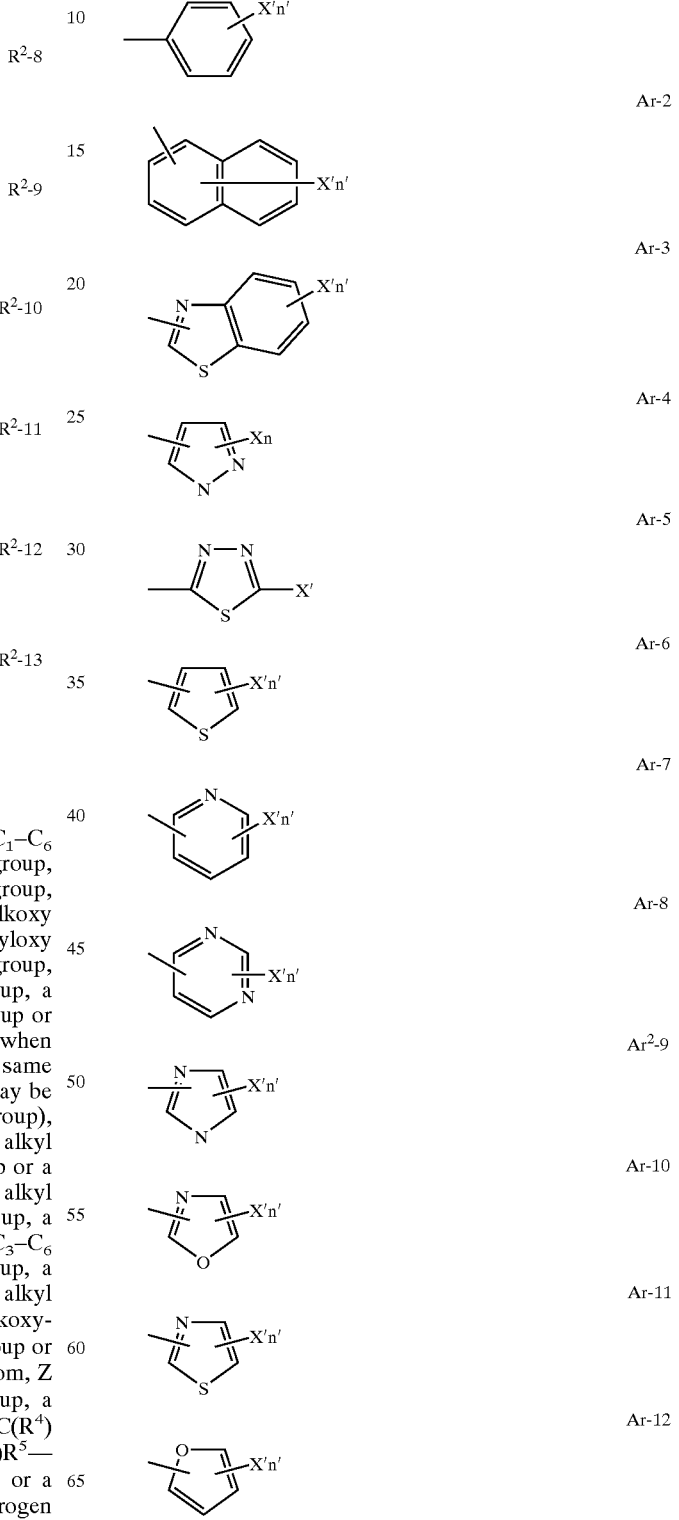

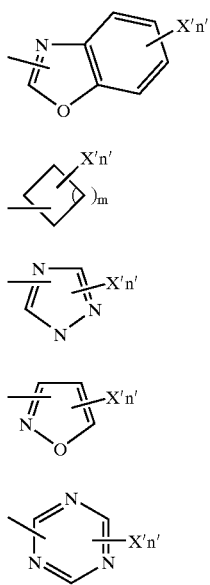

(wherein X' is a hydrogen atom, a halogen atom, a $C_1$–$C_6$ alkyl group, a $C_2$–$C_6$ alkenyl group, a $C_2$–$C_6$ alkynyl group, a $C_1$–$C_6$ alkoxy group, a $C_1$–$C_6$ alkoxy $C_1$–$C_6$ alkyl group, a $NR^9R^{10}$ group, a $CONR^9R^{10}$ group, a $C_1$–$C_4$ haloalkoxy group, a $C_2$–$C_6$ alkenyloxy group, a $C_3$–$C_6$ cycloalkyloxy group, a $C_2$–$C_7$ acyl group, a $C_1$–$C_6$ alkoxycarbonyl group, a $C_1$–$C_6$ alkylthio group, a $C_1$–$C_6$ alkylsulfinyl group, a $C_1$–$C_6$ alkylsufonyl group, a cyano group, a nitro group or a $C_1$–$C_4$ haloalkyl group, n' is an integer of from 1 to 3, m is an integer of from 0 to 3, when n' is an integer of 2 or 3, the plurality of X' may be the same or different, and two adjacent lower alkoxy groups may be bonded to each other to form a $C_1$–$C_3$ alkylenedioxy group), $R^7$ is a hydrogen atom, a halogen atom, a $C_1$–$C_6$ alkyl group, a $C_1$–$C_6$ alkoxy group, a $C_1$–$C_6$ alkylthio group, a $C_1$–$C_4$ haloalkyl group or a $C_3$–$C_6$ cycloalkyl group, and $R^8$ is a hydrogen atom, a $C_1$–$C_6$ alkyl group, a $C_1$–$C_6$ alkylthio group, a $C_1$–$C_4$ haloalkyl group or a $C_3$–$C_6$ cycloalkyl group; and a herbicide containing it as an active ingredient.

Now, definitions of terms used in this specification will be shown below.

The halogen atom represents a fluorine atom, a chlorine atom, a bromine atom or an iodine atom.

The $C_1$–$C_6$ alkyl group means a straight chain or branched chain alkyl group having a carbon number of from 1 to 6, unless otherwise specified, and it may, for example, be a methyl group, an ethyl group, a n-propyl group, an isopropyl group, a n-butyl group, an isobutyl group, a sec-butyl group or a tert-butyl group.

The $C_3$–$C_6$ cycloalkyl group represents a cycloalkyl group having a carbon number of from 3 to 6, and it may, for example, be a cyclopropyl group, a cyclopentyl group or a cyclohexyl group.

The $C_2$–$C_6$ alkenyl group represents a straight chain or branched chain alkenyl group having a carbon number of from 2 to 6, and it may, for example, be an ethenyl group or a 2-propenyl group.

The $C_2$–$C_6$ alkynyl group represents a straight chain or branched chain alkynyl group having a carbon number of from 2 to 6, and it may, for example, be an ethynyl group or a 2-propynyl group.

The $C_1$–$C_4$ haloalkyl group represents a straight chain or branched chain alkyl group having a carbon number of from 1 to 4, which is substituted by from 1 to 9 same or different halogen atoms, unless otherwise specified, and it may, for example, be a chloromethyl group, a trifluoromethyl group or a tetrafluoroethyl group.

The $C_1$–$C_6$ alkoxy group represents an (alkyl)-O-group wherein the alkyl moiety has the above meaning, and it may, for example, be a methoxy group, an ethoxy group or a propoxy group.

The $C_2$–$C_6$ alkenyloxy group represents an (alkenyl)-O-group wherein the alkenyl moiety has the above meaning, and it may, for example, be an ethenyloxy group or a 2-propenyloxy group.

The $C_2$–$C_6$ alkynyloxy group represents an (alkynyl)-O-group wherein the alkynyl moiety has the above meaning, and it may, for example, be an ethynyloxy group or a 2-propynyloxy group.

The $C_3$–$C_6$ cycloalkyloxy group represents a (cycloalkyl)-O-group wherein the cycloalkyl moiety has the above meaning, and it may, for example, be a cyclopropyloxy group, a cyclopentyloxy group or a cyclohexyloxy group.

The $C_1$–$C_6$ alkoxy $C_1$–$C_6$ alkyl group represents an (alkyl)-O-(alkylene)-group, wherein the alkyl moiety has the above meaning, and it may, for example, be a methoxymethyl group or an ethoxymethyl group.

The $C_3$–$C_6$ cycloalkyl $C_1$–$C_6$ alkyl group represents a (cycloalkyl)-($C_1$–$C_6$ alkylene) group wherein the cycloalkyl moiety has the above meaning, and it may, for example, be a cyclopropylmethyl group, a cyclopentylmethyl group, a cyclohexylmethyl group or a cyclohexylethyl group.

The $C_1$–$C_4$ haloalkoxy group represents a (haloalkyl)-O-group wherein the haloalkyl moiety has the above meaning, and it may, for example, be a trifluoromethoxy group or a 2,2,2-trifluoroethoxy group.

The $C_1$–$C_6$ alkylthio group, the $C_1$–$C_6$ alkylsulfinyl group and the $C_1$–$C_6$ alkylsulfonyl group, represent an (alkyl)-S-group, an (alkyl)-SO-group and an (alkyl)-SO$_2$-group, wherein the alkyl moiety has the above meaning, and they may, for example, be a methylthio group, an ethylthio group, a methylsultinyl group, an ethylsulfinyl group, a methylsulfonyl group or an ethylsulfonyl group.

The $C_2$–$C_6$ alkenylthio group, the $C_2$–$C_6$ alkenylsulfinyl group and the $C_2$–$C_6$ alkenylsulfonyl group, represent an (alkenyl)-S-group, an (alkenyl)-SO-group and an (alkenyl)-SO$_2$-group, wherein the alkenyl moiety has the above meaning, and they may, for example, be a propenylthio group, a butenylthio group, a propenylsulfinyl group, a butenylsulfinyl group, a propenylsulfonyl group or a butenylsulfonyl group.

The $C_2$–$C_6$ alkynylthio group, the $C_2$–$C_6$ alkynylsulfinyl group and the $C_2$–$C_6$ alkynylsulfonyl group, represent an (alkynyl)-S-group, an (alkynyl)-SO-group and an (alkynyl)-SO$_2$-group, wherein the alkynyl moiety has the above meaning, and they may, for example, be an ethynylthio group, a 2-propynylthio group, an ethynylsulfinyl group, a 2-propynylsulfinyl group, an ethynylsulfonyl group or a 2-propynylsulfonyl group.

The $C_3$–$C_6$ cycloalkylthio group, the $C_3$–$C_6$ cycloalkylsulfinyl group and the $C_3$–$C_6$ cycloalkylsulfonyl group, represent a (cycloalkyl)-S-group, a (cycloalkyl)-SO-group, and a (cycloalkyl)-SO$_2$-group, wherein the cycloalkyl moiety has the above meaning, and they may, for example, be a cyclopropylthio group, a cyclobutylthio group, a cyclopentylthio group, a cyclohexylthio group, a cyclopropylsulfinyl group, a cyclobutylsulfinyl group, a cyclopentylsulfinyl group, a cyclohexylsulfinyl group, a cyclopropylsulfonyl group, a cyclobutylsulfonyl group, a cyclopentylsulfonyl group or a cyclohexylsulfonyl group.

The $C_1$–$C_6$ alkylthio $C_1$–$C_6$ alkyl group represents an (alkyl)-S-(alkylene) group wherein the alkyl moiety has the above meaning, and it may, for example, be a methylthiomethyl group, an ethylthiomethyl group, a propylthiomethyl group or a methylthioethyl group.

The $C_2$–$C_7$ acyl group represents a $C_1$–$C_6$ alkylcarbonyl group, a $C_2$–$C_6$ alkenylcarbonyl group, a $C_2$–$C_6$ alkynylcarbonyl group, a $C_3$–$C_6$ cycloalkylcarbonyl group or a benzoyl group, and it may, for example, be an acetyl group, a propionyl group, a n-butyryl group, an isobutyryl group, a cyclopropylcarbonyl group or a benzoyl group.

The $C_1$–$C_6$ alkylcarbonyl $C_1$–$C_6$ alkyl group may, for example, be a methylcarbonylmethyl group, an ethylcarbonylmethyl group or a propylcarbonylmethyl group.

The $diC_1$–$C_6$ alkoxy $C_1$–$C_6$ alkyl group may, for example, be a dimethoxymethyl group or a diethoxymethyl group.

The $C_1$–$C_6$ alkoxyimino $C_1$–$C_6$ alkyl group may, for example, be a methoxyiminomethyl group or an ethoxyiminomethyl group.

The hydroxyimino $C_1$–$C_6$ alkyl group may, for example, be a hydroxyiminomethyl group or a hydroxyiminoethyl group.

The cyano $C_1$–$C_6$ alkyl group may, for example, be a cyanomethyl group or a cyanoethyl group.

The $C_1$–$C_6$ hydroxyalkyl group may, for example, be a hydroxymethyl group or a hydroxyethyl group.

The $C_1$–$C_6$ alkoxycarbonyl group may, for example, be a methoxycarbonyl group or an ethoxycarbonyl group.

The $C_1$–$C_6$ alkoxycarbonyl $C_1$–$C_6$ alkyl group may, for example, be a methoxycarbonyl methyl group or an ethoxycarbonyl methyl group.

The carboxyl $C_1$–$C_6$ alkyl group may, for example, be a carboxymethyl group or a carboxyethyl group.

The $diC_1$–$C_6$ alkoxy $C_1$–$C_6$ alkyl group may, for example, be a diethoxymethyl group or a 2-dimethoxyethyl group.

The $diC_1$–$C_6$ alkylamino group is a dialkylamino group wherein the alkylalkyl moiety has the above meaning, and it may, for example, be a dimethylamino group or a diethylamino group.

BEST MODE FOR CARRYING OUT THE INVENTION

Now, typical specific examples of the compound of the present invention represented by the formula (I) will be exemplified in Tables 1 to 39. However, the compound of the present invention is not limited to such compounds. The compound numbers will be referred to in the subsequent description. Further, in a case where the compound of the present invention or the disclosed compound has at least one asymmetric carbon, its all steric isomers are included in the compound of the present invention.

In the tables in this specification, S-isomer and R-isomer represent S-isomer and R-isomer of optical isomers, respectively, and in a case where there is no specific representation even when the compound has an asymmetric carbon, such represents a racemate. Further, in the tables, A-isomer and B-isomer represent diastereomers such that when resolved by silica gel column chromatography, one eluting first is designated as A-isomer, and one eluting later is designated as B-isomer. In a case where there is no representation even if diastereomers exist, such represents a mixture of diastereomers.

The following representations in the tables in this specification represent the respective corresponding groups as shown below.

| | |
|---|---|
| Me: methyl group | Et: ethyl group |
| Pr: n-propyl group | Pr-i: isopropyl group |
| Pr-c: cyclopropyl group | Bu: n-butyl group |
| Bu-i: isobutyl group | Bu-s: sec-butyl group |
| Bu-t: tert-butyl group | Bu-c: cyclobutyl group |
| Pen: n-pentyl group | Pen-i: isopentyl group |
| Pen-c: cyclopentyl group | Hex-c: cyclohexyl group |

TABLE 1

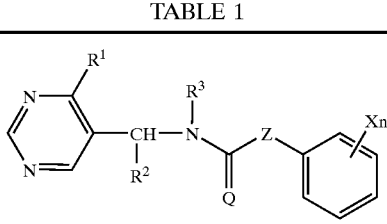

| Compound No. | $R^1$ | $R^2$ | $R^3$ | Z | Xn | Q | Diastereomer | m. p. (° C.) or refractive index ($n_D^{20}$) |
|---|---|---|---|---|---|---|---|---|
| 1-1 | $CClF_2$ | Pr-c | H | $CH_2$ | H | O | | 124–127 |
| 1-2 | $CClF_2$ | Pr-c | H | $CH_2$ | 4-OMe | O | | 116–119 |
| 1-3 | $CClF_2$ | Pr-c | H | $CH_2$ | 4-Cl | O | | 125–128 |
| 1-4 | $CClF_2$ | Pr-c | H | $CH_2$ | 4-$CF_3$ | O | | 111–114 |
| 1-5 | $CF_3$ | Pr-i | H | $CH_2$ | H | O | | 144–146 |
| 1-6 | $CF_3$ | Pr-i | H | $CH_2$ | 4-OMe | O | | 114–117 |
| 1-7 | $CF_3$ | Pr-i | H | CH(Me) | H | O | | 1.5163 |
| 1-8 | $CF_3$ | Pr-i | Me | $CH_2$ | H | O | | 106–109 |
| 1-9 | $CF_3$ | Pr-i | Me | $CH_2$ | 4-OMe | O | | 1.5289 |
| 1-10 | $CF_3$ | Pr-i | Me | S | H | O | | 131–133 |
| 1-11 | $CF_3$ | Pr-i | Me | S | 4-OMe | O | | 156–159 |
| 1-12 | $CF_3$ | Pr-i | Me | $CH_2$ | 4-F | O | | 109–110 |
| 1-13 | $CF_3$ | Pr-i | Me | $CH_2$ | 4-OEt | O | | 1.5151 |
| 1-14 | $CF_3$ | Pr-i | Me | S | 4-Cl | O | | |
| 1-15 | $CClF_2$ | Pr-i | Me | $CH_2$ | H | O | | 109–112 |

TABLE 1-continued

| Compound No. | R¹ | R² | R³ | Z | Xn | Q | Diastereomer | m. p. (° C.) or refractive index ($n_D^{20}$) |
|---|---|---|---|---|---|---|---|---|
| 1-16 | CClF₂ | Pr-i | Me | CH₂ | 4-OMe | O | | Not Measurable |
| 1-17 | CClF₂ | Pr-i | Me | S | H | O | | 127–130 |
| 1-18 | CClF₂ | Pr-i | Me | S | 4-OMe | O | | 136–139 |
| 1-19 | CClF₂ | Pr-i | Me | O | H | O | | 115–118 |
| 1-20 | CF₃ | Pr-i | Me | CH₂ | 2-Cl | O | | 178–181 |
| 1-21 | CF₃ | Pr-i | Me | CH₂ | 3-Cl | O | | 122–125 |
| 1-22 | CF₃ | Pr-i | Me | CH₂ | 4-Cl | O | | 99–101 |
| 1-23 | CF₃ | Pr-i | Me | CH₂ | 4-Me | O | | 76–79 |
| 1-24 | CF₃ | Pr-i | Mo | CH₂ | 4-CF₃ | O | | 105–108 |
| 1-25 | CClF₂ | Pr-i | Me | CH₂ | 4-F | O | | 126–129 |
| 1-26 | CF₃ | Pr-i | Et | CH₂ | H | O | | 87–90 |
| 1-27 | CF₃ | Pr-i | Et | CH₂ | 4-F | O | | 130–132 |
| 1-25 | CF₃ | Pr-i | Me | NH | H | O | | 149–150 |
| 1-29 | CF₃ | Pr-i | Me | NH | 4-Cl | O | | |

TABLE 2

| Compound No. | R¹ | R² | R³ | Z | Xn | Q | Diastereomer | m.p. (° C.) or refractive index ($n_D^{20}$) |
|---|---|---|---|---|---|---|---|---|
| 1-30 | CF₃ | Me | Me | CH₂ | H | O | | 1.5258 |
| 1-31 | CF₃ | Me | Me | CH₂ | 4-F | O | | 1.5202 |
| 1-32 | CF₃ | Et | Me | CH₂ | H | O | | 40–41 |
| 1-33 | CF₃ | Et | Me | CH₂ | 4-F | O | | 72–73 |
| 1-34 | CF₃ | Pr-c | Me | CH₂ | H | O | | Not Measurable |
| 1-35 | CF₃ | Pr-c | Me | CH₂ | 4-F | O | | 97–99 |
| 1-36 | CF₃ | Ph | Me | CH₂ | 4-F | O | | 93–94 |
| 1-37 | CClF₂ | Pr-i | Me | NH | 4-Me | O | | 135–137 |
| 1-38 | CClF₂ | Pr-i | Me | NH | H | O | | 146–147 |
| 1-39 | CF₃ | Pr-i | Me | CH₂ | 3-CF₃ | O | | 119–120 |
| 1-40 | CF₃ | Pr-i | Me | CH₂ | 2,5-F₂ | O | | 145–146 |
| 1-41 | CF₃ | Pr-i | Me | CH₂ | 4-Br | O | | 93–95 |
| 1-42 | CF₃ | Pr-i | Me | CH₂ | 4-I | O | | 102–104 |
| 1-43 | CF₃ | Pr-i | Me | CH₂ | 4-Bu-t | O | | 101–102 |
| 1-44 | CF₃ | Pr-i | Me | CH₂ | 4-SMe | O | | 69–71 |
| 1-45 | CF₃ | Pr-i | Me | CH₂ | 3,4-Cl₂ | O | | 145–146 |
| 1-46 | CF₃ | Pr-i | Me | CH₂ | 2-F,4-Cl | O | | 115–116 |
| 1-47 | CF₃ | Pr-i | Me | CH₂ | 3-OMe,4-Cl | O | | 129–131 |
| 1-48 | CF₃ | Pr-i | Et | CH₂ | 4-Cl | O | | 120–121 |
| 1-49 | CF₃ | Pr-i | Pr | CH₂ | 4-Cl | O | | 140–141 |
| 1-50 | CF₃ | Pr-i | Me | CH₂ | 2-Me | O | | 154–155 |
| 1-51 | CF₃ | Pr-i | Me | CH₂ | 3-Me | O | | 93–94 |
| 1-52 | CF₃ | Pr-i | Me | CH₂ | 4-NO₃ | O | | 146–149 |
| 1-53 | CF₃ | Bu-t | Me | CH₂ | 4-F | O | | 91–92 |
| 1-54 | CF₃ | Bu-t | Me | CH₂ | 4-Cl | O | | 111–112 |
| 1-55 | CF₃ | Bu-t | Me | CH₂ | 4-Me | O | | 84–87 |
| 1-56 | CH₃ | Pr-i | Me | CH₂ | 4-Cl | O | | 118–119 |
| 1-57 | CF₃ | Bu-s | Me | CH₂ | H | O | | 70–71 |
| 1-58 | CF₃ | Bu-s | Me | CH₂ | 4-F | O | | 84–85 |
| 1-59 | CF₃ | Bu-s | Me | CH₂ | 4-Cl | O | | 73–75 |
| 1-60 | CF₃ | Bu-s | Me | CH₂ | 4-Me | O | | 61–64 |
| 1-61 | CF₃ | Pr-i | Et | CH₂ | 4-Me | O | | 92–94 |
| 1-62 | CF₃ | Pr-i | Pr | CH₂ | 4-Me | O | | 83–86 |
| 1-63 | CF₃ | Pr-i | Pr | CH₂ | H | O | | 146–147 |
| 1-64 | CF₃ | Pr-i | Me | CH₂O | H | O | | 117–119 |
| 1-65 | CF₃ | Pr-i | Me | CH₂O | 4-Cl | O | | 141–142 |

TABLE 3

| Compound No. | $R^1$ | $R^2$ | $R^3$ | Z | Xn | Q | Diastereomer | m.p. (° C.) or refractive index ($n_D^{20}$) |
|---|---|---|---|---|---|---|---|---|
| 1-66 | $CF_3$ | Pr-i | Me | $CH_2$ | 3-F | O | | 120–123 |
| 1-67 | $CF_3$ | Pr-i | Me | $CH_2$ | 4-Et | O | | 56–58 |
| 1-68 | $CF_3$ | Pr-i | Me | $CH_2$ | 4-Pr-i | O | | 86–87 |
| 1-69 | Pr-i | Pr-i | Me | $CH_2S$ | H | O | | |
| 1-70 | $CF_8$ | Pr-i | Me | $CH_2$ | 3-Br | O | | 120–121 |
| 1-71 | $CF_3$ | Pr-i | Me | CH(Me) | 4-Cl | O | | 1.5232 |
| 1-72 | $CF_3$ | Pr-i | Me | $CH_2$ | 3,4-$(Me)_2$ | O | | 83–85 |
| 1-73 | Pr-i | Pr-i | Me | $CH_2S$ | 4-Cl | O | | |
| 1-74 | $CF_3$ | Pr-i | Me | $CH_2$ | 3-$NO_2$ | O | | 118–121 |
| 1-75 | $CF_3$ | Pr-i | Me | $CH_2$ | 4-CN | O | | 141–142 |
| 1-76 | $CF_3$ | Pr-i | Me | $CH_2$ | 4-$CH_2$OMe | O | | 58–60 |
| 1-77 | $CF_3$ | Pr-i | Me | $CH_2CH_2$ | H | O | | 79–82 |
| 1-78 | Pr-c | Pr-i | Me | $CH_2$ | 4-Cl | O | | 110–113 |
| 1-79 | Pr-i | Me | Me | $CH_2$ | H | O | | 69–70 |
| 1-80 | $CF_3$ | Pr-i | Pr-c | $CH_2$ | H | O | | 83–86 |
| 1-81 | $CF_3$ | Pr-i | Pr-c | $CH_2$ | 4-Cl | O | | 1.5297 |
| 1-82 | $CF_3$ | Pr-i | Pr-c | $CH_2$ | 4-Me | O | | 1.5218 |
| 1-83 | $CF_3$ | Pr-i | Pr-c | $CH_2$ | 4-F | O | | 81–84 |
| 1-84 | $CF_3$ | Pr-i | Me | $CH_2$ | 4-C≡CMe | O | | 128–132 |
| 1-85 | $CF_3$ | Pr-i | Me | CH=CH | H | O | | 1.5375 |
| 1-86 | $CF_3$ | Pr-i | Me | CH=CH | 4-Cl | O | | 1.5565 |
| 1-87 | Me | Pr-i | Me | $CH_2$ | H | O | | 80–83 |
| 1-88 | Me | Pr-i | Me | $CH_2$ | 4-F | O | | 102–104 |
| 1-89 | Me | Pr-i | Me | $CH_2$ | 4-Me | O | | 106–107 |
| 1-90 | H | Pr-i | Me | $CH_2$ | 4-Cl | O | | 1.5503 |
| 1-91 | $CClF_2$ | Pr-c | Me | $CH_2$ | H | O | | 111–113 |
| 1-92 | $CClF_2$ | Pr-c | Me | $CH_2$ | 4-F | O | | 91–92 |
| 1-93 | $CClF_2$ | Pr-c | Me | $CH_2$ | 4-Me | O | | 87–88 |
| 1-94 | $CClF_2$ | Pr-c | Me | $CH_2$ | 4-Cl | O | | 112–114 |
| 1-95 | $CF_3$ | Pr-i | Me | $CH_2$ | 4-$OCF_3$ | O | | 80–81 |
| 1-96 | $CF_3$ | Pr-i | Me | $CH_2$ | 4-$OCHF_2$ | O | | 54–57 |
| 1-97 | $CF_3$ | Pr-i | Me | $CH_2$ | 4-OPr-i | O | | 74–75 |
| 1-98 | $CF_3$ | Pr-i | Et | $CH_2$ | 4-CN | O | | 139–142 |
| 1-99 | $CF_3$ | Pr-i | Pr | $CH_2$ | 4-CN | O | | 162–163 |
| 1-100 | $CF_3$ | Pr-i | Me | $CH_2$ | 2-F | O | | 163–164 |
| 1-101 | Pr-c | Pr-i | Me | $CH_2$ | 4-F | O | | 111–112 |

TABLE 4

| Compound No. | $R^1$ | $R^2$ | $R^3$ | Z | Xn | Q | Diastereomer | m.p. (° C.) or refractive index ($n_D^{20}$) |
|---|---|---|---|---|---|---|---|---|
| 1-102 | Pr-c | Pr-i | Me | $CH_2$ | 4-Me | O | | 81–83 |
| 1-103 | $CF_3$ | Pr-i | Pr-i | $CH_2$ | H | O | | 1.5131 |
| 1-104 | $CF_3$ | Pr-i | Me | $CH_2$ | 4-$SO_2$Me | O | | 137–139 |
| 1-105 | $CF_3$ | Pr-i | $CH_2$OMe | $CH_2$ | 4-Cl | O | | 142–145 |
| 1-106 | $CF_3$ | Pr-i | $CH_2$OMe | $CH_2$ | 4-Me | O | | 104–106 |
| 1-107 | $CF_3$ | Pr-i | $CH_2$OEt | $CH_2$ | 4-Me | O | | 91–94 |
| 1-108 | $CF_3$ | Pr-i | Me | O | 4-F | O | | |
| 1-109 | $CF_3$ | Pr-i | Me | O | 4-Me | O | | |
| 1-110 | $CF_3$ | Pr-i | Me | O | 4-Cl | O | | |
| 1-111 | $CF_3$ | Pr | Me | $CH_2$ | H | O | | 54–55 |
| 1-112 | $CF_3$ | Pr | Me | $CH_2$ | 4-F | O | | 67–70 |
| 1-113 | $CF_3$ | Pr | Me | $CH_2$ | 4-Me | O | | 63–64 |
| 1-114 | $CF_3$ | Pr | Me | $CH_2$ | 4-Cl | O | | 91–92 |
| 1-115 | $CF_3$ | Pr-i | Me | CH(Me)O | H | O | | 127–130 |
| 1-116 | $CF_3$ | Pr-i | Me | CH(Me)O | 4-Cl | O | | 104–105 |
| 1-117 | $CF_3$ | Pr-i | Me | CH(Me)O | 4-Me | O | | |
| 1-118 | $CF_3$ | Pr-i | Me | $OCH_2$ | H | O | | 1.5028 |
| 1-119 | $CF_3$ | Pr-i | Me | $CH_2$ | S-OMe,4-Me | O | | 1.5109 |
| 1-120 | $CF_3$ | Pr-i | Me | $CH_2$ | 3-Me,4-Cl | O | | 92–94 |
| 1-121 | $CF_3$ | Pr-i | Me | $CH_2$ | 3-Cl,4-Me | O | | 121–122 |
| 1-122 | $CF_3$ | Pr-i | Me | $CH_2$ | 3,4-$F_2$ | O | | 135–136 |
| 1-123 | $CF_3$ | Pr-i | Me | $CH_2$ | 2,6-$F_2$ | O | | 176–177 |
| 1-124 | $CF_3$ | Pr-i | Me | $CH_2$ | 2,4-$Cl_2$ | O | | 147–149 |
| 1-125 | $CF_3$ | Pr-i | Me | $CH_2O$ | 2-F | O | | 157–158 |
| 1-126 | $CF_3$ | Pr-i | Me | $CH_2O$ | 3-F | O | | 127–128 |
| 1-127 | $CF_3$ | Pr-i | Me | $CH_2O$ | 4-F | O | | 119–121 |

TABLE 4-continued

| Compound No. | R¹ | R² | R³ | Z | Xn | Q | Dia-stereo-mer | m.p. (° C.) or refractive index ($n_D^{20}$) |
|---|---|---|---|---|---|---|---|---|
| 1-128 | Pr-i | Pr-i | Me | CH₂ | H | O | | 118–119 |
| 1-129 | Pr-i | Pr-i | Me | CH₂ | 4-F | O | | 125–126 |
| 1-130 | Pr-i | Pr-i | Me | CH₂ | 4-Cl | O | | 123–126 |
| 1-131 | Pr-i | Pr-i | Me | CH₂ | 4-Me | O | | 110–113 |
| 1-132 | CF₃ | Pr-i | Me | CH₂O | 2-Cl | O | | 162–163 |
| 1-133 | CF₃ | Pr-i | Me | CH₂O | 3-Cl | O | | 122–124 |
| 1-134 | CF₃ | Pr-i | Me | CH₂O | 2-Me | O | | 136–138 |
| 1-135 | CF₃ | Pr-i | Me | CH₂O | 3-Me | O | | 117–119 |
| 1-136 | CF₃ | Pr-i | Me | CH₂O | 4-Me | O | | 140–141 |
| 1-137 | CF₃ | Pen-c | Me | CH₂ | H | O | | 72–74 |

TABLE 5

| Compound No. | R¹ | R² | R³ | Z | Xn | Q | Dia-stereo-mer | m.p. (° C.) or refractive index ($n_D^{20}$) |
|---|---|---|---|---|---|---|---|---|
| 1-138 | CF₃ | Pen-c | Me | CH₂ | 4-F | O | | 97–99 |
| 1-139 | CF₃ | Pen-c | Me | CH₂ | 4-Cl | O | | 55–57 |
| 1-140 | CF₃ | Pen-c | Me | CH₂ | 4-Br | O | | 69–71 |
| 1-141 | CF₃ | Pen-c | Me | CH₂ | 4-Me | O | | 76–78 |
| 1-142 | CF₃ | Pr-i | Me | CH₂ | H | S | | 93–94 |
| 1-143 | CF₃ | Pr-i | Me | CH₂ | 4-F | S | | 103–104 |
| 1-144 | CF₃ | Pr-i | Me | CH₂ | 4-Cl | S | | 92–93 |
| 1-145 | CF₃ | Pr-i | Me | CH₂ | 4-Me | S | | 1.5541 |
| 1-146 | CF₃ | Pr-i | Me | CH₂ | 3,4-(-OCH₂O-) | O | | 82–85 |
| 1-147 | CF₃ | Pr-i | Me | CH₂ | 2,4-F₂ | O | | 137–139 |
| 1-148 | CF₃ | Pr-i | Me | CH₂ | 2,3-F₂ | O | | 183–184 |
| 1-149 | CF₃ | Pr-i | Me | CH₂ | 2,3,4-F₃ | O | | |
| 1-150 | SMe | Pr-i | Me | CH₂ | H | O | | 88–89 |
| 1-151 | SMe | Pr-i | Me | CH₂ | 4-Cl | O | | 125–127 |
| 1-152 | SMe | Pr-i | Me | CH₂ | 4-F | O | | 121–124 |
| 1-153 | SMe | Pr-i | Me | CH₂ | 4-Me | O | | 78–79 |
| 1-154 | CF₃ | Pr-i | Me | CH(SMe) | 4-Cl | O | | 148–149 |
| 1-155 | CF₃ | Pr-i | Me | CH(OMe) | 4-Cl | O | | 107–108 |
| 1-156 | CF₃ | Pen-c | Me | CH₂ | 2-F | O | | 111–112 |
| 1-157 | CF₃ | Pr-i | Me | CH₂ | 4-N(Me)₂ | O | | 109–111 |
| 1-158 | CF₃ | Ph(4-F) | Me | CH₂ | 3-F | O | | 85–86 |
| 1-159 | CH₃ | Bu-t | Me | CH₂ | H | O | | 93–95 |
| 1-160 | CH₃ | Bu-t | Me | CH₂ | 4-F | O | | 96–98 |
| 1-161 | CH₃ | Bu-t | Me | CH₂ | 4-Cl | O | | 107–109 |
| 1-162 | CH₃ | Bu-t | Me | CH₂ | 4-Me | O | | 84–86 |
| 1-163 | CHF₂ | Pr-i | Me | CH₂ | H | O | | 62–65 |
| 1-164 | CHF₂ | Pr-i | Me | CH₂ | 4-F | O | | 82–84 |
| 1-165 | CHF₂ | Pr-i | Me | CH₂ | 4-Cl | O | | 85–87 |
| 1-166 | CHF₂ | Pr-i | Me | CH₂ | 4-Me | O | | 83–84 |
| 1-167 | CF₃ | Pr-i | Me | CH₂ | 3,5-F₂ | O | | 156–157 |
| 1-168 | CHF₂ | Pr-i | Et | CH₂ | H | O | | 85–86 |
| 1-169 | CHF₂ | Pr-i | Et | CH₂ | 4-F | O | | 100–103 |
| 1-170 | CHF₂ | Pr-i | Et | CH₂ | 4-Cl | O | | 114–117 |
| 1-171 | CHF₂ | Pr-i | Et | CH₂ | 4-Me | O | | 91–92 |
| 1-172 | CF₃ | Pr-i | CH₂C≡CH | CH₂ | 4-F | O | | 124–128 |

TABLE 6

| Compound No. | R¹ | R² | R³ | Z | Xn | Q | Dia-stereo-mer | m.p. (° C.) or refractive index ($n_D^{20}$) |
|---|---|---|---|---|---|---|---|---|
| 1-173 | CF₃ | Pr-i | Et | CH₂ | 3-F | O | | 119–121 |
| 1-174 | CF₃ | Pr-i | Et | CH₂ | 4-CF₃ | O | | 100–101 |
| 1-175 | CF₃ | Pr-i | Me | C(Me)₂ | 4-Me | O | | 108–110 |
| 1-176 | CF₃ | Pr-i | Me | O | H | O | | 80–81 |
| 1-177 | CF₃ | Pr-i | Me | O | 4-F | O | | 110–112 |
| 1-178 | CF₃ | Pr-i | Me | O | 4-Cl | O | | 112–115 |
| 1-179 | CF₃ | Pr-i | Me | O | 4-Me | O | | 94–97 |
| 1-180 | CF₃ | Pr-i | Me | CH₂ | 3-F,4-Cl | O | | 120–124 |
| 1-181 | CF₃ | Pr-i | Pr | CH₂ | 4-F | O | | 126–127 |
| 1-182 | CF₃ | Pr-i | Me | CH₂S | H | O | | 106–108 |
| 1-183 | CF₃ | Pr-i | Me | CH₂S | 4-Cl | O | | 111–113 |

TABLE 6-continued

| Compound No. | R¹ | R² | R³ | Z | Xn | Q | Diastereomer | m.p. (° C.) or refractive index ($n_D^{20}$) |
|---|---|---|---|---|---|---|---|---|
| 1-184 | CClF₂ | Pr-i | Me | O | 4-F | O | | 119–123 |
| 1-185 | CClF₂ | Pr-i | Me | O | 4-Cl | O | | 99–103 |
| 1-186 | CF₃ | Ph | Me | CH₂ | H | O | | 86–87 |
| 1-187 | CF₃ | Ph | Me | CH₂ | 4-Cl | O | | 146–147 |
| 1-188 | Bu-t | Me | Me | CH₂ | H | O | | 1.5511 |
| 1-189 | Bu-t | Me | Me | CH₂ | 4-F | O | | 88–89 |
| 1-190 | Bu-t | Me | Me | CH₂ | 4-Cl | O | | 1.5582 |
| 1-191 | Bu-t | Me | Me | CH₂ | 4-Me | O | | 1.5471 |
| 1-192 | CF₃ | Pr-i | Me | CH(Me) | 4-OMe | O | | 1.5135 |
| 1-193 | CF₃ | Pr-i | CH₂C≡CH | CH₂ | H | O | | 117–121 |
| 1-194 | CF₃ | Pr-i | CH₂C≡CH | CH₂ | 4-Cl | O | | 119–121 |
| 1-195 | CF₃ | Pr-i | Me | CH(Me) | H | O | | Not Measurable |
| 1-196 | CF₃ | Bu-t | Me | CH₂ | H | O | | 107–109 |
| 1-197 | CF₃ | Ph | Me | CH₂ | 4-Me | O | | 151–154 |
| 1-198 | CF₃ | Pr-i | Me | CH(Me) | 4-F | O | | 1.4992 |
| 1-199 | CF₃ | Pr-i | Me | CH(Me) | 4-Me | O | | |
| 1-200 | CF₃ | 2-thienyl | Me | CH₂ | 4-Cl | O | | 120–121 |
| 1-201 | SMe | Bu-t | Me | CH₂ | H | O | | |
| 1-202 | SMe | Bu-t | Me | CH₂ | 4-F | O | | |
| 1-203 | SMe | Bu-t | Me | CH₂ | 4-Cl | O | | |
| 1-204 | SMe | Bu-t | Me | CH₂ | 4-Me | O | | |
| 1-205 | SMe | Ph | Me | CH₂ | H | O | | |
| 1-206 | SMe | Ph | Me | CH₂ | 4-F | O | | |
| 1-207 | SMe | Ph | Me | CH₂ | 4-Cl | O | | |
| 1-208 | SMe | Ph | Me | CH₂ | 4-Me | O | | |

TABLE 7

| Compound No. | R¹ | R² | R³ | Z | Xn | Q | Diastereomer | m.p. (° C.) or refractive index ($n_D^{20}$) |
|---|---|---|---|---|---|---|---|---|
| 1-209 | Pr-i | Bu-t | Me | CH₂ | H | O | | |
| 1-210 | Pr-i | Bu-t | Me | CH₂ | 4-F | o | | |
| 1-211 | Pr-i | Bu-t | Me | CH₂ | 4-Cl | O | | |
| 1-212 | Pr-i | Bu-t | Me | CH₂ | 4-Me | O | | |
| 1-213 | Pr-i | Ph | Me | CH₂ | H | O | | |
| 1-214 | Pr-i | Ph | Me | CH₂ | 4-F | O | | 90–91 |
| 1-215 | Pr-i | Ph | Me | CH₂ | 4-Cl | O | | |
| 1-216 | Pr-i | Ph | Me | CH₂ | 4-Me | O | | |
| 1-217 | CF₃ | Ph(4-F) | Me | CH₂ | H | O | | 111–112 |
| 1-218 | CF₃ | Ph(4-F) | Me | CH₂ | 4-F | O | | 99–101 |
| 1-219 | CF₃ | Ph(4-F) | Me | CH₂ | 4-Cl | O | | 137–139 |
| 1-220 | CF₃ | Ph(4-F) | Me | CH₂ | 4-Me | O | | 132–134 |
| 1-221 | CF₃ | Ph(4-Cl) | Me | CH₂ | H | O | | 136–137 |
| 1-222 | CF₃ | Ph(4-Cl) | Me | CH₂ | 4-F | O | | 114–115 |
| 1-223 | CF₃ | Ph(4-Cl) | Me | CH₂ | 4-Cl | O | | |
| 1-224 | CF₃ | Ph(4-Cl) | Me | CH₂ | 4-Me | O | | |
| 1-225 | CF₃ | Ph(4-Me) | Me | CH₂ | H | O | | 1.5566 |
| 1-226 | CF₃ | Ph(4-Me) | Me | CH₂ | 4-F | O | | 1.5549 |
| 1-227 | CF₃ | Ph(4-Me) | Me | CH₂ | 4-Cl | O | | |
| 1-228 | CF₃ | Ph(4-Me) | Me | CH₂ | 4-Me | O | | 1.5531 |
| 1-229 | CF₃ | 3-thienyl | Me | CH₂ | H | O | | |
| 1-230 | CF₃ | 3-thienyl | Me | CH₂ | 4-F | O | | |
| 1-231 | CF₃ | 3-thienyl | Me | CH₂ | 4-Cl | O | | |
| 1-232 | CF₃ | 3-thienyl | Me | CH₂ | 4-Me | O | | |
| 1-233 | CF₃ | 2-thienyl | Me | CH₂ | H | O | | |
| 1-234 | CF₃ | 2-thienyl | Me | CH₂ | 4-F | O | | 99–103 |
| 1-235 | CF₃ | 2-thienyl | Me | CH₂ | 4-Cl | O | | |
| 1-236 | CF₃ | 2-thienyl | Me | CH₂ | 4-Me | O | | |
| 1-237 | CF₃ | Ph(3-Cl) | Me | CH₂ | H | O | | |
| 1-238 | CF₃ | Ph(3-Cl) | Me | CH₂ | 4-F | O | | |
| 1-239 | CF₃ | Ph(3-Cl) | Me | CH₂ | 4-Cl | O | | |
| 1-240 | CF₃ | Ph(3-Cl) | Me | CH₂ | 4-Me | O | | |
| 1-241 | CF₃ | Bu-t | Me | CH₂ | 4-Br | O | | |
| 1-242 | CF₃ | Ph | Me | CH₂ | 4-Br | O | | |
| 1-243 | CF₃ | Bu-s | Me | CH₂ | 4-Br | O | | |
| 1-244 | CHF₂ | Pr-i | Me | CH₂ | 4-Br | O | | |

TABLE 8

| Compound No. | R¹ | R² | R³ | Z | Xn | Q | Diastereomer | m.p. (° C.) or refractive index ($n_D^{20}$) |
|---|---|---|---|---|---|---|---|---|
| 1-245 | SMe | Pr-i | Me | CH₂ | 4-Br | O | | |
| 1-246 | Pr-i | Pr-i | Me | CH₂ | 4-Br | O | | |
| 1-247 | Pr-c | Pr-i | Me | CH₂ | 4-Br | O | | |
| 1-248 | Me | Bu-t | Me | CH₂ | 4-Br | O | | |
| 1-249 | CF₃ | Bu-t | Me | CH₂ | 2-F,4-Cl | O | | 101–103 |
| 1-250 | CF₃ | Ph | Me | CH₂ | 2-F,4-Cl | O | | 170—173 |
| 1-251 | CF₃ | Bu-s | Me | CH₂ | 2-F,4-Cl | O | | 84–85 |
| 1-252 | CHF₂ | Pr-i | Me | CH₂ | 2-F,4-Cl | O | | |
| 1-253 | SMe | Pr-i | Me | CH₂ | 2-F,4-Cl | O | | |
| 1-254 | Pr-i | Pr-i | Me | CH₂ | 2-F,4-Cl | O | | 141–142 |
| 1-255 | Pr-c | Pr-i | Me | CH₂ | 2-F,4-Cl | O | | |
| 1-256 | Me | Bu-t | Me | CH₂ | 2-F,4-Cl | O | | |
| 1-257 | CF₃ | Bu-t | Me | CH₂ | 3,4-(Me)₂ | O | | |
| 1-258 | CF₃ | Ph | Me | CH₂ | 3,4-(Me)₂ | O | | |
| 1-259 | CF₃ | Bu-s | Me | CH₂ | 3,4-(Me)₂ | O | | |
| 1-260 | CHF₂ | Pr-i | Me | CH₂ | 3,4-(Me)₂ | O | | |
| 1-261 | SMe | Pr-i | Me | CH₂ | 3,4-(Me)₂ | O | | |
| 1-262 | Pr-i | Pr-i | Me | CH₂ | 3,4-(Me)₂ | O | | |
| 1-263 | Pr-i | Pr-c | Me | CH₂ | 3,4-(Me)₂ | O | | |
| 1-264 | Me | Bu-t | Me | CH₂ | 3,4-(Me)₂ | O | | |
| 1-265 | CF₃ | Bu-t | Me | CH₂ | 3-F | O | | 103–104 |
| 1-266 | CF₃ | Ph | Me | CH₂ | 3-F | O | | 88–90 |
| 1-267 | CF₃ | Bu-s | Me | CH₂ | 3-F | O | | 85–87 |
| 1-268 | CHF₃ | Pr-i | Me | CH₂ | 3-F | O | | |
| 1-269 | SMe | Pr-i | Me | CH₂ | 3-F | O | | |
| 1-270 | Pr-i | Pr-i | Me | CH₂ | 3-F | O | | 151–153 |
| 1-271 | Pr-c | Pr-i | Me | CH₂ | 3-F | O | | |
| 1-272 | Me | Bu-t | Me | CH₂ | 3-F | O | | |
| 1-273 | CF₃ | Bu-t | Me | CH₂ | 2,4-F₂ | O | | 137–140 |
| 1-274 | CF₃ | Ph | Me | CH₂ | 2,4-F₂ | O | | 107–110 |
| 1-275 | CF₃ | Bu-s | Me | CH₂ | 2,4-F₂ | O | | |
| 1-276 | CHF₂ | Pr-i | Me | CH₂ | 2,4-F₂ | O | | |
| 1-277 | SMe | Pr-i | Me | CH₂ | 2,4-F₂ | O | | |
| 1-278 | Pr-i | Pr-i | Me | CH₂ | 2,4-F₂ | O | | |
| 1-279 | Pr-c | Pr-i | Me | CH₂ | 2,4-F₂ | O | | |
| 1-280 | Me | Bu-t | Me | CH₂ | 2,4-F₂ | O | | |

TABLE 9

| Compound No. | R¹ | R² | R³ | Z | Xn | Q | Diastereomer | m.p. (° C.) or refractive index ($n_D^{20}$) |
|---|---|---|---|---|---|---|---|---|
| 1-281 | CF₃ | Bu-t | Me | CH₂ | 3-F,4-Cl | O | | |
| 1-282 | CF₃ | Ph | Me | CH₂ | 3-F,4-Cl | O | | |
| 1-283 | CF₃ | Bu-s | Me | CH₂ | 3-F,4-Cl | O | | |
| 1-284 | CHF₂ | Pr-i | Me | CH₂ | 3-F,4-Cl | O | | |
| 1-285 | SMe | Pr-i | Me | CH₂ | 3-F,4-Cl | O | | |
| 1-286 | Pr-i | Pr-i | Me | CH₂ | 3-F,4-Cl | O | | |
| 1-287 | Pr-c | Pr-i | Me | CH₂ | 3-F,4-Cl | O | | |
| 1-288 | Me | Bu-t | Me | CH₂ | 3-F,4-Cl | O | | |
| 1-289 | CF₃ | Bu-t | Me | CH₂ | 3,4-F₃ | O | | |
| 1-290 | CF₃ | Ph | Me | CH₂ | 3,4-F₃ | O | | |
| 1-291 | CF₃ | Bu-s | Me | CH₂ | 3,4-F₃ | O | | |
| 1-292 | CHF₂ | Pr-i | Me | CH₂ | 3,4-F₃ | O | | |
| 1-293 | SMe | Pr-i | Me | CH₂ | 3,4-F₃ | O | | |
| 1-294 | Pr-i | Pr-i | Me | CH₂ | 3,4-F₃ | O | | |
| 1-295 | Pr-c | Pr-i | Me | CH₂ | 3,4-F₃ | O | | |
| 1-296 | Me | Bu-t | Me | CH₂ | 3,4-F₃ | O | | |
| 1-297 | CF₃ | Bu-t | Me | CH₂ | 3,5-F₃ | O | | |
| 1-298 | CF₃ | Ph | Me | CH₂ | 3,5-F₃ | O | | |
| 1-299 | CF₃ | Bu-s | Me | CH₂ | 3,5-F₃ | O | | |
| 1-300 | CHF₂ | Pr-i | Me | CH₂ | 3,5-F₃ | O | | |
| 1-301 | SMe | Pr-i | Me | CH₂ | 3,5-F₃ | O | | |
| 1-302 | Pr-i | Pr-i | Me | CH₂ | 3,5-F₃ | O | | |
| 1-303 | Pr-c | Pr-i | Me | CH₂ | 3,5-F₃ | O | | |
| 1-304 | Me | Bu-t | Me | CH₂ | 3,5-F₃ | O | | |
| 1-305 | CF₃ | Bu-t | Me | CH₂ | 4-CF₃ | O | | 85–87 |
| 1-306 | CF₃ | Ph | Me | CH₂ | 4-CF₃ | O | | 92–93 |
| 1-307 | CF₃ | Bu-s | Me | CH₂ | 4-CF₃ | O | | 123–125 |
| 1-308 | CHF₂ | Pr-i | Me | CH₂ | 4-CF₃ | O | | |
| 1-309 | SMe | Pr-i | Me | CH₂ | 4-CF₃ | O | | |

TABLE 9-continued

| Compound No. | $R^1$ | $R^2$ | $R^3$ | Z | Xn | Q | Diastereomer | m.p. (° C.) or refractive index ($n_D^{20}$) |
|---|---|---|---|---|---|---|---|---|
| 1-310 | Pr-i | Pr-i | Me | $CH_2$ | 4-$CF_3$ | O | | 139–140 |
| 1-311 | Pr-c | Pr-i | Me | $CH_2$ | 4-$CF_3$ | O | | |
| 1-312 | Me | Bu-t | Me | $CH_2$ | 4-$CF_3$ | O | | |
| 1-313 | $CF_3$ | Bu-t | Me | $CH_2$ | 3-$CF_3$ | O | | |
| 1-314 | $CF_3$ | Ph | Me | $CH_2$ | 3-$CF_3$ | O | | |
| 1-315 | $CF_3$ | Bu-s | Me | $CH_2$ | 3-$CF_3$ | O | | |
| 1-316 | $CHF_2$ | Pr-i | Me | $CH_2$ | 3-$CF_3$ | O | | |

TABLE 10

| Compound No. | $R^1$ | $R^2$ | $R^3$ | Z | Xn | Q | Diastereomer | m.p. (° C.) or refractive index ($n_D^{20}$) |
|---|---|---|---|---|---|---|---|---|
| 1-317 | SMe | Pr-i | Me | $CH_2$ | 3-$CF_3$ | O | | |
| 1-318 | Pr-i | Pr-i | Me | $CH_2$ | 3-$CF_3$ | O | | |
| 1-319 | Pr-c | Pr-i | Me | $CH_2$ | 3-$CF_3$ | O | | |
| 1-320 | Me | Bu-t | Me | $CH_2$ | 3-$CF_3$ | O | | |
| 1-321 | $CF_3$ | Pr-i | Et | $CH_2$ | 2-F,4-Cl | O | | 144–146 |
| 1-322 | Ph | Pr-i | Me | $CH_2$ | H | O | | 82–84 |
| 1-323 | Ph | Pr-i | Me | $CH_2$ | 4-F | O | | 104–105 |
| 1-324 | Ph | Pr-i | Me | $CH_2$ | 4-Cl | O | | 88–90 |
| 1-325 | Ph | Pr-i | Me | $CH_2$ | 4-Me | O | | 79–80 |
| 1-326 | Pr-i | Pr-i | Me | NH | H | O | | 199–200 |
| 1-327 | Pr-i | Pr-i | Me | N(Me) | H | O | | 1.5384 |
| 1-328 | $CF_3$ | Pr-i | Me | C(=O) | H | O | | 101–102 |
| 1-329 | $CF_3$ | Pr-i | Me | $C(Me)_2$ | 4-Cl | O | | Not Measurable |
| 1-330 | $CF_3$ | Bu-i | Me | $CH_2$ | H | O | | 86–87 |
| 1-331 | $CF_3$ | Bu-i | Me | $CH_2$ | 4-F | O | | 97–98 |
| 1-332 | $CF_3$ | Pr-i | OMe | $CH_2$ | H | O | | 1.5071 |
| 1-333 | $CF_3$ | Pr-i | OMe | $CH_2$ | 4-F | O | | 59–62 |
| 1-334 | $CF_3$ | Bu-i | Me | $CH_2$ | 3-F | O | | 93–94 |
| 1-335 | $CF_3$ | Pr-i | Me | C(=O) | 4-Cl | O | | 116–119 |
| 1-336 | Pr-i | Ph | Et | $CH_2$ | 4-Me | O | | |
| 1-337 | $CF_3$ | Ph(4-F) | Et | $CH_2$ | H | O | | |
| 1-338 | $CF_3$ | Ph(4-F) | Et | $CH_2$ | 4-F | O | | |
| 1-339 | $CF_3$ | Ph(4-F) | Et | $CH_2$ | 4-Cl | O | | |
| 1-340 | $CF_3$ | Ph(4-F) | Et | $CH_2$ | 4-Me | O | | |
| 1-341 | $CF_3$ | Ph(4-Cl) | Et | $CH_2$ | H | O | | |
| 1-342 | $CF_3$ | Ph(4-Cl) | Et | $CH_2$ | 4-F | O | | |
| 1-343 | $CF_3$ | Ph(4-Cl) | Et | $CH_2$ | 4-Cl | O | | |
| 1-344 | $CF_3$ | Ph(4-Cl) | Et | $CH_2$ | 4-Me | O | | |
| 1-345 | $CF_3$ | Ph(4-Me) | Et | $CH_2$ | H | O | | |
| 1-346 | $CF_3$ | Ph(4-Me) | Et | $CH_2$ | 4-F | O | | |
| 1-347 | $CF_3$ | Ph(4-Me) | Et | $CH_2$ | 4-Cl | O | | |
| 1-348 | $CF_3$ | Ph(4-Me) | Et | $CH_2$ | 4-Me | O | | |
| 1-349 | $CF_3$ | 3-thienyl | Et | $CH_2$ | H | O | | |
| 1-350 | $CF_3$ | 3-thienyl | Et | $CH_2$ | 4-F | O | | |
| 1-351 | $CF_3$ | 3-thienyl | Et | $CH_2$ | 4-Cl | O | | |
| 1-352 | $CF_3$ | 3-thienyl | Et | $CH_2$ | 4-Me | O | | |

TABLE 11

| Compound No. | $R^1$ | $R^2$ | $R^3$ | Z | Xn | Q | Diastereomer | m.p. (° C.) or refractive index ($n_D^{20}$) |
|---|---|---|---|---|---|---|---|---|
| 1-353 | $CF_3$ | 2-thienyl | Et | $CH_2$ | H | O | | |
| 1-354 | $CF_3$ | 2-thienyl | Et | $CH_2$ | 4-F | O | | |
| 1-355 | $CF_3$ | 2-thienyl | Et | $CH_2$ | 4-Cl | O | | |
| 1-356 | $CF_3$ | 2-thienyl | Et | $CH_2$ | 4-Me | O | | |
| 1-357 | $CF_3$ | Ph(3-Cl) | Et | $CH_2$ | H | O | | |
| 1-358 | $CF_3$ | Ph(3-Cl) | Et | $CH_2$ | 4-F | O | | |
| 1-359 | $CF_3$ | Ph(3-Cl) | Et | $CH_2$ | 4-Cl | O | | |
| 1-360 | $CF_3$ | Ph(3-Cl) | Et | $CH_2$ | 4-Me | O | | |
| 1-361 | $CF_3$ | Ph | Me | CH(Me) | H | O | | |
| 1-362 | $CF_3$ | Ph | Me | CH(Me) | 4-F | O | | |
| 1-363 | $CF_3$ | Ph | Me | CH(Me) | 4-Cl | O | | |
| 1-364 | $CF_3$ | Ph | Me | CH(Me) | 4-Me | O | | |
| 1-365 | $CF_3$ | Ph(4-F) | Me | CH(Me) | H | O | | |

TABLE 11-continued

| Compound No. | R¹ | R² | R³ | Z | Xn | Q | Diastereomer | m.p. (° C.) or refractive index ($n_D^{20}$) |
|---|---|---|---|---|---|---|---|---|
| 1-366 | CF₃ | Ph(4-F) | Me | CH(Me) | 4-F | O | | |
| 1-367 | CF₃ | Ph(4-F) | Me | CH(Me) | 4-Cl | O | | |
| 1-368 | CF₃ | Ph(4-F) | Me | CH(Me) | 4-Me | O | | |
| 1-369 | CF₃ | Ph(4-Cl) | Me | CH(Me) | H | O | | |
| 1-370 | CF₃ | Ph(4-Cl) | Me | CH(Me) | 4-F | O | | |
| 1-371 | CF₃ | Ph(4-Cl) | Me | CH(Me) | 4-Cl | O | | |
| 1-372 | CF₃ | Ph(4-Cl) | Me | CH(Me) | 4-Me | O | | |
| 1-373 | Pr-i | Pr-i | Me | CH(Me) | H | O | | |
| 1-374 | Pr-i | Pr-i | Me | CH(Me) | 4-F | O | | |
| 1-375 | Pr-i | Pr-i | Me | CH(Me) | 4-Cl | O | | |
| 1-376 | Pr-i | Pr-i | Me | CH(Me) | 4-Me | O | | |
| 1-377 | SMe | Pr-i | Me | CH(Me) | H | O | | |
| 1-378 | SMe | Pr-i | Me | CH(Me) | 4-F | O | | |
| 1-379 | SMe | Pr-i | Me | CH(Me) | 4-Cl | O | | |
| 1-380 | SMe | Pr-i | Me | CH(Me) | 4-Me | O | | |
| 1-381 | CF₃ | 3-thienyl | Me | CH(Me) | H | O | | |
| 1-382 | CF₃ | 3-thienyl | Me | CH(Me) | 4-F | O | | |
| 1-383 | CF₃ | 3-thienyl | Me | CH(Me) | 4-Cl | O | | |
| 1-384 | CF₃ | 3-thienyl | Me | CH(Me) | 4-Me | O | | |
| 1-385 | CF₃ | Ph(3-Cl) | Me | CH(Me) | H | O | | |
| 1-386 | CF₃ | Ph(3-Cl) | Me | CH(Me) | 4-F | O | | |
| 1-387 | CF₃ | Ph(3-Cl) | Me | CH(Me) | 4-Cl | O | | |
| 1-388 | CF₃ | Ph(3-Cl) | Me | CH(Me) | 4-Me | O | | |
| 1-389 | Me | Bu-t | Me | CH(Me) | H | O | | |

TABLE 12

| Compound No. | R¹ | R² | R³ | Z | Xn | Q | Diastereomer | m.p. (° C.) or refractive index ($n_D^{20}$) |
|---|---|---|---|---|---|---|---|---|
| 1-390 | Me | Bu-t | Me | CH(Me) | 4-F | O | | |
| 1-391 | Me | Bu-t | Me | CH(Me) | 4-Cl | O | | |
| 1-392 | Me | Bu-t | Me | CH(Me) | 4-Me | O | | |
| 1-393 | CF₃ | Bu-t | Me | CH(Me) | H | O | | |
| 1-394 | CF₃ | Bu-t | Me | CH(Me) | 4-F | O | | |
| 1-395 | CF₃ | Bu-t | Me | CH(Me) | 4-Cl | O | | |
| 1-396 | CF₃ | Bu-t | Me | CH(Me) | 4-Me | O | | |
| 1-397 | CF₃ | 2-thienyl | Me | CH(Me) | H | O | | |
| 1-398 | CF₃ | 2-thienyl | Me | CH(Me) | 4-F | O | | |
| 1-399 | CF₃ | 2-thienyl | Me | CH(Me) | 4-Cl | O | | |
| 1-400 | CF₃ | 2-thienyl | Me | CH(Me) | 4-Me | O | | |
| 1-401 | OMe | Pr-i | Me | CH₂ | H | O | | 1.5439 |
| 1-402 | OMe | Pr-i | Me | CH₂ | 4-F | O | | 1.5332 |
| 1-403 | OMe | Pr-i | Me | CH₂ | 4-Cl | O | | 79–82 |
| 1-404 | OMe | Pr-i | Me | CH₂ | 4-Me | O | | 88–90 |
| 1-405 | CF₃ | Pr-i | OMe | CH₂ | H | O | | |
| 1-406 | CF₃ | Pr-i | OMe | CH₂ | 4-F | O | | |
| 1-407 | CF₃ | Pr-i | OMe | CH₂ | 4-Cl | O | | 1.5159 |
| 1-408 | CF₃ | Pr-i | OMe | CH₂ | 4-Me | O | | |
| 1-409 | CF₃ | 1-MePr-e | Me | CH₂ | H | O | | 78–79 |
| 1-410 | CF₃ | ⟨Me cyclopropyl⟩ | Me | CH₂ | 4-F | O | | 85–87 |
| 1-411 | CF₃ | ⟨Me cyclopropyl⟩ | Me | CH₂ | 4-Cl | O | | 110–111 |
| 1-412 | CF₃ | ⟨Me cyclopropyl⟩ | Me | CH₂ | 4-Me | O | | 88–89 |
| 1-413 | CF₃ | CH₂SMe | Me | CH₂ | 4-F | O | | 65–66 |
| 1-414 | CF₃ | CH₂SMe | Me | CH₂ | 4-Cl | O | | 94–95 |
| 1-415 | CF₃ | CH₂SMe | Me | CH₂ | 4-Br | O | | 109–110 |
| 1-416 | CF₃ | CH(Me)SMe | Me | CH₂ | 4-F | O | | 118–119 |
| 1-417 | CF₃ | Pr-i | Me | CH₂ | 2,3,4-F₃ | O | | 167–169 |
| 1-418 | CF₃ | Pr-i | Me | CH₂ | 3,4,5-F₃ | O | | 181–183 |
| 1-419 | CF₃ | 1-MePr-e | Me | CH₂ | 3-F | O | | 100–101 |
| 1-420 | CF₃ | CH₂SMe | Me | CH₂ | 3-F | O | | 66–67 |

TABLE 12-continued

| Compound No. | R¹ | R² | R³ | Z | Xn | Q | Diastereomer | m.p. (° C.) or refractive index ($n_D^{20}$) |
|---|---|---|---|---|---|---|---|---|
| 1-421 | $CF_3$ | $CH_2SMe$ | Me | $CH_2$ | 4-Me | O | | 87–89 |
| 1-422 | $CF_3$ | $CH_2SMe$ | Me | $CH_2$ | 2-F-4-Cl | O | | 102–103 |

TABLE 13

| Compound No. | R¹ | R² | R³ | Z | Xn | Q | Diastereomer | m.p. (° C.) or refractive index ($n_D^{20}$) |
|---|---|---|---|---|---|---|---|---|
| 1-423 | $CF_3$ | Et | Pr-i | $CH_2$ | 4-Cl | O | | 1.5207 |
| 1-424 | $CF_3$ | Pr-i | Me | N-Me | H | O | | 104–105 |
| 1-425 | $CF_3$ | Pr-i | Me | N-Et | H | O | | 63–65 |
| 1-426 | $CF_3$ | Pr-i | Me | N-Me | 4-F | O | | 84–85 |
| 1-427 | $CF_3$ | Pr-i | Me | N-Me | 4-Cl | O | | 106–108 |
| 1-428 | $CF_3$ | Pr-i | Me | N-Me | 4-Me | O | | 94–96 |
| 1-429 | Pr-i | Pr-i | Me | N-Me | 4-F | O | | 1.5216 |
| 1-430 | Pr-i | Pr-i | Me | N-Me | 4-Cl | O | | 120–123 |
| 1-431 | Pr-i | Pr-i | Me | N-Me | 4-Me | O | | 93–94 |
| 1-432 | Et | Pr-i | Me | $CH_2$ | H | O | | 97–98 |
| 1-433 | Et | Pr-i | Me | $CH_2$ | 4-F | O | | 93–95 |
| 1-434 | Et | Pr-i | Me | $CH_2$ | 4-Cl | O | | 110–111 |
| 1-435 | Et | Pr-i | Me | $CH_2$ | 4-Me | O | | 79–81 |
| 1-436 | Pr-i | Et | Me | $CH_2$ | H | O | | 1.5455 |
| 1-437 | Pr-i | Et | Me | $CH_2$ | 4-F | O | | 66–67 |
| 1-438 | Pr-i | Et | Me | $CH_2$ | 4-Cl | O | | 110–111 |
| 1-439 | Pr-i | Et | Me | $CH_2$ | 4-Me | O | | 98–99 |
| 1-440 | $CF_3$ | 3-thienyl | Me | $CH_2$ | H | O | | |
| 1-441 | $CF_3$ | 3-thienyl | Me | $CH_2$ | 4-F | O | | 109–110 |
| 1-442 | $CF_3$ | 3-thienyl | Me | $CH_2$ | 4-Cl | O | | 135–138 |
| 1-443 | $CF_3$ | 3-thienyl | Me | $CH_2$ | 4-Me | O | | 125–128 |
| 1-444 | $CF_3$ | Pr-i | Me | $CH_2$ | 2,3,5-$F_3$ | O | | 167–169 |
| 1-445 | Pr-n | Pr-i | Me | $CH_2$ | H | O | | 67–69 |
| 1-446 | Pr-n | Pr-i | Me | $CH_2$ | 4-F | O | | 117–118 |
| 1-447 | Pr-n | Pr-i | Me | $CH_2$ | 4-Cl | O | | 122–123 |
| 1-448 | Pr-n | Pr-i | Me | $CH_2$ | 4-Me | O | | 89–90 |
| 1-449 | Pr-i | Pr-n | Me | $CH_2$ | H | O | | 1.5402 |
| 1-450 | Pr-i | Pr-n | Me | $CH_2$ | 4-F | O | | 83–84 |
| 1-451 | Pr-i | Pr-n | Me | $CH_2$ | 4-Cl | O | | 78–79 |
| 1-452 | Pr-i | Pr-n | Me | $CH_2$ | 4-Me | O | | 94–95 |
| 1-453 | $CH(OEt)_2$ | Pr-i | Me | $CH_2$ | H | O | | 1.5253 |
| 1-454 | Pr-i | $CH(OEt)_2$ | Me | $CH_2$ | H | O | | 1.5221 |
| 1-455 | Pr-i | $CH(OEt)_2$ | Me | $CH_2$ | 4-F | O | | 1.5101 |
| 1-456 | Pr-i | $CH(OEt)_2$ | Me | $CH_2$ | 4-Cl | O | | |
| 1-457 | Pr-i | $CH(OEt)_2$ | Me | $CH_2$ | 4-Me | O | | |
| 1-458 | Pr-i | $CH(OEt)_2$ | Me | $OCH_2$ | H | O | | 1.5191 |

TABLE 14

| Compound No. | R¹ | R² | R³ | Z | Xn | Q | Diastereomer | m. p. (° C.) or refractive index ($n_D^{20}$) |
|---|---|---|---|---|---|---|---|---|
| 1-459 | $CF_3$ | Pr-i | Me | N-Me | 4-CN | O | | 144–145 |
| 1-460 | $CF_3$ | Pr-i | Me | N-Me | 4-OMe | O | | 1.5081 |
| 1-461 | $CF_3$ | Pr-i | Me | $NHCH_2$ | H | O | | 92–95 |
| 1-462 | Pr-i | CH=NOMe | Me | $CH_2$ | H | O | | |
| 1-463 | Pr-i | CH=NOMe | Me | $CH_2$ | 4-F | O | | 1.5309 |
| 1-464 | Pr-i | CH=NOMe | Me | $CH_2$ | 4-Cl | O | | 1.5459 |
| 1-465 | Pr-i | CH=NOMe | Me | $CH_2$ | 4-Me | O | | 1.5412 |
| 1-466 | Pr-i | CH=NOMe | Me | $OCH_2$ | H | O | | 1.5352 |
| 1-467 | $CH(OEt)_2$ | Pr-i | Me | $OCH_2$ | H | O | | 1.5236 |
| 1-468 | $CH(OEt)_2$ | Pr-i | Me | $CH_2$ | 4-F | O | | 1.5135 |
| 1-469 | $CH(OEt)_2$ | Pr-i | Me | $CH_2$ | 4-Cl | O | | 1.5282 |
| 1-470 | $CH(OEt)_2$ | Pr-i | Me | $CH_2$ | 4-Me | O | | 116–117 |
| 1-471 | CH=NOMe | Pr-i | Me | $OCH_2$ | H | O | | 1.5481 |

US 6,806,230 B1

TABLE 14-continued

| Compound No. | R¹ | R² | R³ | Z | Xn | Q | Diastereomer | m. p. (° C.) or refractive index ($n_D^{20}$) |
|---|---|---|---|---|---|---|---|---|
| 1-472 |  |  | Me | CH₂ | H | O | | |
| 1-473 |  |  | Me | CH₂ | 4-F | O | | 110–112 |
| 1-474 |  |  | Me | CH₂ | 4-Cl | O | | |
| 1-475 |  |  | CH₂CO₂Et | CH₂ | 4-Me | O | | |
| 1-476 | CF₃ | Pr-i | CH₂CO₂Et | CH₂ | H | O | | 158–159 |
| 1-477 | CF₃ | Pr-i | CH₂CO₂Et | CH₂ | 4-F | O | | |
| 1-478 | CF₃ | Pr-i | CH₂CO₂Et | CH₂ | 4-Cl | O | | |
| 1-479 | CF₃ | Pr-i | CH₂CO₂Et | CH₂ | 4-Me | O | | |
| 1-480 | CF₃ | Pr-i | CH₂CN | CH₂ | H | O | | |
| 1-481 | CF₃ | Pr-i | CH₂CN | CH₂ | 4-F | O | | |
| 1-482 | CF₃ | Pr-i | CH₂CN | CH₂ | 4-Cl | O | | 164–166 |
| 1-483 | CF₃ | Pr-i | CH₂CN | CH₂ | 4-Me | O | | 159–161 |
| 1-484 | CF₃ | Ph(4-OMe) | Me | CH₂ | H | O | | 97–98 |
| 1-485 | CF₃ | Ph(4-OMe) | Me | CH₂ | 4-F | O | | 103–105 |
| 1-486 | CF₃ | Ph(4-OMe) | Me | CH₂ | 4-Cl | O | | 131–133 |
| 1-487 | CF₃ | Ph(4-OMe) | Me | CH₂ | 4-Me | O | | 147–150 |
| 1-488 | CF₃ | Ph(2-OMe) | Me | CH₂ | H | O | | Not Measurable |

TABLE 15

| Compound No. | R¹ | R² | R³ | Z | Xn | Q | Diastereomer | m.p. (° C.) or refractive index ($n_D^{20}$) |
|---|---|---|---|---|---|---|---|---|
| 1-489 | CF₃ | Ph(2-OMe) | Me | CH₂ | 4-F | O | | 1.5474 |
| 1-490 | CF₃ | Ph(2-OMe) | Me | CH₂ | 4-Cl | O | | Not Measurable |
| 1-491 | CF₃ | Ph(2-OMe) | Me | CH₂ | 4-Me | O | | 1.5432 |
| 1-492 | Pr-n | Pr-n | Me | CH₂ | H | O | | 65–66 |
| 1-493 | Pr-n | Pr-n | Me | CH₂ | 4-F | O | | 83–84 |
| 1-494 | Pr-n | Pr-n | Me | CH₂ | 4-Cl | O | | 91–92 |
| 1-495 | Pr-n | Pr-n | Me | CH₂ | 4-Me | O | | 55 . 56 |
| 1-496 | CH=NOMe | Pr-i | Me | CH₂ | H | O | | 113–115 |
| 1-497 | CH=NOMe | Pr-i | Me | CH₂ | 4-F | O | | 155–156 |
| 1-498 | CH=NOMe | Pr-i | Me | CH₂ | 4-Cl | O | | 122–123 |
| 1-499 | CH=NOMe | Pr-i | Me | CH₂ | 4-Me | O | | 1.5468 |
| 1-500 | CH=NOH | Pr-i | Me | CH₂ | H | O | | 171–172 |
| 1-501 | CH=NOH | Pr-i | Me | CH₂ | 4-F | O | | 197–198 |
| 1-502 | CH=NOH | Pr-i | Me | CH₂ | 4-Cl | O | | 183–184 |
| 1-503 | CH=NOH | Pr-i | Me | CH₂ | 4-Me | O | | 155–157 |
| 1-504 | CN | Pr-i | Me | CH₂ | H | O | | 80–81 |
| 1-505 | CN | Pr-i | Me | CH₂ | 4-F | O | | 105–106 |
| 1-506 | CN | Pr-i | Me | CH₂ | 4-Cl | O | | 99–100 |
| 1-507 | CN | Pr-i | Me | CH₂ | 4-Me | O | | 75–76 |
| 1-508 | CN | Pr-i | Me | CH(Me) | 4-Cl | O | | 1.6669 |
| 1-509 | Pr-i | CMe(OMe)₂ | Me | CH₂ | H | O | | 1.5352 |
| 1-510 | Pr-i | CMe(OMe)₂ | Me | CH₂ | 4-F | O | | 112–113 |
| 1-511 | Pr-i | CMe(OMe)₂ | Me | CH₂ | 4-Cl | O | | 106–107 |
| 1-512 | Pr-i | CMe(OMe)₂ | Me | CH₂ | 4-Me | O | | 104–105 |
| 1-513 | Pr-i | COMe | Me | CH₂ | H | O | | 99–100 |
| 1-514 | Pr-i | COMe | Me | CH₂ | 4-F | O | | 114–115 |
| 1-515 | Pr-i | COMe | Me | CH₂ | 4-Cl | O | | 108–109 |
| 1-516 | Pr-i | COMe | Me | CH₂ | 4-Me | O | | 119–120 |
| 1-517 | CMe(OMe)₂ | Pr-i | Me | CH₂ | 4-Cl | O | | 78–79 |

TABLE 15-continued

| Compound No. | R¹ | R² | R³ | Z | Xn | Q | Diastereomer | m.p. (° C.) or refractive index ($n_D^{20}$) |
|---|---|---|---|---|---|---|---|---|
| 1-518 | $CF_3$ | Pr-i | $CH_2CH=CH_2$ | $CH_2$ | H | O | | 121–122 |
| 1-519 | $CF_3$ | Pr-i | $CH_2CH=CH_2$ | $CH_2$ | 4-F | O | | 129–130 |
| 1-520 | $CF_3$ | Pr-i | $CH_2CH=CH_2$ | $CH_2$ | 4-Cl | O | | 124–127 |
| 1-521 | $CF_3$ | Pr-i | $CH_2CH=CH_2$ | $CH_2$ | 4-Me | O | | 98–99 |
| 1-522 | CHO | Pr-i | Me | $CH_2$ | H | O | | |
| 1-523 | CHO | Pr-i | Me | $CH_2$ | 4-F | O | | 1.5466 |
| 1-524 | CHO | Pr-i | Me | $CH_2$ | 4-Cl | O | | 1.5609 |

TABLE 16

| Compound No. | R¹ | R² | R³ | Z | Xn | Q | Diastereomer | m. p. (° C.) or refractive index ($n_D^{20}$) |
|---|---|---|---|---|---|---|---|---|
| 1-525 | CHO | Pr-i | Me | $CH_2$ | 4-Me | O | | 1.5558 |
| 1-526 | COMe | Pr-i | Me | $CH_2$ | H | O | | Not Measurable |
| 1-527 | COMe | Pr-i | Me | $CH_2$ | 4-F | O | | 1.5341 |
| 1-528 | COMe | Pr-i | Me | $CH_2$ | 4-Cl | O | | 1.5501 |
| 1-529 | COMe | Pr-i | Me | $CH_2$ | 4-Me | O | | 1.5423 |
| 1-530 | COMe | Pr-i | Me | CH(Me) | 4-Cl | O | | 1.5395 |
| 1-531 | Pr-i | CH=NOH | Me | $OCH_2$ | H | O | | 1.5365 |
| 1-532 | $CF_3$ | Pr-i | Me | $N(Me)CH_2$ | 4-Cl | O | | 95–96 |
| 1-533 | $CF_3$ | Pr-i | Me | $N(CH_2C\equiv CH)$ | 4-F | O | | 1.5121 |
| 1-534 | $CF_3$ | Pr-i | Me | NHCH(Me) | H | O | | 69–70 |
|  |  |  |  | (R-isomer) |  |  |  |  |
| 1-535 | $CF_3$ | Pr-i | Me | NHCH(Me) | H | O | | 1.5134 |
|  |  |  |  | (S-isomer) |  |  |  |  |
| 1-536 | $CF_3$ | Pr-i | Me | N(Me) | 2-F | O | | 1.5043 |
| 1-537 | $CF_3$ | Pr-i | Me | N(Me) | 2,4-$F_2$ | O | | 1.4936 |
| 1-538 | Et | Pr-i | Me | N(Me) | H | O | | 1.5451 |
| 1-539 | Et | Pr-i | Me | N(Me) | 4-F | O | | 1.5349 |
| 1-540 | Et | Pr-i | Me | N(Me) | 4-Cl | O | | 115–117 |
| 1-541 | Et | Pr-i | Me | N(Me) | 4-Me | O | | 1.5342 |
| 1-542 | $CF_3$ | Pr-i | 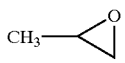 | $CH_2$ | H | O | | 1.5131 |
| 1-543 | $CF_3$ | Pr-i | 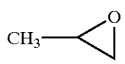 | $CH_2$ | 4-F | O | | 1.5052 |
| 1-544 | $CF_3$ | Pr-i | 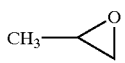 | $CH_2$ | 4-Cl | O | | 1.5215 |
| 1-545 | $CF_3$ | Pr-i | 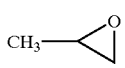 | $CH_2$ | 4-Me | O | | 1.5121 |
| 1-546 | $CF_3$ | Ph(2-F) | Me | $CH_2$ | H | O | | 109–110 |
| 1-547 | $CF_3$ | Ph(2-F) | Me | $CH_2$ | 4-F | O | | 107–108 |
| 1-548 | $CF_3$ | Ph(2-F) | Me | $CH_2$ | 4-Cl | O | | 139–141 |
| 1-549 | $CF_3$ | Ph(2-F) | Me | $CH_2$ | 4-Me | O | | 107–110 |
| 1-550 | $CF_3$ | Ph(2-Me) | Me | $CH_2$ | H | O | | 146–147 |
| 1-551 | $CF_3$ | Ph(2-Me) | Me | $CH_2$ | 4-F | O | | 149–150 |
| 1-552 | $CF_3$ | Ph(2-Me) | Me | $CH_2$ | 4-Cl | | | |
| 1-553 | $CF_3$ | Ph(2-Me) | Me | $CH_2$ | 4-Me | O | | 135–136 |

TABLE 17

| Compound No. | $R^1$ | $R^2$ | $R^3$ | Z | Xn | Q | Diastereomer | m.p. (° C.) or refractive index ($n_D^{20}$) |
|---|---|---|---|---|---|---|---|---|
| 1.554 | $CF_3$ | $Ph(2,4-F_2)$ | Me | $CH_2$ | H | O | | |
| 1.555 | $CF_3$ | $Ph(2,4-F_2)$ | Me | $CH_2$ | 4-F | O | | 102–104 |
| 1.556 | $CF_3$ | $Ph(2,4-F_2)$ | Me | $CH_2$ | 4-Cl | O | | |
| 1.557 | $CF_3$ | $Ph(2,4-F_2)$ | Me | $CH_2$ | 4-Me | O | | |
| 1-558 | Et | Pr-i | $CH_2C{\equiv}CH$ | $CH_2$ | H | O | | 131–132 |
| 1-559 | Et | Pr-i | $CH_2C{\equiv}CH$ | $CH_2$ | 4-F | O | | 93–96 |
| 1-560 | Et | Pr-i | $CH_2C{\equiv}CH$ | $CH_2$ | 4-Cl | O | | 124–125 |
| 1-561 | Et | Pr-i | $CH_2C{\equiv}CH$ | $CH_2$ | 4-Me | O | | 110–111 |
| 1-562 | Et | Pr-i | $CH_2C{\equiv}CH$ | CH(Me) | H | O | | Not Measurable |
| 1-563 | Pr-i | C(Me)=NOMe | Me | $CH_2$ | 4-F | O | | 73–74 |
| 1-564 | Et | Bu-t | Mo | $CH_2$ | H | O | | |
| 1-565 | Et | Bu-t | Me | $CH_2$ | 4-F | O | | 82–83 |
| 1-566 | Et | Bu-t | Me | $CH_2$ | 4-Cl | O | | 98–99 |
| 1-567 | Et | Bu-t | Me | $CH_2$ | 4-Me | O | | 78–80 |
| 1-568 | Pr-i | CN | Me | $OCH_2$ | H | O | | 1.5899 |
| 1-569 | $CF_3$ | Pr-i | $CH_2C{\equiv}CH$ | $CH_2$ | 3-F | O | | 131–133 |
| 1-570 | Bu-t | Et | Me | $CH_2$ | H | O | | |
| 1-571 | Bu-t | Et | Me | $CH_2$ | 4-F | O | | 88–90 |
| 1-572 | Bu-t | Et | Me | $CH_2$ | 4-Cl | O | | 96–97 |
| 1-573 | Bu-t | Et | Me | $CH_2$ | 4-Me | O | | 101–102 |
| 1-574 | $CF_3$ | Pr-i | $CH_2$-Pr-c | $CH_2$ | H | O | | |
| 1-575 | $CF_3$ | Pr-i | $CH_2$-Pr-c | $CH_2$ | 4-F | O | | 108–109 |
| 1-576 | $CF_3$ | Pr-i | $CH_2$-Pr-c | $CH_2$ | 4-Cl | O | | |
| 1-577 | $CF_3$ | Pr-i | $CH_2$-Pr-c | $CH_2$ | 4-Me | O | | |
| 1-578 | $CF_3$ | Pr-i | $CH_2CN$ | $CH_2$ | H | O | | |
| 1-579 | $CF_3$ | Pr-i | $CH_2CN$ | $CH_2$ | 4-F | O | | 162–163 |
| 1-580 | $CF_3$ | Pr-i | $CH_2CN$ | $CH_2$ | 4-Cl | O | | |
| 1-581 | $CF_3$ | Pr-i | $CH_2CN$ | $CH_2$ | 4-Me | O | | |
| 1-582 | Pr-i | $CH_2OMe$ | Me | $CH_2$ | H | O | | |
| 1-583 | Pr-i | $CH_2OMe$ | Me | $CH_2$ | 4-F | O | | |
| 1-584 | Pr-i | $CH_2OMe$ | Me | $CH_2$ | 4-Cl | O | | 1.5391 |
| 1-585 | Pr-i | $CH_2OMe$ | Me | $CH_2$ | 4-Me | O | | |
| 1-586 | Pr-i | $CH_2OMe$ | Me | CH(Me) | 4-Cl | O | | 1.5358 |
| 1-587 | $CH_2OMe$ | Pr-i | Me | $CH_2$ | H | O | | |
| 1-588 | $CH_2OMe$ | Pr-i | Me | $CH_2$ | 4-F | O | | |
| 1-589 | $CH_2OMe$ | Pr-i | Me | $CH_2$ | 4-Cl | O | | 1.5485 |

TABLE 18

| Compound No. | $R^1$ | $R^2$ | $R^3$ | Z | Xn | Q | Diastereomer | m. p. (° C.) or refractive index ($n_D^{20}$) |
|---|---|---|---|---|---|---|---|---|
| 1-590 | $CH_2OMe$ | Pr-i | Me | $CH_2$ | 4-Me | O | | |
| 1-591 | $CH_2OMe$ | Pr-i | Me | CH(Me) | 4-Cl | O | | 1.5382 |
| 1-592 | $CO_2Me$ | Pr-i | Me | CH(Me) | 4-Cl | O | A-isomer | Not Measurable |
| 1-593 | $CO_2Me$ | Pr-i | Me | CH(Me) | 4-Cl | O | B-isomer | Not Measurable |
| 1-594 | $CO_2Et$ | Pr-i | Me | CH(Me) | 4-Cl | O | A-isomer | 1.5406 |
| 1-595 | $CO_2Et$ | Pr-i | Me | CH(Me) | 4-Cl | O | B-isomer | Not Measurable |
| 1-596 | MeO-(dioxolane) | Pr-i | Me | $CH_2$ | H | O | | |
| 1-597 | MeO-(dioxolane) | Pr-i | Me | $CH_2$ | 4-F | O | | 171–173 |
| 1-598 | MeO-(dioxolane) | Pr-i | Me | $CH_2$ | 4-Cl | O | | 167–168 |

TABLE 18-continued

| Compound No. | R¹ | R² | R³ | Z | Xn | Q | Diastereomer | m. p. (° C.) or refractive index ($n_D^{20}$) |
|---|---|---|---|---|---|---|---|---|
| 1-599 | MeO-2-methyl-1,3-dioxolane | Pr-i | Me | CH₂ | 4-Me | O | | 141–142 |
| 1-600 | Pr-i | MeO-2-methyl-1,3-dioxolane | Me | CH(Me) | 4-Cl | O | | 95–98 |
| 1-601 | Pr-i | MeO-2-methyl-1,3-dioxolane | Me | CH₂ | H | O | | |
| 1-602 | Pr-i | MeO-2-methyl-1,3-dioxolane | Me | CH₂ | 4-F | O | | 123–124 |
| 1-603 | Pr-i | MeO-2-methyl-1,3-dioxolane | Me | CH₂ | 4-Cl | O | | 133–134 |
| 1-604 | Pr-i | MeO-2-methyl-1,3-dioxolane | Me | CH₂ | 4-Me | O | | 103–104 |
| 1-605 | Pr-i | MeO-2-methyl-1,3-dioxolane | Me | CH(Me) | 4-Cl | O | | |
| 1-606 | Et | Pr-n | CH₂C≡CH | CH₂ | H | O | | 58–59 |
| 1-607 | Et | Pr-n | CH₂C≡CH | CH₂ | 4-F | O | | 76–77 |
| 1-608 | Et | Pr-n | CH₂C≡CH | CH₂ | 4-Cl | O | | 111–113 |
| 1-609 | Et | Pr-n | CH₂C≡CH | CH₂ | 4-Me | O | | 90–91 |
| 1-610 | Pr-i | Pr-n | CH₂C≡CH | CH₂ | H | O | | |
| 1-611 | Pr-i | Pr-n | CH₂C≡CH | CH₂ | 4-F | O | | 70–71 |
| 1-612 | Pr-i | Pr-n | CH₂C≡CH | CH₂ | 4-Cl | O | | |

TABLE 19

| Compound No. | R¹ | R² | R³ | Z | Xn | Q | Diastereomer | m.p. (° C.) or refractive index ($n_D^{20}$) |
|---|---|---|---|---|---|---|---|---|
| 1-613 | Pr-n | Pr-i | CH₂C≡CH | CH₂ | 4-Me | O | | |
| 1-614 | CF₃ | Pr-i | CH₂C≡CH | CH₂ | 3,4-F₂ | O | | 133–134 |
| 1-615 | CF₃ | Pr-i | CH₂C≡CH | CH₂ | 2-F-4-Cl | O | | 122–124 |
| 1-616 | Pr-n | Pr-i | CH₂C≡CH | CH₂ | H | O | | 118–119 |
| 1-617 | Pr-n | Pr-i | CH₂C≡CH | CH₂ | 4-F | O | | 106–107 |
| 1-618 | Pr-n | Pr-i | CH₂C≡CH | CH₂ | 4-Cl | O | | 111–112 |
| 1-619 | Pr-n | Pr-i | CH₂C≡CH | CH₂ | 4-Me | O | | 98–99 |
| 1-620 | CF₃ | Bu-t | CH₂C≡CH | CH₂ | 4-F | O | | 93–96 |
| 1-621 | Pr-i | Pr-i | CH₂C≡CH | CH₂ | H | O | | 137–138 |
| 1-622 | Pr-i | Pr-i | CH₂C≡CH | CH₂ | 4-F | O | | 159–161 |
| 1-623 | Pr-i | Pr-i | CH₂C≡CH | CH₂ | 4-Cl | O | | 131–134 |
| 1-624 | Pr-i | Pr-i | CH₂C≡CH | CH₂ | 4-Me | O | | 153–154 |
| 1-625 | CH(OMe)₂ | Pr-i | Me | CH(Me) | 4-Cl | O | | 1.5371 |
| 1-626 | Et | Bu-t | CH₂C≡CH | CH₂ | H | O | | 84–88 |
| 1-627 | Et | Bu-t | CH₂C≡CH | CH₂ | 4-F | O | | 127–130 |
| 1-628 | Et | Bu-t | CH₂C≡CH | CH₂ | 4-Cl | O | | |

TABLE 19-continued

| Compound No. | R¹ | R² | R³ | Z | Xn | Q | Diastereomer | m.p. (° C.) or refractive index ($n_D^{20}$) |
|---|---|---|---|---|---|---|---|---|
| 1-629 | Et | Bu-t | CH₂C≡CH | CH₂ | 4-Me | O | | |
| 1-630 | COPr-i | Pr-i | Me | CH(Me) | 4-Cl | O | | 116–117 |
| 1-631 | C(Me)=NOMe | Pr-i | Me | CH(Me) | 4-Cl | O | | 1.5423 |
| 1-632 | CN | Bu-t | Me | CH(Me) | 4-Cl | O | A-isomer | 130–132 |
| 1-633 | COMe | Bu-t | Me | CH(Me) | 4-Cl | O | | 1.5439 |
| 1-634 | CF₃ | Pr-i | Me | CH(Me) (S-isomer) | H | O | A-isomer | 128–131 |
| 1-635 | CF₃ | Pr-i | Me | CH(Me) (S-isomer) | H | O | B-isomer | 1.5091 |
| 1-636 | CF₂Cl | Pr-i | Me | O | 4-Me | O | | 112–115 |
| 1-637 | CF₂Cl | Pr-i | Me | O | 4-OMe | O | | 123–126 |
| 1-638 | CF₂Cl | Pr-i | Me | O | 4-Br | O | | 108–111 |
| 1-639 | CF₂Cl | Pr-i | Me | OCH₂ | H | O | | 1.5251 |
| 1-640 | CF₂Cl | Pr-i | Me | O | 4-NO₂ | O | | 1.5301 |
| 1-641 | CF₂Cl | Pr-i | Me | O | H | S | | 132–135 |
| 1-642 | Et | Pr-i | Me | O | 4-Cl | O | | 80–83 |
| 1-643 | Pr-n | Pr-n | Me | O | 4-Cl | O | | 1.5379 |
| 1-644 | Pr-n | Pr-i | Me | O | 4-Cl | O | | 1.5367 |
| 1-645 | Me | Me | Me | O | 4-Cl | O | | 90–93 |
| 1-646 | Et | Et | Me | O | 4-Cl | O | | 1.5468 |

TABLE 20

| Compound No. | R¹ | R² | R³ | Z | Xn | Q | Diastereomer | m.p. (° C.) or refractive index ($n_D^{20}$) |
|---|---|---|---|---|---|---|---|---|
| 1-647 | Pr-i | Pr-i | Me | O | H | O | | 1.5331 |
| 1-648 | Pr-i | Pr-i | Me | O | 4-Me | O | | 1.5346 |
| 1-649 | Pr-i | Pr-i | Me | O | 4-OMe | O | | 1.5282 |
| 1-650 | Pr-i | Pr-i | Me | O | 4-F | P | | 1.5169 |
| 1-651 | Et | CH(Me)SMe | Me | CH₂ | H | O | | Not Measurable |
| 1-652 | Et | CH(Me)SMe | Me | CH₂ | 4-F | O | | Not Measurable |
| 1-653 | Et | CH(Me)SMe | Me | CH₂ | 4-Cl | O | | 88–91 |
| 1-654 | Et | CH(Me)SMe | Me | CH₂ | 4-Me | O | | 1.5676 |
| 1-655 | NHCO₂CH₃Ph | Pr-i | Me | CH(Me) | 4-Cl | O | | 161–163 |
| 1-656 | Et | C(Me)₂CO₂Me | Me | CH₂ | 4-Cl | O | | 1.5502 |
| 1-657 | SOMe | Pr-i | Me | CH₂ | 4-Cl | O | | |
| 1-658 | SO₂Me | Pr-i | Me | CH₂ | 4-Cl | O | | |
| 1-659 | OEt | Pr-i | Me | CH₂ | H | O | | |
| 1-660 | OEt | Pr-i | Me | CH₂ | 4-F | O | | |
| 1-661 | OEt | Pr-i | Me | CH₂ | 4-Cl | O | | |
| 1-662 | OEt | Pr-i | Me | CH₂ | 4-Me | O | | |
| 1-663 | OCHF₂ | Pr-i | Me | CH₂ | H | O | | |
| 1-664 | OCHF₂ | Pr-i | Me | CH₂ | 4-F | O | | |
| 1-655 | OCHF₂ | Pr-i | Me | CH₂ | 4-Cl | O | | |
| 1-666 | OCHF₂ | Pr-i | Me | CH₂ | 4-Me | O | | |
| 1-667 | SOCH₂CH=CH₂ | Pr-i | Me | CH₂ | 4-Cl | O | | |
| 1-668 | SOCH₂C≡CH | Pr-i | Me | CH₂ | 4-Cl | O | | |
| 1-669 | OCH₂CH=CH₂ | Pr-i | Me | CH₂ | H | O | | |
| 1-670 | OCH₂CH=CH₂ | Pr-i | Me | CH₂ | 4-F | O | | |
| 1-671 | OCH₂CH=CH₂ | Pr-i | Me | CH₂ | 4-Cl | O | | |
| 1-672 | OCH₂CH=CH₂ | Pr-i | Me | CH₂ | 4-Me | O | | |
| 1-673 | OCH₂C≡CH | Pr-i | Me | CH₂ | H | O | | |
| 1-674 | OCH₂C≡CH | Pr-i | Me | CH₂ | 4-F | O | | |
| 1-675 | OCH₂C≡CH | Pr-i | Me | CH₂ | 4-Cl | O | | |
| 1-676 | OCH₃C≡CH | Pr-i | Me | CH₂ | 4-Me | O | | |
| 1-677 | OPr-c | Pr-i | Me | CH₂ | H | O | | |
| 1-678 | OPr-c | Pr-i | Me | CH₂ | 4-F | O | | |
| 1-679 | OPr-c | Pr-i | Me | CH₂ | 4-Cl | O | | |
| 1-680 | OPr-c | Pr-i | Me | CH₂ | 4-Me | O | | |
| 1-681 | SPr-c | Pr-i | Me | CH₂ | 4-Cl | O | | |

TABLE 21

| Compound No. | $R^1$ | $R^2$ | $R^3$ | Z | Xn | Q | Diastereomer | m.p. (° C.) or refractive index ($n_D^{20}$) |
|---|---|---|---|---|---|---|---|---|
| 1-682 | SOPr-c | Pr-i | Me | $CH_2$ | 4-Cl | O | | |
| 1-683 | $SO_2$Pr-c | Pr-i | Me | $CH_2$ | 4-Cl | O | | |
| 1-684 | $N(Me)_2$ | Pr-i | Me | $CH_2$ | 4-Cl | O | | |
| 1-685 | NHMe | Pr-i | Me | $CH_2$ | 4-Cl | O | | |
| 1-686 | $NH(CHF_2)$ | Pr-i | Me | $CH_2$ | 4-Cl | O | | |
| 1-687 | $NH(CH_2OMe)$ | Pr-i | Me | $CH_2$ | 4-Cl | O | | |
| 1-688 | $NH(CH_2SMe)$ | Pr-i | Me | $CH_2$ | 4-Cl | O | | |
| 1-689 | NHPr-c | Pr-i | Me | $CH_2$ | 4-Cl | O | | |
| 1-690 | NHCOMe | Pr-i | Me | $CH_2$ | 4-Cl | O | | |
| 1-691 | $NHSO_2Me$ | Pr-i | Me | $CH_2$ | 4-Cl | O | | |
| 1-692 | $NHCO_2Me$ | Pr-i | Me | $CH_2$ | 4-Cl | O | | |
| 1-693 | $NH(CH_2CH=CH_2)$ | Pr-i | Me | $CH_2$ | 4-Cl | O | | |
| 1-694 | $NH(CH_2C\equiv CH)$ | Pr-i | Me | $CH_2$ | 4-Cl | O | | |
| 1-695 | $CH(Me)CH=CH_2$ | Pr-i | Me | $CH_2$ | 4-Cl | O | | |
| 1-696 | $CH_2C\equiv CH$ | Pr-i | Me | $CH_2$ | 4-Cl | O | | |
| 1-697 | OH | Pr-i | Me | $CH_2$ | 4-Cl | O | | |
| 1-698 | $CO_2H$ | Pr-i | Me | $CH_2$ | 4-Cl | O | | |
| 1-699 | $CON(-C_4H_8)$ | Pr-i | Me | $CH_2$ | 4-Cl | O | | |
| 1-700 | $CONH(CH_2CH=CH_2)$ | Pr-i | Me | $CH_2$ | 4-Cl | O | | |
| 1-701 | Pr-i | $CH(Me)CH=CH_2$ | Me | $CH_2$ | 4-Cl | O | | |
| 1-702 | Pr-i | $CH_2C\equiv CH$ | Me | $CH_2$ | 4-Cl | O | | |
| 1-703 | Et | CHClMe | Me | $CH_2$ | 4-Cl | O | | |
| 1-704 | Et | OEt | Me | $CH_2$ | 4-Cl | O | | |
| 1-705 | Et | CH(Me)CN | Me | $CH_2$ | 4-Cl | O | | |
| 1-706 | Et | $CO_2Me$ | Me | $CH_2$ | 4-Cl | O | | |
| 1-707 | Et | $CHMeN(Me)_2$ | Me | $CH_2$ | 4-Cl | O | | |
| 1-708 | Et | $CON(Me)_2$ | Me | $CH_3$ | 4-Cl | O | | |
| 1-709 | Et | $CHMeCONMe_2$ | Me | $CH_2$ | 4-Cl | O | | |
| 1-710 | Et | Pr-i | Me | $CH_2$ | $4-OCH_2CH=CH_2$ | O | | |
| 1-711 | Et | Pr-i | Me | $CH_2$ | 4-OPr-c | O | | |
| 1-712 | Et | Pr-i | Me | $CH_2$ | 4-COMe | O | | |

TABLE 22

| Compound No. | $R^1$ | $R^2$ | $R^3$ | Z | Xn | Q | Diastereomer | m.p. (° C.) or refractive index ($n_D^{20}$) |
|---|---|---|---|---|---|---|---|---|
| 1-713 | Et | Pr-i | Me | $CH_2$ | $4-CO_2Me$ | O | | |
| 1-714 | Et | Pr-i | Me | $CH_2$ | 4-SOMe | O | | |
| 1-715 | Et | Pr-i | $N(NMe_2)$ | $CH_2$ | 4-Cl | O | | |
| 1-716 | Et | Pr-i | Me | $CH_2$ | $4-CH_2CH=CH_2$ | O | | |
| 1-717 | Et | Pr-i | Me | $CH_2$ | $4-CH_2C\equiv CH$ | O | | |
| 1-718 | $CO_2H$ | Pr-i | N(Me) | CH(Me) | 4-Cl | O | | 168–170 |
| 1-719 | $CH=CHCO_2Et$ | Pr-i | Me | CH(Me) | 4-Cl | O | | 57–59 |
| 1-720 | $CF_3$ | Pr-i | $CH_2C\equiv CH$ | $CH_2$ | 4-Me | O | | 111–113 |
| 1-721 | COEt | Pr-i | Me | CH(Me) | H | O | | |
| 1-722 | COEt | Pr-i | Me | CH(Me) | 4-F | O | | |
| 1-723 | COEt | Pr-i | Me | CH(Me) | 4-Cl | O | | |
| 1-724 | COEt | Pr-i | Me | CH(Me) | 4-Me | O | | |
| 1-725 | COEt | Pr-n | Me | $CH_2$ | H | O | | |
| 1-726 | COEt | Pr-n | Me | $CH_2$ | 4-F | O | | |
| 1-727 | COEt | Pr-n | Me | $CH_2$ | 4-Cl | O | | |
| 1-728 | COEt | Pr-n | Me | $CH_2$ | 4-Me | O | | |
| 1-729 | COEt | Pr-i | $CH_2C\equiv CH$ | CH(Me) | H | O | | |
| 1-730 | COEt | Pr-i | $CH_2C\equiv CH$ | CH(Me) | 4-F | O | | |
| 1-731 | COEt | Pr-i | $CH_2C\equiv CH$ | CH(Me) | 4-Cl | O | | |
| 1-732 | COEt | Pr-i | $CH_2C\equiv CH$ | CH(Me) | 4-Me | O | | |
| 1-733 | COEt | Pr-n | $CH_2C\equiv CH$ | $CH_2$ | H | O | | |
| 1-734 | COEt | Pr-n | $CH_2C\equiv CH$ | $CH_2$ | 4-F | O | | |
| 1-735 | COEt | Pr-n | $CH_2C\equiv CH$ | $CH_2$ | 4-Cl | O | | |
| 1-736 | COEt | Pr-n | $CH_2C\equiv CH$ | $CH_2$ | 4-Me | O | | |
| 1-737 | COMe | Pr-n | Me | $CH_2$ | H | O | | |
| 1-738 | COMe | Pr-n | Me | $CH_2$ | 4-F | O | | |
| 1-739 | COMe | Pr-n | Me | $CH_2$ | 4-Cl | O | | |
| 1-740 | COMe | Pr-n | Me | $CH_2$ | 4-Me | O | | |
| 1-741 | COMe | Pr-i | $CH_2C\equiv CH$ | CH(Me) | H | O | | |

TABLE 22-continued

| Compound No. | $R^1$ | $R^2$ | $R^3$ | Z | Xn | Q | Dia-stereo-mer | m.p. (° C.) or refractive index ($n_D^{20}$) |
|---|---|---|---|---|---|---|---|---|
| 1-742 | COMe | Pr-i | $CH_2C\equiv CH$ | CH(Me) | 4-F | O | | |
| 1-743 | COMe | Pr-i | $CH_2C\equiv CH$ | CH(Me) | 4-Cl | O | | |
| 1-744 | COMe | Pr-i | $CH_2C\equiv CH$ | CH(Me) | 4-Me | O | | |
| 1-745 | COMe | Pr-n | $CH_2C\equiv CH$ | $CH_2$ | H | O | | |
| 1-746 | COMe | Pr-n | $CH_2C\equiv CH$ | $CH_2$ | 4-F | O | | |
| 1-747 | COMe | Pr-n | $CH_2C\equiv CH$ | $CH_2$ | 4-Cl | O | | |
| 1-748 | COMe | Pr-n | $CH_2C\equiv CH$ | $CH_2$ | 4-Me | O | | |

TABLE 23

| Compound No. | $R^1$ | $R^2$ | $R^3$ | Z | Xn | Q | Dia-stereo-mer | m.p. (° C.) or refractive index ($n_D^{20}$) |
|---|---|---|---|---|---|---|---|---|
| 1-749 | COPr-i | Pr-i | Me | CH(Me) | H | O | | |
| 1-750 | COPr-i | Pr-i | Me | CH(Me) | 4-F | O | | |
| 1-751 | COPr-i | Pr-i | Me | CH(Me) | 4-Me | O | | |
| 1-752 | COPr-i | Pr-n | Me | $CH_2$ | H | O | | |
| 1-753 | COPr-i | Pr-n | Me | $CH_2$ | 4-F | O | | |
| 1-754 | COPr-i | Pr-n | Me | $CH_2$ | 4-Cl | O | | |
| 1-755 | COPr-i | Pr-n | Me | $CH_2$ | 4-Me | O | | |
| 1-756 | COPr-i | Pr-i | $CH_2C\equiv CH$ | CH(Me) | H | O | | |
| 1-757 | COPr-i | Pr-i | $CH_2C\equiv CH$ | CH(Me) | 4-F | O | | |
| 1-758 | COPr-i | Pr-i | $CH_2C\equiv CH$ | CH(Me) | 4-Cl | O | | |
| 1-759 | COPr-i | Pr-i | $CH_2C\equiv CH$ | CH(Me) | 4-Me | O | | |
| 1-760 | COPr-i | Pr-n | $CH_2C\equiv CH$ | $CH_2$ | H | O | | |
| 1-761 | COPr-i | Pr-n | $CH_2C\equiv CH$ | $CH_2$ | 4-F | O | | |
| 1-762 | COPr-i | Pr-n | $CH_2C\equiv CH$ | $CH_2$ | 4-Cl | O | | |
| 1-763 | COPr-i | Pr-n | $CH_2C\equiv CH$ | $CH_2$ | 4-Me | O | | |
| 1-764 | OEt | Pr-n | Me | $CH_2$ | H | O | | |
| 1-765 | OEt | Pr-n | Me | $CH_2$ | 4-F | O | | |
| 1-766 | OEt | Pr-n | Me | $CH_2$ | 4-Cl | O | | |
| 1-767 | OEt | Pr-n | Me | $CH_2$ | 4-Me | O | | |
| 1-768 | OEt | Pr-i | $CH_2C\equiv CH$ | CH(Me) | H | O | | |
| 1-769 | OEt | Pr-i | $CH_2C\equiv CH$ | CH(Me) | 4-F | O | | |
| 1-770 | OEt | Pr-i | $CH_2C\equiv CH$ | CH(Me) | 4-Cl | O | | |
| 1-771 | OEt | Pr-i | $CH_2C\equiv CH$ | CH(Me) | 4-Me | O | | |
| 1-772 | OPr-i | Pr-i | Me | CH(Me) | H | O | | |
| 1-773 | OPr-i | Pr-i | Me | CH(Me) | 4-F | O | | |
| 1-774 | OPr-i | Pr-i | Me | CH(Me) | 4-Cl | O | | |
| 1-775 | OPr-i | Pr-i | Me | CH(Me) | 4-Me | O | | |
| 1-776 | OPr-i | Pr-n | Me | $CH_2$ | H | O | | |
| 1-777 | OPr-i | Pr-n | Me | $CH_2$ | 4-F | O | | |
| 1-778 | OPr-i | Pr-n | Me | $CH_2$ | 4-Cl | O | | |
| 1-779 | OPr-i | Pr-n | Me | $CH_2$ | 4-Me | O | | |
| 1-780 | OPr-i | Pr-i | $CH_2C\equiv CH$ | CH(Me) | H | O | | |
| 1-781 | OPr-i | Pr-i | $CH_2C\equiv CH$ | CH(Me) | 4-F | O | | |
| 1-782 | OPr-i | Pr-i | $CH_2C\equiv CH$ | CH(Me) | 4-Cl | O | | |
| 1-783 | OPr-i | Pr-i | $CH_2C\equiv CH$ | CH(Me) | 4-Me | O | | |
| 1-784 | Et | Ph | Me | $CH_2$ | H | O | | |
| 1-785 | Et | Ph | Me | $CH_2$ | 4-F | O | | |

TABLE 24

| Compound No. | $R^1$ | $R^2$ | $R^3$ | Z | Xn | Q | Dia-stereo-mer | m.p. (° C.) or refractive index ($n_D^{20}$) |
|---|---|---|---|---|---|---|---|---|
| 1-786 | Et | Ph | Me | $CH_2$ | 4-Cl | O | | |
| 1-787 | Et | Ph | Me | $CH_2$ | 4-Me | O | | |
| 1-788 | N(Me)$_2$ | Pr-i | Me | $CH_2$ | H | O | | 63–66 |

TABLE 24-continued

| Compound No. | R$^1$ | R$^2$ | R$^3$ | Z | Xn | Q | Dia-stereo-mer | m.p. (° C.) or refractive index ($n_D^{20}$) |
|---|---|---|---|---|---|---|---|---|
| 1-789 | N(Me)$_2$ | Pr-i | Me | CH$_2$ | 4-F | O | | |
| 1-790 | N(Me)$_2$ | Pr-i | Me | CH$_2$ | 4-Me | O | | |
| 1-791 | N(Me)$_2$ | Pr-i | Me | CH(Me) | H | O | | |
| 1-792 | N(Me)$_2$ | Pr-i | Me | CH(Me) | 4-F | O | | |
| 1-793 | N(Me)$_2$ | Pr-i | Me | CH(Me) | 4-Cl | O | | |
| 1-794 | N(Me)$_2$ | Pr-i | Me | CH(Me) | 4-Me | O | | |
| 1-795 | CF$_3$ | Pr-i | Me | N(Me)CH$_2$ | H | O | | |
| 1-796 | CF$_3$ | Pr-i | Me | N(Me)CH$_2$ | 4-F | O | | |
| 1-797 | CF$_3$ | Pr-i | Me | N(Me)CH$_2$ | 4-Me | O | | |
| 1-798 | Et | Pr-i | Me | N(Me)CH$_2$ | H | O | | |
| 1-799 | Et | Pr-i | Me | N(Me)CH$_2$ | 4-F | O | | |
| 1-800 | Et | Pr-i | Me | N(Me)CH$_2$ | 4-Cl | O | | |
| 1-801 | Et | Pr-i | Me | N(Me)CH$_2$ | 4-Me | O | | |
| 1-802 | Pr-i | Pr-i | Me | N(Me)CH$_2$ | H | O | | |
| 1-803 | Pr-i | Pr-i | Me | N(Me)CH$_2$ | 4-F | O | | |
| 1-804 | Pr-i | Pr-i | Me | N(Me)CH$_2$ | 4-Cl | O | | |
| 1-805 | Pr-i | Pr-i | Me | N(Me)CH$_2$ | 4-Me | O | | |
| 1-806 | C(Me)=CH$_2$ | Pr-n | Me | CH$_2$ | H | O | | |
| 1-807 | C(Me)=CH$_2$ | Pr-n | Me | CH$_2$ | 4-F | O | | |
| 1-808 | C(Me)=CH$_2$ | Pr-n | Me | CH$_2$ | 4-Cl | O | | |
| 1-809 | C(Me)=CH$_2$ | Pr-n | Me | CH$_2$ | 4-Me | O | | |
| 1-810 | Pr-n | C(Me)=CH$_2$ | Me | CH$_2$ | H | O | | |
| 1-811 | Pr-n | C(Me)=CH$_2$ | Me | CH$_2$ | 4-F | O | | |
| 1-812 | Pr-n | C(Me)=CH$_2$ | Me | CH$_2$ | 4-Cl | O | | |
| 1-813 | Pr-n | C(Me)=CH$_2$ | Me | CH$_2$ | 4-Me | O | | |
| 1-814 | Et | C(Me)=CH$_2$ | Me | CH$_2$ | H | O | | |
| 1-815 | Et | C(Me)=CH$_2$ | Me | CH$_2$ | 4-F | O | | |
| 1-816 | Et | C(Me)=CH$_2$ | Me | CH$_2$ | 4-Cl | O | | |
| 1-817 | Et | C(Me)=CH$_2$ | Me | CH$_2$ | 4-Me | O | | |
| 1-818 | Et | OEt | Me | CH(Me) | 4-Cl | O | | |
| 1-819 | Et | CH(Me)CN | Me | CH(Me) | 4-Cl | O | | |
| 1-820 | Et | CO$_2$Me | Me | CH(Me) | 4-Cl | O | | |
| 1-821 | Et | CHMeN(Me)$_2$ | Me | CH(Me) | 4-Cl | O | | |

TABLE 25

| Compound No. | R$^1$ | R$^2$ | R$^3$ | Z | Xn | Q | Dia-stereo-mer | m.p. (° C.) or refractive index ($n_D^{20}$) |
|---|---|---|---|---|---|---|---|---|
| 1-822 | Et | CON(Me)$_2$ | Me | CH(Me) | 4-Cl | O | | |
| 1-823 | Et | CHMeCONMe$_2$ | Me | CH(Me) | 4-Cl | O | | |
| 1-824 | Bu-t | Et | CH$_2$C≡CH | CH$_2$ | H | O | | |
| 1-825 | Bu-t | Et | CH$_2$C≡CH | CH$_2$ | 4-F | O | | |
| 1-826 | Bu-t | Et | CH$_2$C≡CH | CH$_2$ | 4-Cl | O | | |
| 1-827 | Bu-t | Et | CH$_2$C≡CH | CH$_2$ | 4-Me | O | | |
| 1-828 | COPr-c | Pr-n | Me | CH$_2$ | H | O | | |
| 1-829 | COPr-c | Pr-n | Me | CH$_2$ | 4-F | O | | |
| 1-830 | COPr-c | Pr-n | Me | CH$_2$ | 4-Cl | O | | |
| 1-831 | COPr-c | Pr-n | Me | CH$_2$ | 4-Me | O | | |
| 1-832 | Et | C(Me)$_2$OH | Me | CH$_2$ | H | O | | |
| 1-833 | Et | C(Me)$_2$OH | Me | CH$_2$ | 4-F | O | | |
| 1-834 | Et | C(Me)$_2$OH | Me | CH$_2$ | 4-Cl | O | | |
| 1-835 | Et | C(Me)$_2$OH | Me | CH$_2$ | 4-Me | O | | |
| 1-836 | Et | C(Me)$_2$Cl | Me | CH$_2$ | H | O | | |
| 1-837 | Et | C(Me)$_2$Cl | Me | CH$_2$ | 4-F | O | | |
| 1-838 | Et | C(Me)$_2$Cl | Me | CH$_2$ | 4-Cl | O | | |
| 1-839 | Et | C(Me)$_2$Cl | Me | CH$_2$ | 4-Me | O | | |
| 1-840 | N(Me)CH$_2$C≡CH | Pr-i | Me | CH$_2$ | H | O | | |
| 1-841 | N(Me)CH$_2$C≡CH | Pr-i | Me | CH$_2$ | 4-F | O | | |
| 1-842 | N(Me)CH$_2$C≡CH | Pr-i | Me | CH$_2$ | 4-Cl | O | | |
| 1-843 | N(Me)CH$_2$C≡CH | Pr-i | Me | CH$_2$ | 4-Me | O | | |
| 1-844 | N(Me)CH$_2$C≡CH | Pr-i | Me | CH(Me) | H | O | | |
| 1-845 | N(Me)CH$_2$C≡CH | Pr-i | Me | CH(Me) | 4-F | O | | |
| 1-846 | N(Me)CH$_2$C≡CH | Pr-i | Me | CH(Me) | 4-Cl | O | | |
| 1-847 | N(Me)CH$_2$C≡CH | Pr-i | Me | CH(Me) | 4-Me | O | | |
| 1-848 | CH$_2$CF$_3$ | Pr-i | Me | CH$_2$ | H | O | | |

TABLE 25-continued

| Compound No. | R¹ | R² | R³ | Z | Xn | Q | Diastereomer | m.p. (° C.) or refractive index ($n_D^{20}$) |
|---|---|---|---|---|---|---|---|---|
| 1-849 | $CH_2CF_3$ | Pr-i | Me | $CH_2$ | 4-F | O | | |
| 1-850 | $CH_2CF_3$ | Pr-i | Me | $CH_2$ | 4-Cl | O | | |
| 1-851 | $CH_2CF_3$ | Pr-i | Me | $CH_2$ | 4-Me | O | | |
| 1-852 | $CF_2CF_3$ | Pr-i | Me | $CH_2$ | H | O | | 106–108 |
| 1-853 | $CF_2CF_3$ | Pr-i | Me | $CH_2$ | 4-F | O | | 118–119 |
| 1-854 | $CF_2CF_3$ | Pr-i | Me | $CH_2$ | 4-Cl | O | | 122–123 |
| 1-855 | $CF_2CF_3$ | Pr-i | Me | $CH_2$ | 4-Me | O | | 68–69 |
| 1-856 | $OCF_3$ | Pr-i | Me | $CH_2$ | H | O | | |
| 1-857 | $OCF_3$ | Pr-i | Me | $CH_2$ | 4-F | O | | |

TABLE 26

| Compound No. | R¹ | R² | R³ | Z | Xn | Q | Diastereomer | m.p. (° C.) or refractive index ($n_D^{20}$) |
|---|---|---|---|---|---|---|---|---|
| 1-858 | $OCF_3$ | Pr-i | Me | $CH_2$ | 4-Cl | O | | |
| 1-859 | $OCF_3$ | Pr-i | Me | $CH_2$ | 4-Me | O | | |
| 1-860 | Et | CH(Me)OMe | Me | $CH_2$ | H | O | | |
| 1-861 | Et | CH(Me)OMe | Me | $CH_2$ | 4-F | O | | |
| 1-862 | Et | CH(Me)OMe | Me | $CH_2$ | 4-Cl | O | | |
| 1-863 | Et | CH(Me)OMe | Me | $CH_2$ | 4-Me | O | | |
| 1-864 | Et | CH(Me)CN | Me | $CH_2$ | H | O | | |
| 1-865 | Et | CH(Me)CN | Me | $CH_2$ | 4-F | O | | |
| 1-866 | Et | CH(Me)CN | Me | $CH_2$ | 4-Me | O | | |
| 1-867 | Et | Pr-i | $CH_2C{\equiv}CH$ | $CH_2$ | 3,4-$F_2$ | O | | |
| 1-868 | Et | Pr-i | $CH_2C{\equiv}CH$ | $CH_2$ | 2,4-$F_2$ | O | | |
| 1-869 | Et | Pr-i | $CH_2C{\equiv}CH$ | $CH_2$ | 3-F | O | | |
| 1-870 | $CF_3$ | Pr-i | $CH_2C{\equiv}CH$ | $CH_2$ | 2,4-$F_2$ | O | λ-isomer | 110–113 |
| 1-871 | $CF_3$ | Pr-i | Me | CH(Me) (R-isomer) | H | O | B-isomer | 144–146 |
| 1-872 | $CF_3$ | Pr-i | Me | CH(Me) (R-isomer) | H | O | | 1.5164 |
| 1-873 | $CClF_2$ | Pr-i | Me | N(Me) | H | O | | 1.5341 |
| 1-874 | $CF_3$ | Pr-i | Me | NHN(Me) | H | O | | 72–75 |
| 1-875 | $CH_2CH(OMe)_2$ | Pr-i | Me | $CH_2$ | 4-Cl | O | | 90–91 |
| 1-876 | $CH_2CN$ | Pr-i | Me | $CH_2$ | 4-Cl | O | | 106–107 |
| 1-877 | 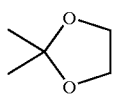 | Et | Me | $CH_2$ | 4-Cl | O | | 1.5552 |
| 1-878 | COMe | Et | Me | $CH_2$ | 4-Cl | O | | 1.5612 |
| 1-879 | CMe=NOMe | Et | Me | $CH_2$ | 4-Cl | O | | 81–83 |
| 1-880 | $CF_3$ | Pr-i | Me | $N(Me)CH_2$ | H | O | | 63–64 |
| 1-881 | CH=NOMe | Pr-n | Me | CH(Me) | 4-Cl | O | | Not Measurable |
| 1-882 | CN | Pr-n | Me | CH(Me) | 4-Cl | O | | 103–106 |
| 1-883 | Et | 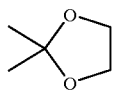 | Me | $CH_2$ | 4-Cl | O | | 161–162 |
| 1-884 | Et | $CMe(OMe)_2$ | Me | $CH_2$ | H | O | | Not Measurable |
| 1-885 | Et | CMe=NOMe | Me | $CH_2$ | H | O | | Not Measurable |
| 1-886 | Et | $CMe(OMe)_2$ | Me | $CH_2$ | 4-F | O | | Not Measurable |
| 1-887 | Et | COMe | Me | $CH_2$ | 4-F | O | | 71–73 |
| 1-888 | Et | CMe=NOMe | Me | $CH_2$ | 4-F | O | | 1.5443 |
| 1-889 | COOH | Pr-i | Me | $CH_2$ | 4-Cl | O | | 139–141 |
| 1-890 | CN | Bu-t | Me | CHMe | 4-Cl | O | | 106–108 |

TABLE 27

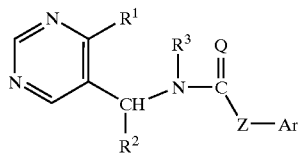

| Compound No. | R¹ | R² | R³ | Z | Ar | Q | m. p. (° C.) or refractive index ($n_D^{20}$) |
|---|---|---|---|---|---|---|---|
| 2-1 | $CF_3$ | Pr-i | Me | $CH_2$ | 2-napthyl | O | 137–138 |
| 2-2 | $CF_3$ | Pr-i | Me | $CH_2$ | 3-thienyl | O | 37–38 |
| 2-3 | $CF_3$ | Pr-i | Me | $CH_2$ | 2-pyridyl | O | 99–100 |
| 2-4 | $CF_3$ | Pr-i | Me | $CH_2$ | 3-pyridyl | O | 93–96 |
| 2-5 | $CF_3$ | Pr-i | Me | $CH_2$ | 4-pyridyl | O | 115–118 |
| 2-6 | $CF_3$ | Pr-i | Me | $CH_2$ | 2-thienyl | O | 51–54 |
| 2-7 | $CHF_2$ | Pr-i | Et | $CH_2$ | 2-thienyl | O | 69–71 |
| 2-8 | $CHF_2$ | Pr-i | Et | $CH_2$ | 3-thienyl | O | 83–85 |
| 2-9 | $CF_3$ | Pr-i | Et | $CH_2$ | 2-thienyl | O | 1.5197 |
| 2-10 | $CF_3$ | Pr-i | Et | $CH_2$ | 3-thienyl | O | 1.5208 |
| 2-11 | $CF_3$ | Bu-s | Me | $CH_2$ | 2-thienyl | O | 1.5215 |
| 2-12 | $CF_3$ | Bu-s | Me | $CH_2$ | 3-thienyl | O | 1.5229 |
| 2-13 | $CF_3$ | Bu-t | Me | $CH_2$ | 2-thienyl | O | 1.5121 |
| 2-14 | $CF_3$ | Bu-t | Me | $CH_2$ | 3-thienyl | O | 58–62 |
| 2-15 | $CF_3$ | Pr-i | Me | CH(Me) | 2-thienyl | O | |
| 2-16 | $CF_3$ | Pr-i | Me | CH(Me) | 3-thienyl | O | |
| 2-17 | $CF_3$ | Bu-t | Me | CH(Me) | 2-thienyl | O | |
| 2-18 | $CF_3$ | Bu-t | Me | CH(Me) | 3-thienyl | O | |
| 2-19 | $CF_3$ | Ph | Me | $CH_2$ | 2-thienyl | O | 139–142 |
| 2-20 | $CF_3$ | Ph | Me | $CH_2$ | 3-thienyl | O | 142–145 |
| 2-21 | SMe | Pr-i | Me | $CH_2$ | 2-thienyl | O | |
| 2-22 | SMe | Pr-i | Me | $CH_2$ | 3-thienyl | O | |
| 2-23 | Pr-i | Pr-i | Me | $CH_2$ | 2-thienyl | O | 79–81 |
| 2-24 | Pr-i | Pr-i | Me | $CH_2$ | 3-thienyl | O | 101–103 |
| 2-25 | $CF_3$ | Pr-i | Me | $CH_2$ | 5-Cl-2-thienyl | O | 94–95 |
| 2-26 | $CF_3$ | Pr-i | Me | $CH_2$ | 5-Me-2-thienyl | O | |
| 2-27 | SMe | Pr-i | Me | $CH_2$ | 5-Cl-2-thienyl | O | |
| 2-28 | SMe | Pr-i | Me | $CH_2$ | 5-Me-2-thienyl | O | |

TABLE 28

| Compound No. | R¹ | R² | R³ | Z | Ar | Q | m.p. (° C.) or refractive index ($n_D^{20}$) |
|---|---|---|---|---|---|---|---|
| 2-29 | Pr-i | Pr-i | Me | $CH_2$ | 5-Cl-2-thienyl | O | |
| 2-30 | Pr-i | Pr-i | Me | $CH_2$ | 5-Me-2-thienyl | O | |
| 2-31 | $CF_3$ | Ph | Me | $CH_2$ | 5-Cl-2-thienyl | O | 79–81 |
| 2-32 | $CF_3$ | Ph | Me | $CH_2$ | 5-Me-2-thienyl | O | 111–113 |
| 2-33 | $CF_3$ | Ph | Me | CH(Me) | 2-thienyl | O | |
| 2-34 | $CF_3$ | Ph | Me | CH(Me) | 3-thienyl | O | |
| 2-35 | $CF_3$ | Pr-i | Me | $CH_2$ | 5-$CF_3$-2-thienyl | O | |
| 2-36 | $CF_3$ | Pr-i | Me | $CH_2$ | 5-F-2-thienyl | O | |
| 2-37 | $CF_3$ | Pr-i | Me | $CH_2$ | 3-Cl-2-thienyl | O | |
| 2-38 | $CF_3$ | Pr-i | Me | $CH_2$ | 3-F-2-thienyl | O | |
| 2-39 | $CF_3$ | Pr-i | Me | $CH_2$ | 5-Cl-3-thienyl | O | |
| 2-40 | $CF_3$ | Pr-i | Me | $CH_2$ | 5-Me-3-thienyl | O | |
| 2-41 | $CF_3$ | Pr-i | Me | $CH_2$ | 4-Br-pyrazol-1-yl | O | 160–161 |
| 2-42 | $CF_3$ | Bu-t | Me | $CH_2$ | 5-Cl-2-thienyl | O | 106–107 |
| 2-43 | $CF_3$ | Pr-i | Me | $CH_2O$ | 5-Cl-2-pyridyl | O | 145–147 |
| 2-44 | $CF_3$ | Pr-i | Me | $CH_2O$ | 5-Cl-3-pyridyl | O | 120–122 |
| 2-45 | $CF_3$ | Pr-i | Me | $CH_2O$ | 3-Cl-5-$CF_3$-pyridin-2-yl | O | 138–141 |
| 2-46 | $CF_3$ | Pr-i | Me | $CH_2O$ | 1-Me-3-$CF_3$5-Pyrazolyl | O | 108–112 |
| 2-47 | $CF_3$ | Pr-i | Me | $CH_2O$ | 5-$CF_3$-1,3,4-thiaziazol-2-yl | O | 121–122 |
| 2-48 | $CF_3$ | Pr-i | Me | $CH_2O$ | 2-benzothiazolyl | O | 192–195 |
| 2-49 | $CF_3$ | Pr-i | Me | $CH_2O$ | 4-$CF_3$-pyridin-2-yl | O | 164–167 |
| 2-50 | $CF_3$ | Pr-i | Me | $CH_2$ | 5-Me-2-thienyl | O | 73–75 |
| 2-51 | $CF_3$ | Bu-i | Me | $CH_2$ | 2-thienyl | O | 68–70 |
| 2-52 | $CF_3$ | Bu-i | Me | $CH_2$ | 3-thienyl | O | 81–82 |
| 2-53 | $CF_3$ | Bu-i | Me | $CH_2$ | 5-Me-2-thienyl | O | 94–98 |
| 2-54 | $CF_3$ | Pr-i | Me | $CH_2$ | Pr-e | O | 86–87 |

TABLE 28-continued

| Compound No. | R¹ | R² | R³ | Z | Ar | Q | m.p. (° C.) or refractive index ($n_D^{20}$) |
|---|---|---|---|---|---|---|---|
| 2-55 | CF₃ | (cyclopropyl with Me,Me) | Me | CH₂ | 2-thienyl | O | 92–93 |
| 2-56 | CF₃ | (cyclopropyl with Me,Me) | Me | CH₂ | 3-thienyl | O | 111–112 |
| 2-57 | CF₃ | Bu-s | Me | CH₂ | 5-Cl-2-thienyl | O | 1.5295 |

TABLE 29

| Compound No. | R¹ | R² | R³ | Z | Ar | Q | m.p. (° C.) or refractive index ($n_D^{20}$) |
|---|---|---|---|---|---|---|---|
| 2-58 | CF₃ | (cyclopropyl with Me,Me) | Me | CH₂ | 5-Cl-2-thienyl | O | Not Measurable |
| 2-59 | CF₃ | (cyclopropyl with Me,Me) | Me | CH₂ | 5-Me-2-thienyl | O | 71–74 |
| 2-60 | CF₃ | Pr-i | Me | CH(Me) | 5-Me-2-thienyl | O | 1.5141 |
| 2-61 | CF₃ | Pr-i | Me | CH(Me) | 5-Br-2-thienyl | O | 1.5331 |
| 2-62 | CF₃ | Pr-i | Me | CH(Me) | 2-thienyl | O | Not more than 30° C. |
| 2-63 | CF₃ | Pr-i | Me | N(Me) | 3-thienyl | O | 1.5244 |
| 2-64 | CF₃ | Pr-i | Me | NH | 2-benzothiazolyl | O | 180–182 |
| 2-65 | CF₃ | Pr-i | Me | N(Me) | 5-Cl-pyridin-2-yl | O | 39–40 |
| 2-66 | CF₃ | Pr-i | Me | NH | cycrohexyl | O | 110–112 |
| 2-67 | CF₃ | Pr-i | Me | N(Me) | 3-Me-5-isoxazolyl | O | 1.4939 |
| 2-68 | CF₃ | Pr-i | Me | N(Me) | 4-MeO-6-Me-pyrimidin-2-yl | O | 107–110 |
| 2-69 | CF₃ | Pr-i | Me | N(Me) | 4,6-(MeO)₂-1,3,5-triazinyl | O | 112–113 |
| 2-70 | CF₃ | Pr-i | Me | N(Me) | 6-MeO-pyridin-3-yl | O | 1.5079 |
| 2-71 | Pr-i | Pr-i | Me | CH₂ | 5-Cl-2-thienyl | O | 112–115 |
| 2-72 | CF₃ | Pr-i | Me | N(Me) | cycrohexyl | O | 98–100 |
| 2-73 | Et | Pr-i | CH₂C≡CH | CH₂ | 5-Cl-2-thienyl | O | 90–91 |
| 2-74 | CF₃ | Pr-i | CH₂C≡CH | CH₂ | 5-Cl-2-thienyl | O | 117–118 |
| 2-75 | Et | Pr-i | Me | CH₂ | 5-Cl-2-thienyl | O | Not Measurable |
| 2-76 | Pr-i | CH₂OMe | Me | CH₂ | 5-Cl-2-thienyl | O | 1.5488 |
| 2-77 | CH₂OMe | Pr-i | Me | CH₂ | 5-Cl-2-thienyl | O | 1.5508 |
| 2-78 | CF₃ | Pr-i | CH₂C≡CH | CH₂ | 3-thienyl | O | 112–114 |
| 2-79 | Pr-i | Pr-i | CH₂C≡CH | CH₂ | 3-thienyl | O | 128–131 |
| 2-80 | CF₂Cl | Pr-i | Me | O | 1-naphtyl | O | 123–126 |
| 2-81 | CF₃ | Pr-i | Me | CH₂ | 5-CF₃-1,3,4-thiadizol-2-yl | O | |
| 2-82 | CF₃ | Pr-i | Me | CH₂ | 4-CF₃-1,3,4-imidazol-2-yl | O | |
| 2-83 | CF₃ | Pr-i | Me | CH₂ | 2-Cl-5-oxazolyl | O | |
| 2-84 | CF₃ | Pr-i | Me | CH₂ | 2-Cl-5-thiazolyl | O | |
| 2-85 | CF₃ | Pr-i | Me | CH₂ | 5-Cl-2-furyl | O | |

TABLE 30

| Compound No. | R¹ | R² | R³ | Z | Ar | Q | m.p. (° C.) or refractive index ($n_D^{20}$) |
|---|---|---|---|---|---|---|---|
| 2-86 | CF₃ | Pr-i | Me | CH₂ | 2-benzoxazolyl | O | |
| 2-87 | Et | Pr-i | Me | CH₂ | 2-thienyl | O | |
| 2-88 | Et | Pr-i | Me | CH₂ | 3-thienyl | O | |
| 2-89 | Et | Pr-i | Me | CH₂ | 5-Me-2-thienyl | O | |
| 2-90 | Et | Pr-i | Me | CH(Me) | 2-thienyl | O | |
| 2-91 | Et | Pr-i | Me | CH(Me) | 3-thienyl | O | |

TABLE 30-continued

| Compound No. | R¹ | R² | R³ | Z | Ar | Q | m.p. (° C.) or refractive index ($n_D^{20}$) |
|---|---|---|---|---|---|---|---|
| 2-92 | Et | Pr-i | Me | CH(Me) | 5-Cl-2-thienyl | O | |
| 2-93 | Et | Pr-i | Me | CH(Me) | 5-Me-2-thienyl | O | |
| 2-94 | Et | Pr-i | CH₂C≡CH | CH₂ | 2-thienyl | O | |
| 2-95 | Et | Pr-i | CH₂C≡CH | CH₂ | 3-thienyl | O | |
| 2-96 | Et | Pr-i | CH₂C≡CH | CH₂ | 5-Me-2-thienyl | O | |
| 2-97 | Et | Bu-s | Me | CH₂ | 2-thienyl | O | |
| 2-98 | Et | Bu-s | Me | CH₂ | 3-thienyl | O | |
| 2-99 | Et | Bu-t | Me | CH₂ | 2-thienyl | O | |
| 2-100 | Et | Bu-t | Me | CH₂ | 3-thienyl | O | |
| 2-101 | Et | Bu-s | CH₂C≡CH | CH₂ | 2-thienyl | O | |
| 2-102 | Et | Bu-s | CH₂C≡CH | CH₂ | 3-thienyl | O | |
| 2-103 | Et | Bu-t | CH₂C≡CH | CH₂ | 2-thienyl | O | |
| 2-104 | Et | Bu-t | CH₂C≡CH | CH₂ | 3-thienyl | O | |
| 2-105 | CF₃ | Pr-i | Me | N(Me) | 2-thienyl | O | |
| 2-106 | CF₃ | Pr-i | Me | N(Me) | 5-Cl-2-thienyl | O | |
| 2-107 | CF₃ | Pr-i | Me | N(Me) | 5-Me-2-thienyl | O | |
| 2-108 | Et | Pr-i | Me | N(Me) | 2-thienyl | O | |
| 2-109 | Et | Pr-i | Me | N(Me) | 3-thienyl | O | |
| 2-110 | Et | Pr-i | Me | N(Me) | 5-Cl-2-thienyl | O | |
| 2-111 | Et | Pr-i | Me | N(Me) | 5-Me-2-thienyl | O | |
| 2-112 | CF₃ | Pr-i | Me | NHCH₂ | 2-thienyl | O | 110–112 |

TABLE 31

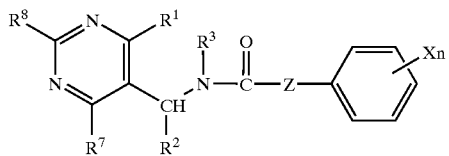

| Compound No. | R₁ | R₂ | R₃ | Z | Xn | R₇ | R₈ | m. p. (° C.) or refractive index ($n_D^{20}$) |
|---|---|---|---|---|---|---|---|---|
| 3-1 | CF₃ | Pr-i | Me | CH₂ | H | H | Me | 99–101 |
| 3-2 | CF₃ | Pr-i | Me | CH₂ | 4-F | H | Me | 74–75 |
| 3-3 | CF₃ | Pr-i | Me | CH₂ | 4-Cl | H | Me | 67–68 |
| 3-4 | CF₃ | Pr-i | Me | CH₂ | 4-Me | H | Me | 85–86 |
| 3-5 | CF₃ | Pr-i | Me | CH₂ | H | H | Pr-c | 144–145 |
| 3-6 | CF₃ | Pr-i | Me | CH₂ | 4-F | H | Pr-c | 131–132 |
| 3-7 | CF₃ | Pr-i | Me | CH₂ | 4-Cl | H | Pr-c | 99–100 |
| 3-8 | CF₃ | Pr-i | Me | CH₂ | 4-Me | H | Pr-c | 82–83 |
| 3-9 | CF₃ | Pr-i | Me | CH₂ | H | Me | H | |
| 3-10 | CF₃ | Pr-i | Me | CH₂ | 4-F | Me | H | |
| 3-11 | CF₃ | Pr-i | Me | CH₂ | 4-Cl | Me | H | |
| 3-12 | CF₃ | Pr-i | Me | CH₂ | 4-Me | Me | H | |
| 3-13 | Me | Pr-i | Me | CH₂ | H | Me | H | |
| 3-14 | Me | Pr-i | Me | CH₂ | 4-F | Me | H | |
| 3-15 | Me | Pr-i | Me | CH₂ | 4-Cl | Me | H | |
| 3-16 | Me | Pr-i | Me | CH₂ | 4-Me | Me | H | |
| 3-17 | Pr-i | Pr-i | Me | CH₂ | H | Me | H | |
| 3-18 | Pr-i | Pr-i | Me | CH₂ | 4-F | Me | H | |
| 3-19 | Pr-i | Pr-i | Me | CH₂ | 4-Cl | Me | H | |
| 3-20 | Pr-i | Pr-i | Me | CH₂ | 4-Me | Me | H | |
| 3-21 | Me | Bu-t | Me | CH₂ | H | Me | H | |
| 3-22 | Me | Bu-t | Me | CH₂ | 4-F | Me | H | |
| 3-23 | Me | Bu-t | Me | CH₂ | 4-Cl | Me | H | |
| 3-24 | Me | Bu-t | Me | CH₂ | 4-Me | Me | H | |
| 3-25 | Et | Et | Me | CH₂ | H | Et | H | |
| 3-26 | Et | Et | Me | CH₂ | 4-F | Et | H | |

TABLE 32

| Compound No. | $R_1$ | $R_2$ | $R_3$ | Z | Xn | $R_7$ | $R_8$ | m.p. (° C.) or refractive index ($n_D^{20}$) |
|---|---|---|---|---|---|---|---|---|
| 3-27 | Et | Et | Me | CH₂ | 4-Cl | Et | H | |
| 3-28 | Et | Et | Me | CH₂ | 4-Me | Et | H | |
| 3-29 | CF₃ | Pr-i | Me | CH₂ | H | H | SMe | |
| 3-30 | CF₃ | Pr-i | Me | CH₂ | 4-F | H | SMe | |
| 3-31 | CF₃ | Pr-i | Me | CH₂ | 4-Cl | H | SMe | |
| 3-32 | CF₃ | Pr-i | Me | CH₂ | 4-Me | H | SMe | |
| 3-33 | CF₃ | Ph | Me | CH₂ | H | Me | H | |
| 3-34 | CF₃ | Ph | Me | CH₂ | 4-F | Me | H | |
| 3-35 | CF₃ | Ph | Me | CH₂ | 4-Cl | Me | H | |
| 3-36 | CF₃ | Ph | Me | CH₂ | 4-Me | Me | H | |
| 3-37 | CF₃ | Pr-i | Me | CH₂ | H | CF₃ | H | |
| 3-38 | CF₃ | Pr-i | Me | CH₂ | 4-F | CF₃ | H | |
| 3-39 | CF₃ | Pr-i | Me | CH₂ | 4-Cl | CF₃ | H | |
| 3-40 | CF₃ | Pr-i | Me | CH₂ | 4-Me | CF₃ | H | |
| 3-41 | OMe | Pr-i | Me | CH₂ | 4-Cl | OMe | H | 107–109 |
| 3-42 | CF₃ | Pr-i | Me | O | 4-Cl | H | Me | 104–107 |
| 3-43 | CF₃ | Pr-i | Me | O | 4-Cl | H | Pr-c | 1.5178 |

TABLE 33

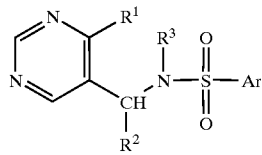

| Compound No. | $R^1$ | $R^2$ | $R^3$ | Ar | m. p. (° C.) or refractive index ($n_D^{20}$) |
|---|---|---|---|---|---|
| 4-1 | CF₃ | Pr-i | Me | Ph(4-Cl) | 1.5246 |
| 4-2 | Et | Pr-i | Me | Ph | 1.5446 |
| 4-3 | Et | Pr-i | Me | Ph(4-F) | 1.5399 |
| 4-4 | Et | Pr-i | Me | Ph(3-F) | 1.541 |
| 4-5 | Et | Pr-i | Me | Ph(2-F) | 1.5441 |
| 4-6 | Et | Pr-i | Me | Ph(4-Cl) | 1.5562 |
| 4-7 | Et | Pr-i | Me | Ph(4-Me) | 1.5475 |
| 4-8 | Et | Pr-i | Me | Ph(4-CN) | 1.5527 |
| 4-9 | Et | Pr-i | Me | Ph(4-OMe) | 102–103 |
| 4-10 | Et | Pr-i | Me | Ph(4-NO₂) | 106–107 |
| 4-11 | Pr-i | Pr-i | Me | Ph(4-F) | 93–95 |
| 4-12 | CH₂OMe | Pr-i | Me | Ph(4-F) | 1.5365 |
| 4-13 | CH(OEt)₂ | Pr-i | Me | Ph(4-F) | 1.5234 |
| 4-14 | Et | Pr | CH₂C≡CH | Ph(4-F) | 1.5445 |
| 4-15 | CF₃ | Pr-i | Me | Ph | 1.518 |
| 4-16 | Pr-i | Pr-i | Me | Ph(4-CF₃) | |
| 4-17 | CF₃ | Pr-i | Me | Ph(4-F) | |
| 4-18 | CF₃ | Pr-i | Me | Ph(3-F) | |
| 4-19 | CF₃ | Pr-i | Me | Ph(2-F) | |
| 4-20 | CF₃ | Pr-i | Me | Ph(4-Me) | |
| 4-21 | CF₃ | Pr-i | Me | Ph(4-CN) | |
| 4-22 | CF₃ | Pr-i | Me | Ph(4-OMe) | |
| 4-23 | CF₃ | Pr-i | Me | Ph(4-NO₂) | |
| 4-24 | CF₃ | Pr-i | CH₂C≡CH | Ph(4-F) | |
| 4-25 | CF₃ | Pr-i | Me | Ph(2-Me) | |
| 4-26 | Et | Pr-i | Me | Ph(2-Me) | 1.5512 |
| 4-27 | CF₃ | Pr-i | M | Ph(3-Me) | |
| 4-28 | Et | Pr-i | Me | Ph(3-Me) | 1.5499 |

TABLE 34

| Compound No. | R¹ | R² | R³ | Ar | m. p. (° C.) or refractive index ($n_D^{20}$) |
|---|---|---|---|---|---|
| 4-29 | CF₃ | Pr-i | CH₂C≡CH | Ph(4-F) | |
| 4-30 | Et | Pr-i | CH₂C≡CH | Ph(4-Cl) | |
| 4-31 | CF₃ | Pr-i | CH₂C≡CH | Ph(4-Cl) | |
| 4-32 | Et | Pr-i | CH₂C≡CH | Ph | |
| 4-33 | CF₃ | Pr-i | CH₂C≡CH | Ph | |
| 4-34 | Et | Pr-i | CH₂C≡CH | Ph(4-Me) | |
| 4-35 | CF₃ | Pr-i | CH₂C≡CH | Ph(4-Me) | |
| 4-36 | CF₂Cl | Pr-i | Me | Ph | 1.5382 |
| 4-37 | CF₂Cl | Pr-i | Me | Ph(4-F) | 1.4929 |
| 4-38 | Pr-i | Pr-i | Me | (3-methyl-1,2,4-triazol-1-yl)-C(O)-N(Et)₂ | 132–133 |
| 4-39 | Pr-i | Pr-i | Me | | |
| 4-40 | Pr-i | Pr-i | Me | Ph(3-F) | |
| 4-41 | Pr-i | Pr-i | Me | Ph(2-F) | |
| 4-42 | Pr-i | Pr-i | Me | Ph(4-Me) | |
| 4-43 | Pr-i | Pr-i | Me | Ph(4-CN) | |
| 4-44 | Pr-i | Pr-i | Me | Ph(4-OMe) | |
| 4-45 | Pr-i | Pr-i | Me | Ph(4-NO₂) | |
| 4-46 | Pr-i | Pr-i | CH₂C≡CH | Ph(4-F) | |
| 4-47 | Pr-i | Pr-i | Me | Ph(2-Me) | |
| 4-48 | Pr-i | Pr-i | Me | Ph(3-Me) | |
| 4-49 | Pr-i | Pr-i | CH₂C≡CH | Ph(4-F) | |
| 4-50 | Pr-i | Pr-i | CH₂C≡CH | Ph(4-Cl) | |
| 4-51 | Pr-i | Pr-i | CH₂C≡CH | Ph | |
| 4-52 | Pr-i | Pr-i | CH₂C≡CH | Ph(4-Me) | |
| 4-53 | Et | Pr-i | Me | Ph(4-CF₃) | 1.5117 |
| 4-54 | Et | Et | Me | Ph(4-F) | 1.5462 |
| 4-55 | Et | Pr-i | Me | 2-thienyl | 109–110 |

TABLE 35

| Compound No. | R¹ | R² | p | Q | q | Xn | m. p. (° C.) or refractive index ($n_D^{20}$) |
|---|---|---|---|---|---|---|---|
| 5-1 | CF₃ | Pr-i | 2 | O | 0 | H | 126–128 |
| 5-2 | CF₃ | Pr-i | 2 | O | 0 | 4-F | 1.5279 |
| 5-3 | CF₃ | Pr-i | 2 | O | 0 | 4-Cl | |
| 5-4 | CF₃ | Pr-i | 2 | O | 0 | 4-Me | |
| 5-5 | CF₃ | Pr-i | 3 | O | 0 | H | |
| 5-6 | CF₃ | Pr-i | 3 | O | 0 | 4-F | |
| 5-7 | CF₃ | Pr-i | 3 | O | 0 | 4-Cl | |
| 5-8 | CF₃ | Pr-i | 3 | O | 0 | 4-Me | |
| 5-9 | CF₃ | Pr-i | 2 | O | 1 | H | 93–95 |
| 5-10 | CF₃ | Pr-i | 2 | O | 1 | 4-F | 1.5090 |
| 5-11 | CF₃ | Pr-i | 2 | O | 1 | 4-Cl | |
| 5-12 | CF₃ | Pr-i | 2 | O | 1 | 4-Me | |
| 5-13 | CF₃ | Pr-i | 3 | O | 1 | H | 1.5181 |
| 5-14 | CF₃ | Pr-i | 3 | O | 1 | 4-F | |
| 5-15 | CF₃ | Pr-i | 3 | O | 1 | 4-Cl | |
| 5-16 | CF₃ | Pr-i | 3 | O | 1 | 4-Me | |
| 5-17 | CF₃ | Pr-i | 3 | S | 0 | H | |
| 5-18 | CF₃ | Pr-i | 3 | S | 0 | 4-F | |
| 5-19 | CF₃ | Pr-i | 3 | S | 0 | 4-Cl | |
| 5-20 | CF₃ | Pr-i | 3 | S | 0 | 4-Me | |
| 5-21 | CF₃ | Pr-i | 3 | S | 1 | H | |
| 5-22 | CF₃ | Pr-i | 3 | S | 1 | 4-F | |
| 5-23 | CF₃ | Pr-i | 3 | S | 1 | 4-Cl | |
| 5-24 | CF₃ | Pr-i | 3 | S | 1 | 4-Me | |
| 5-25 | CF₃ | Pr-i | 2 | S | 1 | H | 138–140 |

TABLE 36

| Compound No. | R¹ | R² | p | Q | q | Xn | m.p. (° C.) or refractive index ($n_D^{20}$) |
|---|---|---|---|---|---|---|---|
| 5-26 | CF₃ | Pr-i | 2 | S | 1 | 4-F | |
| 5-27 | CF₃ | Pr-i | 2 | S | 1 | 4-Cl | |
| 5-28 | CF₃ | Pr-i | 2 | S | 1 | 4-Me | |
| 5-29 | Et | Pr-i | 3 | O | 0 | H | |
| 5-30 | Et | Pr-i | 3 | O | 0 | 4-F | |
| 5-31 | Et | Pr-i | 3 | O | 0 | 4-Cl | |
| 5-32 | Et | Pr-i | 3 | O | 0 | 4-Me | |
| 5-33 | Et | Pr-i | 2 | O | 1 | H | |
| 5-34 | Et | Pr-i | 2 | O | 1 | 4-F | |
| 5-35 | Et | Pr-i | 2 | O | 1 | 4-Cl | |
| 5-36 | Et | Pr-i | 2 | O | 1 | 4-Me | |

TABLE 36-continued

| Compound No. | R¹ | R² | p | Q | q | Xn | m.p. (° C.) or refractive index ($n_D^{20}$) |
|---|---|---|---|---|---|---|---|
| 5-37 | Et | Pr-i | 3 | O | 1 | H | |
| 5-38 | Et | Pr-I | 3 | O | 1 | 4-F | |
| 5-39 | Et | Pr-i | 3 | O | 1 | 4-Cl | |
| 5-40 | Et | Pr-i | 3 | O | 1 | 4-Me | |
| 5-41 | Et | Pr-i | 3 | S | 0 | H | |
| 5-42 | Et | Pr-i | 3 | S | 0 | 4-F | |
| 5-43 | Et | Pr-i | 3 | S | 0 | 4-Cl | |
| 5-44 | Et | Pr-i | 3 | S | 0 | 4-Me | |
| 5-45 | Et | Pr-i | 3 | S | 1 | H | |
| 5-46 | Et | Pr-i | 3 | S | 1 | 4-F | |
| 5-47 | Et | Pr-i | 3 | S | 1 | 4-Cl | |
| 5-48 | Et | Pr-i | 3 | S | 1 | 4-Me | |

TABLE 37

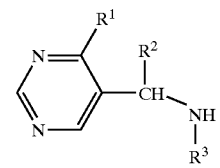

| Compound No. | R¹ | R² | R³ | m. p. (° C.), refractive index ($n_D^{20}$) or NMR (δ(ppm), 300 MHz, CDCl₃) |
|---|---|---|---|---|
| 6-1 | Pr-i | Pr-i | Me | 44–45 |
| 6-2 | Pr-i | Et | Me | 1.4902 |
| 6-3 | Et | Pr-i | Me | 0.86(3H, d); 0.99(3H, d); 1.32(3H, t); 1.65(1H, br); 1.85–1.95(1H, m); 2.23(3H, s); 2.77–2.95(2H, m); 3.58(1H, d); 8.68(1H, s); 9.02(1H, s) |
| 6-4 | Pr | Pr-i | Me | 0.86(3H, d); 0.99(3H, d); 1.00(3H, t); 1.44(1H, br); 1.73–1.83(2H, m); 1.83–1.95(1H, m); 2.23(3H, s); 2.68–2.90(2H, m); 3.59(1H, d); 8.69(1H, s); 9.01(1H, s) |
| 6-5 | Pr-i | Pr | Me | 1.4929 |
| 6-6 | Et | Bu-t | Me | 74–75 |
| 6-7 | Bu-t | Et | Me | 1.02(3H, t); 1.46(9H, s); 1.65–1.72(1H, m); 2.33(3H, s); 4.16(1H, t); 8.85(1H, s); 9.00(1H, s) |
| 6-8 | Pr-i | CH(OEt)₂ | Me | 1.4794 |
| 6-9 | CH(OEt)₂ | Pr-i | Me | 0.85(3H, d); 0.99(3H, d); 1.24(3H, t); 1.45(1H, br); 1.95–2.04(1H, m); 2.23(1H, s); 3.53–3.66(2H, m); 3.72–4.04(2H, m); 4.03(1H, d); 5.57(1H, s); 8.87(1H, s); 9.09(1H, s) |

TABLE 38

| Compound No. | R¹ | R² | R³ | m.p. (° C.), refractive index ($n_D^{20}$) or NMR (δ (ppm), 300 MHz, CDCl₃) |
|---|---|---|---|---|
| 6-10 | CH(OEt)₂ | Pr-n | Me | 1.4811 |
| 6-11 | CH(OEt)₂ | Bu-t | Me | 1.4781 |
| 6-12 | Pr | Pr | Me | 1.4978 |
| 6-13 | Et | Pr | Me | |
| 6-14 | Pr | Et | Me | |
| 6-15 | Pr-i | CH₂OMe | Me | 1.29(3H, d), 1.29(3H, d), 2.29(3H, s), 3.39(3H, s), 3.30–3.46(2H, m), 3.30–3.46(1H, m), 4.1(1H, dd), 8.80(1H, s), 9.07(1H, s) |

TABLE 38-continued

| Compound No. | R¹ | R² | R³ | m.p. (° C.), refractive index ($n_D^{20}$) or NMR (δ (ppm), 300 MHz, CDCl₃) |
|---|---|---|---|---|
| 6-16 | CH₂OMe | Pr-i | Me | 0.83(3H, d); 1.01(3H, d); 1.89–2.63(1H, m); 2.22(3H, s); 3.46(3H, s); 3.61(1H, d); 4.64(2H, q); 8.80(1H, s); 9.10)1H, s) |
| 6-17 | SMe | Pr-i | Me | 1.5509 |
| 6-18 | Pr-i | Pr-i | CH₂C≡CH | 0.86(3H, d); 1.01(3H, d); 1.88–1.95(1H, m); 2.22(1H, t); 2.95(1H, dd); 3.38–3.48(1H, m); 3.38–3.44(1H, dd); 4.04(1H, d); 8.71(1H, s); 9.06(1H, s) |
| 6-19 | Pr-i | Et | CH₂C≡CH | |
| 6-20 | Et | Pr-i | CH₂C≡CH | 1.5185 |
| 6-21 | Pr | Pr-i | CH₂C≡CH | 46–48 |
| 6-22 | Pr-i | Pr | CH₂C≡CH | 0.86(3H, d); 0.93(3H, d); 1.29(3H, d); 1.29(3H, d); 1.27–1.42(2H, m); 1.55–1.70(2H, m): 2.23(1H, t); 3.03(1H, dd); 3.40(1Hdd); 3.37–3.50(1H, m); 4.29(1H, t); 8.74(1H, s); 9.05(1H, s) |
| 6-23 | Et | Bu-t | CH₂C≡CH | 0,95(9H, s); 1.33(3H, t); 2.22(1H, t); 2.88(1F, dd); 2.93(2H, q); 3.41(1H, dd); 4.11(1H, s); 8.79(1H, s); 9.02(1H, s) |

TABLE 39

| Compound No. | R¹ | R² | R³ | m. p. (° C.), refractive index ($n_D^{20}$) or NMR (δ(ppm), 300 MHz, CDCl₃) |
|---|---|---|---|---|
| 6-24 | Bu-t | Et | CH₂C≡CH | |
| 6-25 | Pr | Pr | CH₂C≡CH | |
| 6-26 | Et | Pr | CH₂C≡CH | 0.87(3H, t); 0.94(3H, t); 1.18–1.45(2H, m); 1.33(3H, t); 1.55–1.74(2H, m); 2.45(1H, t); 2.87(2H, q); 3.04(1H, dd); 3.43(1H, dd); 4.25(1H, t); 8.75(1H, s); 9.01(1H, s) |
| 6-27 | Pr | Et | CH₂C≡CH | |
| 6-28 | Et | CH(Me)(SMe) | N(Me) | 0.89(3H, t); 0.94(3H, t); 1.47(1H, br); 1.66(3H, d); 1.68(3H, d); 1.60–1.81(2H, m); 2.05(3H, s); 2.07(3H, s); 2.29(3H, s); 2.33(3H, s); 3.77(1H, t); 3.86(1H, t); 4.33(1H, q); 4.42(1H, q); 8.71(1H, s); 8.77(1H, s); 9.08(1H, s) |
| 6-29 | Ph | Pr-i | N(Me) | 1.5632 |
| 6-30 | Pr-i | Me | N(Me) | 1.5012 |
| 6-31 | Bu-t | Me | N(Me) | 72–73 |
| 6-32 | Pr-i | Ph | N(Me) | 1.5598 |
| 6-33 | CMe(OMe)₂ | Pr-i | N(Me) | 75–76 |
| 6-34 | Pr-i | 2,2-dimethyl-1,3-dioxolane | N(Me) | 79–78 |
| 6-35 | Pr-i | CH=NOMe | N(Me) | 1.5079 |
| 6-36 | 2-methyl-1,3-dioxolan-2-yl | Pr-i | N(Me) | 1.5089 |
| 6-37 | Et | Et | N(Me) | 1.5049 |

The compound of the present invention can be produced, for example, by the following processes, but is not restricted to such processes. Further, syntheses of intermediates will also be described.

Process 1

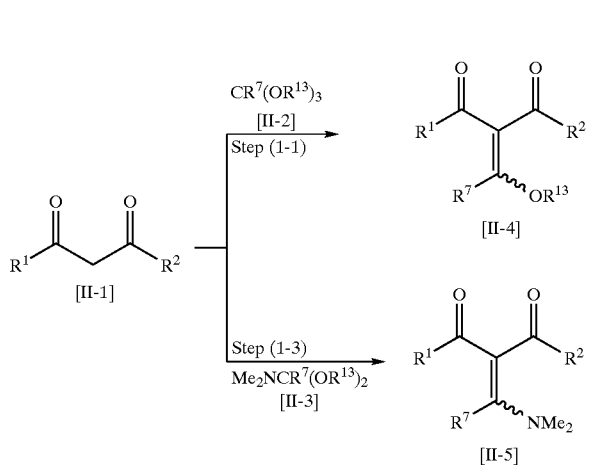
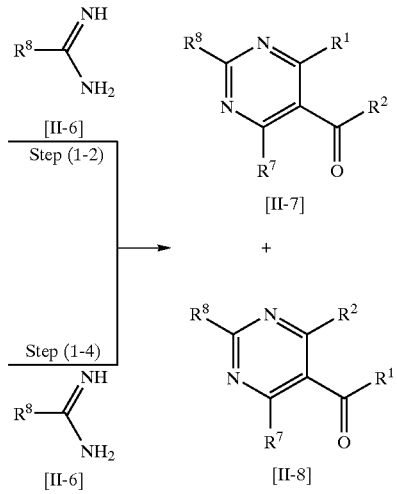

In the formulae, $R^1$, $R^2$, $R^7$ and $R^8$ have the same meanings as defined above, respectively, and $R^{13}$ is a $C_1$–$C_6$ alkyl group.

Namely, in step (1-1), 1 equivalent of a compound represented by the formula [II-1] is reacted with from 1 to 10 equivalents of a compound represented by the formula [II-2] in acetic anhydride to obtain a compound represented by the formula [II-4]. Here, from 0.01 to 1.0 equivalent of a catalyst (such as zinc chloride) may be added, as the case requires.

The reaction is carried out in a nitrogen stream, as the case requires. The reaction is carried out at an optional temperature from room temperature to the reflux temperature in the reaction system and will be completed in from 1 to 100 hours, although it varies depending upon the compound. The desired product can be isolated from the reaction solution by a usual method and may be purified by distillation or column chromatography, as the case requires.

Then, in step (1-2), 1 equivalent of a compound represented by the formula [II-4] is reacted with from 1 to 10 equivalents of a Lewis acid salt of a compound represented by the formula [II-6] in the presence of from 1 to 10 equivalents of a base in an inert solvent to obtain a compound represented by the formula [II-7]. By this reaction, in some cases, a compound represented by the formula [II-8] will also be obtained as a by-product.

Here, the inert solvent may, for example, be an ether such as diethyl ether, tetrahydrofuran or dioxane, or a hydrocarbon such as n-hexane, benzene, toluene or xylene.

The base may, for example, be an alkali metal such as sodium or potassium, an alkali metal alkoxide such as sodium methoxide or potassium tert-butoxide, or an alkali metal hydride such as sodium hydride or potassium hydride.

The Lewis acid may, for example, be acetic acid or hydrochloric acid.

The reaction may be carried out in a nitrogen stream, as the case requires. The reaction is carried out at an optional temperature from −10° C. to the reflux temperature in the reaction system and will be completed in from 1 hour to 24 hours, although it varies depending upon the compound. The desired product can be isolated from the reaction solution by a usual method and may be purified by distillation or column chromatography, as the case requires.

Further, in step (1-3), 1 equivalent of a compound represented by the formula [II-1] is reacted with from 1 to 10 equivalents of a compound represented by the formula [II-3] in an inert solvent or without using any to solvent, to obtain a compound represented by the formula [II-5].

Here, the inert solvent may, for example, be a hydrocarbon such as n-hexane, benzene, toluene or xylene.

The reaction may be carried out in a nitrogen stream, as the case requires. The reaction is carried out at an optional temperature from room temperature to the reflux temperature in the reaction system and will be completed in from 1 to 24 hours, although it varies depending upon the compound. The desired product can be isolated from the reaction solution by a usual method and may be purified by distillation or column chromatography, as the case requires.

Further, in step (1-4), 1 equivalent of a compound represented by the formula [II-5] is reacted with from 1 to 5 equivalents of a Lewis acid salt of a compound represented by the formula [II-6] in an inert solvent in the presence of from 1 to 10 equivalents of a base to obtain a compound represented by the formula [II-7]. In this reaction, sometimes, a compound represented by the formula [II-8] will also be obtained as a by-product.

The inert solvent may, for example, be an ether such as diethyl ether, tetrahydrofuran or dioxane, or a hydrocarbon such as n-hexane, benzene, toluene or xylene.

The base may, for example, be an alkali metal such as sodium or potassium, an alkali metal alkoxide such as sodium methoxide or potassium tert-butoxide, or an alkali metal hydride such as sodium hydride or potassium hydride.

The Lewis acid may, for example, be acetic acid or hydrochloric acid.

The reaction may be carried out in a nitrogen tag stream, as the case requires. The reaction is carried out at an optional temperature from −10° C. to the reflux temperature in the reaction system and will be completed in from 1 to 24 hours, although it varies depending upon the compound. The desired product can be isolated from the reaction solution by a usual method and may be purified by distillation or column chromatography, as the case requires.

Process 2

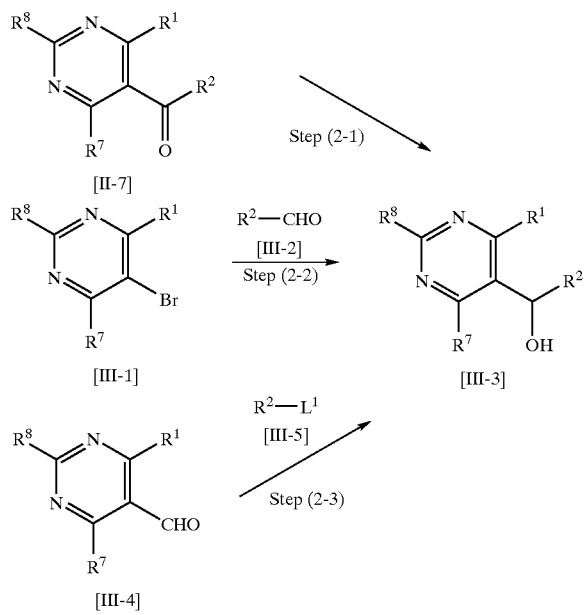

$L^1$ represents a halogen atom, and $R^1$, $R^2$, $R^7$ and $R^8$ in the formulae, have the same meanings as defined above, respectively.

Namely, in step (2-1), 1 equivalent of a compound represented by the formula [II-7] is reduced with from 0.5 to 10 equivalents of a reducing agent (such as a borane-tert-butylamine complex or sodium borohydride) in an inert solvent to obtain a compound represented by the formula [III-3].

The inert solvent may, for example, be an alcohol such as ethyl alcohol, isopropyl alcohol, tert-butyl alcohol or methyl alcohol.

The reaction may be carried out in a nitrogen stream, as the case requires. The reaction is carried out at an optional temperature from −10° C. to the reflux temperature in the reaction system and will be completed in from 1 to 24 hours, although it varies depending upon the compound. The desired product can be isolated from the reaction solution by a usual method and may be purified by distillation or column chromatography, as the case requires.

In step (2-2), 1 equivalent of a compound represented by the formula [III-1] is reacted with from 1 to 10 equivalents of a compound represented by the formula [III-2] in an inert solvent in the presence of from 1 to 10 equivalents of magnesium, or an alkyl lithium such as methyl lithium, ethyl lithium or n-butyllithium, to obtain a compound represented by the formula [III-3].

Here, the inert solvent may, for example, be an ether such as diethyl ether, tetrahydrofuran or dioxane, or a hydrocarbon such as n-hexane, benzene, toluene or xylene.

The reaction may be carried out in a nitrogen stream, as the case requires. The reaction is carried out at an optional temperature from −100° C. to the reflux temperature in the reaction system and will be completed in from 1 to 24 hours, although it varies depending upon the compound. The desired product can be isolated from the reaction solution by a usual method and may be purified by distillation or column chromatography, as the case requires.

Further, the compound represented by the formula [III-1] as the intermediate to be used in the above production process, can be synthesized, for example, by a method disclosed in e.g. the specification of international application WO97/37978.

In step (2-3), 1 equivalent of a compound represented by the formula [III-4] is reacted with from 1 to 10 equivalents of a compound represented by the formula [III-5] in an inert solvent in the presence of from 1 to 10 equivalents of magnesium or an alkyl lithium such as methyl lithium, ethyl lithium or n-butyllithium, to obtain a compound represented by the formula [III-3].

Here, the inert solvent may, for example, be an ether such as diethyl ether, tetrahydrofuran or dioxane, or a hydrocarbon such as n-hexane, benzene, toluene or xylene.

The reaction may be carried out in a nitrogen stream, as the case requires. The reaction is carried out at an optional temperature from −100° C. to the reflux temperature in the reaction system and will be completed in from 1 to 24 hours, although it varies depending upon the compound. The desired product can be isolated from the reaction solution by a usual method and may be purified by distillation or column chromatography, as the case requires.

Process 3

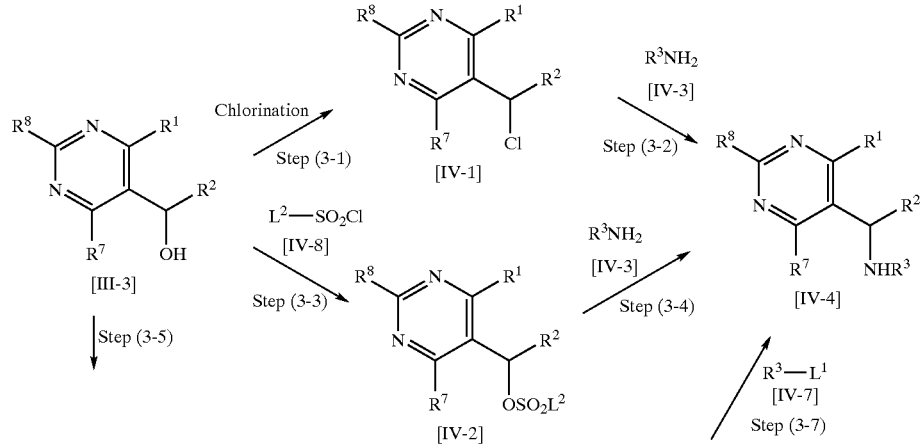

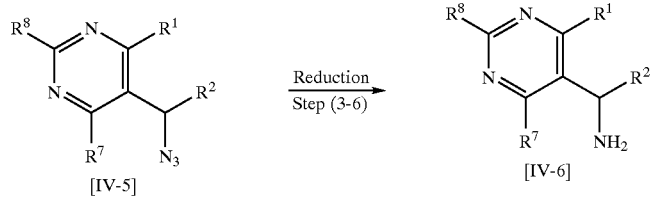

In the formulae, $L^2$ represents a $C_1$–$C_6$ alkyl group or a phenyl group which may be substituted by a $C_1$–$C_6$ alkyl group, and $R^1$, $R^2$, $R^3$, $R^7$, $R^8$ and $L^1$ have the same meanings as defined above, respectively.

Namely, in step (3-1), 1 equivalent of a compound represented by the formula [III-3] is chlorinated with from 1 to 10 equivalents of a chlorinating agent (such as thionyl chloride or hydrogen chloride) in an inert solvent, to obtain a compound represented by the formula [IV-1].

Here, the inert solvent may, for example, be a halogenated hydrocarbon such as chloroform or dichloromethane, an ether such as diethyl ether, tetrahydrofuran or dioxane, or a hydrocarbon such as n-hexane, benzene, toluene or xylene.

The reaction may be carried out in a nitrogen stream, as the case requires. The reaction is carried out at an optional temperature from −10° C. to the reflux temperature in the reaction system and will be completed in from 1 to 24 hours, although it varies depending upon the compound. The desired product can be isolated from the reaction solution by a usual method and may be purified by distillation or column chromatography, as the case requires.

In step (3-2), 1 equivalent of a compound represented by the formula [IV-1] is reacted with from 1 to 10 equivalents of a compound represented by the formula [IV-3] in an inert solvent, to obtain a compound represented by the formula [IV-4].

Here, the inert solvent may, for example, be an alcohol such as ethyl alcohol, isopropyl alcohol or methyl alcohol, an ether such as diethyl ether, tetrahydrofuran or dioxane, a hydrocarbon such as n-hexane, benzene, toluene or xylene, or water.

The reaction may be carried out in a nitrogen stream, as the case requires. The reaction is carried out at an optional temperature from −10° C. to the reflux temperature in the reaction system and will be completed in from 1 to 24 hours, although it varies depending upon the compound. The desired product can be isolated from the reaction solution by a usual method and may be purified by distillation or column chromatography, as the case requires.

Further, in step (3-3), 1 equivalent of a compound represented by the formula [III-3] is reacted with from 1 to 10 equivalents of a compound represented by the formula [IV-8] in an inert solvent in the presence or absence of from 1 to 10 equivalents of a base, to obtain a compound represented by the formula [IV-2].

Here, the inert solvent may, for example, be a halogenated hydrocarbon such as chloroform or dichloromethane, an ether such as diethyl ether, tetrahydrofuran or dioxane, a hydrocarbon such as n-hexane, benzene, toluene or xylene, or a pyridine such as pyridine.

The base may, for example, be sodium hydride, pyridine, triethylamine, 1,8-diazabicyclo[5.4.03]-7-undecene, sodium hydroxide, potassium hydroxide, calcium hydroxide, magnesium hydroxide, sodium carbonate, potassium carbonate, sodium hydrogencarbonate, potassium hydrogencarbonate, sodium methoxide or potassium tert-butoxide.

The reaction may be carried out in a nitrogen stream, as the case requires. The reaction is carried out at an optional temperature from −10° C. to the reflux temperature in the reaction system and will be completed in from 1 to 24 hours, although it varies depending upon the compound. The desired product can be isolated from the reaction solution by a usual method and may be purified by distillation or column chromatography, as the case requires.

Further, in step (3-4), 1 equivalent of a compound represented by the formula [IV-2] is reacted with from 2 to 10 equivalents of a compound represented by the formula [IV-3] in an inert solvent, to obtain a compound represented by the formula [IV-4].

Here, the inert solvent may, for example, be an alcohol such as ethyl alcohol, isopropyl alcohol or methyl alcohol, an ether such as diethyl ether, tetrahydrofuran or dioxane, a hydrocarbon such as n-hexane, benzene, toluene or xylene, a pyridine'such as pyridine, or water.

The reaction may be carried in a nitrogen stream, as the case requires. The reaction is carried out at an optional temperature from −10° C. to the ref lux temperature in the reaction system and will be completed in from 1 to 24 hours, although it varies depending upon the compound. The desired product can be isolated from the reaction solution by a usual method and may be purified by distillation or column chromatography, as the case requires.

In step (3-5), 1 equivalent of a compound represented by the formula [III-3] is azidated with from 1 to 10 equivalents of an azidation agent such as tosyl azide, diphenylphosphoryl azide, sodium azide, lithium azide or hydrogen azide in the presence or absence of boron trifluoridediethylether complex, triphenyl phosphine and trifluoroacetic acid in an inert solvent, to obtain a compound represented by the formula [IV-5].

Here, the inert solvent may, for example, be a halogenated hydrocarbon such as chloroform or dichloromethane, an ether such as diethyl ether, tetrahydrofuran or dioxane, an aprotic polar solvent such as acetonitrile, N,N-dimethylformamide or dimethylsulfoxide, or a hydrocarbon such as n-hexane, benzene, toluene or xylene.

The reaction may be carried out in a nitrogen stream, as the case requires. The reaction is carried out at an optional temperature from −10° C. to the reflux temperature in the reaction system and will be completed in from 1 to 24 hours, although it varies depending upon the compound. The desired product can be isolated from the reaction solution by a usual method and may be purified by distillation or column chromatography, as the case requires.

In step (3-6), 1 equivalent of a compound represented by the formula [IV-5] is treated with from 1 to 10 equivalents of reducing agent such as magnesium, lithium aluminum hydride, sodium borohydride, triphenylphosphine, or iron, or subjected to a hydrogenation catalytic reduction with a catalyst such as palladium carbon, platinum carbon or Raney Nickel, to obtain a compound represented by the formula [IV-6] in an inert solvent.

Here, the inert solvent may, for example, be a halogenated hydrocarbon such as chloroform or dichloromethane, an ether such as diethyl ether, tetrahydrofuran or dioxane, an alcohol such as methyl alcohol or ethyl alcohol, or a hydrocarbon such as n-hexane, benzene, toluene or xylene.

The reaction may be carried out in a nitrogen stream, as the case requires. The reaction is carried out at an optional temperature from −10° C. to the reflux temperature in the reaction system and will be completed in from 1 to 24 hours, although it varies depending upon the compound. The desired product can be isolated from the reaction solution by a usual method and may be purified by distillation or column chromatography, as the case requires.

In step (3-7), 1 equivalent of a compound represented by the formula [IV-6] is reacted with from 1 to 10 equivalents of a compound represented by the formula [IV-7] in an inert solvent in the presence or absence of from 1 to 10 equivalents of a base, to obtain a compound represented by the formula [IV-4].

Here, the inert solvent may, for example, be a halogenatedhydrocarbon such as chloroform or dichloromethane, an ether such as diethyl ether, tetrahydrofuran or dioxane, an alcohol such as methyl alcohol or ethyl alcohol, a hydrocarbon such as n-hexane, benzene, toluene or xylene, an aprotic polar solvent such as acetonitrile, N,N-dimethylformamide or dimethylsulfoxide, a pyridine such as pyridine, or water.

The base may, for example, be sodium hydride, pyridine, triethylamine, 1,8-diazabicyclo[5.4.0]-7-undecene, sodium hydroxide, potassium hydroxide, calcium hydroxide, magnesium hydroxide, sodium carbonate, potassium carbonate, sodium hydrogencarbonate, potassium hydrogencarbonate, sodium methoxide or potassium tert-butoxide.

The reaction may be carried out in a nitrogen stream, as the case requires. The reaction is carried out at an optional temperature from −10° C. to the reflux temperature in the reaction system and will be completed in from 1 to 24 hours, although it varies depending upon the compound. The desired product can be isolated from the reaction solution by a usual method and may be purified by distillation or column chromatography, as the case requires.

Process 4

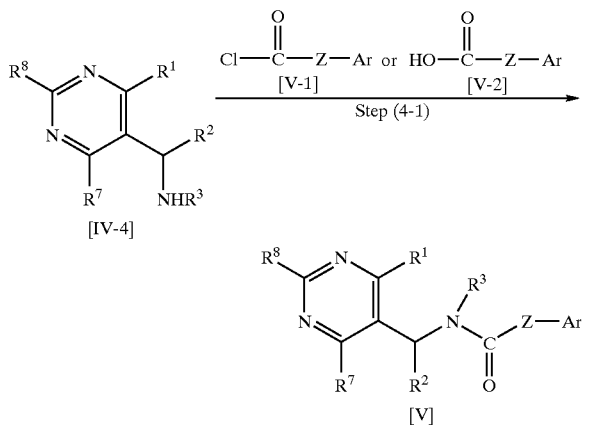

In the formulae, $R^1$, $R^2$, $R^3$, $R^7$, $R^8$, Z and Ar have the same meanings as defined above, respectively.

Namely, in step (4-1), 1 equivalent of a compound represented by the formula [IV-4] is reacted with from 1 to 10 equivalents of a compound represented by the formula [V-1] in an inert solvent in the presence of from 1 to 10 equivalents of a base, or 1 equivalent of a compound represented by the formula [IV-4] is reacted with from 1 to 10 equivalents of a compound represented by the formula [V-2] in an inert solvent in the presence of from 1 to 10 equivalents of a condensing agent (such as 1-ethyl-3-(3-dimethylaminopropyl)carbodiimide hydrochloride or 1,1'-carbonylbis-1H-imidazole), to obtain the desired compound of the present invention represented by the formula [V].

Here, the inert solvent may, for example, be a halogenated hydrocarbon such as chloroform or dichloromethane, an ether such as diethyl ether, diisopropyl ether, tetrahydrofuran or dioxane, a hydrocarbon such as n-hexane, benzene, toluene or xylene, or an aprotic polar solvent such as acetonitrile, N,N-dimethylformamide or dimethylsulfoxide.

The base may, for example,be an inorganic base such as potassium carbonate, sodium carbonate, potassium hydrogencarbonate, sodium hydrogencarbonate, sodium hydroxide or potassium hydroxide, or an organic base such as pyridine or triethylamine.

Each reaction may be carried out in a nitrogen stream, as the case requires. The reaction is carried out at an optional temperature from −10° C. to the reflux temperature in the reaction system and will be completed in from 1 to 100 hours, although it varies depending upon the compound. The desired product can be isolated from the reaction solution by a usual method and may be purified by distillation or column chromatography, as the case requires.

Process 5

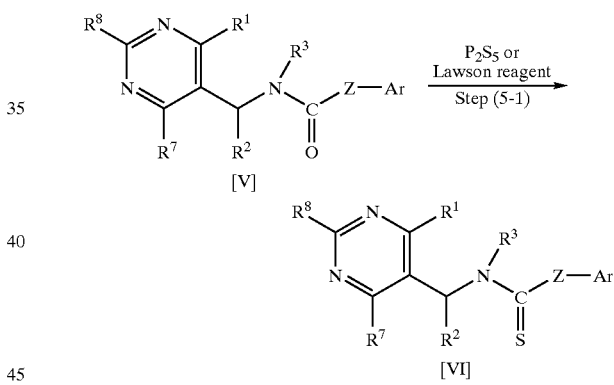

In the formulae, $R^1$, $R^2$, $R^3$, $R^7$, $R^8$, Z and Ar have the same meanings as defined above, respectively.

Namely, in step (5-1), 1 equivalent of the compound of the present invention represented by the formula [V] is reacted with from 0.3 to 10 equivalents of diphosphorus pentasulfide or a Lawson reagent in an inert solvent, to obtain the desired compound of the present invention represented by the formula [VI].

Here, the inert solvent may, for example, be a hydrocarbon such as n-hexane, benzene, toluene or xylene, or a pyridine such as pyridine.

The reaction may be carried out in a nitrogen stream, as the case requires. The reaction is carried out at an optional temperature from −10° C. to the reflux temperature in the reaction system and will be completed in from 1 to 100 hours, although it varies depending upon the compound. The desired product can be isolated from the reaction solution by a usual method and may be purified by distillation or column chromatography, as the case requires.

Process 6

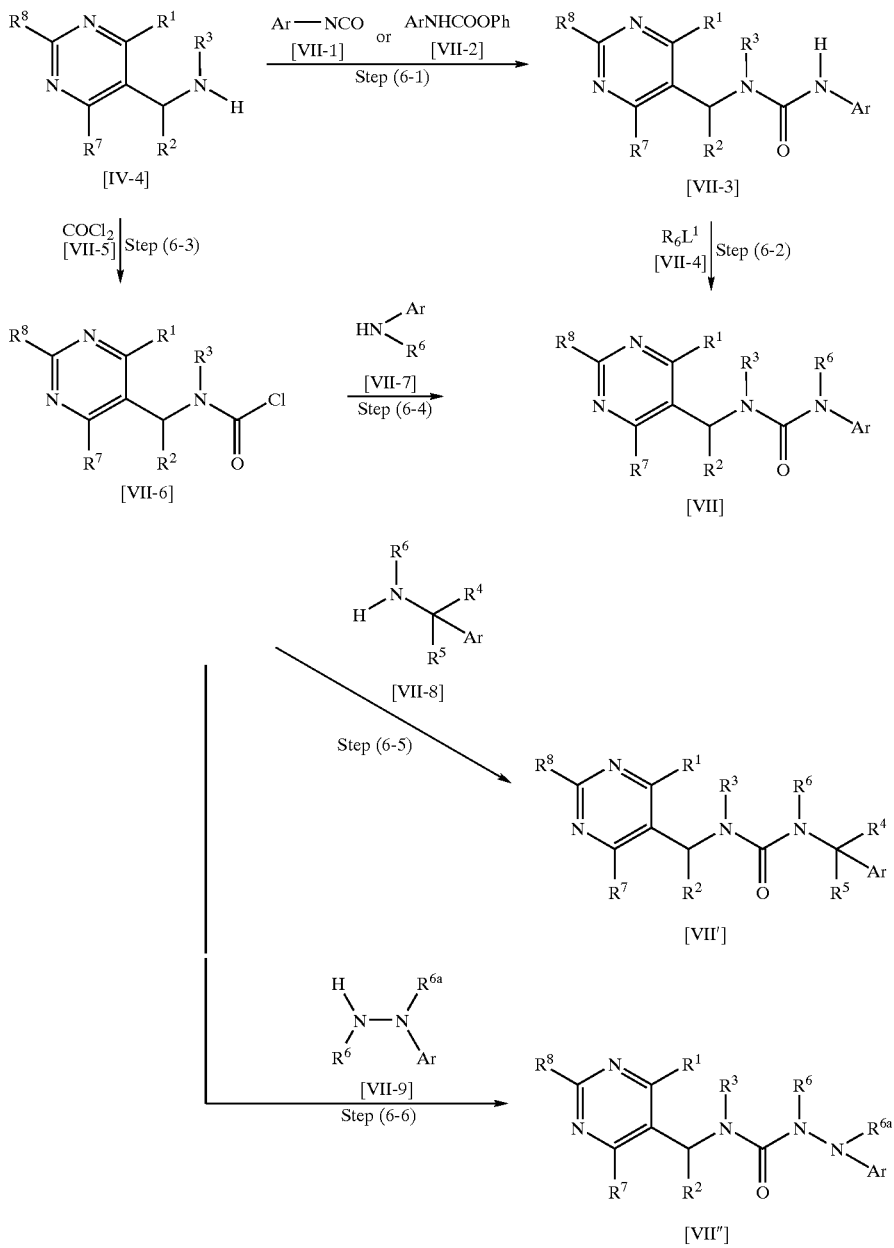

In the formulae, $R^1, R^2, R^3, R^4, R^5, R^6, R^{6a}, R^7, R^8$, Ar and $L^1$ have the same meanings as defined above, respectively.

Namely, in step (6-1), 1 equivalent of a compound of the formula [IV-4] is reacted with from 0.5 to 5 equivalents of a compound represented by the formula [VII-1] or a compound represented by the formula [VII-2] in an inert solvent in the presence or absence of from 1 to 10 equivalents of a base, to obtain the desired compound of the present invention represented by the formula [VII-3].

The base may, for example, be sodium hydride, pyridine, triethylamine, 1,8-diazabicyclo[5.4.0]-7-undecene, sodium hydroxide, potassium hydroxide, calcium hydroxide, magnesium hydroxide, sodium carbonate, potassium carbonate, sodium hydrogencarbonate, potassium hydrogencarbonate, sodium methoxide or potassium tert-butoxide Here, the inert solvent may, for example, be a halogenated hydrocarbon such as chloroform or dichloromethane, an ether such as diethyl ether, tetrahydrofuran or dioxane, an alcohol such as methyl alcohol, isopropyl alcohol or ethyl alcohol, a hydrocarbon such as n-hexane, benzene, toluene or xylene, an aprotic polar solvent such as acetonitrile, N,N-dimethylformamide or dimethylsulfoxide, a pyridine such as pyridine, or water.

The reaction may be carried out in a nitrogen stream, as the case requires. The reaction is carried out at an optional temperature from −10° C. to the reflux temperature in the reaction system and will be completed in from 1 to 24 hours, although it varies depending upon the compound. The desired product can be isolated from the reaction solution by a usual method and may be purified by distillation or column chromatography, as the case requires.

Then, in step (6-2), 1 equivalent of the compound of the present invention represented by the formula [VII-3] is reacted with from 1 to 10 equivalents of a compound represented by the formula [VII-4] in an inert solvent in the presence or absence of from 1 to 10 equivalents of a base, to obtain the desired product of the present to invention represented by the formula [VII].

Here, the inert solvent may, for example, be an alcohol such as ethyl alcohol, isopropyl alcohol or methyl alcohol, an ether such as diethyl ether, tetrahydrofuran or dioxane, an aprotic polar solvent such as acetonitrile, N,N-dimethylformamide or dimethylsulfoxide, a hydrocarbon such as n-hexane, benzene, toluene or xylene, or water.

The base may, for example, be sodium hydride, pyridine, triethylamine, 1,8-diazabicyclo[5.4.0]-7-undecene, sodium hydroxide, potassium hydroxide, calcium hydroxide, magnesium hydroxide, sodium carbonate, potassium carbonate, sodium hydrogencarbonate, potassium hydrogencarbonate, sodium methoxide or potassium tert-butoxide.

The reaction may be carried out in a nitrogen stream, as the case requires. The reaction is carried out at an optional temperature from −10° C. to the reflux temperature in the reaction system and will be completed in from 1 to 24 hours, although it varies depending upon the compound. The desired product can be isolated from the reaction solution by a usual method and may be purified by distillation or column chromatography, as the case requires.

In step (6-3), 1 equivalent of a compound represented by the formula [IV-4] is reacted with from 1 to 10 equivalents of a compound represented by the formula [VII-5] in an inert solvent in the presence or absence of from 1 to 10 equivalents of a base, to obtain a compound represented by the formula [VII-6].

The base may, for example, be sodium hydride, pyridine, triethylamine, 1,8-diazabicyclo[5.4.0]-7-undecene, sodium hydroxide, potassium hydroxide, calcium hydroxide, magnesium hydroxide, sodium carbonate, potassium carbonate, sodium hydrogencarbonate, potassium hydrogencarbonate, sodium methoxide or potassium tert-butoxide.

Here, the inert solvent may, for example, be a halogenated hydrocarbon such as chloroform or dichloromethane, an ether such as diethyl ether, tetrahydrofuran or dioxane, an alcohol such as methyl alcohol or ethyl alcohol, a hydrocarbon such as n-hexane, benzene, toluene or xylene, an aprotic polar solvent such as acetonitrile, N,N-dimethylformamide or dimethylsulfoxide, or water.

The reaction may be carried out in a nitrogen stream, as the case requires. The reaction is carried out at an optional temperature from room temperature to the reflux temperature in the reaction system and will be completed in from 1 to 100 hours, although it varies depending upon the compound. The desired product can be isolated from the reaction solution by a usual method and may be purified by distillation or column chromatography, as the case requires.

Then, in step (6-4), step (6-5) and step (6-6), 1 equivalent of a compound represented by the formula [VII-6] is reacted with from 1 to 10 equivalents of a compound represented by the formula [VII-7], a compound represented by the formula [VII-8] and a compound represented by the formula [VII-9] in an inert solvent in the presence or absence of from 1 to 10 equivalents of a base, to obtain the compound of the present invention represented by the formula [VII], a compound represented by the formula [VII'] and a compound represented by the formula [VII''].

The base may, for example, be sodium hydride, pyridine, triethylamine, 1,8-diazabicyclo[5.4.0]-7-undecene, sodium hydroxide, potassium hydroxide, calcium hydroxide, magnesium hydroxide, sodium carbonate, potassium carbonate, sodium hydrogencarbonate, potassium hydrogencarbonate, sodium methoxide or potassium tert-butoxide.

Here, the inert solvent may, for example, be an alcohol such as ethyl alcohol, isopropyl alcohol or methyl alcohol, an ether such as diethyl ether, tetrahydrofuran or dioxane, an aprotic polar solvent such as acetonitrile, N,N-dimethylformamide or dimethylsulfoxide, a hydrocarbon such as n-hexane, benzene, toluene or xylene, a pyridine such as pyridine, or water.

The reaction may be carried out in a nitrogen stream, as the case requires. The reaction is carried out at an optional temperature from room temperature to the reflux temperature in the reaction system and will be completed in from 1 to 100 hours, although it varies depending upon the compound. The desired product can be isolated from the reaction solution by a usual method and may be purified by distillation or column chromatography, as the case requires.

Process 7

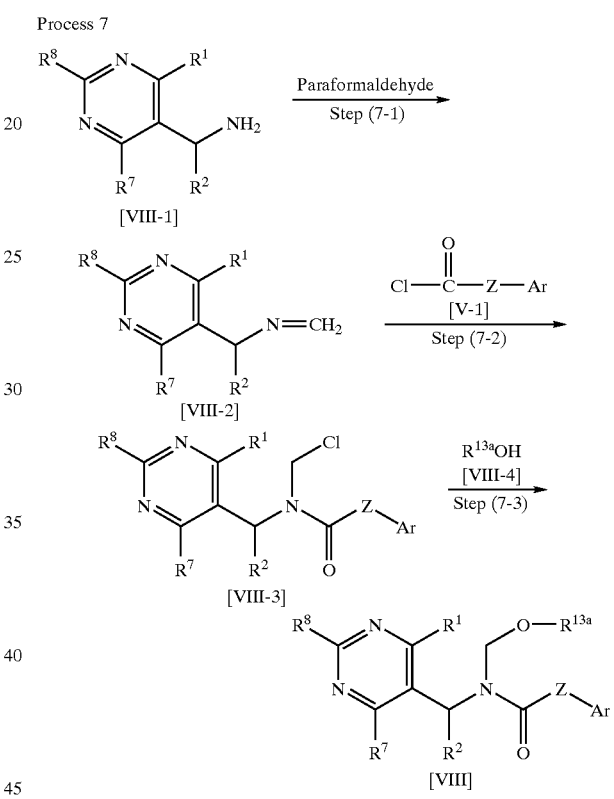

In the formulae, $R^1$, $R^2$, $R^7$, $R^8$, Z and Ar have the same meanings as defined above, respectively, and $R^{13a}$ is a $C_1$–$C_6$ alkyl group.

Namely, in step (7-1), 1 equivalent of a compound represented by the formula [VIII-1] is reacted with from 1 to 10 equivalents of paraformaldehyde in an inert solvent (depending upon the conditions, using a Dean Stark or adding a catalyst), to obtain a compound represented by the formula [VIII-2].

Here, the inert solvent may, for example, be a hydrocarbon such as n-hexane, benzene, toluene or xylene.

The catalyst may, for example, be an organic base such as triethylamine.

The reaction may be carried out in a nitrogen stream, as the case requires. The reaction is carried out at an optional temperature from room temperature to the reflux temperature in the reaction system and will be completed in from 1 to 100 hours, although it varies depending upon the compound. The desired product can be isolated from the reaction solution by a usual method and may be purified by distillation or column chromatography, as the case requires.

Then, in step (7-2), 1 equivalent of the compound represented by the formula [VIII-2] is reacted with from 1 to 10 equivalents of a compound represented by the formula [V-1] in an inert solvent, to obtain a compound represented by the formula [VIII-3].

Here, the inert solvent may, for example, be a hydrocarbon such as n-hexane, benzene, toluene or xylene.

The reaction may be carried out in a nitrogen stream, as the case requires. The reaction is carried out at an optional temperature from −10° C. to the reflux temperature in the reaction system and will be completed in from 1 to 100 hours, although it varies depending upon the compound. The desired product can be isolated from the reaction solution by a usual method and may be purified by distillation or column chromatography, as the case requires.

Further, in step (7-3), 1 equivalent of the compound of the formula [VIII-3] is reacted with from 1 to 4 equivalents of a compound represented by the formula [VIII-4] in an inert solvent in the presence or absence of from 1 to 10 equivalents of a base, to obtain the compound of the present invention, represented by the formula [VIII].

Here, the inert solvent may, for example, be a hydrocarbon such as n-hexane, benzene, toluene or xylene.

The base may, for example, be an inorganic base such as potassium carbonate, sodium carbonate, potassium hydrogencarbonate, sodium hydrogencarbonate, sodium hydroxide or potassium hydroxide, or an organic base such as pyridine or triethylamine.

The reaction may be carried out in a nitrogen stream, as the case requires. The reaction is carried out at an optional temperature from −10° C. to the reflux temperature in the reaction system and will be completed in from 1 to 100 hours, although it varies depending upon the compound. The desired product can be isolated from the reaction solution by a usual method and may be purified by distillation or column chromatography, as the case requires.

Process 8

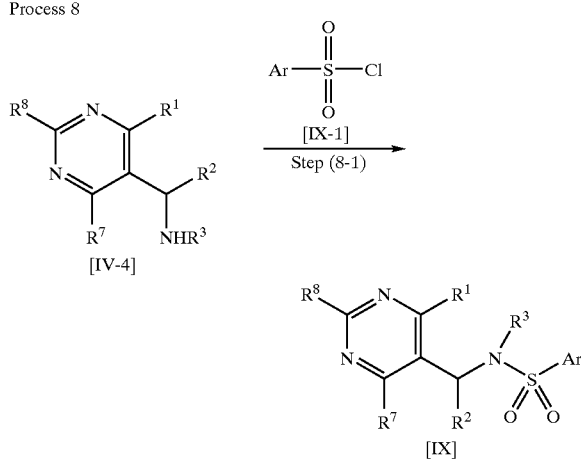

In the formulae, $R^1$, $R^2$, $R^3$, $R^7$, $R^8$ and Ar have the same meanings as defined above, respectively.

Namely, in step (8-1), 1 equivalent of a compound represented by the formula [IV-4] is reacted with from 1 to 10 equivalents of a compound represented by the formula [IX-1] in an inert solvent in the presence or absence of from 1 to 10 equivalents of a base, to obtain the desired compound of the present invention represented by the formula [IX].

The base may, for example, be an inorganic base such as potassium carbonate, sodium carbonate, potassium hydrogencarbonate, sodium hydrogencarbonate, sodium hydroxide or potassium hydroxide, or an organic base such as pyridine or triethylamine.

Here, the inert solvent may, for example, be an alcohol such as ethyl alcohol, isopropyl alcohol or methyl alcohol, an ether such as diethyl ether, tetrahydrofuran or dioxane, an aprotic polar solvent such as acetonitrile, N,N-dimethylformamide or dimethylsulfoxide, a hydrocarbon such as n-hexane, benzene, toluene or xylene, pyridine, or water.

The reaction may be carried out in a nitrogen stream, as the case requires. The reaction is carried out at an optional temperature from room temperature to the reflux temperature in the reaction system and will be completed in from 1 to 100 hours, although it varies depending upon the compound. The desired product can be isolated from the reaction solution by a usual method and may be purified by distillation or column chromatography, as the case requires.

Process 9

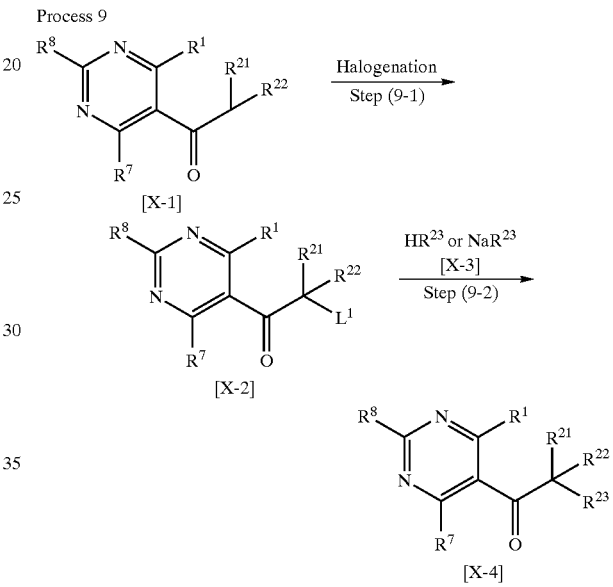

In the formulae, $R^1$, $R^7$, $R^8$ and $L^1$ have the same meanings as defined above, respectively, and each of $R^{21}$ and $R^{22}$ is a hydrogen atom or a $C_1$–$C_6$ alkyl group, $R^{23}$ is a $C_1$–$C_6$ alkoxy group, a $C_2$–$C_6$ alkenyl group, a $C_2$–$C_6$ alkynyl group, a $C_1$–$C_6$ alkylthio group, a cyano group or $NR^9R^{10}$, and $R^9$ and $R^{10}$ have the same meanings as defined above, respectively.

Namely, in step (9-1), 1 equivalent of a compound represented by the formula [X-1] is halogenated with from 1 to 10 equivalents of a chlorinating agent (such as sulfuryl chloride, N-chlorosuccinimide or chlorine) in an inert solvent, to obtain a compound represented by the formula [X-2].

Here, the inert solvent may, for example, be a halogenated hydrocarbon such as chloroform or dichloromethane, an ether such as diethyl ether, tetrahydrofuran or dioxane, or a hydrocarbon such as n-hexane, benzene, toluene or xylene.

The reaction may be carried out in a nitrogen atmosphere, as the case requires. The reaction is carried out at an optional temperature from −10° C. to the reflux temperature in the reaction system and will be completed in from 1 to 24 hours, although it varies depending upon the compound. The desired product can be isolated from the reaction solution by a usual method and may be purified by distillation or column chromatography, as the case requires.

Then, in step (9-2), 1 equivalent of the compound represented by the formula [X-2] is reacted with from 1 to 10 equivalents of a compound represented by the formula [X-3] in an inert solvent in the presence or absence of from 1 to 10 equivalents of a base, to obtain a compound represented by the formula [x-4].

The base may, for example, be sodium hydride, pyridine, triethylamine, 1,8-diazabicyclo[5.4.0]-7-undecene, sodium hydroxide, potassium hydroxide, calcium hydroxide, magnesium hydroxide, sodium carbonate, potassium carbonate, sodium hydrogencarbonate, potassium hydrogencarbonate, sodium methoxide or potassium tert-butoxide.

Here, the inert solvent may, for example, be an alcohol such as ethyl alcohol, isopropyl alcohol or methyl alcohol, an ether such as diethyl ether, tetrahydrofuran or dioxane, a hydrocarbon such as n-hexane, benzene, toluene or xylene or water.

The reaction may be carried out in a nitrogen stream, as the case requires. The reaction is carried out at an optional temperature from −10° C. to the reflux temperature in the reaction system and will be completed in from 1 to 24 hours, although it varies depending upon the compound. The desired product can be isolated from the reaction solution by a usual method and may be purified by distillation or column chromatography, as the case requires.

Process 10

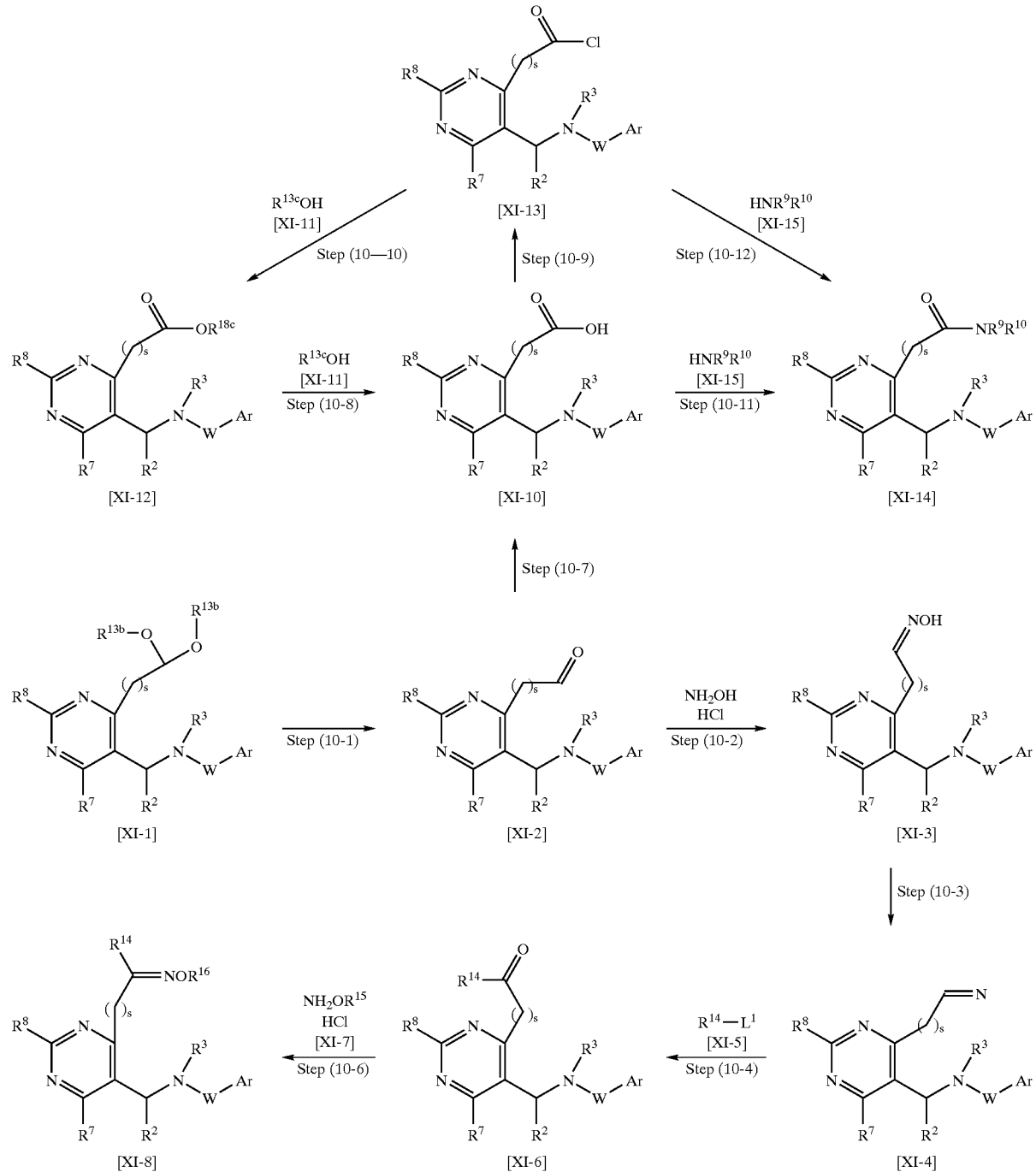

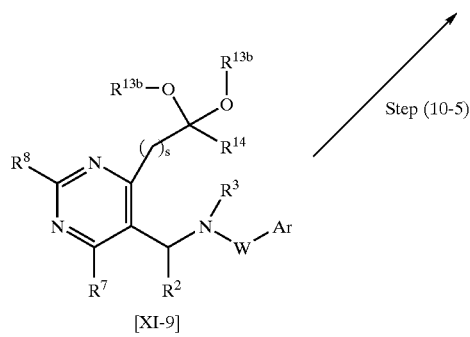

[XI-9]

In the formulae, $R^2$, $R^3$, $R^7$, $R^8$, $R^9$, $R^{10}$, W, $L^1$ and Ar have the same meanings as defined above, respectively, $R^{13b}$ is a $C_1$–$C_6$ alkyl group, or a $C_1$–$C_4$ saturated carbon chain, two of which may be bonded to each other, $R^{13c}$ is a $C_1$–$C_6$ alkyl group, each of $R^{14}$ and $R^{15}$ is a hydrogen atom, a $C_1$–$C_6$ alkyl group, a $C_2$–$C_6$ alkenyl group, a $C_2$–$C_6$ alkynyl group or a $C_3$–$C_6$ cycloalkyl group, and s is 0 or 1.

Namely, in step (10-1), 1 equivalent of a compound represented by the formula [XI-1] is reacted with from 0.9 to 20 equivalents of an acid such as hydrochloric acid or sulfuric acid in an inert solvent, to obtain the desired compound of the present invention represented by the formula [XI-2].

Here, the inert solvent may, for example, be an alcohol such as ethyl alcohol, isopropyl alcohol or methyl alcohol, a ketone such as acetone or methyl ethyl ketone, water, or a mixed solution thereof.

The reaction may be carried out in a nitrogen stream as the case requires. The reaction is carried out at an optional temperature from −10° C. to the reflux temperature in the reaction system and will be completed in from 1 to 24 hours, although it varies depending upon the compound. The desired product can be isolated from the reaction solution by a usual method and may be purified by distillation or column chromatography, as the case requires.

Then, in step (10-2), 1 equivalent of the compound of the present invention represented by the formula [XI-2] is reacted with from 1 to 10 equivalents of hydroxylamine hydrochloride in an inert solvent in the presence of sodium acetate, potassium acetate, sodium carbonate or potassium carbonate, to obtain the desired compound of the present invention represented by the formula [XI-3].

Here, the inert solvent may, for example, be an alcohol such as ethyl alcohol, isopropyl alcohol or methyl alcohol, an ether such as diethyl ether, tetrahydrofuran or dioxane, an aprotic polar solvent such as acetonitrile, N,N-dimethylformamide, or a diethylsulfoxide, a hydrocarbon such as n-hexane, benzene, toluene or xylene, a pyridine such as pyridine, or water.

The reaction may be carried out in a nitrogen stream, as the case requires. The reaction is carried out at an optional temperature from room temperature to the reflux temperature in the reaction system and will be completed in from 1 to 100 hours, although it varies depending upon the compound. The desired product can be isolated from the reaction solution by a usual method and may be purified by distillation or column chromatography, as the case requires.

Then, in step (10-3), 1 equivalent of a compound represented by the formula [XI-3] is reacted with from 1 to 10 equivalents of a dehydrating agent in an inert solvent, to obtain the compound of the present invention represented by the formula [XI-4].

The dehydrating agent may, for example, be 1-[3-(dimethylamino)propyl]-3-ethylcarbodiimide hydrochloride, 1,1'-carbonyldiimidazole, thionyl chloride, phosphorus pentachloride, methanesulfonyl chloride, diphosgene, p-toluene sulfonyl chloride, or acetic anhydride.

Here, the inert solvent may, for example, be a halogenated hydrocarbon such as dichloromethane, chloroform or carbon tetrachloride, an alcohol such as ethyl alcohol, isopropyl alcohol or methyl alcohol, an ether such as diethyl ether, tetrahydrofuran or dioxane, an aprotic polar solvent such as acetonitrile, N,N-dimethylformamide or dimethylsulfoxide, a hydrocarbon such as n-hexane, benzene, toluene or xylene, or water.

The reaction may be carried out in a nitrogen stream, as the case requires. The reaction is carried out at an optional temperature from room temperature to the reflux temperature in the reaction system and will be completed in from 1 to 100 hours, although it varies depending upon the compound. The desired product can be isolated from the reaction solution by a usual method and may be purified by distillation or column chromatography, as the case requires.

Then, in step (10-4), 1 equivalent of the compound of the present invention represented by the formula [XI-4] is reacted with from 1 to 10 equivalents of a compound represented by the formula [XI-5] and with of from 1 to 10 equivalents of an alkyl lithium such as methyl lithium, ethyl lithium or n-butylithium, or magnesium in an inert solvent, to obtain a compound represented by the formula [XI-6].

The reaction may be carried out in a nitrogen stream, as the case requires. The reaction is carried out at an optional temperature from room temperature to the reflux temperature in the reaction system and will be completed in from 1 to 100 hours, although it varies depending upon the compound. The desired product can be isolated from the reaction solution by a usual method and may be purified by distillation or column chromatography, as the case requires.

Here, the inert solvent may, for example be an ether such as diethyl ether, tetrahydrofuran or dioxane, a hydrocarbon such as n-hexane, benzene, toluene or xylene, or water.

Further, in step (10-5), 1 equivalent of the compound of the present invention represented by the formula [XI-9] is reacted with from 0.9 to 20 equivalents of an acid such as hydrochloric acid or sulfuric acid in an inert solvent, to obtain the desired compound of the present invention represented by the formula [XI-6].

Here, the inert solvent may, for example, be an alcohol such as ethyl alcohol, isopropyl alcohol or methyl alcohol, a ketone such as acetone or methyl ethyl ketone, water, or a mixed solution thereof.

The reaction may be carried out in a nitrogen stream, as the case requires. The reaction is carried out at an optional temperature from −10° C. to the reflux temperature in the reaction system and will be completed in from 1 to 24 hours, although it varies depending upon the compound. The desired product can be isolated from the reaction solution by a usual method and may be purified by distillation or column chromatography, as the case requires.

Then, in step (10-6), 1 equivalent of the compound of the present invention represented by the formula [XI-6] is reacted with from 1 to 10 equivalents of a compound represented by the formula [XI-7] in an inert solvent in the presence of 1 to 10 equivalents of sodium acetate, potassium acetate, sodium carbonate or potassium carbonate, to obtain the desired compound of the present invention represented by the formula [XI-8].

Here, the inert solvent may, for example be an alcohol such as ethyl alcohol, isopropyl alcohol or methyl alcohol, an ether such as diethyl ether, tetrahydrofuran or dioxane, an aprotic polar solvent such as acetonitrile, N,N-dimethylformamide or dimethylsulfoxide, a hydrocarbon such as n-hexane, benzene, toluene or xylene, a pyridine such as pyridine, or water.

The reaction may be carried out in a nitrogen stream, as the case requires. The reaction is carried out at an optional temperature from room temperature to the reflux temperature in the reaction system and will be completed in from 1 to 100 hours, although it varies depending upon the compound. The desired product can be isolated from the reaction solution by a usual method and may be purified by distillation or column chromatography, as the case requires.

Then, in step (10-7), 1 equivalent of the compound of the present invention represented by the formula [XI-2] is reacted with from 1 to 10 equivalents of an oxidizing agent such as potassium permanganate, peracetic acid, hydrogen peroxide, m-chloroperbenzoic acid or sodium hypochlorite in an inert solvent in the presence or absence of from 1 to 10 equivalents of a base such as sodium hydroxide or potassium hydroxide, to obtain the desired compound of the present invention represented by the formula [XI-10].

Here, the inert solvent may, for example, be a ketone such as acetone or methyl ethyl ketone, an alcohol such as ethyl alcohol, isopropyl alcohol or methyl alcohol, an ether such as diethyl ether, tetrahydrofuran or dioxane, water or a mixed solution thereof.

The reaction may be carried out in a nitrogen stream, as the case requires. The reaction is carried out at an optional temperature from room temperature to the reflux temperature in the reaction system and will be completed in from 1 to 100 hours, although it varies depending upon the compound. The desired product can be isolated from the reaction solution by a usual method and may be purified by distillation or column chromatography, as the case requires.

Then, in step (10-8), 1 equivalent of the compound of the present invention represented by the formula [XI-10] is reacted with from 1 to 50 equivalents of a compound represented by the formula [XI-11] in an inert solvent or without using any solvent in the presence of e.g. sulfuric acid or p-toluene sulfonic acid, to obtain the desired compound of the present invention represented by the formula [XI-12].

Here, the inert solvent may, for example, be an alcohol such as ethyl alcohol, isopropyl alcohol or methyl alcohol, an ether such as diethyl ether, tetrahydrofuran or dioxane, an aprotic polar solvent such as acetonitrile, N,N-dimethylformamide or dimethylsulfoxide, or a hydrocarbon such as n-hexane, benzene, toluene or xylene.

The reaction may be carried out in a nitrogen stream, as the case requires. The reaction is carried out at an optional temperature from room temperature to the reflux temperature in the reaction system and will be completed in from 1 to 100 hours, although it varies depending upon the compound. The desired product can be isolated from the reaction solution by a usual method and may be purified by distillation or column chromatography, as the case requires.

In step (10-9), 1 equivalent of the compound of the present invention represented by the formula [XI-10] is reacted with from 1 to 10 equivalents of a chlorinating agent such as thionyl chloride in an inert solvent, to obtain a compound represented by the formula [XI-13].

Here, the inert solvent may, for example, be a halogenated hydrocarbon such as dichloromethane, chloroform or carbon tetrachloride, an ether such as diethyl ether, tetrahydrofuran or dioxane, or a hydrocarbon such as n-hexane, benzene, toluene or xylene.

The reaction may be carried out in a nitrogen stream, as the case requires. The reaction is carried out at an optional temperature from room temperature to the reflux temperature in the reaction system and will be completed in from 1 to 100 hours, although it varies depending upon the compound. The desired product can be isolated from the reaction solution by a usual method and may be purified by distillation or column chromatography, as the case requires.

Then, in step (10-10), 1 equivalent of the compound represented by the formula [XI-13] is reacted with from 1 to 3 equivalents of a compound represented by the formula [XI-11] in an inert solvent in the presence or absence of from 1 to 6 equivalents of a base, to obtain the desired compound of the present invention represented by the formula [XI-12].

The base may, for example, be sodium hydride, pyridine, triethylamine, 1,8-diazabicyclo[5.4.0]-7-undecene, sodium hydroxide, potassium hydroxide, calcium hydroxide, magnesium hydroxide, sodium carbonate, potassium carbonate, sodium hydrogencarbonate, potassium hydrogencarbonate, sodium methoxide or potassium tert-butoxide.

Here, the inert solvent may, for example, be an alcohol such as ethyl alcohol, isopropyl alcohol or methyl alcohol, an ether such as diethyl ether, tetrahydrofuran or dioxane, an aprotic polar solvent such as acetonitrile, N,N-dimethylformamide or dimethylsulfoxide, a hydrocarbon such as n-hexane, benzene, toluene or xylene, a pyridine such as pyridine, or water.

The reaction may be carried out in a nitrogen stream, as the case requires. The reaction is carried out at an optional temperature from room temperature to the reflux temperature in the reaction system and will be completed in from 1 to 100 hours, although it varies depending upon the compound. The desired product can be isolated from the reaction solution by a usual method and may be purified by distillation or column chromatography, as the case requires.

Further, in step (10-11), 1 equivalent of the compound of the present invention represented by the formula [XI-10] is reacted with from 1 to 3 equivalents of a compound represented by the formula [XI-15] in an inert solvent in the presence or absence of from 1 to 6 equivalents of a base by using a peptidizing agent such as 1,1'-carbonylbis-1H-imidazole or N,N'-dicyclohexylcarbodiimide, to obtain the desired compound of the present invention represented by the formula [XI-14].

The base may, for example, be sodium hydride, pyridine, triethylamine, 1,8-diazabicyclo[5.4.0]-7-undecene, sodium hydroxide, potassium hydroxide, calcium hydroxide, magnesium hydroxide, sodium carbonate, potassium carbonate, sodium hydrogencarbonate, potassium hydrogencarbonate, sodium methoxide or potassium tert-butoxide.

Here, the inert solvent may, for example, be a halogenated hydrocarbon such as dichloromethane, chloroform or carbon tetrachloride, an alcohol such as ethyl alcohol, isopropyl alcohol or methyl alcohol, an ether such as diethyl ether, tetrahydrofuran or dioxane, an aprotic polar solvent such as acetonitrile, N,N-dimethylformamide or dimethylsulfoxide, a hydrocarbon such as n-hexane, benzene, toluene or xylene, a pyridine such as pyridine, or water.

The reaction may be carried out in a nitrogen stream, as the case requires. The reaction is carried out at an optional temperature from room temperature to the reflux temperature in the reaction system and will be completed in from 1 to 100 hours, although it varies depending upon the compound. The desired product can be isolated from the reaction solution by a usual method and may be purified by distillation or column chromatography, as the case requires.

In step (10-12), 1 equivalent of the compound represented by the formula [XI-13] is reacted with from 1 to 3 equivalents of a compound represented by the formula [XI-15] in an inert solvent in the presence or absence of from 1 to 10 equivalents of a base, to obtain the desired compound of the present invention represented by the formula [XI-14].

The base may, for example, be sodium hydride, pyridine, triethylamine, 1,8-diazabicyclo[5.4.0]-7-undecene, sodium hydroxide, potassium hydroxide, calcium hydroxide, magnesium hydroxide, sodium carbonate, potassium carbonate, sodium hydrogencarbonate, potassium hydrogencarbonate, sodium methoxide or potassium tert-butoxide.

Here, the inert solvent may, for example, be an alcohol such as ethyl alcohol, isopropyl alcohol or methyl alcohol, an ether such as diethyl ether, tetrahydrofuran or dioxane, an aprotic polar solvent such as acetonitrile, N,N-dimethylformamide or dimethylsulfoxide, a hydrocarbon such as n-hexane, benzene, toluene or xylene, a pyridine such as pyridine, or water.

The reaction may be carried out in a nitrogen stream, as the case requires. The reaction is carried out at an optional temperature from room temperature to the reflux temperature in the reaction system and will be completed in from 1 to 100 hours, although it varies depending upon the compound. The desired product can be isolated from the reaction solution by a usual method and may be purified by distillation or column chromatography, as the case requires.

3 equivalents of a compound represented by the formula [XII-1] in an inert solvent in the presence or absence of from 1 to 10 equivalents of a base, to obtain a compound represented by the formula [XII-2].

The base may, for example, be sodium hydride, pyridine, triethylamine, 1,8-diazabicyclo[5.4.0]-7-undecene, sodium hydroxide, potassium hydroxide, calcium hydroxide, magnesium hydroxide, sodium carbonate, potassium carbonate, sodium hydrogencarbonate, potassium hydrogencarbonate, sodium methoxide or potassium tert-butoxide.

Here, the inert solvent may, for example, be an alcohol such as ethyl alcohol, isopropyl alcohol or methyl alcohol, an ether such as diethyl ether, tetrahydrofuran or dioxane, an aprotic polar solvent such as acetonitrile, N,N-dimethylformamide or dimethylsulfoxide, a hydrocarbon such as n-hexane, benzene, toluene or xylene, a pyridine such as pyridine, or water.

The reaction may be carried out in a nitrogen stream, as the case requires. The reaction is carried out at an optional temperature from −10° C. to the reflux temperature in the reaction system and will be completed in from 1 to 24 hours, although it varies depending upon the compound. The desired product can be isolated from the reaction solution by a usual method and may be purified by distillation or column chromatography, as the case requires.

Then, in step (11-3), 1 equivalent of the compound represented by the formula [XII-2] is reacted with from 1 to 10 equivalents of phosgene or thiophosgene in an inert solvent in the presence or absence of from 1 to 10 equivalents of a base, to obtain the desired compound of the present invention, as represented by the formula [XII].

The base may, for example, be sodium hydride, pyridine, triethylamine, 1,8-diazabicyclo[5.4.0]-7-undecene, sodium

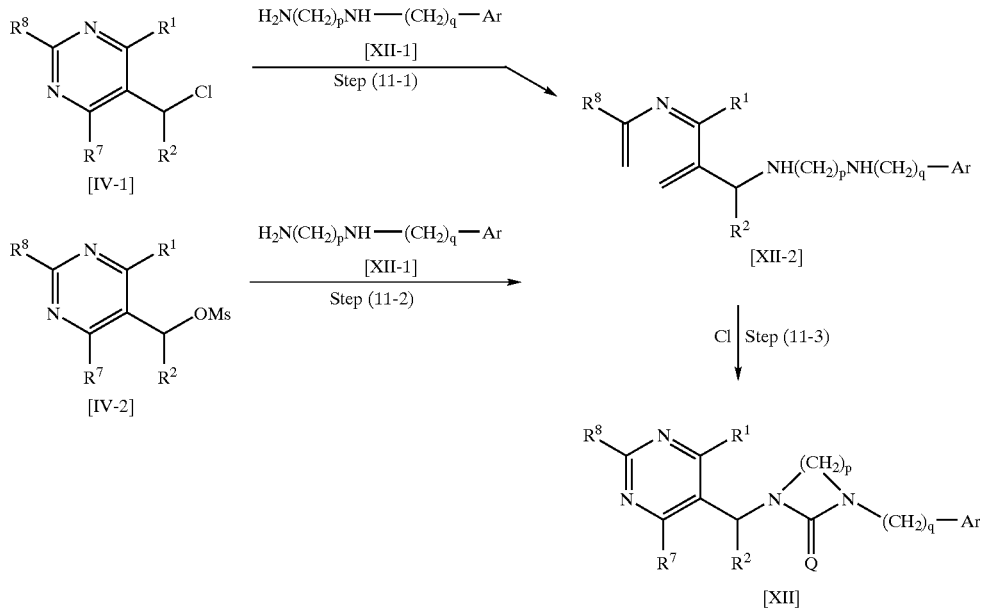

Process 11

In the formulae, $R^1$, $R^2$, $R^7$, $R^8$, Q and Ar have the same meanings as defined above, respectively, Ms is a methanesulfonyl group, p is 2, 3 or 4, and q is 1 or 0.

Namely, in steps (11-1) and (11-2), 1 equivalent of a compound represented by the formula [IV-1] or a compound represented by the formula [IV-2] is reacted with from 0.9 to hydroxide, potassium hydroxide, calcium hydroxide, magnesium hydroxide, sodium carbonate, potassium carbonate, sodium hydrogencarbonate, potassium hydrogencarbonate, sodium methoxide or potassium tert-butoxide.

Here, the inert solvent may, for example, be an ether such as diethyl ether, tetrahydrofuran or dioxane, a halogenated hydrocarbon such as dichloromethane, chloroform or carbon tetrachloride, a hydrocarbon such as n-hexane, benzene, toluene or xylene, or water.

The reaction may be carried out in a nitrogen stream, as the case requires. The reaction is carried out at an optional temperature from −10° C. to the reflux temperature in the reaction system and will be completed in from 1 to 24 hours, although it varies depending upon the compound. The desired product can be isolated from the reaction solution by a usual method and may be purified by distillation or column chromatography, as the case requires.

The base may, for example, be sodium hydride, pyridine, triethylamine, 1,8-diazabicyclo[5.4.0]-7-undecene, sodium hydroxide, potassium hydroxide, calcium hydroxide, magnesium hydroxide, sodium carbonate, potassium carbonate, sodium hydrogencarbonate, potassium hydrogencarbonate, sodium methoxide or potassium tert-butoxide.

Here, the solvent may, for example, be an alcohol such as ethyl alcohol, isopropyl alcohol or methyl alcohol, an ether such as diethyl ether, tetrahydrofuran or dioxane, an aprotic polar solvent such as acetonitrile, N,N-dimethylformamide Process 12

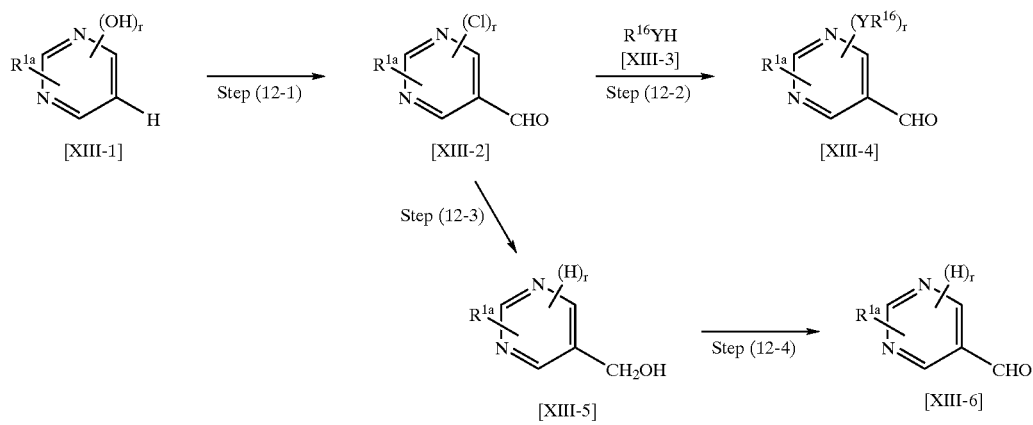

In the formulae, $R^{1a}$ is a hydrogen atom, a $C_1$–$C_6$ alkyl group, a $C_2$–$C_6$ alkenyl group, a $C_2$–$C_6$ alkynyl group, a $C_1$–$C_6$ alkoxy $C_1$–$C_6$ alkyl group, a $C_3$–$C_6$ cycloalkyl group, a phenyl group or a $C_1$–$C_4$ haloalkyl group, $R^{16}$ is a hydrogen atom, a $C_1$–$C_6$ alkyl group, a $C_2$–$C_6$ alkenyl group, a $C_2$–$C_6$ alkynyl group, a $C_1$–$C_6$ alkoxy $C_1$–$C_6$ alkyl group, a $C_3$–$C_6$ cycloalkyl group or a phenyl group, Y is an oxygen atom, a sulfur atom or $NR^9$, $R^9$ has the same meaning as defined above, and r is 1 or 2.

Namely, in step (12-1), 1 equivalent of a compound represented by the formula [XIII-1] is reacted with from 1 to 10 equivalents of N-methylformanilide or N,N-dimethylformamide and from 1 to 20 equivalents of phosphorusoxychloride in an inert solvent or without using any solvent, to obtain a compound represented by the formula [XIII-2].

Here, the inert solvent may, for example, be an ether such as diethyl ether, tetrahydrofuran or dioxane, a halogenated hydrocarbon such as dichloromethane, chloroform, carbon tetrachloride, chlorobenzene or dichlorobenzene, a hydrocarbon such as n-hexane, benzene, toluene or xylene, or water.

The reaction may be carried out in a nitrogen stream, as the case requires. The reaction is carried out at an optional temperature from −10° C. to the reflux temperature in the reaction system and will be completed in from 1 to 24 hours, although it depends upon the compound. The desired product can be isolated from the reaction solution by a usual method and may be purified by distillation or column chromatography, as the case requires.

Then, in step (12-2), 1 equivalent of the compound represented by the formula [XIII-2] is reacted with from 1 to 3 equivalents of a compound represented by the formula [XIII-3] in an inert solvent in the presence or absence of from 1 to 10 equivalents of a base, to obtain a compound represented by the formula [XIII-4].

or dimethylsulfoxide, a hydrocarbon such as n-hexane, benzene, toluene or xylene, a pyridine such as pyridine, or water.

The reaction may be carried out in a nitrogen stream, as the case requires. The reaction is carried out at an optional temperature from −10OC to the reflux temperature in the reaction system and will be completed in from 1 to 24 hours, although it varies depending upon the compound. The desired product can be isolated from the reaction solution by a usual method and may be purified by distillation or column chromatography, as the case requires.

Further, in step (12-3), 1 equivalent of the compound represented by the formula [XIII-2] is subjected to hydrogenation and reacted in an inert solvent by using from 1 to 8 equivalents of manganese oxide and from 0.01 to 4 equivalents of a catalyst such as palladium carbon or Raney Nickel, to obtain a compound represented by the formula [XIII-5].

Here, the inert solvent may, for example, be an alcohol such as ethyl alcohol, isopropyl alcohol or methyl alcohol, an ether such as diethyl ether, tetrahydrofuran or dioxane, a hydrocarbon such as n-hexane, benzene, toluene or xylene, a pyridine such as pyridine or water.

The reaction is carried out at an optional temperature from −10° C. to the reflux temperature in the reaction system and will be completed in from 1 to 24 hours, although it varies depending upon the compound. The desired product can be isolated from the reaction solution by a usual method and may be purified by distillation or column chromatography, as the case requires.

Then, in step (12-4), 1 equivalent of the compound represented by the formula [XIII-5] is subjected to an oxidation reaction in an inert solvent by using from 1 to 10 equivalents of oxalyl chloride, from 1 to 10 equivalents of dimethylsulfoxide and from 1 to 10 equivalents of triethylamine or the like, to obtain a compound represented by the formula [XIII-63].

Here, the inert solvent may, for example, be a halogenated hydrocarbon such as dichloromethane, chloroform or carbon tetrachloride, an alcohol such as ethyl alcohol, isopropyl alcohol or methyl alcohol, an ether such as diethyl ether, tetrahydrofuran or dioxane, an aprotic polar solvent such as acetonitrile, N,N-dimethylformamide or dimethylsulfoxide, a hydrocarbon such as n-hexane, benzene, toluene or xylene, a pyridine such as pyridine, or water.

The reaction may be carried out in a nitrogen stream, as the case requires. The reaction is carried out at an optional temperature from −80° C. to the reflux temperature in the reaction system and will be completed in from 1 to 24 hours, although it varies depending upon the compound. The desired product can be isolated from the reaction solution by a usual method and may be purified by distillation or column chromatography, as the case requires.

Now, the processes for production, a formulation method and the application of the compound of the present invention will be described in detail with reference to Examples. Further, the processes for production of intermediates in the synthesis of the compound of the present invention will also be described.

PREPARATION EXAMPLE 1

Preparation of N-methyl-N-[2-methyl-1-(4-trifluoromethylpyrimidin-5-yl)propyl] phenylacetamide (Compound No. 1–8 of the Present Invention)

6 g (26 mmol) of 4-trifluoromethyl-5-[1-(N-methylamino)-2-methylpropyl]pyrimidine and 3.6 g (26 mmol) of potassium carbonate were dissolved in 150 ml of acetonitrile, and 4 g (26 mmol) of phenylacetyl chloride was dropwise added, followed by stirring at room temperature for 3 hours. To the reaction solution, 200 ml of water was added, followed by extraction with ethyl acetate. The obtained organic layer was washed with water and then dried over anhydrous magnesium sulfate. Ethyl acetate was distilled off under reduced pressure, and the obtained crude crystals were washed with n-hexane to obtain 7.7 g (yield: 85%) of N-methyl-N-[2-methyl-1-(4-trifluoromethylpyrimidin-5-yl)propyl]phenylacetamide as colorless transparent crystals (melting point: 106–109° C.).

PREPARATION EXAMPLE 2

Preparation of N-methyl-N-[2-methyl-1-(4-trifluoromethylpyrimidin-5-yl)propyl]-2-pyridylacetamide (Compound No. 2–3 of the Present Invention)

0.3 g (1.7 mmol) of 2-pyrimidinylacetate hydrochloride and 0.18 g (1.8 mmol) of triethylamine were dissolved in 30 ml of tetrahydrofuran, and 0.28 g (1.7 mmol) of 1,1'-carbonylbis-1H-imidazole was added, followed by stirring at room temperature for 1 hour. Then, 0.4 g (1.7 mmol) of 4-trifluoromethyl-5-[1-(N-methylamino)-2-methylpropyl] pyrimidine was added, followed by heating and refluxing for further 3 hours. To the reaction solution, 100 ml of water was added, followed by extraction with ethyl acetate. The obtained organic layer was washed with water and then dried over anhydrous magnesium sulfate. Ethyl acetate was distilled off under reduced pressure, and the obtained crude product was purified by silica gel column chromatography (developing solvent/n-hexane:ethyl acetate:methanol= 4.5:4.5:1) to obtain 0.2 g (yield: 33%) of N-methyl-N-[2-methyl-1-(4-trifluoromethylpyrimidin-5-yl)propyl]-2-pyridylacetamide as colorless transparent crystals (melting point: 99–100° C.).

PREPARATION EXAMPLE 3

Preparation of N-methyl-N-[2-methyl-1-(4-trifluoromethylpyrimidin-5-yl)propyl] phenylthioacetamide (Compound No. 1–142 of the Present Invention)

0.45 g (1.3 mmol) of N-methyl-N-[2-methyl-1-(4-trifluoromethylpyrimidin-5-yl)propyl]phenylthioacetamide and 0.52 g (1.3 mmol) of a Lawson reagent were dissolved in 30 ml of toluene, followed by heating and refluxing for 30 hours. To the reaction solution, 100 ml of water was added, followed by extraction with ethyl acetate. The obtained organic layer was washed with water and then dried with anhydrous magnesium sulfate. Ethyl acetate m was distilled off under reduced pressure, and the obtained crude product was purified by silica gel column chromatography (developing solvent/n-hexane:ethyl acetate=3:1) to obtain 0.12 g (yield: 26%) of N-methyl-N-[2-methyl-1-(4-trifluoromethylpyrimidin-5-yl)propyl]phenylthioacetamide as slightly yellow crystals (melting point: 93–94° C.).

PREPARATION EXAMPLE 4

Preparation of N-methoxymethyl-N-[2-methyl-1-(4-trifluoromethylpyrimidin-5-yl)propyl]-4-chlorophenylacetamide (Compound No. 1-105 of the Present Invention)

1.0 g (4.6 mmol) of 4-trifluoromethyl-5-[1-amino-2-methylpropyl]pyrimidine, 0.23 g (6.9 mmol)of paraformaldehyde and 0.1 g (9.9 mmol) of triethylamine were dissolved in 50 ml of toluene. Heating and refluxing were carried out for 1 hour while removing water from the reaction system by means of Dean's Stark. The reaction solution was returned to room temperature, and 0.86 g (4.6 mmol) of 4-chlorophenylacetylchloride was dropwise added, followed by stirring for further 2 hours. To this solution, 10 ml of a toluene solution containing 0.2 g (6.2 mmol) of methanol and 0.5 g (4.9 mmol) of triethylamine, was dropwise added, followed by stirring at room temperature for 1 hour. To the reaction solution, 100 mg of water was added, followed by extraction with ethyl acetate. The obtained organic layer was washed with water and then dried over anhydrous magnesium sulfate. Ethyl acetate was distilled off under reduced pressure, and the obtained crude product was purified by silica gel column chromatography (developing solvent/n-hexane:ethyl acetate=3:1) to obtain 0.5 g (yield: 26%) of N-methoxymethyl-N-[2-methyl-1-(4-trifluoromethylpyrimidin-5-yl)propyl]-4-chlorophenylacetamide as colorless transparent crystals (melting point: 142–145° C.).

PREPARATION EXAMPLE 5

Preparation of N-methyl-N-[2-methyl-1-(4-chlorodifluoromethylpyrimidin-5-yl)propyl]-N'-(4-methylphenyl)urea (Compound No. 1-37 of the Present Invention)

0.50 g (2.1 mmol) of 4-chlorodifluoromethyl-5-[1-(N-methylamino)-2-methylpropyl]pyrimidine and 0.28 g (2.1 mmol) of 4-methylphenyl isocyanate were dissolved in 30 ml of isopropyl ether, followed by stirring at room temperature for 1 hour. Precipitated crystals were collected by filtration to obtain 0.65 g (yield: 84%) of N-methyl-N-[2-methyl-1-(4-chlorodifluoromethylpyrimidin-5-yl)propyl]-N'-(4-methylphenyl)urea as colorless transparent crystals (melting point: 135–137° C.).

PREPARATION EXAMPLE 6

Preparation of 1,3-dimethyl-1-[2-methyl-1-(4-trifluoromethyl-pyrimidin-5-yl)-propyl]-3-phenylurea (Compound No. 1-424 of the Present Invention)

0.8 g (3.4 mmol) of 4-trifluoromethyl-5-[1-(N-methylamino)-2-methylpropyl]pyridine was dissolved in 30 ml of chloroform, and 5 mg of a chloroform solution of 0.45 g (3.8 mmol) of phenyl isocyanate was dropwise added, followed by stirring at room temperature for 10 hours. To the reaction solution, 50 ml of water was added, followed by extraction with ethyl acetate. The obtained organic layer was washed with water and then dried over anhydrous magnesium sulfate. Ethyl acetate was distilled off under reduced pressure, and the obtained crude crystals were washed with n-hexane to obtain 1.0 g (yield: 83%) of 1-methyl-1-[2-methyl-1-(4-trifluoromethyl-pyrimidin-5-yl)-propyl]-3-phenylurea. 0.5 g (1.4 mmol) of the obtained 1-methyl-1-(2-methyl-1-(4-trifluoromethyl-pyrimidin-5-yl)-propyl)-3-phenylurea was dissolved in 30 mg of tetrahydrofuran, and 0.06 g (2.5 mmol) of sodium hydride was added, followed by stirring at room temperature for 0.5 hour. Then, 0.22 g (1.6 mmol) of methyl iodide was dropwise added, followed by stirring at room temperature for 4 hours. To the reaction solution, 50 ml of water was added, followed by extraction with ethyl acetate. The obtained organic layer was washed with water and then dried over anhydrous magnesium sulfate. Ethyl acetate was distilled off under reduced pressure, and the obtained crude product was purified by silica gel chromatography (developing solvent/n-hexane:ethyl acetate 9:1 to 3:1) to obtain 0.28 g (yield: 53.8%) of 1,3-dimethyl-1-[2-methyl-1-(4-trifluoromethyl-pyrimidin-5-yl)-propyl-3-phenylurea as colorless crystals (melting point: 104–105° C.).

PREPARATION EXAMPLE 7

Preparation of N-[1-(4-ethyl-pyrimidin-5-yl)-2-methylpropyl]-4-fluoro-N-methyl-benzenesulfonamide (Compound No. 4-3 of the Present Invention)

0.4 g (0.2 mmol) of [1-(4-ethyl-pyrimidin-5-yl)-propyl]-methyl-amine was dissolved in 20 ml of pyridine, and 0.43 g (0.22 mmol) of p-fluorobenzenesulfonyl chloride was dropwise added, followed by stirring at room temperature for 10 hours. To the reaction solution, 50 ml of water was added, followed by extraction with diethyl ether. The obtained organic phase was washed twice with 30 ml of a dilute citric acid aqueous solution and then dried over anhydrous magnesium sulfate. Diethyl ether was distilled off under reduced pressure, and the obtained crude product was purified by silica gel chromatography (developing solvent/n-hexane:ethyl acetate 4:1 to 1:1) to obtain 0.4 g (yield: 56%) of (N-[1-(4-ethyl-pyrimidin-5-yl)-2-methylpropyl]-4-fluoro-N-methyl-benzenesulfonamide as a colorless oil ($n_D^{20}$=1.5399).

PREPARATION EXAMPLE 8

Preparation of 1-(4-chlorobenzyl)-1,3-dimethyl-3-[2-methyl-1-(4-trifluoromethyl-pyrimidin-5-yl)-propyl]-urea (Compound No. 1-532 of the Present Invention)

0.16 g (1.0 mmol) of (4-chlorobenzyl)-methylamine was dissolved in 30 ml of pyridine, and 0.3 g (1.0 mmol) of N-methyl-N-(2-methyl-1-(4-trifluoromethyl-pyrimidin-5-yl)-propyl]-carbamoyl chloride was dropwise added, followed by stirring at room temperature for 10 hours. To the reaction solution, 50 ml of water was added, followed by extraction with diethyl ether. The obtained organic phase was washed twice with 30 ml of a dilute citric acid aqueous solution, followed by drying over anhydrous magnesium sulfate. Diethyl ether was distilled off under reduced pressure, and the obtained crude product was purified by silica gel chromatography (developing solvent/n-hexane:ethyl acetate=8:1 to 3:1) to obtain 0.22 g (yield: 52%) of 1-(4-chlorobenzyl)-1,3-dimethyl-3-[2-methyl-1-(4-trifluoromethyl-pyrimidin-5-yl)-propyl]-urea as colorless crystals (melting point: 95–98° C.).

PREPARATION EXAMPLE 9

Preparation of N-[1-(4-diethoxymethylpyrimidin-5-yl)-2-methylpropyl]-N-methyl-2-phenyl acetamide (Compound No. 1-453 of the Present Invention)

8.3 g (0.031 mol) of [1-(4-diethoxymethylpyrimidin-5-yl)-2-methylpropyl]methylamine and 6.4 g (46 mmol) of potassium carbonate were added to 100 ml of acetonitrile, and then 5.8 g (0.038 mol) of phenylacetyl chloride was dropwise added at room temperature and reacted for 2 hours. After completion of the reaction, the product was poured into water and extracted with ethyl acetate. The organic layer was washed with an aqueous citric acid solution, water and an aqueous sodium chloride solution in this order, dried and concentrated, and the obtained oily product was purified by silica gel column chromatography (ethyl acetate:n-hexane=1:5 to ethyl acetate), to obtain 8.4 g (yield: 70%) of N-[1-(4-diethoxymethylpyrimidin-5-yl)-2-methylpropyl]-N-methyl-2-phenyl acetamide as colorless viscous liquid ($n_D^2$=1.5253)

PREPARATION EXAMPLE 10

Preparation of N-[1-(4-formylpyrimidin-5-yl)-2-methylpropyll-N-methyl-4-fluorophenylacetamide (Compound No. 1-523 of the Present Invention)

8.4 g (2.1 mmol) of N-[1-(4-diethoxymethylpyrimidin-5-yl)-2-methylpropyl]-N-methy4-fluorophenylacetamide was dissolved in 100 ml of acetone, and 13 ml of 6N hydrochloric acid was added and reacted at room temperature for 5 hours. After completion of the reaction, the reaction solution was concentrated, and an aqueous sodium hydrogencarbonate solution was added to alkaline, followed by extraction with ethyl acetate. The organic layer was washed with an aqueous citric acid solution, water and an aqueous sodium chloride solution, in this order, dried and concentrated, and the obtained oily product was purified by silica gel column chromatography (ethyl acetate:n-hexane=1:5 to ethyl acetate) to obtain 5.3 g (yield: 77%) of N-[1-(4-formylpyrimidin-5-yl)-2-methylpropyl]-N-methyl-4-fluorophenylacetamide as colorless viscous liquid ($n_D^{20}$=1.5466).

PREPARATION EXAMPLE 11

Preparation of N-[1-(4-hydroxyiminomethylpyrimidin-5-yl)-2-methylpropyl]-N-methylphenylacetamide (Compound No. 1-500 of the Present Invention)

1.0 g (3.2 mmol) of N-(1-(4-formylpyrimidin-5-yl)-2-methylpropyl]-N-methylphenylacetamide was dissolved in 30 ml of methanol, and 0.45 g (6.5 mmol) of hydroxylamine hydrochloride and 0.63 g (6.4 mmol) of potassium acetate were added and reacted at room temperature for 1 hour. After completion of the reaction, the product was poured into water and extracted with ethyl acetate. The organic layer was washed with an aqueous sodium hydrogencarbonate solution, an aqueous citric acid solution, water and an aqueous sodium chloride solution, in this order, dried and concentrated, and the obtained oily product was purified by silica gel column chromatography (ethyl acetate:n-hexane= 1:1 to ethyl acetate) to obtain 0.45 g (yield: 43%) of N-[1-(4-hydroxyiminomethylpyrimidin-5-yl)-2-methylpropyl]-N-methylphenylacetamide as colorless crystals (melting point: 171–172° C.).

PREPARATION EXAMPLE 12

Preparation of N-[1-(4-cyanopyrimidin-5-yl)-2-methylpropyl]-N-methylphenylacetamide (Compound No. 1-504 of the Present Invention)

0.25 g (0.77 mmol) of N-[1-(4-hydroxyiminomethylpyrimidin-5-yl)-2-methylpropyl]-N-methylphenylacetamide was dissolved in 30 ml of chloroform, and 0.16 g (0.83 mmol) of 1-(3-(dimethylamino)propyl]-3-ethylcarbodilmide hydrochloride was added and reacted at room temperature for 8 hours. After completion of the reaction, the solvent was distilled off, and water was added, followed by extraction with ethyl acetate. The organic layer was washed with water and an aqueous sodium chloride solution in this order, dried and concentrated, and the obtained oily product was purified by silica gel column chromatography (ethyl acetate:n-hexane= 1:1 to ethyl acetate) to obtain 0.19 g (yield: 88%) of N-[1-(4-cyanopyrimidin-5-yl)-2-methylpropyl]-N-methylphenylacetamide as colorless crystals (melting point: 80–81° C.).

PREPARATION EXAMPLE 13

Preparation of 2-(4-chlorophenyl)-N-[1-(4,6-dimethoxypyrimidin-5-yl)-2-methylpropyl]-N-methyl acetamide (Compound No. 3-41 of the Present Invention)

0.80 g (3.8 mmol) of 1-(4,6-dimethoxypyrimidin-5-yl)-2-methylpropylamine, 0.59 g (4.2 mmol) of methyl iodide and 0.46 g (4.6 mmol) of triethylamine were added to 10 ml of N,N-dimethylacetamide and reacted at 80° C. for 1 hour. After completion of the reaction, the product was poured into water and extracted with toluene. The organic layer was washed with water and an aqueous sodium chloride solution in this order, dried and concentrated, and the obtained oily product was supplied to the subsequent reaction without purification. 0.20 g (0.89 mmol) of this oily product and 0.22 g (1.6 mmol) of potassium carbonate were added to 20 ml of acetonitrile, and then 0.30 g (1.6 mmol) of 4-chlorophenylacetyl chloride was added at room temperature and reacted overnight. After completion of the reaction, the product was poured into water and extracted with ethyl acetate. The organic layer was washed with an aqueous citric acid solution, water and an aqueous sodium chloride solution in this order, dried and concentrated, and the obtained oily product was purified by preparative HPLC (ethyl acetate:n-hexane=1:1) to obtain 0.21 g (yield: 15%, 2 steps) of 2-(4-chlorophenyl)-N-[1(4,6-dimethoxypyrimidin-5-yl)-2-methylpropyl]-N-methyl acetamide as colorless crystals (melting point: 107–109° C.).

PREPARATION EXAMPLE 14

Preparation of 1-[2-methyl-1-(4-trifluoromethyl-pyrimidin-5-yl)-propyl]-3-phenylimidazolin-2-one (Compound No. 5-1 of the Present Invention)

1.05 g (4.2 mol) of 5-(1-chloro-2-methylpropyl)-4-trifluoromethylpyrimidine and 0.61 (4.2 mol) of N-phenylethylenediamine were added to 10 ml of isopropyl alcohol, followed by stirring at room temperature for 6 hours. After completion of the reaction, the reaction solution was concentrated, then poured into water and extracted with ethyl acetate, and purified by silica gel column chromatography (ethyl acetate:n-hexane=1:1 to ethyl acetate) to obtain 0.38 g of N-[2-methyl-1-(4-trifluoromethylpyrimidin-5-yl)-propyl]-N'-phenylethane-1,2-diamine. Then, 0.38 g (1 mmol) of N-[2-methyl-1-(4-trifluoromethylpyrimidin-5-yl)-propyl]-N'-phenylethane-1,2-diamine and 0.5 g (5 mmol) of triethylamine were added to 10 ml of dichloromethane, and a dichloromethane solution containing 0.2 g (2 mmol) of phosgene was dropwise added under cooling with ice. After the dropwise addition, stirring was further continued at room temperature for 1 hour to terminate the reaction. After termination of the reaction, the product was poured into water, washed with an aqueous sodium hydrogencarbonate solution, dried and concentrated, and the obtained oily product was purified by silica gel column chromatography (ethyl acetate:n-hexane=1:1 to ethyl acetate) to obtain 0.25 g (yield: 61%) of 1-[2-methyl-1-(4-trifluoromethyl-pyrimidin-5-yl)-propyl]-3-phenylimidazolin-2-one as colorless crystals (melting point: 126–128° C.).

PREPARATION EXAMPLE 15

Preparation of 5-(1-{[2-(4-chlorophenyl)-propionyl] methylamino}-2-methylpropyl)-pyrimidine-4-carboxylic acid (Compound No. 1-718 of the Present Invention)

A solution comprising 1.0 g (3.2 mmol) of N-[1-(4-formylpyrimidin-5-yl)-2-methylpropyl]-N-methylphenylacetamide and 10 ml of tetrahydrofuran, was added to a solution comprising 0.23 g (4.1 mmol) of potassium hydroxide and 10 ml of water. Then, 0.88 g (5.56 mmol) of potassium permanganate was further added. Then, the mixture was heated at 80° C. for 3 hours. After completion of the reaction, sodium sulfite was added, followed by filtration. The filtrate was acidified with hydrochloric acid and then extracted with ethyl acetate, and the extract was washed with an aqueous sodium chloride solution, dried over anhydrous magnesium sulfate and concentrated to obtain a crude product. This crude product was dissolved in a mixed solution of toluene, ether and acetone, followed by extraction with an aqueous potassium hydroxide solution. Then, extract was acidified with diluted hydrochloric acid and extracted with ethyl acetate. The extract was dried over magnesium sulfate, concentrated and further washed with isopropyl ether to obtain 0.33 g (yield: 32%) of 5-(1-{[2-(4-chlorophenyl)-propionyl]methylamino}-2-methylpropyl)-pyrimidine-4-carboxylic acid (diastereomer A-isomer) as slightly blown crystals (melting point: 168–170° C.).

PREPARATION EXAMPLE 16

Preparation of 5-(1-{[2-(4-chlorophenyl)-propionyl] methylamino}-2-methylpropyl)-pyrimidine-4-carboxylic acid methyl ester (diastereomer A-isomer) (Compound No. 1-592 of the Present Invention)

A few drops of concentrated sulfuric acid were added to a methanol solution of 2.00 g (5.32 mmol) of 5-(1-{[2-(4-chlorophenyl)-propionyl]methylamino}-2-methylpropyl)-pyrimidine-4-carboxylic acid, followed by heating and refluxing for 5 hours. After completion of the reaction, water was added, followed by extraction with ethyl acetate, and the extract was washed with an aqueous sodium chloride solution, dried over magnesium sulfate and concentrated, and the obtained oily product was purified by silica gel column chromatography (ethyl acetate:n-hexane=1:1 to ethyl acetate) to obtain 0.59 g (yield: 28%) of 5-(1-{[2-(4-chlorophenyl)-propionyl]methylamino}-2-methylpropyl)-pyrimidine-4-carboxylic acid methyl ester (diastereomer A-isomer) as colorless oily product.

Examples for Preparation of Intermediates

REFERENCE EXAMPLE 1

Preparation of 3-ethoxymethylene-1,1,1-trifluoro-5-methyl-2,4-hexanedione

A mixture comprising 213 g (1.17 mol) of 1,1,1-trifluoro-5-methyl-2,4-hexanedione, 242 g (1.64 mol) of ethyl orthoformate and 166 g (1.63 mol) of acetic anhydride, was heated and refluxed for 6 hours. The solvent was distilled off under reduced pressure to obtain 146 g (yield: 67%) of 3-ethoxymethylene-1,1,1-trifluoro-5-methyl-2,4-hexanedione.

REFERENCE EXAMPLE 2

Preparation of 5-isopropylcarbonyl-4-trifluoromethylpyrimidine 46 g (0.85 mol) of sodium methoxide was dissolved in 700 ml of methanol, and 76 g (0.73 mol) of formamidine acetate was added, followed by stirring at room temperature for 15 minutes. Then, 146 g (0.61 mol) of 3-ethoxymethylene-1,1,1-trifluoro-5-methyl-2,4-hexanedione was added under cooling with ice, followed by heating and refluxing for further 2 hours. The solvent was distilled off under reduced pressure, and 1,000 ml of ice water was added, followed by extraction with ethyl acetate. The obtained organic layer was washed with water and then dried over anhydrous magnesium sulfate. Ethyl acetate was distilled off under reduced pressure, and the obtained crude product was purified by silica gel column chromatography (developing solvent/n-hexane:ethyl acetate=6:1) to obtain 89 g (yield: 67%) of 5-isopropylcarbonyl-4-trifluoromethylpyrimidine as slightly yellow liquid.

REFERENCE EXAMPLE 3

Preparation of 5-(1-hydroxy-2-methylpropyl)-4-trifluoromethylpyrimidine 25 g (115 mmol) of 5-isopropylcarbonyl-4-trifluorometylpyrimidine was dissolved in 100 ml of ethanol, and under cooling with ice, 6 g (69 mmol) of a borane-tert-butylamine complex was added, followed by stirring for 2 hours. Further, 20 ml of acetone was added, followed by stirring for 0.5 hour. The solvent was distilled off under reduced pressure, and the residue was purified by silica gel column chromatography (developing solvent/n-hexane:ethyl acetate=1:1) to obtain 22 g (yield: 87%) of 5-(1-hydroxy-2-methylpropyl)-4-trifluoromethylpyrimidine as slightly yellow liquid ($n_D^{20}$=1.4481)

REFERENCE EXAMPLE 4

Preparation of 5-(1-chloro-2-methylpropyl)-4-trifluoromethylpyrimidine 22 g (100 mmol) of 5-(1-hydroxy-2-methylpropyl)-4-trifluoromethylpyrimidine was dissolved in 150 ml of chloroform, and 25 ml (342 mmol) of thionyl chloride was added. The reaction mixture was heated and refluxed for 2 hours. The solvent and thionyl chloride was distilled off under reduced pressure, and the residue was purified by silica gel column chromatography (developing solvent/n-hexane:ethyl acetate=6:1) to obtain 11.6 g (yield: 49%) of 5-(1-chloro-2-methylpropyl)-4-trifluoromethylpyrimidine as brown liquid (refractive index $n_D^{20}$: 1.4558).

REFERENCE EXAMPLE 5

Preparation of 5-[1-(N-methylamino)-2-methylpropyl]-4-trifluoromethylpyrimidine 4.5 g (19 mmol) of 5-(1-chloro-2-methylpropyl)-4-trifluoromethylpyrimidine was dissolved in 50 ml of isopropyl alcohol, and 10 ml (161 mmol) of a 50% methylamine aqueous solution was added, followed by stirring at room temperature for 8 hours. The solvent was distilled off under reduced pressure, and 100 ml of water was added, followed by extraction with ethyl acetate. The obtained organic layer was washed with water and then dried over anhydrous magnesium sulfate. Ethyl acetate was distilled off under reduced pressure to obtain 3.4 g (yield: 77%) of 5-(1-(N-methylamino)-2-methylpropyl]-4-trifluoromethylpyrimidine as slightly yellow liquid (refractive index $n_D^{20}$: 1.4529).

REFERENCE EXAMPLE 6

Preparation of 4-ethoxymethylene-2,6-dimethyl-3,5-heptanedione

A mixture comprising 17.2 g (110 mmol) of 2,6-dimethyl-3,5-heptanedione, 22.8 g (153 mmol) of ethyl orthoformate and 31.5 g (309 mmol) of acetic anhydride, was reacted for 2 hours at 110° C. The solvent was distilled off under reduced pressure to obtain 11.5 g (yield: 49%) of 4-ethoxymethylene-2,6-dimethyl-3,5-heptanedione.

REFERENCE EXAMPLE 7

Preparation of 5-isopropylcarbonyl-4-isopropylpyrimidine 11.5 g (60 mmol) of a 28% sodium methoxide solution was dissolved in 100 ml of methanol, and 5.6 g (54 mmol) of formamidine acetate was added, followed by stirring at room temperature for 15 minutes. Then, 11.5 g (54 mmol) of 4-ethoxymethylene-2,6-dimethyl-3,5-heptanedione was added under cooling with ice. The reaction mixture was further reacted at 50° C. for one hour. The solvent was distilled off under reduced pressure, and 200 ml of water was added, followed by extraction with ethyl acetate. The obtained organic layer was washed with water and then dried over anhydrous magnesium sulfate. Ethyl acetate was distilled off under reduced pressure, and the residue was purified by silica gel column chromatography (developing solvent/n-hexane:ethyl acetate=4:1) to obtain 9.2 g (yield: 89%) of 5-isopropylcarbonyl-4-isopropylpyrimidine as slightly yellow liquid.

REFERENCE EXAMPLE 8

Preparation of 5-(1-hydroxy-2-methylpropyl)-4-isopropylpyrimidine 9.2 g (48 mmol) of 5-isopropylcarbonyl-4-isopropylpyrimidine was dissolved in 50 ml of ethanol, and under cooling with ice, 2.5 g (29 mmol) of a borane-tert-butylamine complex was added, followed by stirring for 2 hours. Further, 20 ml of acetone was added, followed by stirring for 0.5 hour. The solvent was distilled off under reduced pressure, and 200 ml of water was added, followed by extraction with ethyl acetate. The obtained organic layer was washed with water and then dried over anhydrous magnesium sulfate. Ethyl acetate was distilled off under reduced pressure to obtain 8.3 g (yield: 89%) of the desired product i.e. 5-(1-hydroxy-2-methylpropyl)-4-isopropylpyrimidine.

REFERENCE EXAMPLE 9

Preparation of 5-(1-methylsulfonyloxy-2-methylpropyl)-4-isopropylpyrimidine 8.3 g (43 mmol) of 5-(1-hydroxy-2-methylpropyl)-4-isopropylpyrimidine was dissolved in 10 ml of pyridine, and under cooling with ice, 9.8 g (86 mmol) of methylsulfonyl chloride was dropwise added. The reaction mixture was reacted at room temperature for 2 hours, and then, 100 ml of ice water was added, followed by extraction with ethyl acetate. The obtained organic layer was washed with an aqueous citric acid solution and water and then dried over anhydrous magnesium sulfate. Ethyl acetate was distilled off under reduced pressure to obtain 10.6 g (yield: 90%) of 5-(1-methylsulfonyloxy-2-methylpropyl)-4-isopropylpyrimidine.

[$^1$H-NMR (300 MHz CDCl$_3$, TMS δ (ppm)) 0.91 (3 H, d), 1.14 (3H, d), 1.31 (3H, dd), 2.1–2.2 (1H, m), 2.89 (3H, s), 3.2–3.3 (3H, m) 5.56 (1H, d), 8.68 (1H, s), 9.14 (1H, s)],

REFERENCE EXAMPLE 10

Preparation of 5-[1-(N-methylamino)-2-methylpropyl]-4-isopropylpyrimidine 10.6 g (39 mmol) of 5-(1-methylsulfonyloxy-2-methylpropyl)-4-isopropylpyrimidine was dissolved in 50 ml of isopropyl alcohol, and 10 ml (129 mmol) of a 40% methylamine aqueous solution was added, followed by stirring at room temperature for 8 hours. After completion of the reaction, the solvent was distilled off under reduced pressure, and 100 ml of water was added, followed by extraction with ethyl acetate. The obtained organic layer was washed with water and then dried over anhydrous magnesium sulfate. Ethyl acetate was distilled off under reduced pressure, and the residue was purified by silica gel column chromatography (developing solvent=ethyl acetate) to obtain 2.9 g (yield: 36%) of 5-[1-(N-methylamino)-2-methylpropyl]-4-isopropylpyrimidine as slightly yellow crystals (melting point: 37–39° C.).

REFERENCE EXAMPLE 11

Preparation of 5-(1-hydroxy-2-methylpropyl)-4-methylthiopyrimidine 10.6 g (52 mmol) of 5-bromo-4-methylthiopyrimidine was dissolved in 100 ml of tetrahydrofuran, and at −60° C., 36 ml of a n-butyllithium hexane solution (1.6 mol/l) was dropwise added. After stirring at −60° C. for 30 minutes, 4.1 g (57 mmol) of isobutylaldehyde was dropwise added and further reacted for 1 hour. The reaction solution was poured into water and extracted with ethyl acetate. The obtained organic layer was washed with water and then dried over anhydrous magnesium sulfate. Ethyl acetate was distilled off under reduced pressure, and the residue was purified by silica gel column chromatography (developing solvent/n-hexane:ethyl acetate=3:2) to obtain 2.9 g (yield: 28%) of 5-(1-hydroxy-2-methylpropyl)-4-methylthiopyrimidine as slightly yellow crystals (melting point: 123–127° C.).

REFERENCE EXAMPLE 12

Preparation of 2-bromo-1-(4-ethylpyrimidin-5-yl)-propan-1-one 49.2 g (0.30 mol) of 1-(4-ethylpyrimidin-5-yl)propan-1-one was dissolved in 500 ml of carbon tetrachloride, and 53 g (0.30 mol) of N-bromosuccinimide and 0.3 g of azoisobutyronitrile were added, followed by refluxing for 2 hours. After cooling, crystals were removed by filtration, and the filtrate was concentrated and the obtained oily product was purified by column chromatography (ethyl acetate:n-hexane=1:4 to 1:2) to obtain 64.3 g (yield: 89%) of 2-bromo-1-(4-ethylpyrimidin-5-yl)-propan-1-one as yellow liquid.

REFERENCE EXAMPLE 13

Preparation of 1-(4-ethylpyrimidin-5-yl)-2-methylthio-propan-1-one 10.0 g (0.041 mol) of 2-bromo-1-(4-ethylpyrimidin-5-yl) propan-1-one was dissolved in 40 ml of isopropyl alcohol, and 21 g (0.045 mol) of a 15% sodium methythiolate aqueous solution was added under cooling with ice and then reacted at room temperature for 1 hour. After completion of the reaction, the product was poured into water and extracted with ethyl acetate. The organic layer was washed with an aqueous sodium chloride solution, dried and concentrated to obtain 9.5 g of crude 1-(4-ethylpyrimidin-5-yl)-2-methylthio-propan-1-one. The product was used for the subsequent reaction without purification.

REFERENCE EXAMPLE 14

Preparation of 4,6-dichloropyrimidine-5-carboaldehyde

To 65.0 g (0.89 mol) of N,N-dimethylformamide, 356 g (2.3 mol) of phosphorus oxychloride was added at a temperature of at most 20° C. under cooling with ice, followed by stirring at room temperature for 10 minutes. 50.0 g (0.45 mol) of 4,6-dihydroxypyrimidine was slowly added under cooling with ice. After completion of the addition, when the temperature-rising was terminated, the mixture was reacted at 90° C. for 3 hours. Excess phosphorus oxychloride was distilled off under reduced pressure, and 300 ml of chloroform was added, and the mixture was slowly added into ice water. The organic layer was washed with an aqueous sodium hydrogencarbonate solution, water and an aqueous sodium chloride solution in this order, dried and concentrated, and the obtained crude crystals were washed with n-hexane to obtain 43.8 g (yield: 55%) of 4,6-dichloropyrimidine-5-carboaldehyde as brown crystals (melting point: 65–66° C.).

REFERENCE EXAMPLE 15

Preparation of 4,6-dimethoxypyrimidine-5-carboaldehyde 43.6 g (246 mmol) of 4,6-dichloropyrimidine-5-carboaldehyde was dissolved in 200 ml of methanol, and 120 g (622 mmol) of 28% sodium methoxide was added under cooling with ice and then reacted for 2 hours at room temperature. After completion of the reaction, the solvent was distilled off, and an aqueous citric acid solution was added, followed by extraction with ethyl acetate. The organic layer was washed with an aqueous sodium hydrogencarbonate solution, an aqueous citric acid solution, water and an aqueous sodium chloride solution in this order, dried and concentrated, and the obtained crude crystals were washed with isopropyl ether to obtain 8.3 g (yield: 20%) of 4,6-dimethoxypyrimidine-5-carboaldehyde.

REFERENCE EXAMPLE 16

Preparation of 1-(4,6-dimethoxypyrimidin-5-yl)-3-methylbutan-2-ol 0.81 g (33 mmol) of magnesium was added to 30 ml of tetrahydrofuran, and 4.1 g (33 mmol) of 2-bromopropane was added to prepare a tetrahydrofuran solution of isopropyl magnesium bromide. 2.8 g (17 mmol) of 4,6-dimethoxypyrimidine-5-carboaldehyde was dissolved in 50 ml of tetrahydrofuran, and the solution was added to the above tetrahydrofuran solution at room temperature and reacted overnight. The reaction solution was poured into an aqueous ammonium chloride solution and extracted with ethyl acetate. The organic layer was washed with an aqueous citric acid solution, water and an aqueous sodium chloride solution in this order, dried and concentrated, and the obtained oily product was purified by column chromatography (ethyl acetate:n-hexane=1:4) to obtain 1.9 g (yield: 54%) of 1-(4,6-dimethoxy pyrimidin-5-yl)-3-methylbutan-2-ol as slightly yellow crystals.

REFERENCE EXAMPLE 17

Preparation of 5-(2-azide-3-methylbutyl)-4,6-dimethoxypyrimidine 1.05 g (5 mmol) of 1-(4,6-dimethoxypyrimidin-5-yl)-3-methylbutan-2-ol was dissolved in 10 ml of toluene, and under cooling with ice, 1.01 g (10 mmol) of trimethylsilylazide and 1.42 g (10 mmol) of boron trifluoride diethyl ether complex were added sequentially and then reacted for 7 hours at room temperature. After completion of the reaction, the product was poured into water and extracted with toluene. The organic layer was washed with an aqueous sodium hydrogencarbonate solution, water and an aqueous sodium chloride solution in this order, dried and concentrated, and the obtained oily product was purified by column chromatography (ethyl actate:n-hexane=1:9) to obtain 1.22 g (yield: 100%) of 5-(2-azide-3-methylbutyl)-4,6-dimethoxypyrimidine as colorless liquid.

[$^1$H-NMR (300 MHz CDCl$_3$, TMS δ (ppm)) 0.70 (3 H, d), 1.13 (3H, d), 2.44 (1H, m), 4.00 (6H, s), 4.38 (1H, d), 8.39 (1H, s)].

REFERENCE EXAMPLE 18

Preparation of 1-(4,6-dimethoxypyrimidin-5-yl)-2-methylpropylamine 1.2 g (5.1 mmol) of 5-(2-azide-3-methylbutyl)-4,6-dimethoxypyrimidine was dissolved in 20 ml of methanol, and under cooling with ice, 1.5 g (0.062 mol) of magnesium was added and reacted overnight. After completion of the reaction, the solvent was distilled off, and ether was added. Insolubles were filtered off, followed by extraction with diluted hydrochloric acid. An aqueous sodium hydroxide solution was added to alkaline, followed by extraction with toluene. The organic layer was washed with water and an aqueous sodium chloride solution in this order, dried and concentrated, and the obtained oily product was purified by column chromatography (ethyl acetate:n-hexane=1:1) to obtain 0.80 g (yield: 75%) of 1-(4,6-dimethoxypyrimidin-5-yl)-2-methylpropylamine as colorless crystals.

[$^1$H-NMR (300 MHz, CDCl$_3$, TMS δ (ppm)) 0.70 (3 H, d), 1.07 (3H, d), 1.71 (2H, s), 2.02 (1H, m), 3.78 (1H, d), 3.97 (6H, s), 8.33 (1H, s)].

Now, the physical properties ($^1$H-NMR values (CDCl$_3$/TMS δ (ppm)) of the compounds of the present invention prepared in accordance with the methods disclosed in processes 1 to 12, will be shown in Tables 40 to 43.

TABLE 40

| Compound No. | NMR (δ(ppm), 300MHz, TMS-CDCl$_3$) |
|---|---|
| 1-016 | 0.81(3H, d), 1.01(3H, d), 2.75–2.87(1 H, m), 2.90(1H, s), 3.60(2H, dd), 3.78(3 H, s), 5.44(1H, d), 6.83(2H, d), 7.11(2 H, d), 9.23(1H, s), 9.25(1H, s) |
| 1-034 | 0.29–0.32(1H, m), 0.75–0.77(3H, m), 1.48–1.60(1H, m), 2.99(3H, s), 3.70(2H, s), 4.84(1H, d), 7.17–7.33(5H, m), 9.25 (1H, s), 9.31(1H, s) |
| 1-195 | 0.76–0.81(3H, t, 3H, t), 0.91–0.98(3 H, t, 3H, t), 1.36–1.41(3H, d, 3H, d), 2.64–2.90(1H, m, 1H, m), 2.75(3H, s), 2.85 (3H, s), 3.69–3.80(1H, q, 1H, q), 5.13(1 H, d), 5.51(1H, d), 7.17–7.31(5H, m, 5H, m), 9.22(1H, s), 9.23(1H, s), 9.27(1H, s), 9.30(1H, s), mixture of diastereoisomers |
| 1-329 | 0.80(3H, d), 1.07(3H, d), 1.45(3H, s), 1.50(3H, s), 2.39(3H, s), 2.67–2.80(1 H, m), 5.58(1H, d), 7.08(2H, d), 7.25(2 H, d), 9.15(1H, s), 9.27(1H, s) |
| 1-488 | 2.76(3H, s), 2.88(3H, s), 3.70(3H, s), 3.72(3H, s), 3.77(2H, s), 3.79(2H, s), 7.36–7.73(9H, m, 9H, m), 8.57(1H, s), 8.61(1H, s), 9.25(1H, s), 9.27(1H, s), mixture of diastereoisomers |
| 1-490 | 2.76(3H, s), 2.88(3H, s), 3.70(3H, s), 3.72(3H, s), 3.77(2H, s), 3.79(2H, s), 6.70–7.40(8H, m, 8H, m), 8.55(1H, s), 8.60(1H, s), 9.25(1H, s), 9.27(1H, s), mixture of diastereoisomers |
| 1-526 | 0.89(3H, d), 0.98(3H, d), 2.48–2.60(1 H, m), 2.68(3H, s), 2.92(3H, s), 3.63(2 H, s), 5.38(1H, d), 7.05–7.28(5H, m), 8.94(1H, s), 9.13(1H, s) |

TABLE 41

| Compound No. | NMR (δ(ppm), 300MHz, TMS-CDCl$_3$) |
|---|---|
| 1-562 | 0.79(3H, d), 0.89(3H, d), 0.89(3H, d), 1.12(3H, t), 1.16(3H, d), 1.29(3H, t), 1.25(3H, d), 1.52(3H, d), 1.88(1H, t), 2.27(1H, t), 2.04–2.94(3H, m, 3H, m), 3.44–3.56(1H, m, 1H, m), 3.69–3.81(2H, m), 3.90–4.00(2H, m), 5.77(2H, d, 2H, d), 7.19–7.35(5H, m, 5H, m), 8.59(1H, s), 8.61(1H, s), 9.00(1H, s), 9.08(1H, s), mixture of diastereoisomers |
| 1-592 | 0.90(3H, d), 1.01(3H, d), 1.36(3H, d), 2.53–2.65(1H, m), 2.73(3H, s), 3.78(1 H, q), 4.01(3H, s), 5.70(1H, d), 6.99(2 H, d), 7.18(2H, d), 8.89(1H, s), 9.16(1 H, s) |
| 1-593 | 0.80(3H, d), 0.92(3H, d), 1.36(3H, d), 2.40–2.50(1H, m), 2.62(3H, s), 3.68(1 H, q), 4.02(3H, s), 5.76(1H, d), 7.14(2 H, d), 7.27(2H, d), 8.92(1H, s), 9.19(1 H, s) |
| 1-595 | 0.80(3H, d), 0.91(3H, d), 1.35(3H, d), 1.45(3H, t), 2.40–2.50(1H, m), 2.63(3 |

TABLE 41-continued

| Compound No. | NMR (δ(ppm), 300MHz, TMS-CDCl₃) |
|---|---|
| | H, s), 3.67(1H, q), 4.51(2H, q), 5.78(1 H, d), 7.14(2H, d), 7.27(2H, d), 8.92(1 H, s), 9.19(1H, s) |
| 1-651 | 0.94(3H, t, 3H, t), 1.47(3H, d), 1.66(3 H, d), 1.88–1.98(2H, m, 2, m), 2.08(3H, s), 2.09(3H, s), 2.61(3H, s), 2.68(3H, s), 3.74(2H, dd, 2H, dd), 4.29(1H, q, 1H, q), 6.03(1H, t), 6.12(1H, t), 7.23–7.37 (5H, m, 5H, m), 8.61(1H, s), 8.63(1H, s), 9.09(1H, s), 9.11(1H, s), mixture of diastereoisomers |
| 1-652 | 0.94(3H, t, 3H, t), 1.49(3H, d), 1.65(3 H, d), 1.91–1.99(2H, m, 2H, m), 2.07(3H, s), 2.63(3H, s), 2.70(3H, s), 3.70(2H, s, 2H, s), 4.25–4.32(1H, m, 1H, m), 6.01 (1H, t), 6.11(1H, t), 6.99–7.28(4H, m, 4 H, m), 8.62(1H, s), 8.64(1H, s), 9.10(1 H, s), 9.11(1H, s), mixture of diastereoisomers |

TABLE 42

| Compound No. | NMR (δ(ppm), 300MHz, TMS-CDCl₃) |
|---|---|
| 1-872 | 0.77(3H, d), 0.97(3H, d), 1.37(3H, d), 2.85(3H, s), 2.81–2.91(1H, m), 3.77(1 H, q)5.14(1H, d), 7.16–7.29(5H, m)9.22 (1H, s), 9.29(1H, s) |
| 1-873 | 0.80(3H, d), 1.15(3H, d), 2.43(3H, s), 2.76–2.84(1H, m), 3.18(3H, s), 5.23(1 H, d), 6.77(2H, d), 7.02(1H, t), 7.15(2 H, d), 9.16(1H, s), 9.26(1H, s) |
| 1-877 | 0.82(3H, t), 0.93(3H, t), 1.72(3H, s), 1.78(3H, s), 1.86–1.92(2H, m), 2.77(3 H, s), 3.01(3H, s), 3.70(2H, s), 4.06(2 H, s), 3.70–4.20(4H, m), 5.86(1H, t), 6.09(1H, t), 7.14–7.30(4H, m), 8.70(1H, s), 8.80(1H, s), 9.13(1H, s), 9.22(1H, s) |
| 1-878 | 0.89(3H, t), 0.97(3H, t), 1.70–1.90(2 H, m), 1.90–2.10(2H, m), 2.66(3H, s), 2.70(3H, s), 2.94(3H, s), 3.00(3H, s), 3.62 (2H, s), 3.73(2H, dd), 5.62(1H, t), 5.70–5.79(1H, m), 7.05–7.27(4H, m, 4H, m), 8.68(1H, s), 8.83(1H, s), 9.15(1H, s), 9.20(1H, s) |
| 2-58 | 0.44–0.53(2H, m), 0.55–0.65(H, m), 1.16(3H, s), 3.13(3H, s), 3.80(2H, s), 5.64 (1H, s), 6.63(1H, d), 6.75(1H, d), 9.12 (1H, s), 9.26(1H, s) |
| 2-75 | 0.89(3H, d), 0.99(3H, d), 1.23(3H, t), 2.43–2.51(1H, m), 2.71–3.05(2H, m), 2.77(3H, s), 3.80(2H, dd), 5.72(1H, d), 6.65 (1H, d), 6.74(1H, d), 8.61(1H, s), 9.06 (1H, s) |

TABLE 43

| Compound No. | NMR (δ(ppm), 300MHz, TMS-CDCl₃) |
|---|---|
| 4-26 | 0.78(3H, t), 1.11–1.21(3H, m), 1.31(3 H, t), 2.36(3H, s), 2.58(3H, s), 2.44–2.67 (1H, m), 2.77(3H, s), 2.86(3H, s), 2.88–3.16 (2H, m), 5.02(1H, dd), 7.04–7.45 (4H, m), 8.52(1H, s), 8.69(1H, s), 9.01 (1H, s), 9.10(1H, s) |
| 4-28 | 0.77(3H, d), 1.15(3H, d), 1.31(3H, t), 2.31(3H, s), 2.33–2.43(1H, m)2.80(3H, s), 2.89–3.17(2H, m), 5.02(1H, d), 7.22–7.35 (4H, m), 8.52(1H, s), 9.01(1H, s) |
| 4-36 | 0.77(3H, d), 1.12(3H, d), 2.48–2.58(1 H, m), 3.04(3H, s), 5.09(1H, d), 7.35–7.39 (2H, m), 7.46–7.54(3.H, m)9.05(1H, s), 9.21(1H, s) |
| 4-37 | 0.77(3H, d), 1.13(3H, d), 2.53–2.59(1 H,), 3.02(3H, s), 5.1(1H, d), 7.04–7.08 (2H, m), 7.54–7.58(2H, m)9.06(1H, s), 9.24(1H, s) |
| 4-54 | 0.86(3H, t), 1.34(3H, t), 1.63–2.09(2 H, m), 2.76(3H, s), 2.91–3.09(2H, m), 5.27 (1H, dd)7.17–7.21(2H, m)7.72–7.79 (2H, m), 8.47(1H, s), 9.06(1H, s) |
| 5-13 | 0.79(3H, d), 1.16(3H, d), 1.83–1.90(2H, m), 2.91–2.99(1H, m), 3.07–3.14(3H, m), 3.32–3.40(1H, m), 4.40(1H, d), 4.68(1H, d), 5.02(1H, d)7.20–7.33(5H, m), 9.25 (1H, s), 9.46(1H, s) |

The herbicide of the present invention comprises the pyrimidine derivative represented by the formula [I] as an active ingredient.

In order to use the compound of the present invention as a herbicide, the compound of the present invention may be used by itself, but it may be used as formulated in e.g. a dust, a wettable powder, an emulsifiable concentrate, a microgranule or a granule by incorporating a carrier, a surfactant, a dispersant or an adjuvant which are commonly used for formulations. The carrier to be used for formulation may, for example, be a solid carrier such as talc, bentonite, clay, kaolin, diatomaceous earth, white carbon, vermiculite, calcium carbonate, slaked lime, silica sand, ammonium sulfate or urea, or a liquid carrier such as isopropyl alcohol, xylene, cyclohexane or methylnaphthalene.

The surfactant and the dispersant may, for example, be a metal salt of an alkylbenzene sulfonic acid, a metal salt of dinaphthylmethanedisulfonic acid, an alcohol/sulfuric acid ester, an alkylaryl sulfonate, lignin sulfonate, polyoxyethylene glycol ether, polyoxyethylene alkylaryl ether, and polyoxyethylene sorbitan monoalkylate. The adjuvant may, for example, be carboxymethylcellulose, polyethylene glycol or gum Arabic. In the actual use, it may be applied as diluted to a proper concentration or may be directly applied.

The herbicide of the present invention can be used by application to foliage, application to soil or application to water surface. The blend proportion of the active ingredient may suitably be selected, as the case requires. However, in the case of a dust or a granule, it is preferably selected within a range of from 0.01 to 10% (weight), preferably from 0.05 to 5% (weight). Further, in the case of an emulsifiable concentrate and a wettable powder, it is preferably selected within a range of from 1 to 50% (weight), preferably from 5 to 30% (weight).

The dose of the herbicide of the present invention varies depending upon the type of the compound to be used, the objective weeds, the germination tendency, the environmental conditions as well as the formulation to be used. However, when it is used as it is, in the case of a dust or a granule, the dose is preferably selected within a range of from 0.1 g to 5 kg, preferably from 1 g to 1 kg, per 10 ares as an active ingredient. Further, in a case where it is used in a liquid state as in the case of an emulsifiable concentrate or wettable powder, the dose is preferably selected within a range of from 0.1 to 50,000 ppm, preferably from 10 to 10,000 ppm.

Further, the compound of the present invention may be used in combination with an insecticide, a fungicide, another herbicide, a plant growth regulator, a fertilizer, etc., as the case requires.

Now, the formulation method will be described in detail with reference to typical Formulation Examples. However, the compounds, the types of the additives and the blend ratios are not limited thereto and may be varied within wide ranges. In the following description, "parts" means "parts by weight".

FORMULATION EXAMPLE 1: WETTABLE POWDER

To 10 parts of compound (1-8), 0.5 part of polyoxyethyleneoctylphenyl ether, 0.5 part of a sodium salt of β-naphthalene sulfonic acid formalin condensate, 20 parts of diatomaceous earth and 69 parts of clay were mixed and pulverized to obtain a wettable powder.

FORMULATION EXAMPLE 2: WETTABLE POWDER

To 10 parts of compound (1-8), 0.5 part of polyoxyethyleneoctylphenyl ether, 0.5 part of a sodium salt of β-naphthalene sulfonic acid formalin condensate, 20 parts of diatomaceous earth, 5 parts of white carbon and 64 parts of clay were mixed and pulverized to obtain a wettable powder.

FORMULATION EXAMPLE 3: WETTABLE POWDER

To 10 parts of compound (1-8), 0.5 part of polyoxyethyleneoctylphenyl ether, 0.5 part of a sodium salt of β-naphthalene sulfonic acid formalin condensate, 20 parts of diatomaceous earth, 5 parts of white carbon and 64 parts of calcium carbonate, were mixed and pulverized to obtain a wettable powder.

FORMULATION EXAMPLE 4: EMULSIFIABLE CONCENTRATE

To 30 parts of compound (1-8), 60 parts of a mixture of equal amounts of xylene and isophorone, and 10 parts of a mixture comprising a surfactant polyoxyethylenesorbitan alkylate, a polyoxyethylene alkylaryl polymer and an alkylaryl sulfonate, were added, followed by thorough stirring to obtain an emulsifiable concentrate.

FORMULATION EXAMPLE 5: GRANULE 10 parts of compound (1-8), 80 parts of an extender having talc and bentonite mixed in a ratio of 1:3, 5 parts of white carbon, 5 parts of a mixture comprising a surfactant polyoxyethylenesorbitan alkylate, a polyoxyethylene alkylaryl polymer and an alkylaryl sulfonate, and 10 parts of water were mixed and thoroughly kneaded to obtain a paste, which was extruded through a screen having openings having a diameter of 0.7 mm, then dried and cut into a length of from 0.5 to 1 mm to obtain a granule.

Now, the effects of the compound of the present invention will be described with reference to Test Examples.

TEST EXAMPLE 1: TESTS OF HERBICIDAL EFFECTS BY FLOODED PADDY FIELD TREATMENT

In a 100 cm² plastic pot, paddy field soil was filled and paddled. Then, seeds of barnyard grass (Eo) and monochoria (Mo) were sown, and water was introduced to a depth of 3 cm. Next day, a wettable powder prepared in accordance with Formulation Example 1 was diluted with water and dropwise applied to the water surface. The dose was 100 g of the active ingredient per 10 ares. Thereafter, cultivation was carried out in a green house, and on the 21st day after the treatment, the herbicidal effects were examined in accordance with the standards as identified in Table 44. The results are shown in Tables 45 to 52.

TABLE 44

| Index number | Herbicidal effects (growth-inhibition degree) and phytotoxicity |
|---|---|
| 5 | Herbicidal effect or phytotoxicity for controlling more than 90% |
| 4 | Herbicidal effect or phytotoxicity of at least 70% and less than 90% |
| 3 | Herbicidal effect or phytotoxicity of at least 50% and less than 70% |
| 2 | Herbicidal effect or phytotoxicity of at least 30% and less than 50% |
| 1 | Herbicidal effect or phytotoxicity of at least 10% and less than 30% |
| 0 | Herbicidal effect or phytotoxicity of at least 0% and less than 10% |

TABLE 45

| Compound No. | Dose (gai/10a) | Eo | Mo |
|---|---|---|---|
| 1-4 | 100 | 5 | 5 |
| 1-8 | 100 | 5 | 5 |
| 1-9 | 100 | 5 | 5 |
| 1-10 | 100 | 5 | 5 |
| 1-12 | 100 | 5 | 5 |
| 1-13 | 100 | 5 | 5 |
| 1-15 | 100 | 5 | 5 |
| 1-16 | 100 | 5 | 5 |
| 1-17 | 100 | 5 | 5 |
| 1-18 | 100 | 5 | 5 |
| 1-19 | 100 | 5 | 5 |
| 1-20 | 100 | 5 | 5 |
| 1-21 | 100 | 5 | 5 |
| 1-22 | 100 | 5 | 5 |
| 1-23 | 100 | 5 | 5 |
| 1-24 | 100 | 5 | 5 |
| 1-25 | 100 | 5 | 5 |
| 1-26 | 100 | 5 | 5 |
| 1-27 | 100 | 5 | 5 |
| 1-32 | 100 | 5 | 5 |
| 1-33 | 100 | 5 | 5 |
| 1-34 | 100 | 5 | 5 |
| 1-35 | 100 | 5 | 5 |
| 1-36 | 100 | 5 | 5 |
| 1-37 | 100 | 5 | 5 |
| 1-38 | 100 | 5 | 5 |
| 1-39 | 100 | 5 | 5 |
| 1-40 | 100 | 5 | 5 |
| 1-41 | 100 | 5 | 5 |
| 1-42 | 100 | 5 | 5 |
| 1-43 | 100 | 5 | 5 |
| 1-44 | 100 | 5 | 5 |
| 1-45 | 100 | 5 | 5 |
| 1-46 | 100 | 5 | 5 |
| 1-47 | 100 | 5 | 5 |
| 1-48 | 100 | 5 | 5 |
| 1-49 | 100 | 5 | 5 |
| 1-50 | 100 | 5 | 5 |

TABLE 45-continued

| Compound No. | Dose (gai/10a) | Eo | Mo |
|---|---|---|---|
| 1-51 | 100 | 5 | 5 |
| 1-52 | 100 | 5 | 5 |
| 1-53 | 100 | 5 | 5 |
| 1-54 | 100 | 5 | 5 |
| 1-55 | 100 | 5 | 5 |
| 1-56 | 100 | 5 | 5 |
| 1-57 | 100 | 5 | 5 |
| 1-58 | 100 | 5 | 5 |
| 1-59 | 100 | 5 | 5 |
| 1-60 | 100 | 5 | 5 |
| 1-61 | 100 | 5 | 5 |
| 1-62 | 100 | 5 | 5 |
| 1-63 | 100 | 5 | 5 |
| 1-64 | 100 | 5 | 5 |
| 1-65 | 100 | 5 | 5 |

TABLE 46

| Compound No. | Dose (gai/10a) | Eo | Mo |
|---|---|---|---|
| 1-66 | 100 | 5 | 5 |
| 1-67 | 100 | 5 | 5 |
| 1-68 | 100 | 5 | 5 |
| 1-70 | 100 | 5 | 5 |
| 1-71 | 100 | 5 | 5 |
| 1-72 | 100 | 5 | 5 |
| 1-74 | 100 | 5 | 5 |
| 1-75 | 100 | 5 | 5 |
| 1-76 | 100 | 5 | 5 |
| 1-78 | 100 | 5 | 5 |
| 1-80 | 100 | 5 | 5 |
| 1-81 | 100 | 5 | 5 |
| 1-82 | 100 | 5 | 5 |
| 1-83 | 100 | 5 | 5 |
| 1-84 | 100 | 5 | 5 |
| 1-85 | 100 | 5 | 5 |
| 1-86 | 100 | 5 | 5 |
| 1-87 | 100 | 5 | 5 |
| 1-88 | 100 | 5 | 5 |
| 1-89 | 100 | 5 | 5 |
| 1-90 | 100 | 5 | 5 |
| 1-91 | 100 | 5 | 5 |
| 1-93 | 100 | 5 | 5 |
| 1-94 | 100 | 5 | 5 |
| 1-95 | 100 | 5 | 5 |
| 1-96 | 100 | 5 | 5 |
| 1-97 | 100 | 5 | 5 |
| 1-98 | 100 | 5 | 5 |
| 1-99 | 100 | 5 | 5 |
| 1-100 | 100 | 5 | 5 |
| 1-101 | 100 | 5 | 5 |
| 1-102 | 100 | 5 | 5 |
| 1-103 | 100 | 5 | 5 |
| 1-104 | 100 | 5 | 5 |
| 1-105 | 100 | 5 | 5 |
| 1-106 | 100 | 5 | 5 |
| 1-107 | 100 | 5 | 5 |
| 1-111 | 100 | 5 | 4 |
| 1-112 | 100 | 5 | 5 |
| 1-113 | 100 | 5 | 5 |
| 1-114 | 100 | 5 | 5 |
| 1-115 | 100 | 5 | 5 |
| 1-116 | 100 | 5 | 5 |
| 1-118 | 100 | 5 | 5 |
| 1-119 | 100 | 5 | 5 |
| 1-120 | 100 | 5 | 5 |
| 1-121 | 100 | 5 | 5 |
| 1-122 | 100 | 5 | 5 |
| 1-123 | 100 | 5 | 5 |
| 1-124 | 100 | 5 | 5 |
| 1-125 | 100 | 5 | 5 |
| 1-126 | 100 | 5 | 5 |
| 1-127 | 100 | 5 | 5 |

TABLE 47

| Compound No. | Dose (gai/10a) | Eo | Mo |
|---|---|---|---|
| 1-128 | 100 | 5 | 4 |
| 1-129 | 100 | 5 | 5 |
| 1-130 | 100 | 5 | 5 |
| 1-131 | 100 | 5 | 5 |
| 1-132 | 100 | 5 | 5 |
| 1-133 | 100 | 5 | 5 |
| 1-134 | 100 | 5 | 5 |
| 1-135 | 100 | 5 | 5 |
| 1-136 | 100 | 5 | 5 |
| 1-137 | 100 | 5 | 5 |
| 1-138 | 100 | 5 | 5 |
| 1-139 | 100 | 5 | 5 |
| 1-140 | 100 | 5 | 5 |
| 1-141 | 100 | 5 | 5 |
| 1-142 | 100 | 5 | 5 |
| 1-143 | 100 | 5 | 5 |
| 1-144 | 100 | 5 | 5 |
| 1-145 | 100 | 5 | 5 |
| 1-146 | 100 | 5 | 5 |
| 1-147 | 100 | 5 | 5 |
| 1-148 | 100 | 5 | 5 |
| 1-150 | 100 | 5 | 5 |
| 1-151 | 100 | 5 | 5 |
| 1-152 | 100 | 5 | 5 |
| 1-153 | 100 | 5 | 5 |
| 1-154 | 100 | 5 | 5 |
| 1-155 | 100 | 5 | 5 |
| 1-156 | 100 | 5 | 5 |
| 1-159 | 100 | 5 | 5 |
| 1-160 | 100 | 5 | 5 |
| 1-161 | 100 | 5 | 5 |
| 1-162 | 100 | 5 | 5 |
| 1-163 | 100 | 5 | 5 |
| 1-164 | 100 | 5 | 5 |
| 1-165 | 100 | 5 | 5 |
| 1-166 | 100 | 5 | 5 |
| 1-167 | 100 | 5 | 5 |
| 1-168 | 100 | 5 | 5 |
| 1-169 | 100 | 5 | 5 |
| 1-170 | 100 | 5 | 5 |
| 1-171 | 100 | 5 | 5 |
| 1-172 | 100 | 5 | 5 |
| 1-173 | 100 | 5 | 5 |
| 1-174 | 100 | 5 | 5 |
| 1-175 | 100 | 5 | 5 |
| 1-177 | 100 | 5 | 5 |
| 1-178 | 100 | 5 | 4 |
| 1-180 | 100 | 5 | 5 |
| 1-181 | 100 | 5 | 5 |
| 1-182 | 100 | 5 | 5 |
| 1-183 | 100 | 5 | 5 |
| 1-184 | 100 | 5 | 5 |
| 1-185 | 100 | 5 | 5 |

TABLE 48

| Compound No. | Dose (gai/10a) | Eo | Mo |
|---|---|---|---|
| 1-186 | 100 | 5 | 5 |
| 1-187 | 100 | 5 | 5 |
| 1-188 | 100 | 5 | 5 |
| 1-189 | 100 | 5 | 5 |
| 1-190 | 100 | 5 | 5 |
| 1-191 | 100 | 5 | 5 |
| 1-192 | 100 | 5 | 5 |
| 1-193 | 100 | 5 | 5 |
| 1-194 | 100 | 5 | 5 |
| 1-195 | 100 | 5 | 5 |
| 1-196 | 100 | 5 | 5 |
| 1-197 | 100 | 5 | 5 |
| 1-198 | 100 | 5 | 5 |
| 1-200 | 100 | 5 | 5 |

TABLE 48-continued

| Compound No. | Dose (gai/10a) | Eo | Mo |
|---|---|---|---|
| 1-214 | 100 | 5 | 5 |
| 1-217 | 100 | 5 | 5 |
| 1-218 | 100 | 5 | 5 |
| 1-219 | 100 | 5 | 5 |
| 1-220 | 100 | 5 | 5 |
| 1-221 | 100 | 5 | 5 |
| 1-222 | 100 | 5 | 5 |
| 1-225 | 100 | 5 | 5 |
| 1-226 | 100 | 5 | 5 |
| 1-228 | 100 | 5 | 5 |
| 1-234 | 100 | 5 | 5 |
| 1-249 | 100 | 5 | 5 |
| 1-250 | 100 | 5 | 5 |
| 1-251 | 100 | 5 | 5 |
| 1-254 | 100 | 5 | 5 |
| 1-265 | 100 | 5 | 5 |
| 1-266 | 100 | 5 | 5 |
| 1-267 | 100 | 5 | 5 |
| 1-270 | 100 | 5 | 5 |
| 1-273 | 100 | 5 | 5 |
| 1-274 | 100 | 5 | 5 |
| 1-305 | 100 | 5 | 5 |
| 1-306 | 100 | 5 | 5 |
| 1-307 | 100 | 5 | 5 |
| 1-310 | 100 | 5 | 5 |
| 1-321 | 100 | 5 | 5 |
| 1-322 | 100 | 5 | 5 |
| 1-323 | 100 | 5 | 5 |
| 1-324 | 100 | 5 | 5 |
| 1-325 | 100 | 5 | 5 |
| 1-327 | 100 | 5 | 5 |
| 1-328 | 100 | 5 | 5 |
| 1-329 | 100 | 5 | 5 |
| 1-330 | 100 | 5 | 5 |
| 1-331 | 100 | 5 | 5 |
| 1-333 | 100 | 5 | 5 |
| 1-334 | 100 | 5 | 5 |
| 1-335 | 100 | 5 | 5 |
| 1-401 | 100 | 5 | 5 |

TABLE 49

| Compound No. | Dose (gai/10a) | Eo | Mo |
|---|---|---|---|
| 1-402 | 100 | 5 | 5 |
| 1-403 | 100 | 5 | 5 |
| 1-404 | 100 | 5 | 5 |
| 1-407 | 100 | 5 | 5 |
| 1-409 | 100 | 5 | 5 |
| 1-410 | 100 | 5 | 5 |
| 1-411 | 100 | 5 | 5 |
| 1-412 | 100 | 5 | 5 |
| 1-413 | 100 | 5 | 5 |
| 1-414 | 100 | 5 | 5 |
| 1-415 | 100 | 5 | 5 |
| 1-416 | 100 | 5 | 5 |
| 1-417 | 100 | 5 | 5 |
| 1-418 | 100 | 5 | 5 |
| 1-419 | 100 | 5 | 5 |
| 1-420 | 100 | 5 | 5 |
| 1-421 | 100 | 5 | 5 |
| 1-422 | 100 | 5 | 5 |
| 1-424 | 100 | 5 | 5 |
| 1-425 | 100 | 5 | 5 |
| 1-426 | 100 | 5 | 5 |
| 1-427 | 100 | 5 | 5 |
| 1-428 | 100 | 5 | 5 |
| 1-429 | 100 | 5 | 5 |
| 1-430 | 100 | 5 | 5 |
| 1-431 | 100 | 5 | 5 |
| 1-432 | 100 | 5 | 5 |
| 1-433 | 100 | 5 | 5 |
| 1-434 | 100 | 5 | 5 |

TABLE 49-continued

| Compound No. | Dose (gai/10a) | Eo | Mo |
|---|---|---|---|
| 1-435 | 100 | 5 | 5 |
| 1-436 | 100 | 5 | 5 |
| 1-437 | 100 | 5 | 5 |
| 1-438 | 100 | 5 | 5 |
| 1-439 | 100 | 5 | 5 |
| 1-441 | 100 | 5 | 5 |
| 1-442 | 100 | 5 | 5 |
| 1-443 | 100 | 5 | 5 |
| 1-444 | 100 | 5 | 5 |
| 1-445 | 100 | 5 | 5 |
| 1-446 | 100 | 5 | 5 |
| 1-447 | 100 | 5 | 5 |
| 1-448 | 100 | 5 | 5 |
| 1-449 | 100 | 5 | 5 |
| 1-450 | 100 | 5 | 5 |
| 1-451 | 100 | 5 | 5 |
| 1-452 | 100 | 5 | 5 |
| 1-454 | 100 | 5 | 5 |
| 1-455 | 100 | 5 | 5 |
| 1-458 | 100 | 5 | 5 |
| 1-459 | 100 | 5 | 5 |
| 1-460 | 100 | 5 | 5 |
| 1-461 | 100 | 5 | 5 |
| 1-463 | 100 | 5 | 5 |

TABLE 50

| Compound No. | Dose (gai/10a) | Eo | Mo |
|---|---|---|---|
| 1-464 | 100 | 5 | 5 |
| 1-465 | 100 | 5 | 5 |
| 1-469 | 100 | 5 | 5 |
| 1-473 | 100 | 5 | 5 |
| 1-476 | 100 | 5 | 5 |
| 1-482 | 100 | 5 | 5 |
| 1-483 | 100 | 5 | 5 |
| 1-484 | 100 | 5 | 5 |
| 1-485 | 100 | 5 | 5 |
| 1-486 | 100 | 5 | 5 |
| 1-487 | 100 | 5 | 5 |
| 1-488 | 100 | 5 | 5 |
| 1-489 | 100 | 5 | 5 |
| 1-490 | 100 | 5 | 5 |
| 1-491 | 100 | 5 | 5 |
| 1-492 | 100 | 5 | 5 |
| 1-493 | 100 | 5 | 5 |
| 1-494 | 100 | 5 | 5 |
| 1-495 | 100 | 5 | 5 |
| 1-496 | 100 | 5 | 5 |
| 1-497 | 100 | 5 | 5 |
| 1-498 | 100 | 5 | 5 |
| 1-499 | 100 | 5 | 5 |
| 1-500 | 100 | 5 | 5 |
| 1-501 | 100 | 5 | 5 |
| 1-502 | 100 | 5 | 5 |
| 1-504 | 100 | 5 | 5 |
| 1-505 | 100 | 5 | 5 |
| 1-506 | 100 | 5 | 5 |
| 1-507 | 100 | 5 | 5 |
| 1-510 | 100 | 5 | 5 |
| 1-511 | 100 | 5 | 5 |
| 1-517 | 100 | 5 | 5 |
| 1-518 | 100 | 5 | 5 |
| 1-519 | 100 | 5 | 5 |
| 1-520 | 100 | 5 | 5 |
| 1-521 | 100 | 5 | 5 |
| 1-524 | 100 | 5 | 5 |
| 1-526 | 100 | 5 | 5 |
| 1-527 | 100 | 5 | 5 |
| 1-528 | 100 | 5 | 5 |
| 1-529 | 100 | 5 | 5 |
| 1-530 | 100 | 5 | 5 |
| 1-532 | 100 | 5 | 5 |

TABLE 50-continued

| Compound No. | Dose (gai/10a) | Eo | Mo |
|---|---|---|---|
| 1-533 | 100 | 5 | 5 |
| 1-535 | 100 | 5 | 5 |
| 1-536 | 100 | 5 | 5 |
| 1-537 | 100 | 5 | 5 |
| 1-538 | 100 | 5 | 5 |
| 1-539 | 100 | 5 | 5 |
| 1-540 | 100 | 5 | 5 |
| 1-541 | 100 | 5 | 5 |
| 1-546 | 100 | 5 | 5 |

TABLE 51

| Compound No. | Dose (gai/10a) | Eo | Mo |
|---|---|---|---|
| 1-547 | 100 | 5 | 5 |
| 1-548 | 100 | 5 | 5 |
| 1-549 | 100 | 5 | 5 |
| 1-550 | 100 | 5 | 5 |
| 1-551 | 100 | 5 | 5 |
| 1-553 | 100 | 5 | 5 |
| 1-555 | 100 | 5 | 5 |
| 1-558 | 100 | 5 | 5 |
| 1-559 | 100 | 5 | 5 |
| 1-560 | 100 | 5 | 5 |
| 1-561 | 100 | 5 | 5 |
| 1-562 | 100 | 5 | 5 |
| 1-563 | 100 | 5 | 5 |
| 1-565 | 100 | 5 | 5 |
| 1-566 | 100 | 5 | 5 |
| 1-567 | 100 | 5 | 5 |
| 1-569 | 100 | 5 | 5 |
| 1-571 | 100 | 5 | 4 |
| 1-572 | 100 | 5 | 5 |
| 1-573 | 100 | 5 | 5 |
| 1-579 | 100 | 5 | 5 |
| 1-584 | 100 | 5 | 5 |
| 1-586 | 100 | 5 | 5 |
| 1-589 | 100 | 5 | 5 |
| 1-591 | 100 | 5 | 5 |
| 1-592 | 100 | 5 | 5 |
| 1-593 | 100 | 5 | 5 |
| 1-594 | 100 | 5 | 5 |
| 1-595 | 100 | 5 | 5 |
| 1-597 | 100 | 5 | 5 |
| 1-598 | 100 | 5 | 5 |
| 1-599 | 100 | 5 | 5 |
| 1-600 | 100 | 5 | 5 |
| 1-602 | 100 | 5 | 5 |
| 1-603 | 100 | 5 | 5 |
| 1-604 | 100 | 5 | 5 |
| 1-606 | 100 | 5 | 5 |
| 1-607 | 100 | 5 | 5 |
| 1-608 | 100 | 5 | 5 |
| 1-609 | 100 | 5 | 5 |
| 1-611 | 100 | 5 | 5 |
| 1-614 | 100 | 5 | 5 |
| 1-615 | 100 | 5 | 5 |
| 1-624 | 100 | 5 | 5 |
| 1-626 | 100 | 5 | 5 |
| 1-627 | 100 | 5 | 5 |
| 1-637 | 100 | 5 | 5 |
| 1-639 | 100 | 5 | 5 |
| 1-640 | 100 | 5 | 5 |
| 1-641 | 100 | 5 | 5 |
| 2-1 | 100 | 5 | 5 |
| 2-2 | 100 | 5 | 5 |
| 2-3 | 100 | 5 | 5 |

TABLE 52

| Compound No. | Dose (gai/10a) | Eo | Mo |
|---|---|---|---|
| 2-5 | 100 | 5 | 5 |
| 2-6 | 100 | 5 | 5 |
| 2-7 | 100 | 5 | 5 |
| 2-8 | 100 | 5 | 5 |
| 2-9 | 100 | 5 | 5 |
| 2-10 | 100 | 5 | 5 |
| 2-11 | 100 | 5 | 5 |
| 2-12 | 100 | 5 | 5 |
| 2-13 | 100 | 5 | 5 |
| 2-14 | 100 | 5 | 5 |
| 2-19 | 100 | 5 | 5 |
| 2-20 | 100 | 5 | 5 |
| 2-23 | 100 | 5 | 5 |
| 2-24 | 100 | 5 | 5 |
| 2-25 | 100 | 5 | 5 |
| 2-31 | 100 | 5 | 5 |
| 2-32 | 100 | 5 | 5 |
| 2-41 | 100 | 5 | 5 |
| 2-42 | 100 | 5 | 5 |
| 2-44 | 100 | 5 | 5 |
| 2-46 | 100 | 5 | 5 |
| 2-48 | 100 | 5 | 5 |
| 2-50 | 100 | 5 | 5 |
| 2-51 | 100 | 5 | 5 |
| 2-52 | 100 | 5 | 5 |
| 2-53 | 100 | 5 | 5 |
| 2-54 | 100 | 5 | 5 |
| 2-55 | 100 | 5 | 5 |
| 2-56 | 100 | 5 | 5 |
| 2-57 | 100 | 5 | 5 |
| 2-58 | 100 | 5 | 5 |
| 2-59 | 100 | 5 | 5 |
| 2-60 | 100 | 5 | 5 |
| 2-61 | 100 | 5 | 5 |
| 2-62 | 100 | 5 | 5 |
| 2-63 | 100 | 5 | 5 |
| 2-71 | 100 | 5 | 5 |
| 2-72 | 100 | 5 | 5 |
| 2-73 | 100 | 5 | 5 |
| 2-74 | 100 | 5 | 5 |
| 2-75 | 100 | 5 | 5 |
| 2-77 | 100 | 5 | 5 |
| 2-78 | 100 | 5 | 5 |
| 2-80 | 100 | 5 | 4 |
| 4-1 | 100 | 5 | 5 |
| 4-2 | 100 | 5 | 5 |

TEST EXAMPLE 2: TEST OF HERBICIDAL EFFECTS BY UPLAND SOIL TREATMENT

In a 80 cm² plastic pot, upland soil was filled, and seeds of barnyard grass (Ec) and green foxtail (Se) were sown and covered with soil. A wettable powder prepared in accordance with Formulation Example 1 was diluted with water and uniformly applied to the soil surface by means of a small size spray at a rate of 100 l per 10 ares, so that the dose of the active ingredient would be 100 g per 10 ares. Thereafter, cultivation was carried out in a green house, and on the 21st day after the treatment, the herbicidal effects were examined in accordance with the standards as identified in Table 44. The results are shown in Tables 53 to 60.

TABLE 53

| Compound No. | Dose (gai/10a) | Ec | Se |
|---|---|---|---|
| 1-8 | 100 | 5 | 5 |
| 1-9 | 100 | 5 | 5 |
| 1-10 | 100 | 4 | 4 |

TABLE 53-continued

| Compound No. | Dose (gai/10a) | Ec | Se |
|---|---|---|---|
| 1-12 | 100 | 5 | 5 |
| 1-13 | 100 | 5 | 5 |
| 1-15 | 100 | 5 | 5 |
| 1-16 | 100 | 4 | 5 |
| 1-17 | 100 | 4 | 4 |
| 1-20 | 100 | 5 | 5 |
| 1-21 | 100 | 5 | 5 |
| 1-22 | 100 | 5 | 5 |
| 1-23 | 100 | 5 | 5 |
| 1-24 | 100 | 5 | 5 |
| 1-25 | 100 | 5 | 5 |
| 1-26 | 100 | 5 | 5 |
| 1-27 | 100 | 5 | 5 |
| 1-32 | 100 | 5 | 5 |
| 1-33 | 100 | 5 | 5 |
| 1-34 | 100 | 5 | 5 |
| 1-35 | 100 | 5 | 5 |
| 1-36 | 100 | 5 | 5 |
| 1-37 | 100 | 5 | 5 |
| 1-38 | 100 | 5 | 4 |
| 1-40 | 100 | 5 | 4 |
| 1-41 | 100 | 5 | 5 |
| 1-42 | 100 | 5 | 5 |
| 1-45 | 100 | 5 | 5 |
| 1-46 | 100 | 5 | 5 |
| 1-47 | 100 | 5 | 5 |
| 1-48 | 100 | 5 | 5 |
| 1-49 | 100 | 5 | 4 |
| 1-50 | 100 | 5 | 5 |
| 1-51 | 100 | 5 | 5 |
| 1-52 | 100 | 5 | 5 |
| 1-53 | 100 | 5 | 5 |
| 1-54 | 100 | 5 | 5 |
| 1-55 | 100 | 5 | 5 |
| 1-56 | 100 | 5 | 5 |
| 1-57 | 100 | 5 | 5 |
| 1-58 | 100 | 5 | 5 |
| 1-59 | 100 | 5 | 5 |
| 1-60 | 100 | 5 | 5 |
| 1-61 | 100 | 5 | 5 |
| 1-62 | 100 | 4 | 4 |
| 1-63 | 100 | 5 | 5 |
| 1-64 | 100 | 5 | 5 |
| 1-65 | 100 | 5 | 5 |
| 1-66 | 100 | 5 | 5 |
| 1-67 | 100 | 5 | 5 |
| 1-68 | 100 | 5 | 5 |
| 1-70 | 100 | 5 | 5 |
| 1-71 | 100 | 5 | 5 |
| 1-72 | 100 | 5 | 4 |

TABLE 54

| Compound No. | Dose (gai/10a) | Ec | Se |
|---|---|---|---|
| 1-74 | 100 | 5 | 5 |
| 1-75 | 100 | 5 | 5 |
| 1-76 | 100 | 5 | 5 |
| 1-77 | 100 | 5 | 5 |
| 1-78 | 100 | 5 | 5 |
| 1-80 | 100 | 5 | 5 |
| 1-81 | 100 | 5 | 5 |
| 1-83 | 100 | 5 | 5 |
| 1-85 | 100 | 5 | 5 |
| 1-87 | 100 | 5 | 5 |
| 1-88 | 100 | 5 | 5 |
| 1-89 | 100 | 5 | 5 |
| 1-90 | 100 | 5 | 5 |
| 1-91 | 100 | 4 | 5 |
| 1-92 | 100 | 5 | 5 |
| 1-95 | 100 | 5 | 5 |
| 1-96 | 100 | 5 | 5 |
| 1-97 | 100 | 5 | 5 |

TABLE 54-continued

| Compound No. | Dose (gai/10a) | Ec | Se |
|---|---|---|---|
| 1-98 | 100 | 5 | 5 |
| 1-99 | 100 | 5 | 5 |
| 1-100 | 100 | 5 | 5 |
| 1-101 | 100 | 5 | 5 |
| 1-102 | 100 | 5 | 5 |
| 1-103 | 100 | 5 | 5 |
| 1-105 | 100 | 5 | 5 |
| 1-106 | 100 | 5 | 4 |
| 1-11 | 100 | 5 | 5 |
| 1-112 | 100 | 5 | 5 |
| 1-113 | 100 | 5 | 4 |
| 1-114 | 100 | 5 | 5 |
| 1-115 | 100 | 5 | 5 |
| 1-116 | 100 | 5 | 4 |
| 1-118 | 100 | 5 | 5 |
| 1-119 | 100 | 5 | 4 |
| 1-120 | 100 | 5 | 4 |
| 1-121 | 100 | 5 | 4 |
| 1-122 | 100 | 5 | 5 |
| 1-123 | 100 | 5 | 5 |
| 1-124 | 100 | 5 | 5 |
| 1-125 | 100 | 5 | 5 |
| 1-126 | 100 | 5 | 5 |
| 1-127 | 100 | 5 | 5 |
| 1-128 | 100 | 5 | 5 |
| 1-130 | 100 | 5 | 5 |
| 1-131 | 100 | 5 | 5 |
| 1-133 | 100 | 5 | 5 |
| 1-134 | 100 | 5 | 5 |
| 1-135 | 100 | 5 | 5 |
| 1-136 | 100 | 5 | 5 |
| 1-137 | 100 | 5 | 5 |
| 1-138 | 100 | 5 | 5 |
| 1-139 | 100 | 5 | 5 |
| 1-140 | 100 | 5 | 5 |

TABLE 55

| Compound No. | Dose (gai/10a) | Ec | Se |
|---|---|---|---|
| 1-141 | 100 | 5 | 5 |
| 1-142 | 100 | 5 | 5 |
| 1-143 | 100 | 5 | 5 |
| 1-144 | 100 | 5 | 5 |
| 1-145 | 100 | 5 | 5 |
| 1-146 | 100 | 4 | 4 |
| 1-147 | 100 | 5 | 5 |
| 1-148 | 100 | 5 | 5 |
| 1-150 | 100 | 5 | 5 |
| 1-151 | 100 | 5 | 5 |
| 1-152 | 100 | 5 | 5 |
| 1-153 | 100 | 5 | 5 |
| 1-155 | 100 | 4 | 4 |
| 1-159 | 100 | 5 | 5 |
| 1-160 | 100 | 5 | 5 |
| 1-161 | 100 | 5 | 5 |
| 1-162 | 100 | 5 | 4 |
| 1-163 | 100 | 5 | 5 |
| 1-164 | 100 | 5 | 5 |
| 1-165 | 100 | 5 | 5 |
| 1-166 | 100 | 5 | 5 |
| 1-167 | 100 | 5 | 5 |
| 1-168 | 100 | 5 | 5 |
| 1-169 | 100 | 5 | 5 |
| 1-170 | 100 | 5 | 5 |
| 1-171 | 100 | 5 | 4 |
| 1-172 | 100 | 5 | 5 |
| 1-173 | 100 | 5 | 5 |
| 1-174 | 100 | 5 | 5 |
| 1-177 | 100 | 4 | 4 |
| 1-180 | 100 | 5 | 5 |
| 1-181 | 100 | 5 | 5 |
| 1-182 | 100 | 5 | 5 |

TABLE 55-continued

| Compound No. | Dose (gai/10a) | Ec | Se |
|---|---|---|---|
| 1-186 | 100 | 5 | 5 |
| 1-187 | 100 | 5 | 5 |
| 1-190 | 100 | 4 | 4 |
| 1-192 | 100 | 5 | 5 |
| 1-193 | 100 | 5 | 5 |
| 1-194 | 100 | 5 | 5 |
| 1-195 | 100 | 5 | 5 |
| 1-196 | 100 | 5 | 5 |
| 1-197 | 100 | 5 | 5 |
| 1-198 | 100 | 5 | 5 |
| 1-200 | 100 | 5 | 5 |
| 1-214 | 100 | 5 | 5 |
| 1-217 | 100 | 5 | 5 |
| 1-218 | 100 | 5 | 5 |
| 1-219 | 100 | 5 | 5 |
| 1-220 | 100 | 5 | 5 |
| 1-222 | 100 | 5 | 5 |
| 1-225 | 100 | 5 | 5 |
| 1-226 | 100 | 5 | 4 |
| 1-228 | 100 | 5 | 5 |

TABLE 56

| Compound No. | Dose (gai/10a) | Ec | Se |
|---|---|---|---|
| 1-234 | 100 | 5 | 5 |
| 1-249 | 100 | 5 | 5 |
| 1-250 | 100 | 4 | 5 |
| 1-251 | 100 | 5 | 5 |
| 1-254 | 100 | 5 | 5 |
| 1-265 | 100 | 5 | 5 |
| 1-266 | 100 | 5 | 5 |
| 1-267 | 100 | 5 | 5 |
| 1-270 | 100 | 5 | 5 |
| 1-273 | 100 | 5 | 5 |
| 1-274 | 100 | 5 | 5 |
| 1-305 | 100 | 5 | 5 |
| 1-306 | 100 | 5 | 5 |
| 1-307 | 100 | 5 | 5 |
| 1-310 | 100 | 5 | 5 |
| 1-321 | 100 | 5 | 5 |
| 1-323 | 100 | 4 | 4 |
| 1-326 | 100 | 4 | 4 |
| 1-327 | 100 | 5 | 5 |
| 1-328 | 100 | 5 | 5 |
| 1-329 | 100 | 5 | 5 |
| 1-330 | 100 | 5 | 5 |
| 1-331 | 100 | 5 | 5 |
| 1-332 | 100 | 5 | 5 |
| 1-333 | 100 | 5 | 5 |
| 1-334 | 100 | 5 | 5 |
| 1-335 | 100 | 5 | 5 |
| 1-401 | 100 | 5 | 5 |
| 1-402 | 100 | 5 | 5 |
| 1-403 | 100 | 5 | 5 |
| 1-404 | 100 | 5 | 5 |
| 1-407 | 100 | 5 | 5 |
| 1-409 | 100 | 5 | 5 |
| 1-410 | 100 | 5 | 5 |
| 1-411 | 100 | 5 | 5 |
| 1-412 | 100 | 5 | 5 |
| 1-414 | 100 | 4 | 5 |
| 1-416 | 100 | 5 | 5 |
| 1-417 | 100 | 5 | 5 |
| 1-418 | 100 | 5 | 5 |
| 1-419 | 100 | 5 | 5 |
| 1-424 | 100 | 5 | 5 |
| 1-425 | 100 | 5 | 5 |
| 1-426 | 100 | 5 | 5 |
| 1-427 | 100 | 5 | 5 |
| 1-428 | 100 | 5 | 5 |
| 1-429 | 100 | 5 | 5 |
| 1-430 | 100 | 5 | 5 |

TABLE 56-continued

| Compound No. | Dose (gai/10a) | Ec | Se |
|---|---|---|---|
| 1-431 | 100 | 5 | 5 |
| 1-432 | 100 | 5 | 5 |
| 1-433 | 100 | 5 | 5 |
| 1-434 | 100 | 5 | 5 |
| 1-435 | 100 | 5 | 5 |

TABLE 57

| Compound No. | Dose (gai/10a) | Ec | Se |
|---|---|---|---|
| 1-436 | 100 | 5 | 5 |
| 1-437 | 100 | 5 | 5 |
| 1-438 | 100 | 5 | 5 |
| 1-439 | 100 | 5 | 4 |
| 1-441 | 100 | 5 | 5 |
| 1-442 | 100 | 5 | 5 |
| 1-443 | 100 | 5 | 5 |
| 1-444 | 100 | 5 | 5 |
| 1-445 | 100 | 5 | 5 |
| 1-446 | 100 | 5 | 5 |
| 1-447 | 100 | 5 | 5 |
| 1-448 | 100 | 5 | 4 |
| 1-449 | 100 | 5 | 5 |
| 1-450 | 100 | 5 | 5 |
| 1-451 | 100 | 5 | 5 |
| 1-452 | 100 | 5 | 5 |
| 1-454 | 100 | 4 | 5 |
| 1-455 | 100 | 5 | 5 |
| 1-458 | 100 | 5 | 4 |
| 1-459 | 100 | 5 | 5 |
| 1-460 | 100 | 5 | 5 |
| 1-461 | 100 | 5 | 5 |
| 1-463 | 100 | 4 | 5 |
| 1-464 | 100 | 5 | 5 |
| 1-465 | 100 | 5 | 5 |
| 1-466 | 100 | 4 | 4 |
| 1-471 | 100 | 5 | 4 |
| 1-473 | 100 | 5 | 4 |
| 1-476 | 100 | 5 | 5 |
| 1-482 | 100 | 5 | 5 |
| 1-483 | 100 | 5 | 4 |
| 1-484 | 100 | 5 | 5 |
| 1-485 | 100 | 5 | 5 |
| 1-488 | 100 | 5 | 5 |
| 1-489 | 100 | 5 | 5 |
| 1-490 | 100 | 5 | 5 |
| 1-492 | 100 | 5 | 5 |
| 1-493 | 100 | 5 | 5 |
| 1-494 | 100 | 5 | 5 |
| 1-495 | 100 | 5 | 5 |
| 1-496 | 100 | 5 | 4 |
| 1-497 | 100 | 5 | 5 |
| 1-498 | 100 | 5 | 5 |
| 1-499 | 100 | 5 | 4 |
| 1-502 | 100 | 4 | 4 |
| 1-504 | 100 | 5 | 5 |
| 1-505 | 100 | 5 | 5 |
| 1-506 | 100 | 5 | 5 |
| 1-507 | 100 | 5 | 5 |
| 1-508 | 100 | 5 | 5 |
| 1-511 | 100 | 4 | 4 |
| 1-517 | 100 | 5 | 5 |
| 1-518 | 100 | 5 | 5 |

TABLE 58

| Compound No. | Dose (gai/10a) | Ec | Se |
|---|---|---|---|
| 1-519 | 100 | 5 | 5 |
| 1-520 | 100 | 5 | 5 |

TABLE 58-continued

| Compound No. | Dose (gai/10a) | Ec | Se |
|---|---|---|---|
| 1-521 | 100 | 5 | 5 |
| 1-523 | 100 | 4 | 5 |
| 1-524 | 100 | 5 | 5 |
| 1-526 | 100 | 5 | 5 |
| 1-527 | 100 | 5 | 5 |
| 1-528 | 100 | 5 | 5 |
| 1-529 | 100 | 5 | 5 |
| 1-530 | 100 | 5 | 5 |
| 1-531 | 100 | 4 | 4 |
| 1-532 | 100 | 5 | 5 |
| 1-533 | 100 | 5 | 5 |
| 1-535 | 100 | 5 | 5 |
| 1-536 | 100 | 5 | 5 |
| 1-537 | 100 | 5 | 5 |
| 1-538 | 100 | 5 | 5 |
| 1-539 | 100 | 5 | 5 |
| 1-540 | 100 | 5 | 5 |
| 1-541 | 100 | 5 | 4 |
| 1-546 | 100 | 5 | 5 |
| 1-547 | 100 | 5 | 5 |
| 1-548 | 100 | 5 | 5 |
| 1-549 | 100 | 5 | 5 |
| 1-550 | 100 | 5 | 5 |
| 1-551 | 100 | 5 | 5 |
| 1-553 | 100 | 5 | 5 |
| 1-555 | 100 | 5 | 5 |
| 1-558 | 100 | 5 | 5 |
| 1-559 | 100 | 5 | 5 |
| 1-560 | 100 | 5 | 5 |
| 1-561 | 100 | 5 | 4 |
| 1-562 | 100 | 5 | 5 |
| 1-563 | 100 | 5 | 5 |
| 1-565 | 100 | 5 | 5 |
| 1-566 | 100 | 5 | 5 |
| 1-567 | 100 | 5 | 5 |
| 1-569 | 100 | 5 | 5 |
| 1-571 | 100 | 5 | 5 |
| 1-572 | 100 | 5 | 5 |
| 1-573 | 100 | 5 | 4 |
| 1-579 | 100 | 5 | 5 |
| 1-584 | 100 | 5 | 5 |
| 1-586 | 100 | 5 | 5 |
| 1-589 | 100 | 5 | 5 |
| 1-591 | 100 | 5 | 5 |
| 1-592 | 100 | 5 | 5 |
| 1-594 | 100 | 5 | 5 |
| 1-597 | 100 | 4 | 4 |
| 1-598 | 100 | 5 | 4 |
| 1-600 | 100 | 4 | 5 |
| 1-602 | 100 | 5 | 5 |
| 1-603 | 100 | 4 | 4 |

TABLE 59

| Compound No. | Dose (gai/10a) | Ec | Se |
|---|---|---|---|
| 1-604 | 100 | 5 | 4 |
| 1-606 | 100 | 5 | 5 |
| 1-607 | 100 | 4 | 4 |
| 1-608 | 100 | 5 | 5 |
| 1-609 | 100 | 5 | 4 |
| 1-611 | 100 | 5 | 5 |
| 1-614 | 100 | 5 | 5 |
| 1-616 | 100 | 5 | 5 |
| 1-617 | 100 | 5 | 5 |
| 1-618 | 100 | 5 | 5 |
| 1-619 | 100 | 5 | 5 |
| 1-620 | 100 | 5 | 5 |
| 1-621 | 100 | 5 | 5 |
| 1-622 | 100 | 4 | 5 |
| 1-623 | 100 | 5 | 4 |
| 1-624 | 100 | 5 | 5 |
| 1-625 | 100 | 4 | 5 |

TABLE 59-continued

| Compound No. | Dose (gai/10a) | Ec | Se |
|---|---|---|---|
| 1-626 | 100 | 5 | 4 |
| 1-627 | 100 | 5 | 5 |
| 1-636 | 100 | 4 | 4 |
| 1-639 | 100 | 5 | 5 |
| 1-640 | 100 | 4 | 4 |
| 1-641 | 100 | 5 | 4 |
| 1-642 | 100 | 4 | 4 |
| 1-646 | 100 | 4 | 4 |
| 2-1 | 100 | 5 | 4 |
| 2-2 | 100 | 5 | 4 |
| 2-6 | 100 | 5 | 4 |
| 2-7 | 100 | 5 | 5 |
| 2-8 | 100 | 5 | 5 |
| 2-9 | 100 | 5 | 5 |
| 2-10 | 100 | 5 | 5 |
| 2-11 | 100 | 5 | 5 |
| 2-12 | 100 | 5 | 5 |
| 2-13 | 100 | 5 | 5 |
| 2-14 | 100 | 5 | 5 |
| 2-19 | 100 | 5 | 5 |
| 2-20 | 100 | 5 | 5 |
| 2-23 | 100 | 5 | 5 |
| 2-24 | 100 | 5 | 5 |
| 2-25 | 100 | 5 | 5 |
| 2-31 | 100 | 5 | 5 |
| 2-32 | 100 | 5 | 5 |
| 2-44 | 100 | 5 | 5 |
| 2-46 | 100 | 5 | 5 |
| 2-47 | 100 | 4 | 5 |
| 2-50 | 100 | 5 | 5 |
| 2-51 | 100 | 5 | 5 |
| 2-52 | 100 | 5 | 5 |
| 2-53 | 100 | 5 | 5 |
| 2-54 | 100 | 5 | 5 |
| 2-55 | 100 | 5 | 5 |
| 2-56 | 100 | 5 | 5 |

TABLE 60

| Compound No. | Dose (gai/10a) | Ec | Se |
|---|---|---|---|
| 2-57 | 100 | 5 | 5 |
| 2-58 | 100 | 5 | 5 |
| 2-59 | 100 | 5 | 4 |
| 2-60 | 100 | 5 | 5 |
| 2-61 | 100 | 5 | 5 |
| 2-62 | 100 | 5 | 5 |
| 2-63 | 100 | 5 | 4 |
| 2-71 | 100 | 5 | 5 |
| 2-72 | 100 | 5 | 5 |
| 2-73 | 100 | 5 | 5 |
| 2-74 | 100 | 5 | 5 |
| 2-75 | 100 | 5 | 5 |
| 2-77 | 100 | 5 | 5 |
| 2-78 | 100 | 5 | 5 |
| 2-79 | 100 | 5 | 5 |
| 4-1 | 100 | 5 | 5 |
| 4-2 | 100 | 5 | 4 |

TEST EXAMPLE 3: TEST OF HERBICIDAL EFFECTS BY FOLIAGE TREATMENT IN UPLAND FIELD

In a 80 cm$^2$ plastic pot, upland soil was filled, and seeds of barnyard grass (Ec) and green foxtail (Se) were sown and cultured in a green house for 2 weeks. Then, a wettable powder prepared in accordance with Formulation Example 1 was diluted with water and applied to the entire foliage from above the plants by means of a small size spray at a rate of 100 l per 10 ares so that the dose of the active ingredient would be 100 g per 10 ares. Thereafter, cultivation was carried out in a green house, and on the 14th day after the treatment, the herbicidal effects were examined in accordance with the standards of Table 44. The results are shown in Tables 61 to 64.

TABLE 61

| Compound No. | Dose (gai/10A) | Ec | Se |
|---|---|---|---|
| 1-1 | 100 | 4 | 4 |
| 1-8 | 100 | 5 | 4 |
| 1-9 | 100 | 5 | 4 |
| 1-10 | 100 | 4 | 4 |
| 1-12 | 100 | 5 | 4 |
| 1-13 | 100 | 5 | 4 |
| 1-21 | 100 | 4 | 4 |
| 1-22 | 100 | 4 | 4 |
| 1-24 | 100 | 4 | 4 |
| 1-26 | 100 | 4 | 4 |
| 1-27 | 100 | 4 | 4 |
| 1-41 | 100 | 5 | 4 |
| 1-42 | 100 | 4 | 4 |
| 1-46 | 100 | 4 | 4 |
| 1-47 | 100 | 4 | 4 |
| 1-48 | 100 | 5 | 4 |
| 1-50 | 100 | 4 | 4 |
| 1-53 | 100 | 4 | 4 |
| 1-54 | 100 | 5 | 4 |
| 1-55 | 100 | 4 | 4 |
| 1-56 | 100 | 4 | 4 |
| 1-57 | 100 | 5 | 4 |
| 1-58 | 100 | 4 | 4 |
| 1-59 | 100 | 4 | 4 |
| 1-60 | 100 | 4 | 4 |
| 1-61 | 100 | 4 | 4 |
| 1-66 | 100 | 5 | 4 |
| 1-78 | 100 | 5 | 4 |
| 1-81 | 100 | 4 | 4 |
| 1-83 | 100 | 5 | 4 |
| 1-87 | 100 | 4 | 4 |
| 1-88 | 100 | 4 | 4 |
| 1-89 | 100 | 5 | 4 |
| 1-92 | 100 | 5 | 4 |
| 1-95 | 100 | 5 | 5 |
| 1-96 | 100 | 5 | 5 |
| 1-98 | 100 | 4 | 4 |
| 1-100 | 100 | 5 | 5 |
| 1-107 | 100 | 4 | 4 |
| 1-111 | 100 | 4 | 4 |
| 1-112 | 100 | 4 | 5 |
| 1-113 | 100 | 4 | 4 |
| 1-122 | 100 | 4 | 4 |
| 1-127 | 100 | 4 | 4 |
| 1-129 | 100 | 5 | 5 |
| 1-133 | 100 | 5 | 4 |
| 1-137 | 100 | 5 | 4 |
| 1-142 | 100 | 4 | 4 |
| 1-143 | 100 | 4 | 4 |
| 1-144 | 100 | 4 | 4 |
| 1-152 | 100 | 4 | 4 |
| 1-153 | 100 | 4 | 4 |
| 1-164 | 100 | 4 | 4 |

TABLE 62

| Compound No. | Dose (gai/10d) | Ec | Se |
|---|---|---|---|
| 1-172 | 100 | 5 | 5 |
| 1-186 | 100 | 5 | 4 |
| 1-192 | 100 | 4 | 4 |
| 1-193 | 100 | 5 | 4 |
| 1-194 | 100 | 5 | 4 |
| 1-195 | 100 | 5 | 4 |
| 1-196 | 100 | 5 | 4 |
| 1-198 | 100 | 4 | 4 |
| 1-214 | 100 | 4 | 4 |
| 1-218 | 100 | 4 | 4 |
| 1-220 | 100 | 5 | 5 |
| 1-221 | 100 | 4 | 4 |
| 1-251 | 100 | 4 | 4 |
| 1-267 | 100 | 4 | 4 |
| 1-270 | 100 | 4 | 4 |
| 1-330 | 100 | 4 | 4 |
| 1-331 | 100 | 4 | 4 |
| 1-333 | 100 | 4 | 4 |
| 1-334 | 100 | 4 | 4 |
| 1-401 | 100 | 5 | 5 |
| 1-402 | 100 | 5 | 4 |
| 1-403 | 100 | 4 | 4 |
| 1-404 | 100 | 5 | 4 |
| 1-407 | 100 | 4 | 4 |
| 1-409 | 100 | 4 | 4 |
| 1-410 | 100 | 4 | 4 |
| 1-411 | 100 | 4 | 4 |
| 1-412 | 100 | 4 | 4 |
| 1-416 | 100 | 5 | 4 |
| 1-417 | 100 | 4 | 5 |
| 1-419 | 100 | 4 | 5 |
| 1-424 | 100 | 4 | 4 |
| 1-426 | 100 | 4 | 4 |
| 1-427 | 100 | 4 | 4 |
| 1-428 | 100 | 4 | 4 |
| 1-430 | 100 | 4 | 4 |
| 1-431 | 100 | 4 | 4 |
| 1-432 | 100 | 5 | 4 |
| 1-434 | 100 | 4 | 4 |
| 1-435 | 100 | 4 | 4 |
| 1-436 | 100 | 4 | 4 |
| 1-437 | 100 | 4 | 4 |
| 1-441 | 100 | 4 | 4 |
| 1-442 | 100 | 4 | 4 |
| 1-445 | 100 | 5 | 5 |
| 1-446 | 100 | 5 | 4 |
| 1-447 | 100 | 5 | 4 |
| 1-449 | 100 | 4 | 4 |
| 1-450 | 100 | 4 | 4 |
| 1-451 | 100 | 4 | 4 |
| 1-452 | 100 | 4 | 4 |
| 1-454 | 100 | 4 | 4 |
| 1-455 | 100 | 4 | 4 |

TABLE 63

| Compound No. | Dose (gai/10a) | Ec | Se |
|---|---|---|---|
| 1-459 | 100 | 4 | 4 |
| 1-461 | 100 | 4 | 4 |
| 1-463 | 100 | 4 | 4 |
| 1-464 | 100 | 4 | 4 |
| 1-473 | 100 | 5 | 4 |
| 1-482 | 100 | 5 | 4 |
| 1-484 | 100 | 5 | 5 |
| 1-486 | 100 | 4 | 4 |
| 1-488 | 100 | 5 | 4 |
| 1-489 | 100 | 4 | 4 |
| 1-490 | 100 | 4 | 4 |
| 1-492 | 100 | 5 | 4 |
| 1-493 | 100 | 4 | 4 |
| 1-494 | 100 | 5 | 4 |
| 1-496 | 100 | 4 | 4 |
| 1-497 | 100 | 4 | 4 |
| 1-504 | 100 | 5 | 4 |
| 1-505 | 100 | 5 | 5 |
| 1-506 | 100 | 4 | 4 |
| 1-507 | 100 | 4 | 4 |
| 1-508 | 100 | 4 | 4 |
| 1-517 | 100 | 4 | 4 |
| 1-519 | 100 | 4 | 4 |
| 1-526 | 100 | 5 | 4 |

TABLE 63-continued

| Compound No. | Dose (gai/10a) | Ec | Se |
|---|---|---|---|
| 1-527 | 100 | 4 | 4 |
| 1-528 | 100 | 4 | 4 |
| 1-529 | 100 | 5 | 4 |
| 1-530 | 100 | 4 | 4 |
| 1-532 | 100 | 5 | 4 |
| 1-536 | 100 | 4 | 4 |
| 1-537 | 100 | 4 | 4 |
| 1-538 | 100 | 4 | 4 |
| 1-539 | 100 | 4 | 4 |
| 1-540 | 100 | 4 | 4 |
| 1-541 | 100 | 4 | 4 |
| 1-546 | 100 | 4 | 4 |
| 1-547 | 100 | 4 | 4 |
| 1-558 | 100 | 4 | 4 |
| 1-559 | 100 | 4 | 4 |
| 1-560 | 100 | 4 | 4 |
| 1-661 | 100 | 5 | 4 |
| 1-563 | 100 | 5 | 4 |
| 1-565 | 100 | 5 | 4 |
| 1-566 | 100 | 4 | 4 |
| 1-569 | 100 | 5 | 4 |
| 1-571 | 100 | 4 | 4 |
| 1-572 | 100 | 4 | 4 |
| 1-579 | 100 | 4 | 4 |
| 1-584 | 100 | 4 | 4 |
| 1-586 | 100 | 5 | 4 |
| 1-589 | 100 | 4 | 4 |
| 1-591 | 100 | 4 | 4 |
| 1-592 | 100 | 5 | 4 |

TABLE 64

| Compound No. | Dose (gai/10a) | Ec | Se |
|---|---|---|---|
| 1-594 | 100 | 5 | 5 |
| 1-598 | 100 | 4 | 4 |
| 1-600 | 100 | 5 | 4 |
| 1-602 | 100 | 4 | 4 |
| 1-606 | 100 | 4 | 4 |
| 1-607 | 100 | 4 | 4 |
| 1-609 | 100 | 4 | 4 |
| 1-611 | 100 | 4 | 4 |
| 1-617 | 100 | 4 | 4 |
| 1-619 | 100 | 4 | 4 |
| 1-622 | 100 | 4 | 4 |
| 1-642 | 100 | 4 | 4 |
| 2-11 | 100 | 5 | 4 |
| 2-12 | 100 | 5 | 4 |
| 2-23 | 100 | 4 | 4 |
| 2-25 | 100 | 5 | 4 |
| 2-46 | 100 | 4 | 4 |
| 2-50 | 100 | 4 | 4 |
| 2-51 | 100 | 4 | 4 |
| 2-53 | 100 | 4 | 4 |
| 2-57 | 100 | 5 | 5 |
| 2-60 | 100 | 4 | 4 |
| 2-61 | 100 | 4 | 4 |
| 2-62 | 100 | 4 | 4 |
| 2-71 | 100 | 5 | 4 |
| 2-74 | 100 | 4 | 4 |
| 2-75 | 100 | 5 | 4 |
| 2-79 | 100 | 4 | 4 |
| 4-2 | 100 | 5 | 4 |

TEST EXAMPLE 4: TEST OF SELECTIVITY FOR A CROP PLANT BY FLOODED PADDY FIELD TREATMENT

In a 100 cm² plastic pot, a paddy field soil was filled and paddled. Then, seeds of barnyard grass (Eo) and monochoria (Mo) were sown, and rice (Or) of second leaf stage was transplanted, and water was introduced to a depth of 3 cm. Next day, a wettable powder prepared in accordance with Formulation Example 1 was diluted with water and drop-wise applied to the water surface. The dose was 25 g of the active ingredient per 10 ares. Thereafter, cultivation was carried out in a green house, and on the 21st day after the treatment, the herbicidal effects were examined in accordance with the standards of Table 44. The results are shown in Tables 65 to 69.

TABLE 65

| Compound No. | Dose (gai/10s) | Eo | Mo | Or |
|---|---|---|---|---|
| 1-4 | 25 | 5 | 4 | 1 |
| 1-13 | 25 | 5 | 5 | 1 |
| 1-16 | 25 | 5 | 5 | 1 |
| 1-17 | 25 | 5 | 5 | 1 |
| 1-18 | 25 | 5 | 4 | 1 |
| 1-20 | 25 | 5 | 5 | 1 |
| 1-21 | 25 | 5 | 5 | 1 |
| 1-22 | 25 | 5 | 5 | 1 |
| 1-23 | 25 | 5 | 5 | 1 |
| 1-26 | 25 | 5 | 5 | 1 |
| 1-33 | 25 | 5 | 5 | 1 |
| 1-34 | 25 | 5 | 5 | 1 |
| 1-36 | 25 | 5 | 5 | 1 |
| 1-38 | 25 | 5 | 5 | 0 |
| 1-39 | 25 | 5 | 5 | 0 |
| 1-40 | 25 | 5 | 5 | 0 |
| 1-41 | 25 | 5 | 5 | 0 |
| 1-42 | 25 | 5 | 5 | 0 |
| 1-43 | 25 | 5 | 5 | 1 |
| 1-44 | 25 | 5 | 5 | 0 |
| 1-45 | 25 | 5 | 5 | 0 |
| 1-46 | 25 | 5 | 5 | 0 |
| 1-47 | 25 | 5 | 5 | 0 |
| 1-48 | 25 | 5 | 5 | 1 |
| 1-49 | 25 | 5 | 5 | 0 |
| 1-50 | 25 | 5 | 5 | 1 |
| 1-51 | 25 | 5 | 5 | 1 |
| 1-52 | 25 | 5 | 5 | 1 |
| 1-53 | 25 | 5 | 5 | 1 |
| 1-54 | 25 | 5 | 5 | 1 |
| 1-55 | 25 | 5 | 5 | 1 |
| 1-59 | 25 | 5 | 5 | 0 |
| 1-60 | 25 | 5 | 5 | 1 |
| 1-61 | 25 | 5 | 5 | 1 |
| 1-62 | 25 | 5 | 5 | 1 |
| 1-63 | 25 | 5 | 5 | 1 |
| 1-67 | 25 | 5 | 5 | 1 |
| 1-72 | 25 | 5 | 5 | 0 |
| 1-74 | 25 | 5 | 5 | 0 |
| 1-76 | 25 | 5 | 5 | 0 |
| 1-78 | 25 | 5 | 5 | 1 |
| 1-81 | 25 | 5 | 5 | 0 |
| 1-82 | 25 | 5 | 5 | 0 |
| 1-83 | 25 | 5 | 5 | 1 |
| 1-84 | 25 | 5 | 5 | 0 |
| 1-85 | 25 | 5 | 5 | 0 |
| 1-86 | 25 | 5 | 5 | 0 |
| 1-87 | 25 | 5 | 5 | 1 |
| 1-89 | 25 | 5 | 5 | 0 |
| 1-91 | 25 | 5 | 5 | 1 |
| 1-93 | 25 | 5 | 5 | 0 |
| 1-97 | 25 | 5 | 5 | 0 |
| 1-98 | 25 | 5 | 5 | 1 |

TABLE 66

| Compound No. | Dose (gai/10a) | Eo | Mo | Or |
|---|---|---|---|---|
| 1-99 | 25 | 5 | 5 | 1 |
| 1-103 | 25 | 5 | 5 | 1 |
| 1-104 | 25 | 5 | 5 | 1 |
| 1-106 | 25 | 5 | 5 | 0 |

TABLE 66-continued

| Compound No. | Dose (gai/10a) | Eo | Mo | Or |
|---|---|---|---|---|
| 1-107 | 25 | 5 | 5 | 0 |
| 1-113 | 25 | 5 | 5 | 0 |
| 1-116 | 25 | 5 | 5 | 0 |
| 1-118 | 25 | 5 | 3 | 0 |
| 1-119 | 25 | 5 | 5 | 0 |
| 1-120 | 25 | 5 | 5 | 0 |
| 1-121 | 25 | 5 | 5 | 1 |
| 1-123 | 25 | 5 | 5 | 1 |
| 1-124 | 25 | 5 | 5 | 0 |
| 1-125 | 25 | 5 | 5 | 0 |
| 1-126 | 25 | 5 | 5 | 1 |
| 1-130 | 25 | 5 | 5 | 1 |
| 1-131 | 25 | 5 | 5 | 1 |
| 1-132 | 25 | 5 | 5 | 0 |
| 1-133 | 25 | 5 | 5 | 1 |
| 1-134 | 25 | 5 | 5 | 0 |
| 1-135 | 25 | 5 | 5 | 1 |
| 1-136 | 25 | 5 | 5 | 1 |
| 1-137 | 25 | 5 | 5 | 1 |
| 1-139 | 25 | 5 | 5 | 0 |
| 1-140 | 25 | 5 | 5 | 0 |
| 1-141 | 25 | 5 | 5 | 1 |
| 1-144 | 25 | 5 | 5 | 1 |
| 1-145 | 25 | 5 | 5 | 1 |
| 1-146 | 25 | 5 | 5 | 1 |
| 1-147 | 25 | 5 | 5 | 1 |
| 1-150 | 25 | 5 | 5 | 1 |
| 1-152 | 25 | 5 | 5 | 1 |
| 1-153 | 25 | 5 | 5 | 1 |
| 1-161 | 25 | 5 | 5 | 0 |
| 1-162 | 25 | 5 | 5 | 0 |
| 1-166 | 25 | 5 | 5 | 1 |
| 1-167 | 25 | 5 | 5 | 1 |
| 1-168 | 25 | 5 | 5 | 1 |
| 1-169 | 25 | 5 | 5 | 1 |
| 1-170 | 25 | 5 | 5 | 1 |
| 1-171 | 25 | 5 | 5 | 1 |
| 1-172 | 25 | 5 | 5 | 1 |
| 1-175 | 25 | 5 | 5 | 0 |
| 1-180 | 25 | 5 | 5 | 1 |
| 1-181 | 25 | 5 | 5 | 1 |
| 1-182 | 25 | 5 | 5 | 1 |
| 1-183 | 25 | 5 | 5 | 0 |
| 1-188 | 25 | 5 | 5 | 0 |
| 1-189 | 25 | 5 | 5 | 0 |
| 1-190 | 25 | 5 | 5 | 0 |
| 1-197 | 25 | 5 | 5 | 0 |
| 1-200 | 25 | 5 | 5 | 1 |
| 1-217 | 25 | 5 | 5 | 1 |

TABLE 67

| Compound No. | Dose (gai/10a) | Eo | Mo | Or |
|---|---|---|---|---|
| 1-218 | 25 | 5 | 5 | 1 |
| 1-219 | 25 | 5 | 5 | 1 |
| 1-220 | 25 | 5 | 5 | 1 |
| 1-221 | 25 | 5 | 5 | 1 |
| 1-225 | 25 | 5 | 5 | 0 |
| 1-226 | 25 | 5 | 5 | 1 |
| 1-228 | 25 | 5 | 5 | 0 |
| 1-234 | 25 | 5 | 5 | 1 |
| 1-250 | 25 | 5 | 5 | 1 |
| 1-251 | 25 | 5 | 5 | 1 |
| 1-306 | 25 | 5 | 5 | 1 |
| 1-321 | 25 | 5 | 5 | 1 |
| 1-324 | 25 | 5 | 5 | 1 |
| 1-325 | 25 | 5 | 5 | 1 |
| 1-329 | 25 | 5 | 5 | 1 |
| 1-333 | 25 | 5 | 5 | 1 |
| 1-334 | 25 | 5 | 5 | 0 |
| 1-401 | 25 | 5 | 5 | 1 |
| 1-404 | 25 | 5 | 5 | 1 |

TABLE 67-continued

| Compound No. | Dose (gai/10a) | Eo | Mo | Or |
|---|---|---|---|---|
| 1-412 | 25 | 5 | 5 | 1 |
| 1-416 | 25 | 5 | 5 | 1 |
| 1-417 | 25 | 5 | 5 | 1 |
| 1-418 | 25 | 5 | 5 | 1 |
| 1-425 | 25 | 5 | 5 | 1 |
| 1-436 | 25 | 5 | 5 | 1 |
| 1-439 | 25 | 5 | 5 | 1 |
| 1-441 | 25 | 5 | 5 | 1 |
| 1-442 | 25 | 5 | 5 | 1 |
| 1-443 | 25 | 5 | 5 | 1 |
| 1-444 | 25 | 5 | 5 | 1 |
| 1-448 | 25 | 5 | 5 | 1 |
| 1-452 | 25 | 5 | 5 | 0 |
| 1-454 | 25 | 5 | 5 | 1 |
| 1-455 | 25 | 5 | 5 | 1 |
| 1-459 | 25 | 5 | 5 | 1 |
| 1-461 | 25 | 5 | 5 | 1 |
| 1-465 | 25 | 5 | 5 | 0 |
| 1-473 | 25 | 5 | 5 | 1 |
| 1-483 | 25 | 5 | 5 | 1 |
| 1-484 | 25 | 5 | 5 | 1 |
| 1-485 | 25 | 5 | 5 | 1 |
| 1-486 | 25 | 5 | 5 | 1 |
| 1-487 | 25 | 5 | 5 | 1 |
| 1-489 | 25 | 5 | 5 | 1 |
| 1-490 | 25 | 5 | 5 | 0 |
| 1-491 | 25 | 5 | 5 | 0 |
| 1-492 | 25 | 5 | 5 | 0 |
| 1-493 | 25 | 5 | 5 | 1 |
| 1-494 | 25 | 5 | 5 | 1 |
| 1-495 | 25 | 5 | 5 | 0 |
| 1-496 | 25 | 5 | 5 | 1 |
| 1-498 | 25 | 5 | 5 | 0 |
| 1-504 | 25 | 5 | 5 | 1 |

TABLE 68

| Compound No. | Dose (gai/10a) | Eo | Mo | Or |
|---|---|---|---|---|
| 1-505 | 25 | 5 | 5 | 0 |
| 1-506 | 25 | 5 | 5 | 1 |
| 1-507 | 25 | 5 | 5 | 1 |
| 1-511 | 25 | 5 | 5 | 0 |
| 1-517 | 25 | 5 | 5 | 1 |
| 1-519 | 26 | 5 | 5 | 1 |
| 1-520 | 25 | 5 | 5 | 1 |
| 1-521 | 25 | 5 | 5 | 1 |
| 1-527 | 25 | 5 | 5 | 1 |
| 1-528 | 25 | 5 | 5 | 1 |
| 1-529 | 25 | 5 | 5 | 1 |
| 1-530 | 25 | 5 | 5 | 1 |
| 1-532 | 25 | 5 | 5 | 1 |
| 1-533 | 25 | 5 | 5 | 1 |
| 1-541 | 25 | 5 | 5 | 1 |
| 1-547 | 25 | 5 | 5 | 1 |
| 1-548 | 25 | 5 | 5 | 1 |
| 1-549 | 25 | 5 | 5 | 0 |
| 1-551 | 25 | 5 | 5 | 0 |
| 1-553 | 25 | 5 | 5 | 1 |
| 1-558 | 25 | 5 | 5 | 1 |
| 1-566 | 25 | 5 | 5 | 1 |
| 1-567 | 25 | 5 | 5 | 1 |
| 1-569 | 25 | 5 | 5 | 1 |
| 1-572 | 25 | 5 | 5 | 1 |
| 1-573 | 25 | 5 | 5 | 1 |
| 1-579 | 25 | 5 | 5 | 1 |
| 1-584 | 25 | 5 | 5 | 1 |
| 1-559 | 25 | 5 | 5 | 1 |
| 1-591 | 25 | 5 | 5 | 1 |
| 1-593 | 25 | 5 | 4 | 0 |
| 1-594 | 25 | 5 | 5 | 1 |
| 1-598 | 25 | 5 | 5 | 1 |
| 1-599 | 25 | 5 | 5 | 1 |

TABLE 68-continued

| Compound No. | Dose (gai/10a) | Eo | Mo | Or |
|---|---|---|---|---|
| 1-604 | 25 | 5 | 5 | 1 |
| 1-606 | 25 | 5 | 5 | 1 |
| 1-607 | 25 | 5 | 5 | 1 |
| 1-608 | 25 | 5 | 5 | 1 |
| 1-609 | 25 | 5 | 5 | 1 |
| 1-611 | 25 | 5 | 5 | 1 |
| 1-614 | 25 | 5 | 5 | 1 |
| 1-615 | 25 | 5 | 5 | 1 |
| 1-624 | 25 | 5 | 5 | 1 |
| 1-626 | 25 | 5 | 5 | 1 |
| 1-627 | 25 | 5 | 5 | 1 |
| 1-639 | 25 | 5 | 4 | 1 |
| 2-1 | 25 | 5 | 5 | 0 |
| 2-2 | 25 | 5 | 5 | 1 |
| 2-7 | 25 | 5 | 5 | 1 |
| 2-8 | 25 | 5 | 5 | 0 |
| 2-19 | 25 | 5 | 5 | 1 |
| 2-20 | 25 | 5 | 5 | 1 |
| 2-25 | 25 | 5 | 5 | 1 |

TABLE 69

| Compound No. | Dose (gai/10a) | Eo | Mo | Or |
|---|---|---|---|---|
| 2-31 | 25 | 5 | 5 | 0 |
| 2-32 | 25 | 5 | 5 | 1 |
| 2-42 | 25 | 5 | 5 | 0 |
| 2-48 | 25 | 5 | 5 | 1 |
| 2-50 | 25 | 5 | 5 | 1 |
| 2-55 | 25 | 5 | 5 | 1 |
| 2-56 | 25 | 5 | 5 | 1 |
| 2-57 | 25 | 5 | 5 | 1 |
| 2-58 | 25 | 5 | 5 | 1 |
| 2-71 | 25 | 5 | 5 | 1 |
| 2-73 | 25 | 5 | 5 | 1 |
| 2-74 | 25 | 5 | 5 | 1 |
| 2-75 | 25 | 5 | 5 | 1 |
| 2-78 | 25 | 5 | 5 | 1 |
| 4-1 | 25 | 5 | 5 | 1 |
| 4-2 | 25 | 5 | 5 | 1 |

TEST EXAMPLE 5: TEST OF SELECTIVITY FOR A CROP PLANT BY SOIL TREATMENT IN UPLAND FIELD

In a 80 cm² plastic pot, upland soil was filled, and seeds of barnyard grass (Ec), green foxtail (Se), soybean (G1), wheat (Tr) and corn (Ze) were sown and covered with soil. A wettable powder prepared in accordance with Formulation Example 1 was diluted with water and uniformly applied to the soil surface by a small size spray at a rate of 100 l per 10 ares so that the dose of the active ingredient would be 25 g per 10 ares. Thereafter, cultivation was carried out in a green house, and on the 21st day after the treatment, the herbicidal effects were examined in accordance with the standards of Table 44. The results are shown in Table 70.

TABLE 70

| Compound No. | Dose (gai/10a) | Ec | Se | Gl | Tr | Ze |
|---|---|---|---|---|---|---|
| 1-15 | 25 | 5 | 5 | — | 1 | 1 |
| 1-23 | 25 | 5 | 5 | — | 2 | 1 |
| 1-33 | 25 | 4 | 4 | 0 | 2 | 1 |
| 1-42 | 25 | 5 | 5 | 0 | 0 | 0 |
| 1-45 | 25 | 4 | 5 | 0 | 2 | 0 |

TABLE 70-continued

| Compound No. | Dose (gai/10a) | Ec | Se | Gl | Tr | Ze |
|---|---|---|---|---|---|---|
| 1-46 | 25 | 5 | 5 | 1 | 3 | 0 |
| 1-48 | 25 | 4 | 5 | 0 | 1 | 0 |
| 1-49 | 25 | 5 | 5 | 1 | 0 | 3 |
| 1-50 | 25 | 4 | 5 | 3 | 3 | 0 |
| 1-51 | 25 | 5 | 5 | 0 | 1 | 0 |
| 1-53 | 25 | 4 | 5 | 1 | 2 | 0 |
| 1-54 | 25 | 4 | 5 | 0 | 1 | 0 |
| 1-55 | 25 | 5 | 4 | 1 | 1 | 0 |
| 1-56 | 25 | 5 | 5 | 0 | 4 | 3 |
| 1-58 | 25 | 5 | 5 | 0 | 3 | 0 |
| 1-59 | 25 | 5 | 5 | 0 | 1 | 0 |
| 1-60 | 25 | 5 | 5 | 1 | 2 | 0 |
| 1-61 | 25 | 5 | 5 | 1 | 3 | 0 |
| 1-64 | 25 | 4 | 4 | 2 | 3 | 0 |
| 1-65 | 25 | 5 | 5 | 0 | 0 | 0 |
| 1-68 | 25 | 4 | 4 | 0 | 2 | 2 |
| 1-70 | 25 | 5 | 4 | 1 | 4 | 1 |
| 1-71 | 25 | 5 | 5 | — | 3 | 0 |
| 1-75 | 25 | 4 | 4 | 0 | 3 | 2 |
| 1-76 | 25 | 4 | 4 | 0 | 2 | 2 |
| 1-77 | 25 | 5 | 5 | 1 | 3 | 2 |
| 1-78 | 25 | 5 | 5 | 0 | 1 | 0 |
| 1-80 | 25 | 5 | 5 | 0 | 5 | 1 |
| 1-81 | 25 | 4 | 4 | 0 | 1 | 0 |
| 1-83 | 25 | 5 | 5 | 1 | 2 | 1 |
| 1-84 | 25 | 4 | 4 | 0 | 1 | 0 |
| 1-85 | 25 | 4 | 4 | 0 | 1 | 0 |
| 1-89 | 25 | 4 | 5 | 0 | 2 | 2 |
| 1-95 | 25 | 5 | 5 | 1 | 0 | 0 |
| 1-97 | 25 | 4 | 4 | 3 | 1 | 0 |
| 1-98 | 25 | 4 | 5 | 0 | 1 | 1 |
| 1-99 | 25 | 4 | 4 | 0 | 3 | 0 |
| 1-100 | 25 | 5 | 5 | 0 | 2 | 2 |

Industrial Applicability

The compound of the present invention represented by the formula [I] exhibits excellent herbicidal effects over a wide range from preemergence to the growing period of various weeds which are problematic in upland fields, including, for example, broad leaf weeds such as smartweed, slender amaranth, lambsquaters, chickweed, velvetleaf, prickly sida, hemp sesbania, morning glory and cocklebur, perenial and annual cyperaceous weeds such as purple nutsedge, yellow nutsedge, himekugu, chufa and rice flatsedge, and glass weeds such as barnyard grass, crab grass, green foxtail, annual bluegrass, Johnson grass, water foxtail and wild oat. Further, it can control annual weeds such as barnyard grass, umbrella plant and monochoria, and perenial weeds such as Japanese ribbon wapato, arrowhead, water nutgrass, water chestnut, Japanese bulrush and narrowleaf waterplaintain, which germinate in paddy fields. On the other hand, the herbicide of the present invetion has high safety to crop plants and exhibits particularly high safety to rice, wheat, barley, corn, grain solgum, soybean, cotton, beet, etc.

What is claimed is:

1. A pyrimidine derivative represented by the formula (I)

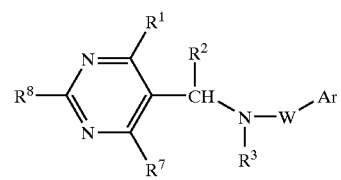

(I)

wherein $R^1$ is a hydrogen atom (except for a case where $R^2$ hydrogen atom, and W=$SO_2$), a halogen atom, a C₁–C₆ alkyl group, a C₁–C₆ alkylcarbonyl C₁–C₆ alkyl group, a hydroxyl group, a C₂–C₆ alkenyl group, a C₂–C₆ alkynyl group, a C₃–C₆ cycloalkyl group (this group may be substituted by a halogen atom, a C₁–C₆ alkyl group, a C₁–C₆ alkoxy group or a C₁–C₄ haloalkyl group), a C₁–C₄ haloalkyl group, a C₁–C₆ alkoxy group, a C₁–C₄ haloalkoxy group, a C₂–C₆ alkenyloxy group, a C₂–C₆ alkynyloxy group, a C₃–C₆ cycloalkyloxy group, a phenyl group (this group may be substituted by a halogen atom, a C₁–C₆ alkyl group, a C₁–C₆ alkoxy group, a C₁–C₄ haloalkyl group, a C₁–C₄ haloalkoxy group, a cyano group, a cyano C₁–C₆ alkyl group, a nitro group, a C₁–C₆ alkylthio group, a C₁–C₆ alkylsulfinyl group or a C₁–C₆ alkylsulfonyl group), a C₁–C₆ alkylthio group (except for a case where R²=phenyl group, and W=SO₂), a C₂–C₆ alkenylthio group, a C₂–C₆ alkynylthio group, a C₃–C₆ cycloalkylthio group, a C₁–C₆ alkylsulfinyl group, a C₂–C₆ alkenylsulfinyl group, a C₂–C₆ alkynylsulfinyl group, a C₃–C₆ cycloalkylsulfinyl group, a C₁–C₆ alkylsulfonyl group, a C₂–C₆ alkenylsulfonyl group, a C₂–C₆ alkynylsulfonyl group, a C₃–C₆ cycloalkylsulfonyl group, a C₁–C₆ hydroxyalkyl group, a C₂–C₇ acyl group, a C₁–C₆ alkoxy C₁–C₆ alkyl group, a cyano group, a C₁–C₆ alkoxycarbonyl group, a C₁–C₆ alkoxycarbonyl C₁–C₆ alkyl group, a C₁–C₆ alkoxycarbonyl C₂–C₆ alkenyl group, a carboxyl group, a carboxyl C₁–C₆ alkyl group, a di C₁–C₆ alkoxy C₁–C₆ alkyl group, a C₁–C₆ alkoxyimino C₁–C₆ alkyl group, a hydroxyimino C₁–C₆ alkyl group, a dioxolanyl group (this group may be substituted by a C₁–C₆ alkyl group), an aldehyde group, an oxiranyl group, a NR⁹R¹⁰ group or a CONR⁹R¹⁰ group, and R⁹ is a hydrogen atom, a C₁–C₆ alkyl group, a C₂–C₆ alkenyl group, a C₂–C₆ alkynyl group, a C₁–C₄ haloalkyl group, a C₁–C₆ alkoxy C₁–C₆ alkyl group, a C₁–C₆ alkylthio C₁–C₆ alkyl group, a C₃–C₆ cycloalkyl group, a C₂–C₇ acyl group or a C₁–C₆ alkylsulfonyl group, and R¹⁰ is a C₁–C₆ alkyl group, a C₂–C₆ alkenyl group, a C₂–C₆ alkynyl group, a C₁–C₄ haloalkyl group, a C₁–C₆ alkoxy C₁–C₆ alkyl group, a C₁–C₆ alkylthio C₁–C₆ alkyl group, a C₃–C₆ cycloalkyl group, a C₂–C₇ acyl group, a C₁–C₆ alkylsulfonyl group, a C₁–C₆ alkoxycarbonyl group or a benzyloxycarbonyl group;

R² is a hydrogen atom, a C₁–C₆ alkyl group, a C₂–C₆ alkenyl group, a C₂–C₆ alkynyl group, a C₁–C₆ alkylthio group, a C₁–C₄ haloalkyl group, a C₁–C₆ alkoxy group, a C₁–C₆ alkoxy C₁–C₆ alkyl group, a C₁–C₆ alkylthio C₁–C₆ alkyl group, a C₃–C₆ cycloalkyl group (this group may be substituted by a halogen atom, a C₁–C₆ alkyl group, a C₁–C₆ alkoxy group or a C₁–C₄ haloalkyl group), a C₂–C₇ acyl group, a cyano group, a di C₁–C₆ alkoxy C₁–C₆ alkyl group, a C₁–C₆ alkoxyimino C₁–C₆ alkyl group, a hydroxyimino C₁–C₆ alkyl group, a a cyano C₁–C₆ alkyl group, a C₁–C₆ hydroxyalkyl group, a C₁–C₆ alkoxycarbonyl group, a C₁–C₆ alkoxycarbonyl C₁–C₆ alkyl group, a CR¹¹R¹²NR⁹R¹⁰ group, a CONR⁹R¹⁰ group, a CR¹¹R¹²CONR⁹R¹⁰ group or a group represented by the formulae R²-1 or R²-2:

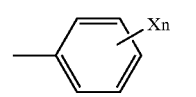

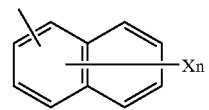

and wherein X is a hydrogen atom, a halogen atom, a C₁–C₆ alkyl group, a C₂–C₆ alkenyl group, a C₂–C₆ alkynyl group, a C₁–C₆ alkoxy group, a C₁–C₆ alkoxy C₁–C₆ alkyl group, a NR⁹R¹⁰ group, a CONR⁹R¹⁰ group, a C₁–C₄ haloalkoxy group, a C₂–C₆ alkenyloxy group, a C₃–C₆ cycloalkyloxy group, C₂–C₇ acyl group, a C₁–C₆ alkoxycarbonyl group, a C₁–C₆ alkylthio group, a C₁–C₆ alkylsulfinyl group, a C₁–C₆ alkylsufonyl group, a cyano group, a nitro group or a C₁–C₄ haloalkyl group, and n is an integer of from 1 to 3, and when n is an integer of 2 or 3, the plurality of X may be the same or different, and two adjacent lower alkoxy groups may be bonded to each other to form a C₁–C₃ alkylenedioxy group;

each of R¹¹ and R¹² is a hydrogen atom, a C₁–C₆ alkyl group, a C₂–C₆ alkenyl group, a C₂–C₆ alkynyl group or a C₁–C₆ alkoxy group;

R³ is a hydrogen atom, a C₁–C₆ alkyl group, a C₂–C₆ alkenyl group, a C₂–C₆ alkynyl group, a C₁–C₆ alkoxy group, a di C₁–C₆ alkylamino group, a C₃–C₆ cycloalkyl group, a C₁–C₆ alkoxy C₁–C₆ alkyl group, a cyano C₁–C₆ alkyl group, a C₃–C₆ cycloalkyl C₁–C₆ alkyl group, an oxiranyl C₁–C₆ alkyl group or a C₁–C₆ alkoxycarbonyl C₁–C₆ alkyl group;

W is a —C(=Q)Z— group or a —SO₂— group, Q is an oxygen atom or a sulfur atom, Z is an oxygen atom, a sulfur atom, a —NR⁶— group, a —CH₂CH₂— group, a —CH=CH— group, a —C(R⁴)R⁵— group, a —C(R⁴)R⁵—Q— group, a —Q—C(R⁴)R⁵— group, a —C(=Q)— group, a —NR⁶NR⁶ᵃ— group or a —NR⁶C(R⁴)R⁵— group, and each of R⁴ and R⁵ is a hydrogen atom, a C₁–C₆ alkyl group, a halogen atom, a C₁–C₆ alkoxy group or a C₁–C₆ alkylthio group, each of R⁶ and R⁶ᵃ is a hydrogen atom, a C₁–C₆ alkyl group, a C₂–C₆ alkenyl group or a C₂–C₆ alkynyl group;

Ar is a group represented by the formulae Ar-1 or Ar-2:

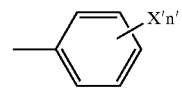

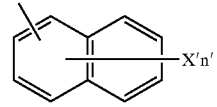

and wherein X' is a hydrogen atom, a halogen atom, a C₁–C₆ alkyl group, a C₂–C₆ alkenyl group, a C₂–C₆ alkynyl group, a C₁–C₆ alkoxy group, a C₁–C₆ alkoxy C₁–C₆ alkyl group, a NR⁹R¹⁰ group, a CONR⁹R¹⁰ group, a $C_1$–$C_4$ haloalkoxy group, a $C_2$–$C_6$ alkenyloxy group, a $C_3$–$C_6$ cycloalkyloxy group, a $C_2$–$C_7$ acyl group, a $C_1$–$C_6$ alkoxycarbonyl group, a $C_1$–$C_6$ alkylthio group, a $C_1$–$C_6$ alkylsulfinyl group, a $C_1$–$C_6$ alkylsufonyl group, a cyano group, a nitro group or a $C_1$–$C_4$ haloalkyl group, n' is an integer of from 1 to 3, and when n' is an integer of 2 or 3, the plurality of X' may be the same or different, and two adjacent lower alkoxy groups may be bonded to each other to form a $C_1$–$C_3$ alkylenedioxy group;

$R^7$ is a hydrogen atom, a halogen atom, a $C_1$–$C_6$ alkyl group, a $C_1$–$C_6$ alkoxy group, a $C_1$–$C_6$ alkylthio group, (except for a case where $R^1$ is a hydrogen atom and $R^2$ is a phenyl group and W is $SO_2$), a $C_1$–$C_4$ haloalkyl group or a $C_3$–$C_6$ cycloalkyl group; and $R^8$ is a hydrogen atom, a $C_1$–$C_6$ alkyl group, a $C_1$–$C_6$ alkylthio group, a $C_1$–$C_4$ haloalkyl group or a $C_3$–$C_6$ cycloalkyl group.

2. A pyrimidine derivative represented by the formula

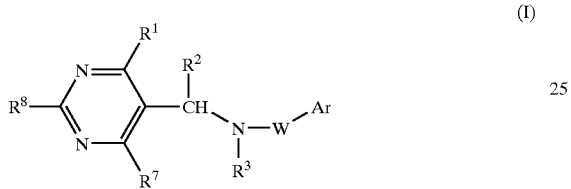

(I)

wherein $R^1$ is a hydrogen atom, a halogen atom, a $C_1$–$C_6$ alkyl group, a $C_1$–$C_6$ alkylcarbonyl $C_1$–$C_6$ alkyl group, a hydroxyl group, a $C_2$–$C_6$ alkenyl group, a $C_2$–$C_6$ alkynyl group, a $C_3$–$C_6$ cycloalkyl group (this group may be substituted by a halogen atom, a $C_1$–$C_6$ alkyl group, a $C_1$–$C_6$ alkoxy group or a $C_1$–$C_4$ haloalkyl group), a $C_1$–$C_4$ haloalkyl group, a $C_1$–$C_6$ alkoxy group, a $C_1$–$C_4$ haloalkoxy group, a $C_2$–$C_6$ alkenyloxy group, a $C_2$–$C_6$ alkynyloxy group, a $C_3$–$C_6$ cycloalkyloxy group, a phenyl group (this group may be substituted by a halogen atom, a $C_1$–$C_6$ alkyl group, a $C_1$–$C_6$ alkoxy group, a $C_1$–$C_4$ haloalkyl group, a $C_1$–$C_4$ haloalkoxy group, a cyano group, a nitro group, a $C_1$–$C_6$ alkylthio group, a $C_1$–$C_6$ alkylsulfinyl group or a $C_1$–$C_6$ alkylsulfonyl group), a $C_1$–$C_6$ alkylthio group, a $C_2$–$C_6$ alkenylthio group, a $C_2$–$C_6$ atkynylthio group, a $C_3$–$C_6$ cycloalkylthio group, a $C_1$–$C_6$ alkylsulfinyl group, a $C_2$–$C_6$ alkenylsulfinyl group, a $C_2$–$C_6$ alkynylsulfinyl group, a $C_3$–$C_6$ cycloalkylsulfinyl group, a $C_1$–$C_6$ alkylsulfonyl group, a $C_2$–$C_6$ alkenylsulfonyl group, a $C_2$–$C_6$ alkynylsulfonyl group, a $C_3$–$C_6$ cycloalkylsulfonyl group, a hydroxyalkyl group, a $C_2$–$C_7$ acyl group, a $C_1$–$C_6$ alkoxy $C_1$–$C_6$ alkyl group, a cyano group, a cyano $C_1$–$C_6$ alkyl group, a $C_1$–$C_6$ alkoxycarbonyl group, a $C_1$–$C_6$ alkoxycarbonyl $C_1$–$C_6$ alkyl group, a $C_1$–$C_6$ alkoxycarbonyl $C_2$–$C_6$ alkenyl group, a carboxyl group, a carboxyl $C_1$–$C_6$ alkyl group, a di $C_1$–$C_6$ alkoxy $C_1$–$C_6$ alkyl group, a $C_1$–$C_6$ alkoxyimino $C_1$–$C_6$ alkyl group, a hydroxyimino $C_1$–$C_6$ alkyl group, a dioxolanyl group (this group may be substituted by a $C_1$–$C_6$ alkyl group), an aldehyde group, an oxiranyl group, a $NR^9R^{10}$ group or a $CONR^9R^{10}$ group, and $R^9$ is a hydrogen atom, a $C_1$–$C_6$ alkyl group, a $C_2$–$C_6$ alkenyl group, a $C_2$–$C_6$ alkynyl group, a $C_1$–$C_4$ haloalkyl group, a $C_1$–$C_6$ alkoxy $C_1$–$C_6$ alkyl group, a $C_1$–$C_6$ alkylthio $C_1$–$C_6$ alkyl group, a $C_3$–$C_6$ cycloalkyl group, a $C_2$–$C_7$ acyl group or a $C_1$–$C_6$ alkylsulfonyl group, and $R^{10}$ is a $C_1$–$C_6$ alkyl group, a $C_2$–$C_6$ alkenyl group, a $C_2$–$C_6$ alkynyl group, a $C_1$–$C_4$ haloalkyl group, a $C_1$–$C_6$ alkoxy $C_1$–$C_6$ alkyl group, a $C_1$–$C_6$ alkylthio $C_1$–$C_6$ alkyl group, a $C_3$–$C_6$ cycloalkyl group, a $C_2$–$C_7$ acyl group, a $C_1$–$C_6$ alkylsulfonyl group, a $C_1$–$C_6$ alkoxycarbonyl group or a benzyloxycarbonyl group;

$R^2$ is a hydrogen atom, a $C_1$–$C_6$ alkyl group, a $C_2$–$C_6$ alkenyl group, a $C_2$–$C_6$ alkynyl group, a $C_1$–$C_6$ alkylthio group, a $C_1$–$C_4$ haloalkyl group, a $C_1$–$C_6$ alkoxy group, a $C_1$–$C_6$ alkoxy $C_1$–$C_6$ alkyl group, a $C_1$–$C_6$ alkylthio $C_1$–$C_6$ alkyl group, a $C_3$–$C_6$ cycloalkyl group (this group may be substituted by a halogen atom, a $C_1$–$C_6$ alkyl group, a $C_1$–$C_6$ alkoxy group or a $C_1$–$C_4$ haloalkyl group), a $C_2$–$C_7$ acyl group, a cyano group, a di $C_1$–$C_6$ alkoxy $C_1$–$C_6$ alkyl group, a $C_1$–$C_6$ alkoxyimino $C_1$–$C_6$ alkyl group, a hydroxyimino $C_1$–$C_6$ alkyl group, a a cyano $C_1$–$C_6$ alkyl group, a $C_1$–$C_6$ hydroxyalkyl group, a $C_1$–$C_6$ alkoxycarbonyl group, a $C_1$–$C_6$ alkoxycarbonyl $C_1$–$C_6$ alkyl group, a $CR^{11}R^{12}NR^9R^{10}$ group, a $CONR^9R^{10}$ group, a $CR^{11}R^{12}CONR^9R^{10}$ group or a group represented by the formulae $R^2$-1 or $R^2$-2:

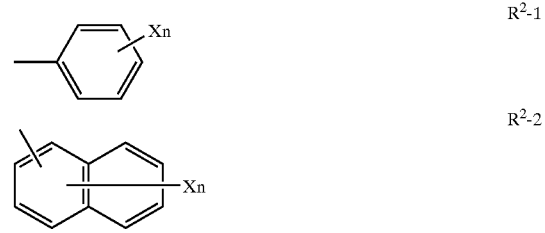

and wherein X is a hydrogen atom, a halogen atom, a $C_1$–$C_6$ alkyl group, a $C_2$–$C_6$ alkenyl group, a $C_2$–$C_6$ alkynyl group, a $C_1$–$C_6$ alkoxy group, a $C_1$–$C_6$ alkoxy $C_1$–$C_6$ alkyl group, a $NR^9R^{10}$ group, a $CONR^9R^{10}$ group, a $C_1$–$C_4$ haloalkoxy group, a $C_2$–$C_6$ alkenyloxy group, a $C_3$–$C_6$ cycloalkyloxy group, a $C_2$–$C_7$ acyl group, a $C_1$–$C_6$ alkoxycarbonyl group, a $C_1$–$C_6$ alkylthio group, a $C_1$–$C_6$ alkylsulfinyl group, a $C_1$–$C_6$ alkylsufonyl group, a cyano group, a nitro group or a $C_1$–$C_4$ haloalkyl group, n is an integer of from 1 to 3, and when n is an integer of 2 or 3, the plurality of X may be the same or different, and two adjacent lower alkoxy groups may be bonded to each other to form a $C_1$–$C_3$ alkylenedioxy group, and each of $R^{11}$ and $R^{12}$ is a hydrogen atom, a $C_1$–$C_6$ alkyl group, a $C_2$–$C_6$ alkenyl group, a $C_2$–$C_6$ alkynyl group or a $C_1$–$C_6$ alkoxy group;

$R^3$ is a hydrogen atom, a $C_1$–$C_6$ alkyl group, a $C_2$–$C_6$ alkenyl group, a $C_2$–$C_6$ alkynyl group, a $C_1$–$C_6$ alkoxy group, a di $C_1$–$C_6$ alkylamino group, a $C_3$–$C_6$ cycloalkyl group, a $C_1$–$C_6$ alkoxy $C_1$–$C_6$ alkyl group, a cyano $C_1$–$C_6$ alkyl group, a $C_3$–$C_6$ cycloalkyl $C_1$–$C_6$ alkyl group, an oxiranyl $C_1$–$C_6$ alkyl group or a $C_1$–$C_6$ alkoxycarbonyl $C_1$–$C_6$ alkyl group;

W is a —C(=Q)Z— group, Q is an oxygen atom or a sulfur atom, Z is an oxygen atom, a sulfur atom, a —$NR^6$— group, a —$CH_2CH_2$— group, a —CH=CH— group, a —C($R^4$)$R^5$— group, a —C($R^4$)$R^5$—Q— group, a —Q—C($R^4$)$R^5$— group, a —C(=Q)— group, a —$NR^6NR^{6a}$ group or a —$NR^6C$ ($R^4$)$R^5$— group, each of $R^4$ and $R^5$ is a hydrogen atom, a $C_1$–$C_6$ alkyl group, a halogen atom, a $C_1$–$C_6$ alkoxy group or a $C_1$–$C_6$ alkylthio group, each of $R^6$ and $R^{6a}$ is a hydrogen atom, a $C_1$–$C_6$ alkyl group, a $C_2$–$C_6$ alkenyl group or a $C_2$–$C_6$ alkynyl group;

Ar is a group represented by the formulae Ar to Ar-1 or Ar-2:

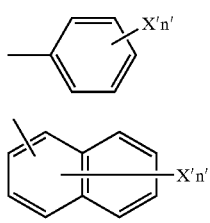

and wherein X' is a hydrogen atom, a halogen atom, a $C_1$–$C_6$ alkyl group, a $C_2$–$C_6$ alkenyl group, a $C_2$–$C_6$ alkynyl group, a $C_1$–$C_6$ alkoxy group, a $C_1$–$C_6$ alkoxy $C_1$–$C_6$ alkyl group, a $NR^9R^{10}$ group, a $CONR^9R^{10}$ group, a $C_1$–$C_4$ haloalkoxy group, a $C_2$–$C_6$ alkenyloxy group, a $C_3$–$C_6$ cycloalkyloxy group, a $C_2$–$C_7$ acyl group, a $C_1$–$C_6$ alkoxycarbonyl group, a $C_1$–$C_6$ alkylthio group, a $C_1$–$C_6$ alkylsulfinyl group, a $C_1$–$C_6$ alkylsufonyl group, a cyano group, a nitro group or a $C_1$–$C_4$ haloalkyl group, n' is an integer of from 1 to 3, and when n' is an integer of 2 or 3, the plurality of X' may be the same or different, and two adjacent lower alkoxy groups may be bonded to each other to form a $C_1$–$C_3$ alkylenedioxy group);

$R^7$ is a hydrogen atom, a halogen atom, a $C_1$–$C_6$ alkyl group, a $C_1$–$C_6$ alkoxy group, a $C_1$–$C_6$ alkylthio group, a $C_1$–$C_4$ haloalkyl group or a $C_3$–$C_6$ cycloalkyl group; and $R^8$ is a hydrogen atom, a $C_1$–$C_6$ alkyl group, a $C_1$–$C_6$ alkylthio group, a $C_1$–$C_4$ haloalkyl group or a $C_3$–$C_6$ cycloalkyl group.

3. A pyrimidine derivative represented by the formula

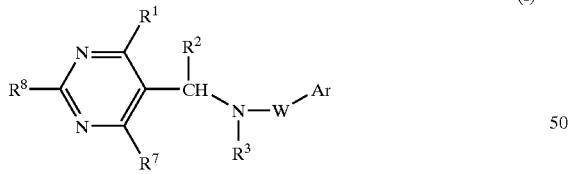

(I)

wherein $R^1$ is a halogen atom, a $C_1$–$C_6$ alkyl group, an oxo $C_1$–$C_6$ alkyl group, a hydroxyl group, a $C_2$–$C_6$ alkenyl group, a $C_2$–$C_6$ alkynyl group, a $C_3$–$C_6$ cycloalkyl group (this group may be substituted by a halogen atom, a $C_1$–$C_6$ alkyl group, a $C_1$–$C_6$ alkoxy group or a $C_1$–$C_4$ haloalkyl group), a $C_1$–$C_4$ haloalkyl group, a $C_1$–$C_6$ alkoxy group, a $C_1$–$C_4$ haloalkoxy group, a $C_2$–$C_6$ alkenyloxy group, a $C_2$–$C_6$ alkynyloxy group, a $C_3$–$C_6$ cycloalkyloxy group, a phenyl group (this group may be substituted by a halogen atom, a $C_1$–$C_6$ alkyl group, a $C_1$–$C_6$ alkoxy group, a $C_1$–$C_4$ haloalkyl group, a $C_1$–$C_4$ haloalkoxy group, a cyano group, a nitro group, a $C_1$–$C_6$ alkylthio group, a $C_1$–$C_6$ alkylsulfinyl group or a $C_1$–$C_6$ alkylsulfonyl group), a $C_2$–$C_6$ alkenylthio group, a $C_2$–$C_6$ alkynylthio group, a $C_3$–$C_6$ cycloalkylthio group, a $C_1$–$C_6$ alkylsulfinyl group, a $C_2$–$C_6$ alkenylsulfinyl group, a $C_2$–$C_6$ alkynylsulfinyl group, a $C_3$–$C_6$ cycloalkylsulfinyl group, a $C_1$–$C_6$ alkylsulfonyl group, a $C_2$–$C_6$ alkenylsulfonyl group, a $C_2$–$C_6$ alkynylsulfonyl group, a $C_3$–$C_6$ cycloalkylsulfonyl group, a hydroxyalkyl group, a $C_2$–$C_7$ acyl group, a $C_1$–$C_6$ alkoxy $C_1$–$C_6$ alkyl group, a cyano group, a cyano $C_1$–$C_6$ alkyl group, a $C_1$–$C_6$ alkoxycarbonyl group, a $C_1$–$C_6$ alkoxycarbonyl $C_1$–$C_6$ alkyl group, a $C_1$–$C_6$ alkoxycarbonyl $C_2$–$C_6$ alkenyl group, a carboxyl group, a carboxyl $C_1$–$C_6$ alkyl group, a di $C_1$–$C_6$ alkoxy $C_1$–$C_6$ alkyl group, a $C_1$–$C_6$ alkoxyimino $C_1$–$C_6$ alkyl group, a hydroxyimino $C_1$–$C_6$ alkyl group, a dioxolanyl group (this group may be substituted by a $C_1$–$C_6$ alkyl group), an aldehyde group, an oxiranyl group, a $NR^9R^{10}$ group or a $CONR^9R^{10}$ group, and $R^9$ is a hydrogen atom, a $C_1$–$C_6$ alkyl group, a $C_2$–$C_6$ alkenyl group, a $C_2$–$C_6$ alkynyl group, a $C_1$–$C_4$ haloalkyl group, a $C_1$–$C_6$ alkoxy $C_1$–$C_6$ alkyl group, a $C_1$–$C_6$ alkylthio $C_1$–$C_6$ alkyl group, a $C_3$–$C_6$ cycloalkyl group, a $C_2$–$C_7$ acyl group or a $C_1$–$C_6$ alkylsulfonyl group, and $R^{10}$ is a $C_1$–$C_6$ alkyl group, a $C_2$–$C_6$ alkenyl group, a $C_2$–$C_6$ alkynyl group, a $C_1$–$C_4$ haloalkyl group, a $C_1$–$C_6$ alkoxy $C_1$–$C_6$ alkyl group, a $C_1$–$C_6$ alkylthio $C_1$–$C_6$ alkyl group, a $C_3$–$C_6$ cycloalkyl group, a $C_2$–$C_7$ acyl group, a $C_1$–$C_6$ alkylsulfonyl group, a $C_1$–$C_6$ alkoxycarbonyl group or a benzyloxycarbonyl group;

$R^2$ is a hydrogen atom, a $C_1$–$C_6$ alkyl group, a $C_2$–$C_6$ alkenyl group, a $C_2$–$C_6$ alkynyl group, a $C_1$–$C_6$ alkylthio group, a $C_1$–$C_4$ haloalkyl group, a $C_1$–$C_6$ alkoxy group, a $C_1$–$C_6$ alkoxy $C_1$–$C_6$ alkyl group, a $C_1$–$C_6$ alkylthio $C_1$–$C_6$ alkyl group, a $C_3$–$C_6$ cycloalkyl group (this group may be substituted by a halogen atom, a $C_1$–$C_6$ alkyl group, a $C_1$–$C_6$ alkoxy group or a $C_1$–$C_4$ haloalkyl group), a $C_2$–$C_7$ acyl group, a cyano group, a di $C_1$–$C_6$ alkoxy $C_1$–$C_6$ alkyl group, a $C_1$–$C_6$ alkoxyimino $C_1$–$C_6$ alkyl group, a hydroxyimino $C_1$–$C_6$ alkyl group, a a cyano $C_1$–$C_6$ alkyl group, a $C_1$–$C_6$ hydroxyalkyl group, a $C_1$–$C_6$ alkoxycarbonyl group, a $C_1$–$C_6$ alkoxycarbonyl $C_1$–$C_6$ alkyl group, a $CR^{11}R^{12}NR^9R^{10}$ group, a $CONR^9R^{10}$ group, a $CR^{11}R^{12}CONR^9R^{10}$ group or a group represented by the formulae $R^2$-1 or $R^2$-2:

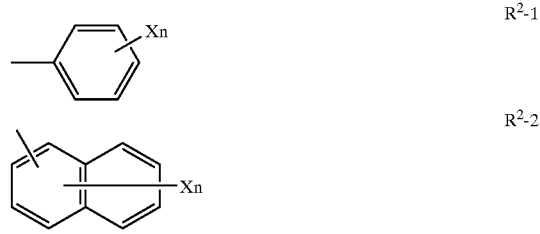

and (wherein X is a hydrogen atom, a halogen atom, a $C_1$–$C_6$ alkyl group, a $C_2$–$C_6$ alkenyl group, a $C_2$–$C_6$ alkynyl group, a $C_1$–$C_6$ alkoxy group, a $C_1$–$C_6$ alkoxy $C_1$–$C_6$ alkyl group, a $NR^9R^{10}$ group, a $CONR^9R^{10}$ group, a $C_1$–$C_4$ haloalkoxy group, a $C_2$–$C_6$ alkenyloxy group, a $C_3$–$C_6$ cycloalkyloxy group, a $C_2$–$C_7$ acyl group, a $C_1$–$C_6$ alkoxycarbonyl group, a $C_1$–$C_6$ alkylthio group, a $C_1$–$C_6$ alkylsulfinyl group, a $C_1$–$C_6$ alkylsufonyl group, a cyano group, a nitro group or a $C_1$–$C_4$ haloalkyl group, n is an integer of from 1 to 3, and when n is an integer of 2 or 3, the plurality of X may be the same or different, and two adjacent lower alkoxy groups may be bonded to each other to form a $C_1$–$C_3$ alkylenedioxy group), and each of $R^{11}$ and $R^{12}$ is a hydrogen atom, a $C_1$–$C_6$ alkyl group, a $C_2$–$C_6$ alkenyl group, a $C_2$–$C_6$ alkynyl group or a $C_1$–$C_6$ alkoxy group;

$R^3$ is a hydrogen atom, a $C_1$–$C_6$ alkyl group, a $C_2$–$C_6$ alkenyl group, a $C_2$–$C_6$ alkynyl group, a $C_1$–$C_6$ alkoxy group, a di $C_1$–$C_6$ alkylamino group, a $C_3$–$C_6$ cycloalkyl group, a $C_1$–$C_6$ alkoxy $C_1$–$C_6$ alkyl group, a cyano $C_1$–$C_6$ alkyl group, a $C_3$–$C_6$ cycloalkyl $C_1$–$C_6$ alkyl group, an oxiranyl $C_1$–$C_6$ alkyl group or a $C_1$–$C_6$ alkoxycarbonyl $C_1$–$C_6$ alkyl group;

W is a —$SO_2$— group;

Ar is a group represented by the formulae Ar-1 or Ar-2:

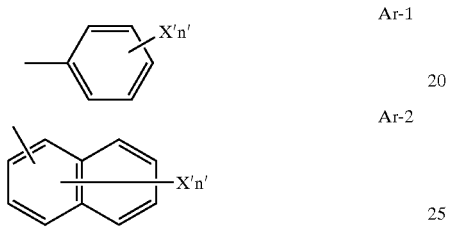

and wherein X' is a hydrogen atom, a halogen atom, an alkyl group, a $C_2$–$C_6$ alkenyl group, a $C_2$–$C_6$ alkynyl group, a $C_1$–$C_6$ alkoxy group, a $C_1$–$C_6$ alkoxy $C_1$–$C_6$ alkyl group, a $NR^9R^{10}$ group, a $CONR^9R^{10}$ group, a $C_1$–$C_4$ haloalkoxy group, a $C_2$–$C_6$ alkenyloxy group, a $C_3$–$C_6$ cycloalkyloxy group, a $C_2$–$C_7$ acyl group, a $C_1$–$C_6$ alkoxycarbonyl group, a $C_1$–$C_6$ alkylthio group, a $C_1$–$C_6$ alkylsulfinyl group, a $C_1$–$C_6$ alkylsufonyl group, a cyano group, a nitro group or a $C_1$–$C_4$ haloalkyl group, n' is an integer of from 1 to 3, and when n' is an integer of 2 or 3, the plurality of X' may be the same or different, and two adjacent lower alkoxy groups may be bonded to each other to form a $C_1$–$C_3$ alkylenedioxy group;

$R^7$ is a hydrogen atom, a halogen atom, a $C_1$–$C_6$ alkyl group, a $C_1$–$C_6$ alkoxy group, a $C_1$–$C_6$ alkylthio group, a $C_1$–$C_4$ haloalkyl group or a $C_3$–$C_6$ cycloalkyl group; and $R^8$ is a hydrogen atom, a $C_1$–$C_6$ alkyl group, a $C_1$–$C_6$ alkylthio group, a $C_1$–$C_4$ haloalkyl group or a $C_3$–$C_6$ cycloalkyl group.

4. A pyrimidine derivative represented by the formula

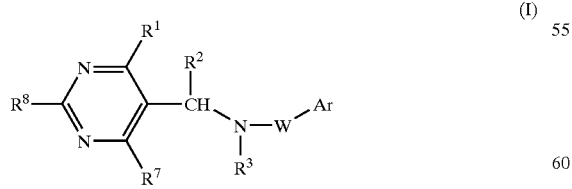

(I)

wherein $R^1$ is a halogen atom, a $C_1$–$C_6$ alkyl group, a $C_1$–$C_6$ alkylcarbonyl $C_1$–$C_6$ alkyl group, a hydroxyl group, a $C_2$–$C_6$ alkenyl group, a $C_2$–$C_6$ alkynyl group, a $C_3$–$C_6$ cycloalkyl group (this group may be substituted by a halogen atom, a $C_1$–$C_6$ alkyl group, a $C_1$–$C_6$ alkoxy group or a $C_1$–$C_4$ haloalkyl group), a $C_1$–$C_4$ haloalkyl group, a $C_1$–$C_6$ alkoxy group, a $C_1$–$C_4$ haloalkoxy group, a $C_2$–$C_6$ alkenyloxy group, a $C_2$–$C_6$ alkynyloxy group, a $C_3$–$C_6$ cycloalkyloxy group, a phenyl group (this group may be substituted by a halogen atom, a $C_1$–$C_6$ alkyl group, a $C_1$–$C_6$ alkoxy group, a $C_1$–$C_4$ haloalkyl group, a $C_1$–$C_4$ haloalkoxy group, a cyano group, a nitro group, a $C_1$–$C_6$ alkylthio group, a $C_1$–$C_6$ alkylsulfinyl group or a $C_1$–$C_6$ alkylsulfonyl group), a $C_1$–$C_6$ alkylthio group (except for a case where $R^2$ =phenyl group, and W=$SO_2$), a $C_2$–$C_6$ alkenylthio group, a $C_2$–$C_6$ alkynylthio group, a $C_3$–$C_6$ cycloalkylthio group, a $C_1$–$C_6$ alkylsulfinyl group, a $C_2$–$C_6$ alkenylsulfinyl group, a $C_2$–$C_6$ alkynylsulfinyl group, a $C_3$–$C_6$ cycloalkylsulfinyl group, a $C_1$–$C_6$ alkylsulfonyl group, a $C_2$–$C_6$ alkenylsulfonyl group, a $C_2$–$C_6$ alkynylsulfonyl group, a $C_3$–$C_6$ cycloalkylsulfonyl group, a $C_1$–$C_6$ hydroxyalkyl group, a $C_2$–$C_7$ acyl group, a $C_1$–$C_6$ alkoxy $C_1$–$C_6$ alkyl group, a cyano group, a cyano $C_1$–$C_6$ alkyl group, a $C_1$–$C_6$ alkoxycarbonyl group, a $C_1$–$C_6$ alkoxycarbonyl $C_1$–$C_6$ alkyl group, a $C_1$–$C_6$ alkoxycarbonyl $C_2$–$C_6$ alkenyl group, a carboxyl group, a carboxyl $C_1$–$C_6$ alkyl group, a di $C_1$–$C_6$ alkoxy $C_1$–$C_6$ alkyl group, a $C_1$–$C_6$ alkoxyimino $C_1$–$C_6$ alkyl group, a hydroxyimino $C_1$–$C_6$ alkyl group, a dioxolanyl group (this group may be substituted by a $C_1$–$C_6$ alkyl group), an aldehyde group, an oxiranyl group, a $NR^9R^{10}$ group or a $CONR^9R^{10}$ group, and $R^9$ is a hydrogen atom, a $C_1$–$C_6$ alkyl group, a $C_2$–$C_6$ alkenyl group, a $C_2$–$C_6$ alkynyl group, a $C_1$–$C_4$ haloalkyl group, a $C_1$–$C_6$ alkoxy $C_1$–$C_6$ alkyl group, a $C_1$–$C_6$ alkylthio $C_1$–$C_6$ alkyl group, a $C_3$–$C_6$ cycloalkyl group, a $C_2$–$C_7$ acyl group or a $C_1$–$C_6$ alkylsulfonyl group, and $R^{10}$ is a $C_1$–$C_6$ alkyl group, a $C_2$–$C_6$ alkenyl group, a $C_2$–$C_6$ alkynyl group, a $C_1$–$C_4$ haloalkyl group, a $C_1$–$C_6$ alkoxy $C_1$–$C_6$ alkyl group, a $C_1$–$C_6$ alkylthio $C_1$–$C_6$ alkyl group, a $C_3$–$C_6$ cycloalkyl group, a $C_2$–$C_7$ acyl group, a $C_1$–$C_6$ alkylsulfonyl group, a $C_1$–$C_6$ alkoxycarbonyl group or a benzyloxycarbonyl group;

$R^2$ is a $C_1$–$C_6$ alkyl group, a $C_2$–$C_6$ alkenyl group, a $C_2$–$C_6$ alkynyl group, a $C_1$–$C_6$ alkylthio group, a $C_1$–$C_4$ haloalkyl group, a $C_1$–$C_6$ alkoxy group, a $C_1$–$C_6$ alkoxy $C_1$–$C_6$ alkyl group, a $C_1$–$C_6$ alkylthio $C_1$–$C_6$ alkyl group, a $C_3$–$C_6$ cycloalkyl group (this group may be substituted by a halogen atom, a $C_1$–$C_6$ alkyl group, a $C_1$–$C_6$ alkoxy group or a $C_1$–$C_4$ haloalkyl group), a $C_2$–$C_7$ acyl group, a cyano group, a di $C_1$–$C_6$ alkoxy $C_1$–$C_6$ alkyl group, a $C_1$–$C_6$ alkoxyimino $C_1$–$C_6$ alkyl group, a hydroxyimino $C_1$–$C_6$ alkyl group, a a cyano $C_1$–$C_6$ alkyl group, a $C_1$–$C_6$ hydroxyalkyl group, a $C_1$–$C_6$ alkoxycarbonyl group, a $C_1$–$C_6$ alkoxycarbonyl $C_1$–$C_6$ alkyl group, a $CR^{11}R^{12}NR^9R^{10}$ group, a $CONR^9R^{10}$ group, a $CR^{11}R^{12}CONR^9R^{10}$ group or a group represented by the formulae $R^2$-1 or $R^2$-2:

-continued

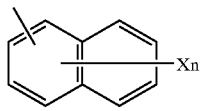

R²-2 and wherein X is a hydrogen atom, a halogen atom, a $C_1$–$C_6$ alkyl group, a $C_2$–$C_6$ alkenyl group, a $C_2$–$C_6$ alkynyl group, a $C_1$–$C_6$ alkoxy group, a $C_1$–$C_6$ alkoxy $C_1$–$C_6$ alkyl group, a $NR^9R^{10}$ group, a $CONR^9R^{10}$ group, a $C_1$–$C_4$ haloalkoxy group, a $C_2$–$C_6$ alkenyloxy group, a $C_3$–$C_6$ cycloalkyloxy group, a $C_2$–$C_7$ acyl group, a $C_1$–$C_6$ alkoxycarbonyl group, a $C_1$–$C_6$ alkylthio group, a $C_1$–$C_6$ alkylsulfinyl group, a $C_1$–$C_6$ alkylsufonyl group, a cyano group, a nitro group or a $C_1$–$C_4$ haloalkyl group, n is an integer of from 1 to 3, and when n is an integer of 2 or 3, the plurality of X may be the same or different, and two adjacent lower alkoxy groups may be bonded to each other to form a $C_1$–$C_3$ alkylenedioxy group, and each of $R^{11}$ and $R^{12}$ is a hydrogen atom, a $C_1$–$C_6$ alkyl group, a $C_2$–$C_6$ alkenyl group, a $C_2$–$C_6$ alkynyl group or a $C_1$–$C_6$ alkoxy group;

$R^3$ is a hydrogen atom, a $C_1$–$C_6$ alkyl group, a $C_2$–$C_6$ alkenyl group, a $C_2$–$C_6$ alkynyl group, a $C_1$–$C_6$ alkoxy group, a di $C_1$–$C_6$ alkylamino group, a $C_3$–$C_6$ cycloalkyl group, a $C_1$–$C_6$ alkoxy $C_1$–$C_6$ alkyl group, a cyano $C_1$–$C_6$ alkyl group or a $C_3$–$C_6$ cycloalkyl $C_1$–$C_6$ alkyl group;

W is a —C(=Q)Z— group or a —SO$_2$— group, Q is an oxygen atom or a sulfur atom, Z is an oxygen atom, a sulfur atom, a —NR$^6$— group, a —C(R)R$^5$— group, a —C(R$^4$)R$^5$—Q— group, a —NR$^6$NR$^6$— group or a —NR$^6$C(R$^4$)R$^5$— group, and each of $R^4$ and $R^5$ is a hydrogen atom, a $C_1$–$C_6$ alkyl group, a halogen atom or a $C_1$–$C_6$ alkoxy group, and each of $R^6$ and $R^{6a}$ is a hydrogen atom, a $C_1$–$C_6$ alkyl group, a $C_2$–$C_6$ alkenyl group or a $C_2$–$C_6$ alkynyl group;

Ar is a group represented by any one of the formulae Ar-1 or Ar-2:

Ar-1

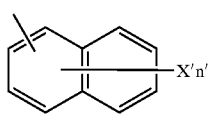

Ar-2 and wherein X' is a hydrogen atom, a halogen atom, a $C_1$–$C_6$ alkyl group, a $C_2$–$C_6$ alkenyl group, a $C_2$–$C_6$ alkynyl group, a $C_1$–$C_6$ alkoxy group, a $C_1$–$C_6$ alkoxy $C_1$–$C_6$ alkyl group, a $NR^9R^{10}$ group, a $CONR^9R^{10}$ group, a $C_1$–$C_4$ haloalkoxy group, a $C_2$–$C_6$ alkenyloxy group, a $C_3$–$C_6$ cycloalkyloxy group, a $C_2$–$C_7$ acyl group, a $C_1$–$C_6$ alkoxycarbonyl group, a $C_1$–$C_6$ alkylthio group, a $C_1$–$C_6$ alkylsulfinyl group, a $C_1$–$C_6$ alkylsufonyl group, a cyano group, a nitro group or a $C_1$–$C_4$ haloalkyl group, n' is an integer of from 1 to 3, and when n' is an integer of 2 or 3, the plurality of X' may be the same or different, and two adjacent lower alkoxy groups may be bonded to each other to form a $C_1$–$C_3$ alkylenedioxy group;

$R^7$ is a hydrogen atom or a halogen atom; and $R^8$ is a hydrogen atom.

5. A pyrimidine derivative represented by the formula

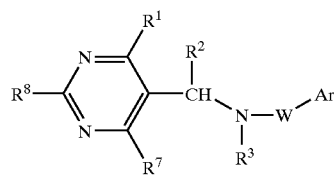

(I)

wherein $R^1$ is a $C_1$–$C_6$ alkyl group, a $C_1$–$C_6$ alkylcarbonyl $C_1$–$C_6$ alkyl group, a $C_3$–$C_6$ cycloalkyl group (this group may be substituted by a halogen atom, a $C_1$–$C_6$ alkyl group, a $C_1$–$C_6$ alkoxy group or a $C_1$–$C_4$ haloalkyl group), a $C_1$–$C_4$ haloalkyl group, a $C_1$–$C_6$ alkoxy group, a phenyl group (this group may be substituted by a halogen atom, a $C_1$–$C_6$ alkyl group, a $C_1$–$C_6$ alkoxy group, a $C_1$–$C_4$ haloalkyl group, a $C_1$–$C_4$ haloalkoxy group, a cyano group, a nitro group, a $C_1$–$C_6$ alkylthio group, a $C_1$–$C_6$ alkylsulfinyl group or a $C_1$–$C_6$ alkylsulfonyl group), a $C_1$–$C_6$ alkylthio group (except for a case where $R^2$=phenyl group, and W=SO$_2$), a $C_1$–$C_6$ alkylsulfinyl group, a $C_2$–$C_7$ acyl group, a $C_1$–$C_6$ alkoxy $C_1$–$C_6$ alkyl group, a cyano group, a cyano $C_1$–$C_6$ alkyl group, a $C_1$–$C_6$ alkoxycarbonyl group, a $C_1$–$C_6$ alkoxycarbonyl $C_2$–$C_6$ alkenyl group, a carboxyl group, a di $C_1$–$C_6$ alkoxy $C_1$–$C_6$ alkyl group or a $C_1$–$C_6$ alkoxyimino $C_1$–$C_6$ alkyl group;

$R^2$ is a $C_1$–$C_6$ alkyl group, a $C_1$–$C_4$ haloalkyl group, a $C_1$–$C_6$ alkoxy $C_1$–$C_6$ alkyl group, a $C_1$–$C_6$ alkylthio $C_1$–$C_6$ alkyl group, a $C_3$–$C_6$ cycloalkyl group (this group may be substituted by a halogen atom, a $C_1$–$C_6$ alkyl group, a $C_1$–$C_6$ alkoxy group or a $C_1$–$C_4$ haloalkyl group) a $C_2$–$C_7$ acyl group, or a group represented by the formula R²-1:

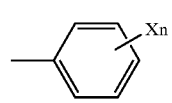

R²-1 and wherein X is a hydrogen atom, a halogen atom, a $C_1$–$C_6$ alkyl group, a $C_2$–$C_6$ alkenyl group, a $C_2$–$C_6$ alkynyl group, a $C_1$–$C_6$ alkoxy group, a $C_1$–$C_6$ alkoxy $C_1$–$C_6$ alkyl group, a $NR^9R^{10}$ group, a $CONR^9R^{10}$ group, a $C_1$–$C_4$ haloalkoxy group, a $C_2$–$C_6$ alkenyloxy group, a $C_3$–$C_6$ cycloalkyloxy group, a $C_2$–$C_7$ acyl group, a $C_1$–$C_6$ alkoxycarbonyl group, a $C_1$–$C_6$ alkylthio group, a $C_1$–$C_6$ alkylsulfinyl group, a $C_1$–$C_6$ alkylsufonyl group, a cyano group, a nitro group or a $C_1$–$C_4$ haloalkyl group, n is an integer of from 1 to 3, and when n is an integer of 2 or 3, the plurality of X may be the same or different, and two adjacent lower alkoxy groups may be bonded to each other to form a $C_1$–$C_3$ alkylenedioxy group, and $R^9$ is a hydrogen atom, a $C_1$–$C_6$ alkyl group, a $C_2$–$C_6$ alkenyl group, a $C_2$–$C_6$ alkynyl group, a $C_1$–$C_4$ haloalkyl group, a $C_1$–$C_6$ alkoxy $C_1$–$C_6$ alkyl group, a $C_1$–$C_6$ alkylthio $C_1$–$C_6$ alkyl group, a $C_3$–$C_6$ cycloalkyl group, a $C_2$–$C_7$ acyl group or a $C_1$–$C_6$ alkylsulfonyl group, and $R^{10}$ is a $C_1$–$C_6$ alkyl group, a $C_2$–$C_6$ alkenyl group, a $C_2$–$C_6$ alkynyl group, a $C_1$–$C_4$ haloalkyl group, a $C_1$–$C_6$ alkoxy $C_1$–$C_6$ alkyl group, a $C_1$–$C_6$ alkylthio $C_1$–$C_6$ alkyl group, a $C_3$–$C_6$ cycloalkyl group, a $C_2$–$C_7$ acyl group, a $C_1$–$C_6$ alkylsulfonyl group, a $C_1$–$C_6$ alkoxycarbonyl group or a benzyloxycarbonyl group, and each of $R^{11}$ and $R^{12}$ is a hydrogen atom, a $C_1$–$C_6$ alkyl group, a $C_2$–$C_6$ alkenyl group, a $C_2$–$C_6$ alkynyl group or a $C_1$–$C_6$ alkoxy group;

$R^3$ is a $C_1$–$C_6$ alkyl group, a $C_2$–$C_6$ alkenyl group, a $C_2$–$C_6$ alkynyl group, a $C_1$–$C_6$ alkoxy group, a $C_3$–$C_6$ cycloalkyl group, a $C_1$–$C_6$ alkoxy $C_1$–$C_6$ alkyl group or a cyano $C_1$–$C_6$ alkyl group;

W is a —C(=Q)Z— group or a —SO$_2$— group, Q is an oxygen atom or a sulfur atom, Z is a —NR$^6$— group, a —C(R$^4$)R$^5$— group, a —C(R$^4$)R$^5$—Q— group, a —NRR$^{6a}$— group or a —NR$^6$C(R$^4$)R$^5$— group, and each of $R^4$ and $R^5$ is a hydrogen atom, a $C_1$–$C_6$ alkyl group, a halogen atom or a $C_1$–$C_6$ alkoxy group, and each of $R^6$ and $R^{6a}$ is a hydrogen atom, a $C_1$–$C_6$ alkyl group, a $C_2$–$C_6$ alkenyl group or a $C_2$–$C_6$ alkynyl group;

Ar is a group represented by formula Ar-1,

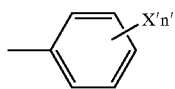

Ar-1 and wherein X' is a hydrogen atom, a halogen atom, a $C_1$–$C_6$ alkyl group, a $C_2$–$C_6$ alkenyl group, a $C_2$–$C_6$ alkynyl group, a $C_1$–$C_6$ alkoxy group, a $C_1$–$C_6$ alkoxy $C_1$–$C_6$ alkyl group, a NR$^9$R$^{10}$ group, a CONR$^9$R$^{10}$ group, a $C_1$–$C_4$ haloalkoxy group, a $C_2$–$C_6$ alkenyloxy group, a $C_3$–$C_6$ cycloalkyloxy group, a $C_2$–$C_7$ acyl group, a $C_1$–$C_6$ alkoxycarbonyl group, a $C_1$–$C_6$ alkylthio group, a $C_1$–$C_6$ alkylsulfinyl group, a $C_1$–$C_6$ alkylsufonyl group, a cyano group, a nitro group or a $C_1$–$C_4$ haloalkyl group, n' is an integer of from 1 to 3, and when n' is an integer of 2 or 3, the plurality of X' may be the same or different, and two adjacent lower alkoxy groups may be bonded to each other to form a $C_1$–$C_3$ alkylenedioxy group;

$R^7$ is a hydrogen atom, a halogen atom, a $C_1$–$C_6$ alkyl group, a $C_1$–$C_6$ alkoxy group, a $C_1$–$C_6$ alkylthio group, a $C_1$–$C_4$ haloalkyl group or a $C_3$–$C_6$ cycloalkyl group, and $R^8$ is a hydrogen atom, a $C_1$–$C_6$ alkyl group, a $C_1$–$C_6$ alkylthio group, a $C_1$–$C_4$ haloalkyl group or a $C_3$–$C_6$ cycloalkyl group.

6. A herbicide containing the pyrimidine derivative as defined in claim 1, as an active ingredient.

7. A herbicide containing the pyrimidine derivative as defined in claim 2, as an active ingredient.

8. A herbicide containing the pyrimidine derivative as defined in claim 3, as an active ingredient.

9. A herbicide containing the pyrimidine derivative as defined in claim 4, as an active ingredient.

10. A herbicide containing the pyrimidine derivative as defined in claim 5, as an active ingredient.

* * * * *